(12) United States Patent
Hasslacher et al.

(10) Patent No.: US 8,877,473 B2
(45) Date of Patent: Nov. 4, 2014

(54) FORMULATIONS OF RECOMBINANT FURIN

(75) Inventors: Meinhard Hasslacher, Vienna (AT); Andrzej Citkowicz, Fremont, CA (US); Catherine White, Albany, CA (US); Ken Franke, Davis, CA (US)

(73) Assignees: Baxter International Inc., Deerfield, IL (US); Baxter Healthcare SA, Glattpark (Opfikon) (CH)

( * ) Notice: Subject to any disclaimer, the term of this patent is extended or adjusted under 35 U.S.C. 154(b) by 0 days.

(21) Appl. No.: 13/488,324

(22) Filed: Jun. 4, 2012

(65) Prior Publication Data

US 2012/0329128 A1 Dec. 27, 2012

Related U.S. Application Data

(60) Provisional application No. 61/492,712, filed on Jun. 2, 2011.

(51) Int. Cl.
| | | |
|---|---|---|
| *C12N 9/96* | (2006.01) | |
| *C12N 9/64* | (2006.01) | |
| *A61K 9/19* | (2006.01) | |
| *A61K 47/26* | (2006.01) | |
| *A61K 9/08* | (2006.01) | |
| *A61K 9/00* | (2006.01) | |

(52) U.S. Cl.
CPC ....... *C12Y 304/21075* (2013.01); *C12N 9/6454* (2013.01); *A61K 9/19* (2013.01); *A61K 47/26* (2013.01); *A61K 9/08* (2013.01); *A61K 9/0019* (2013.01)
USPC ........................................................ 435/188

(58) Field of Classification Search
USPC ........................................................ 435/188
See application file for complete search history.

(56) References Cited

U.S. PATENT DOCUMENTS

| | | |
|---|---|---|
| 6,210,929 B1 | 4/2001 | Schlokat et al. |
| 6,596,526 B1 | 7/2003 | Plaimauer et al. |
| 8,124,737 B2 * | 2/2012 | Lichte et al. .................. 530/383 |
| 2009/0181423 A1 * | 7/2009 | Plaimauer et al. ........... 435/68.1 |
| 2009/0304669 A1 | 12/2009 | Matthiessen et al. |

FOREIGN PATENT DOCUMENTS

| | | |
|---|---|---|
| EP | 1 825 865 A2 | 8/2007 |
| WO | WO 91/06314 A2 | 5/1991 |
| WO | WO 92/09698 A1 | 6/1992 |
| WO | WO 2005/058283 A2 | 6/2005 |
| WO | WO 2005/058283 A3 | 6/2005 |
| WO | WO 2005058283 A2 * | 6/2005 |

OTHER PUBLICATIONS

Human Recombinant Furin F2677. Datasheet [online]. Sigma Aldrich [retrieved on Feb. 26, 2013]. Retrieved from the Internet: <URL: http://www.sigmaaldrich.com/etc/medialib/docs/Sigma/Datasheet/7/f2677dat.Par.0001.File.tmp/f2677dat.pdf>.*

Bravo, D.A. et al., "Accurate and Efficient Cleavage of the Human Insulin Proreceptor by the Human Proprotein-processing Protease Furin," *The Journal of Biological Chemistry*, Oct. 14, 1994, vol. 269, No. 41, pp. 25830-25837.

Hosaka, M. et al., "Arg-X-Lys/Arg-Arg Motif as a Signal for Precursor Cleavage Catalyzed by Furin within the Constitutive Secretory Pathway," *The Journal of Biological Chemistry*, Jul. 5, 1991, vol. 266, No. 19, pp. 12127-12130.

International Search Report for International Patent Application No. PCT/US2012/040790 mailed Nov. 5, 2012, 5 pages.

Molloy, S.S. et al., "Human Furin is a Calcium-dependent Serine Endoprotease That Recognizes the Sequence Arg-X-X-Arg and Efficiently Cleaves Anthrax Toxin Protective Antigen," *The Journal of Biological Chemistry*, Aug. 15, 1992, vol. 267, No. 23, pp. 16396-16402.

* cited by examiner

*Primary Examiner* — Jon P Weber
*Assistant Examiner* — Kara Johnson
(74) *Attorney, Agent, or Firm* — Morgan, Lewis & Bockius LLP

(57) ABSTRACT

The present application provides stabilized formulations of furin (e.g., rfurin) containing a sugar, sugar alcohol, and/or non-ionic surfactant. As compared to non-stabilized compositions, the furin formulations disclosed herein retain greater amounts of furin activity and monomeric furin content, while reducing furin aggregation when stored and/or subjected to mechanical stress. Also provided are methods for stably diluting furin (e.g., rfurin) compositions.

28 Claims, 45 Drawing Sheets

FORMULATIONS OF RECOMBINANT FURIN

CROSS-REFERENCES TO RELATED APPLICATIONS

The present application claims the benefit of U.S. Provisional Application No. 61/492,712, filed Jun. 2, 2011, the content of which is expressly incorporated herein by reference in its entirety for all purposes.

FIELD OF THE APPLICATION

This application generally relates to the field of protein formulations.

BACKGROUND OF THE INVENTION

The family of the proteolytic mammalian subtilisin-like proprotein convertases (SPC or PC) is homologous with bacterial subtilisins and yeast Kex2p. To date seven distinct members of the SPC family have been identified, including furin, PC1 (also known as PC3), PC2, PACE4, PC4, PC5 (also known as PC6), PC7 (LPC, PC8, or SPC7), each of which exhibits unique tissue distribution.

Furin, also termed PACE (paired basic amino acid cleavage enzyme) is ubiquitously expressed in all mammalian tissues and cell lines and is capable of processing a wide range of bioactive precursor proteins in the secretory pathway, including also hormones, growth factors, receptors, viral and bacterial proteins, and plasma proteins. It is a calcium-dependent serine endoprotease structurally arranged into several domains, namely a signal peptide, propeptide, catalytic domain, middle domain, (also termed homo-B or P-domain), the C-terminally located cysteine-rich domain, transmembrane domain and the cytoplasmic tail. The furin protease cleavage site comprises a recognition sequence which is characterized by the amino acid sequence Arg-X-Lys/Arg-Arg (Hosaka et al., J Biol Chem. 1991; 266:12127-30).

Furin belongs to the family of the pro-protein convertases and is dependent on calcium ($Ca^{2+}$). Furin specifically cleaves the C-terminal peptide bond of arginine within a specific sequence, containing arginine at positions −1 and −4. This sequence can be found in numerous human proteins, showing that furin plays a major role in the maturation of a number of human pro-proteins. Accordingly, furin is a proprotein convertase that processes latent precursor proteins into their biologically active products. Furin is a calcium-dependent serine endoprotease that cleaves precursor proteins at their paired basic amino acid processing sites. One substrate for furin is von Willebrand Factor (vWF).

Furin (e.g., rfurin) is capable of converting pro-VWF (pro-von Willebrand factor) into mature VWF by cleaving the Arg741-Ser742 peptide bond of VWF. This maturation step is part of, for example, a rVWF production process which provides a therapy for von Willebrand Disease Type B. The production of activated recombinant proteins is of high clinical and diagnostic importance. For example, active or mature proteins, like mature VWF, may be used to control blood coagulation.

Furin formulations, particularly recombinant furin (rfurin) formulations, often have low shelf life (less than 6 months) due to a loss of rfurin activity from protein degradation (often from self-cleavage of the furin protein). In addition, when used in certain production processes, such as production of mature vWF, rfurin formulations are diluted, often by 200-fold, and the diluted rfurin generally shows a disproportionate loss of activity. Accordingly, there is a need in the field for methods and formulations that stabilize furin (e.g., rfurin) compositions, as well as methods for diluting concentrated furin (e.g., rfurin) compositions without losing a substantial fraction of furin activity.

BRIEF SUMMARY OF THE INVENTION

The present disclosure fulfills these and other needs in the field of furin (e.g., rfurin) formulation, storage, and manipulation, by providing methods and formulations for stabilizing furin (e.g., rfurin compositions). These needs are met, at least in part, by the discovery that the addition of sugars, sugar alcohols, and/or non-ionic surfactants significantly increases the stability of furin (e.g., rfurin) compositions during storage and mechanical stress.

Accordingly, the present invention provides highly stabilized furin formulations, particularly highly stabilized rfurin formulations that show increased stability under conditions of high temperature, agitation, and varying pH as compared to the starting (control) furin formulations.

In one aspect, the present disclosure provides a stabilized aqueous composition of recombinant furin (rfurin), the composition comprising: from 8,000 U/mL to 500,000 U/mL rfurin; from 100 mM to 300 mM of a pharmaceutically acceptable salt; from 0.5 mM to 2 mM calcium; from 2% to 20% sugar or sugar alcohol; from 10 to 200 ppm non-ionic surfactant; from 10 to 200 mM buffering agent; and a pH from 5.5 to 7.5.

In one embodiment, the compositions provided above include 150 mM to 250 mM of a pharmaceutically acceptable salt. In another embodiment, the compositions provided above include 190±10 mM of a pharmaceutically acceptable salt. In another embodiment, the compositions provided above include 190 mM of a pharmaceutically acceptable salt.

In one embodiment of the compositions provided above, the pharmaceutically acceptable salt is sodium chloride. In another embodiment of the compositions provided above, the pharmaceutically acceptable salt is potassium chloride.

In one embodiment, the compositions provided above include 0.9±0.2 mM calcium. In another embodiment, the compositions provided above include 0.92 mM calcium.

In one embodiment, the compositions provided above include from 5% to 15% sugar or sugar alcohol. In another embodiment, the compositions provided above include 10±2% sugar or sugar alcohol. In another embodiment, the compositions provided above include 10% sugar or sugar alcohol.

In one embodiment of the compositions provided above, the sugar or sugar alcohol is selected from the group consisting of sucrose, trehalose, mannitol, and a combination thereof. In another embodiment of the compositions provided above, the sugar or sugar alcohol is trehalose. In another embodiment of the compositions provided above, the sugar or sugar alcohol is sucrose.

In one embodiment, the compositions provided above include from 10 ppm to 100 ppm non-ionic surfactant. In another embodiment, the compositions provided above include from 50 ppm to 100 ppm non-ionic surfactant. In another embodiment, the compositions provided above include 75 ppm non-ionic surfactant.

In one embodiment of the compositions provided above, the non-ionic surfactant is polysorbate-80.

In one embodiment, the compositions provided above include from 50 mM to 150 mM buffering agent. In another embodiment, the compositions provided above include 90±10 mM buffering agent. In another embodiment, the compositions provided above include 91 mM buffering agent.

In one embodiment of the compositions provided above, the buffering agent comprises acetate. In another embodiment of the compositions provided above, the buffering agent comprises HEPES. In another embodiment of the compositions provided above, the buffering agent comprises MES. In another embodiment of the compositions provided above, the buffering agent comprises acetate and HEPES.

In one embodiment, the compositions provided above include from 25 mM to 75 mM acetate and from 25 to 75 mM HEPES. In another embodiment, the compositions provided above include 45±5 mM acetate and 45±5 mM HEPES. In another embodiment, the compositions provided above include 45 mM acetate and 46 mM HEPES.

In one embodiment, the compositions provided above have a pH from 5.5 to 7.0. In another embodiment, the compositions provided above have a pH from 5.5 to 6.5. In another embodiment, the compositions provided above have a pH of 6.0±0.2. In another embodiment, the compositions provided above have a pH of 6.0.

In one embodiment of the compositions provided above, the composition has increased stability when stored at 37° C. as compared to a rfurin composition that does not contain a sugar or sugar alcohol.

In one embodiment of the compositions provided above, the composition maintains a higher percentage of rfurin activity when stored at 37° C. as compared to a rfurin composition that does not contain a sugar or sugar alcohol.

In one embodiment of the compositions provided above, the composition maintains a higher percentage of rfurin monomer content when stored at 37° C. as compared to a rfurin composition that does not contain a sugar or sugar alcohol.

In one embodiment of the compositions provided above, the composition has increased stability when agitated as compared to a rfurin composition that does not contain a non-ionic surfactant.

In one embodiment of the compositions provided above, the composition maintains a higher percentage of rfurin activity when agitated as compared to a rfurin composition that does not contain a non-ionic surfactant.

In one embodiment of the compositions provided above, the composition maintains a higher percentage of rfurin monomer content when agitated as compared to a rfurin composition that does not contain a non-ionic surfactant.

In one embodiment of the compositions provided above, the composition has increased stability when diluted as compared to a rfurin composition that does not contain a non-ionic surfactant.

In one embodiment of the compositions provided above, the composition maintains a higher percentage of rfurin activity when diluted as compared to a rfurin composition that does not contain a non-ionic surfactant.

In one embodiment of the compositions provided above, the composition maintains a higher percentage of rfurin monomer content when diluted as compared to a rfurin composition that does not contain a non-ionic surfactant.

In one aspect, the present disclosure provides a stabilized aqueous composition of recombinant furin (rfurin), the composition comprising: from 8,000 U/mL to 500,000 U/mL rfurin; 190 mM sodium chloride; 0.92 mM calcium; 10% trehalose; 75 ppm polysorbate 80; 45 mM acetic acid; 46 mM HEPES; and a pH from 5.5 to 7.5.

In one embodiment, the compositions provided above have a pH from 5.5 to 7.0. In another embodiment, the compositions provided above have a pH from 5.5 to 6.5. In another embodiment, the compositions provided above have a pH of 6.0±0.2. In another embodiment, the compositions provided above have a pH of 6.0.

In one aspect, the present disclosure provides a method for diluting an aqueous rfurin composition, the method comprising adding a dilution buffer comprising from 10 ppm to 200 ppm of a non-ionic surfactant to the aqueous rfurin composition, thereby forming a diluted rfurin composition.

In one embodiment of the methods provided above, the dilution buffer comprises from 10 ppm to 100 ppm of a non-ionic surfactant. In another embodiment of the methods provided above, the dilution buffer comprises from 50 ppm to 100 ppm of a non-ionic surfactant. In another embodiment of the methods provided above, the dilution buffer comprises 75 ppm of a non-ionic surfactant.

In one embodiment of the methods provided above, the dilution buffer has a pH of from 5.5 to 7.5. In another embodiment of the methods provided above, the dilution buffer has a pH of from 5.5 to 6.5. In another embodiment of the methods provided above, the dilution buffer has a pH of 6.0±0.2. In another embodiment of the methods provided above, the dilution buffer has a pH of 6.0.

In one embodiment of the methods provided above, the diluted rfurin composition comprises at least 50% of rfurin activity present in the aqueous rfurin composition prior to dilution.

In one embodiment of the methods provided above, the diluted rfurin composition comprises at least 75% of rfurin activity present in the aqueous rfurin composition prior to dilution.

In one aspect, the present disclosure provides a highly stabilized formulation of recombinant furin (rfurin), said formulation comprising: 8,000-52,000 U/mL rfurin; 1 mM to 300 mM of a pharmaceutically acceptable salt; 0.1 mM to 2 mM calcium chloride; 1% to 20% sugar and/or sugar dihydrate; 50 to 100 ppm of a surfactant; and 1 mM to 100 mM of a carboxylic acid, a buffering agent in sufficient concentration for maintaining a pH of 4.0-7.0, or both said carboxylic acid and said buffering agent.

In one embodiment, the formulations provided above include 180-200 mM salt.

In one embodiment of the formulations provided above, the salt is sodium chloride.

In one embodiment, the formulations provided above include 0.5-1.0 mM calcium.

In one embodiment, the formulations provided above include 5-15% sugar or sugar dihydrate.

In one embodiment of the formulations provided above, the sugar or sugar dihydrate is selected from the group consisting of sucrose, trehalose, mannitol, and a combination thereof.

In one embodiment of the formulations provided above, the surfactant is polysorbate 80.

In one embodiment of the formulations provided above, the surfactant is present at a concentration of about 65 to about 85 ppm.

In one embodiment of the formulations provided above, the carboxylic acid is acetic acid.

In one embodiment of the formulations provided above, the carboxylic acid is in a concentration of 35-55 mM.

In one embodiment of the formulations provided above, the buffering agent is HEPES.

In one embodiment of the formulations provided above, the buffering agent is in a concentration of about 20 to about 100 mM.

In one embodiment of the formulations provided above, the formulation shows improved stability after storage at 37° C. as compared to a formulation that does not contain a sugar or sugar dihydrate.

In one embodiment of the formulations provided above, the formulation is prepared by adding rfurin to a composition comprising 1% polysorbate 80, 500 mM HEPES, 400 mM acetic acid, 1 mM calcium chloride, and trehalose dihydrate powder, wherein said composition has a pH of 6.0 prior to addition to said rfurin.

In one aspect, the present disclosure provides a highly stabilized formulation of recombinant furin (rfurin), said formulation comprising: 8,000-57,000 U/mL rfurin; 190 mM sodium chloride; 0.92 mM calcium chloride; 10% w/w trehalose dihydrate; 75 ppm polysorbate 80; 45 mM acetic acid; and 46 mM HEPES.

In one aspect, the present disclosure provides a highly stabilized formulation of recombinant furin (rfurin) that includes: (a) 8,000-52,000 U/mL rfurin; (b) 1 mM to 300 mM of a pharmaceutically acceptable salt; (c) 0.1 mM to 2 mM calcium chloride; (d) 1% to 20% sugar and/or sugar dihydrate; (e) 50 to 100 ppm of a surfactant; and (f) 1 mM to 100 mM of a carboxylic acid or a buffering agent in sufficient concentration for maintaining a pH of 4.0-7.0 or both the carboxylic acid and the buffering agent.

BRIEF DESCRIPTION OF THE DRAWINGS

FIG. 1. rFurin in the control formulation—a temperature study analyzed using the furin activity assay. rFurin samples in the control formulation were incubated at: room temperature, 37° C., or 45° C. for up to seven days. The activities of rfurin samples are plotted against the number of days of incubation. Error bars are ±1 standard deviation; n=4.

FIG. 2. rFurin in the control formulation—a temperature study analyzed using SEC. The same samples as in FIG. 1 were analyzed using SEC. Relative rfurin peak heights are plotted against the number of days of incubation. The relative peak heights were calculated as the percentages of the rfurin peak height at time zero.

FIG. 3. rFurin in the control formulation incubated at 37° C. analyzed using SEC. rFurin samples in the control formulation were incubated at 37° C. for seven days. FIG. 3 shows an overlay of SEC absorption profiles at 280 nm of six time points. The same study as in FIG. 1.

FIG. 4. rFurin in the control formulation incubated at room temperature and 37° C. analyzed using Western Blotting. The same study as in FIG. 1. Lane: (1) MWM marker; (2) T=0; (3) rfurin incubated at room temperature for 1 day; (4) rfurin incubated at room temperature for 2 days; (5) rfurin incubated at room temperature for 3 days; (6) rfurin incubated at room temperature for 7 days; (7) MWM marker; (8) rfurin incubated at 37° C. for 1 day; (9) rfurin incubated at 37° C. for 2 days; (10) rfurin incubated at 37° C. for 3 days; and (11) rfurin incubated at 37° C. for 7 days.

FIG. 5. rFurin in the control formulation—a freeze/thaw study analyzed using the furin activity assay. rFurin activity is plotted against the number of freeze/thaw cycles. Error bars are ±1 standard deviation; n=4.

FIG. 6. rFurin in the control formulation—a freeze/thaw study analyzed using SEC. rFurin peak heights are plotted against the number of freeze/thaw cycles.

FIG. 7. rFurin in the control formulation—an agitation study analyzed using the activity assay. rFurin activity is plotted against the time of agitation. Error bars are ±1 standard deviation; n=4.

FIG. 8. rFurin in the control formulation—an agitation study analyzed using SEC. rFurin peak heights are plotted against the time of agitation.

FIG. 9. Comparison of different lots of rfurin using Western Blotting. Various lots of rfurin were analyzed using Western Blotting. Production order is denoted alphabetically. Lane: (1) MWM marker; (2) furin reference; (3) 03-04-09 (lot 018342, 2 mL vial); (4) 03-08-09 (lot 018365, 2 mL vial); (5) 03-15-09 (lot 018366, 2 mL vial); (6) 03-01-09 (lot 018315, 2 mL vial); (7) 07-26-10 (lot X572, 200 mL bottle); (8) 03-06-09 (lot 018365, 200 mL bottle); (9) 08-01-10 (lot X576, 200 mL bottle); (10) 03-09-09 (lot 018366, 200 mL bottle); (11) MWM marker; (12) furin reference; (13) 08-03-10 (lot X577, 200 mL bottle); (14) 07-24-10 (lot X573, 200 mL bottle); (15) 07-30-10 (lot X575, 200 mL bottle); (16) 018346 (QC Stability at −80° C.); (17) 018346 (QC Stability at −25° C.); (18) 018315 (QC Stability at −80° C.); and (19) 018315 (QC Stability at −25° C.).

FIG. 10. Impact of thawing method on rfurin activity analyzed using the furin activity assay. rFurin sample activities are shown as bars for various lots of rfurin thawed at either: 4° C. (left) or room temperature (RT; right). Error bars are ±1 standard deviation; n=4.

FIG. 11. Effect of pH 5 and 5.5 on rfurin activity analyzed using the furin activity assay. rFurin samples were incubated at 37° C. at either pH: 5.0, 5.5, or 6.0 (control formulation) for up to seven days. The activities of rfurin samples are plotted against the number of days of incubation. Error bars are ±1 standard deviation; n=4.

FIG. 12. Effect of pH 5 and 5.5 on rfurin activity analyzed using SEC. rFurin samples were incubated at 37° C. at either pH: 5.0, 5.5 or 6.0 (control formulation). Relative peak heights of rfurin are plotted against the number of days of incubation. The relative peak heights were calculated as the percentage of the rfurin peak height at time zero.

FIG. 13. rFurin stability at 37° C. in the control formulation analyzed using SEC. A rfurin sample in the control formulation was incubated for four days at 37° C. The overlay of 280 nm absorption profiles shows three time points: T=0, 1 day, and 4 days of incubation.

FIG. 14. rFurin stability in MES pH 6.0 analyzed using SEC. A rfurin sample was spiked with MES (final C=100 mM, pH 6.0) and incubated for four days at 37° C. An overlay of 280 nm absorption profiles shows three time points: T=0, 1 day, and 4 days of incubation.

FIG. 15. rFurin stability in HEPES pH 7.0 analyzed using SEC. A rfurin sample was spiked with HEPES (final C=100 mM, pH 7.0) and incubated for four days at 37° C. The overlay of 280 nm absorption profiles shows three time points: T=0, 1 day, and 4 days of incubation.

FIG. 16. rFurin stability in HEPES pH 8.0 analyzed using SEC. A rfurin sample was spiked with HEPES (final C=100 mM, pH 8.0) and incubated for four days at 37° C. The overlay of 280 nm absorption profiles shows three time points: T=0, 1 day, and 4 days of incubation.

FIG. 17. Effects of sucrose and polysorbate 80 additives on rfurin stability at 37° C. analyzed using SEC. The samples were incubated at 37° C. for four days. Relative peak heights of rfurin are plotted against the time of incubation. The relative peak heights were calculated as the percentages of the rfurin peak height at time zero.

FIG. 18. Effects of sucrose and polysorbate 80 on rfurin stability in the control formulation at 37° C. analyzed using the furin activity assay. The relative activities of rfurin samples are plotted against the number of days of incubation to compare the following samples: control formulation without additives, control formulation plus 10% sucrose, and control formulation plus 10% sucrose plus 25 ppm polysorbate 80. The relative activity values were calculated as the percentages of the furin activity at time zero. Error bars are ±1 standard deviation=4.

Figure 19:
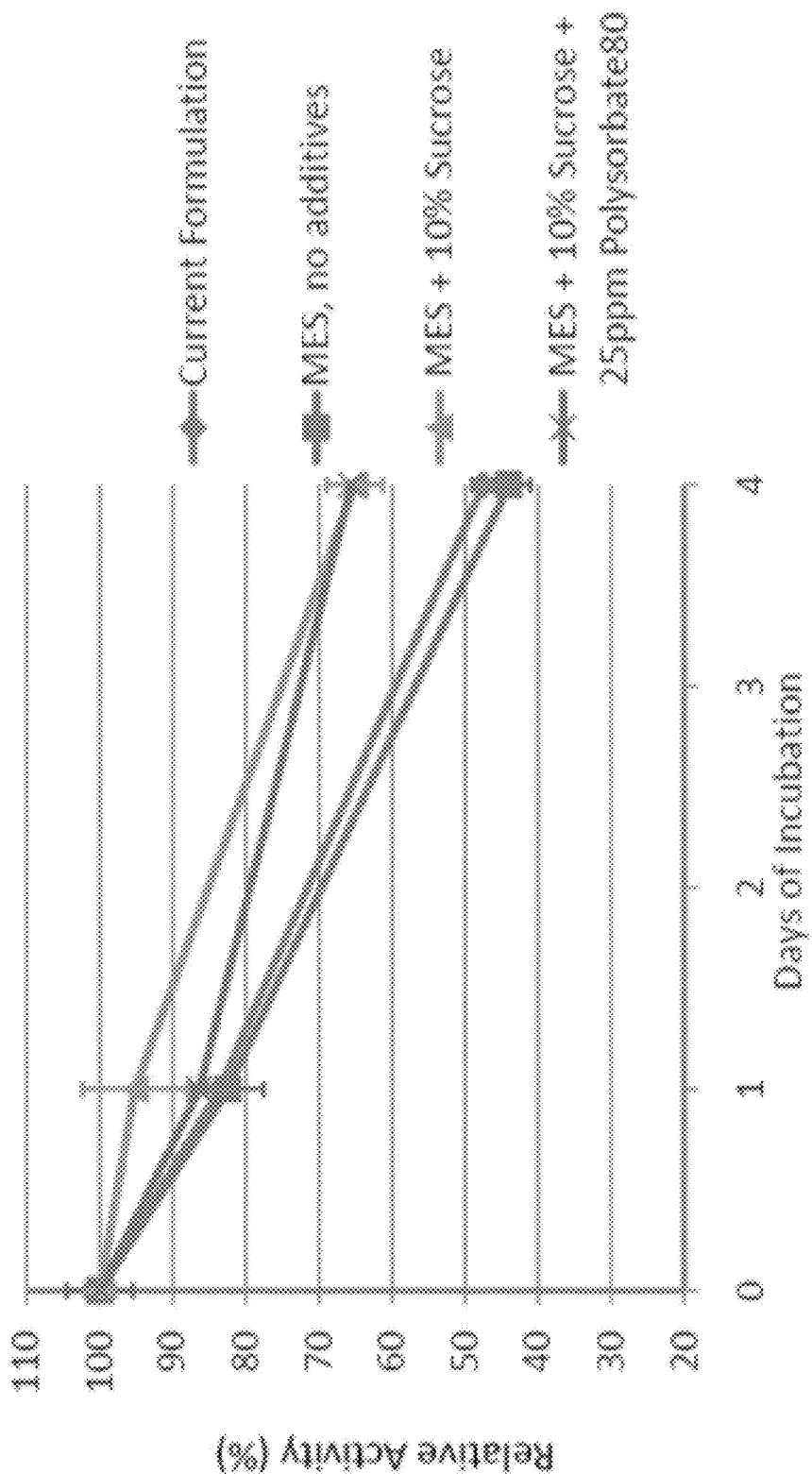

FIG. 19. Effects of sucrose and polysorbate 80 on rfurin stability in MES buffer at 37° C. analyzed using the furin activity assay. The relative activities of rfurin samples are plotted against the number of days of incubation to compare the following samples: control formulation without additives, spiked with MES (final C=100 mM, pH 6.0), spiked with MES (final C=100 mM, pH 6. plus 10% sucrose, and spiked with MES (final C=100 mM, pH 6.0) plus 10% sucrose plus 25 ppm polysorbate 80. The relative activity values were calculated as the percentages of the furin activity at time zero. Error bars are ±1 standard deviation; n=4.

Figure 20:
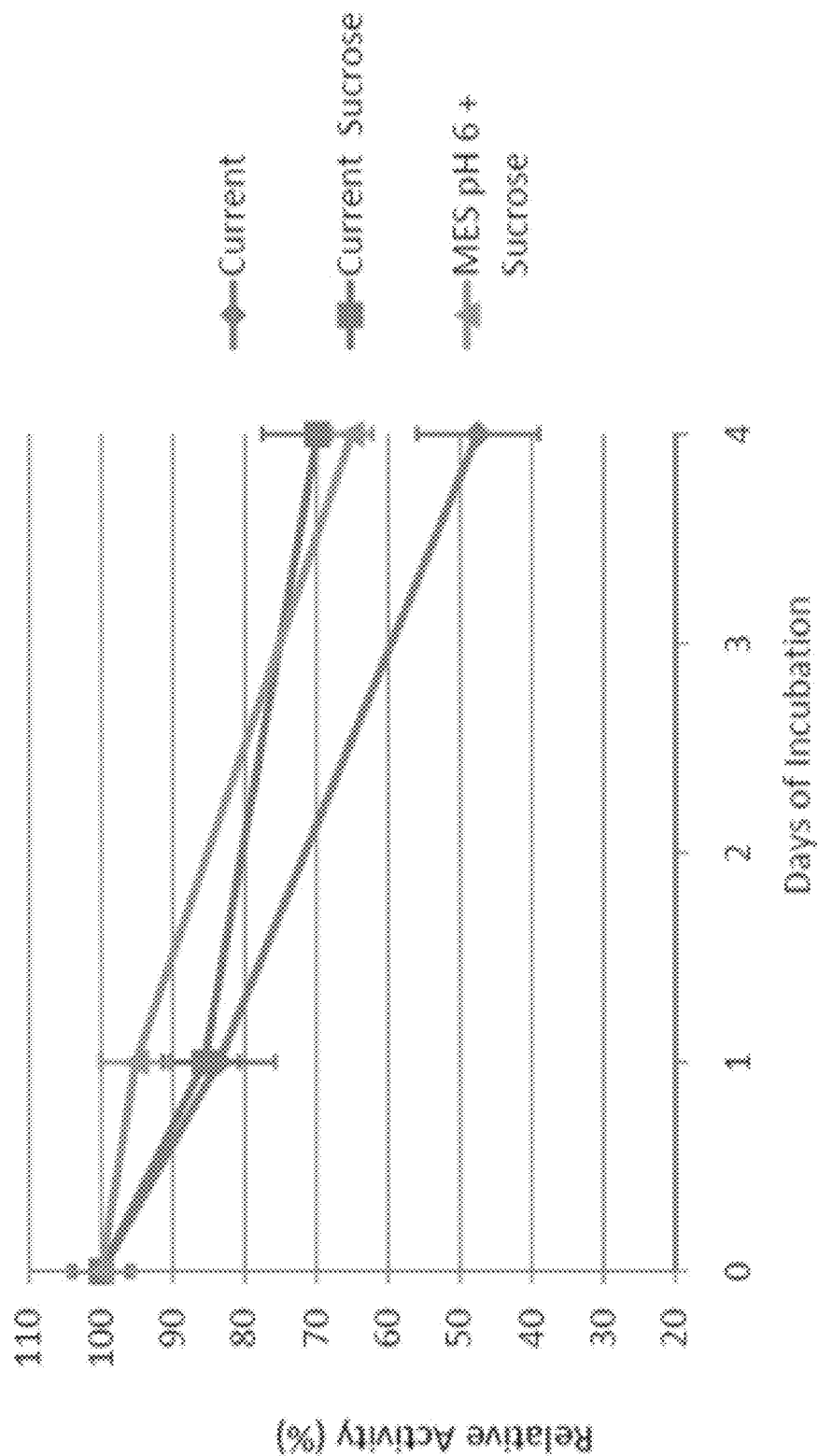

FIG. 20. Comparison of rfurin stability at 37° C. in the control formulation to the formulation in MES buffer analyzed using the furin activity assay. The relative activities of rfurin samples are plotted against the number of days of incubation to compare the following samples: control formulation without additives, control formulation plus 10% sucrose, and spiked with MES (final C=100 mM, pH 6.0) plus 10% sucrose. The relative activity values were calculated as the percentages of the furin activity at time zero. Error bars are ±1 standard deviation; n=4.

Figure 21:
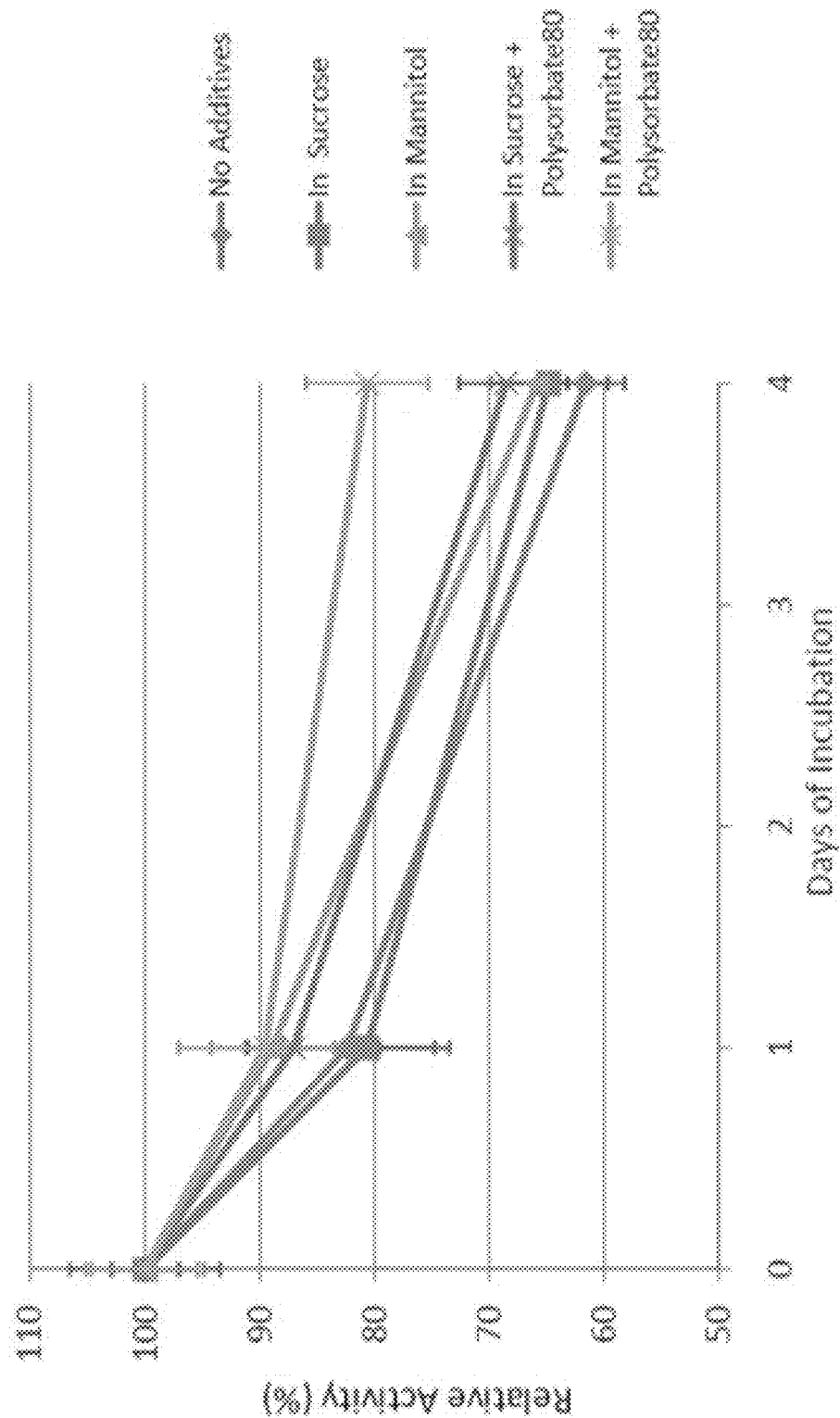

FIG. 21. Comparison of rfurin stability at 37° C. in sucrose to mannitol analyzed using the furin activity assay. All samples were spiked with HEPES/acetic acid, pH 6.0. The relative activities of rfurin samples are plotted against the number of days of incubation to compare the following samples: no additives, 10% sucrose, 10% mannitol, 10% sucrose plus 25 ppm of polysorbate 80, and 10% mannitol plus 25 ppm of polysorbate 80. The relative activity values were calculated as the percentages of the furin activity at time zero. Error bars are ±1 standard deviation; n=4.

Figure 22:
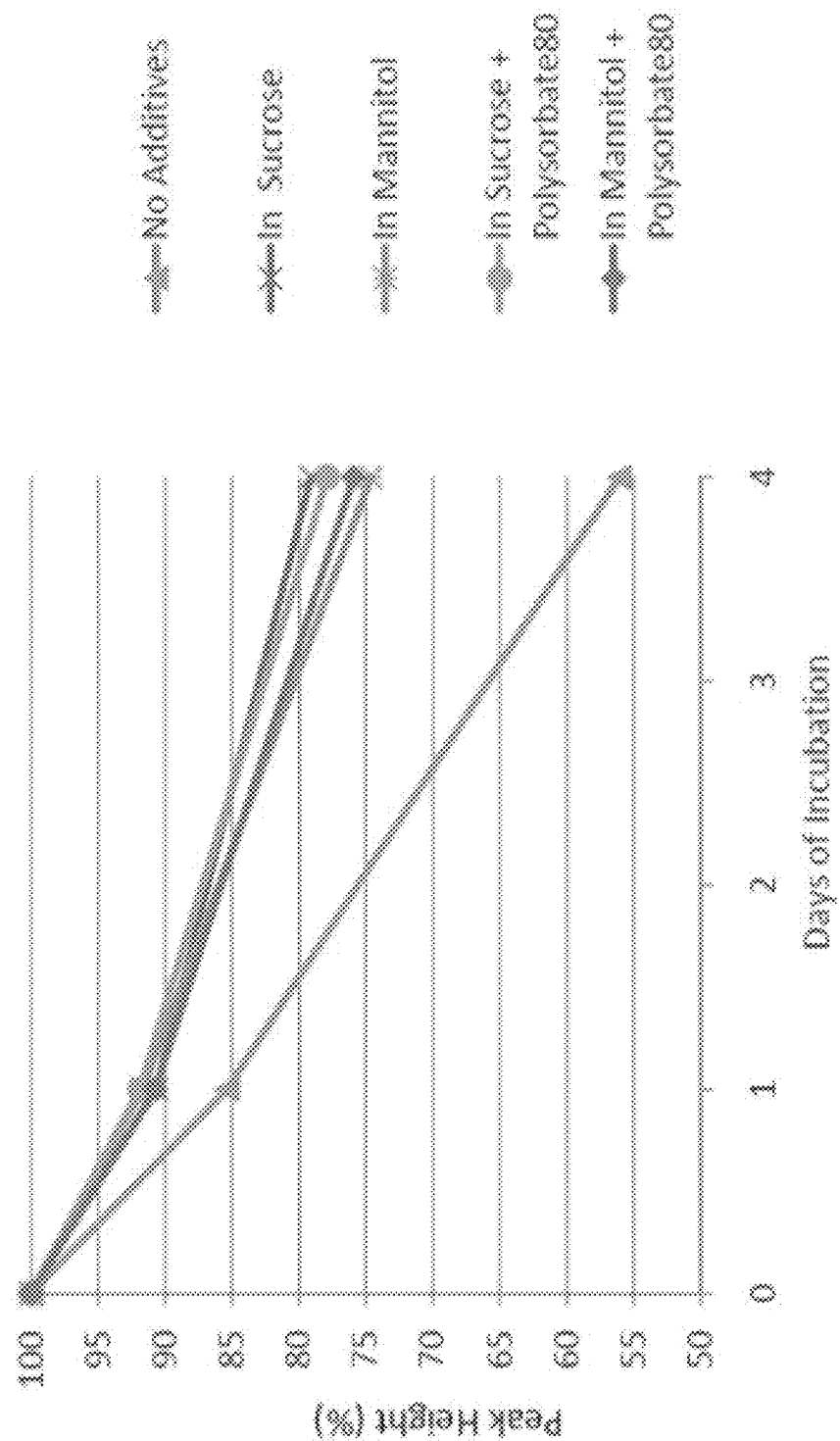

FIG. 22. rFurin Stability at 37° C.: sucrose vs. mannitol analyzed using SEC. The same samples as in FIG. 21 were analyzed using SEC. Relative rfurin peak heights are plotted against the time of incubation. The relative peak heights were calculated as the percentages of the rfurin peak height at time zero.

Figure 23:
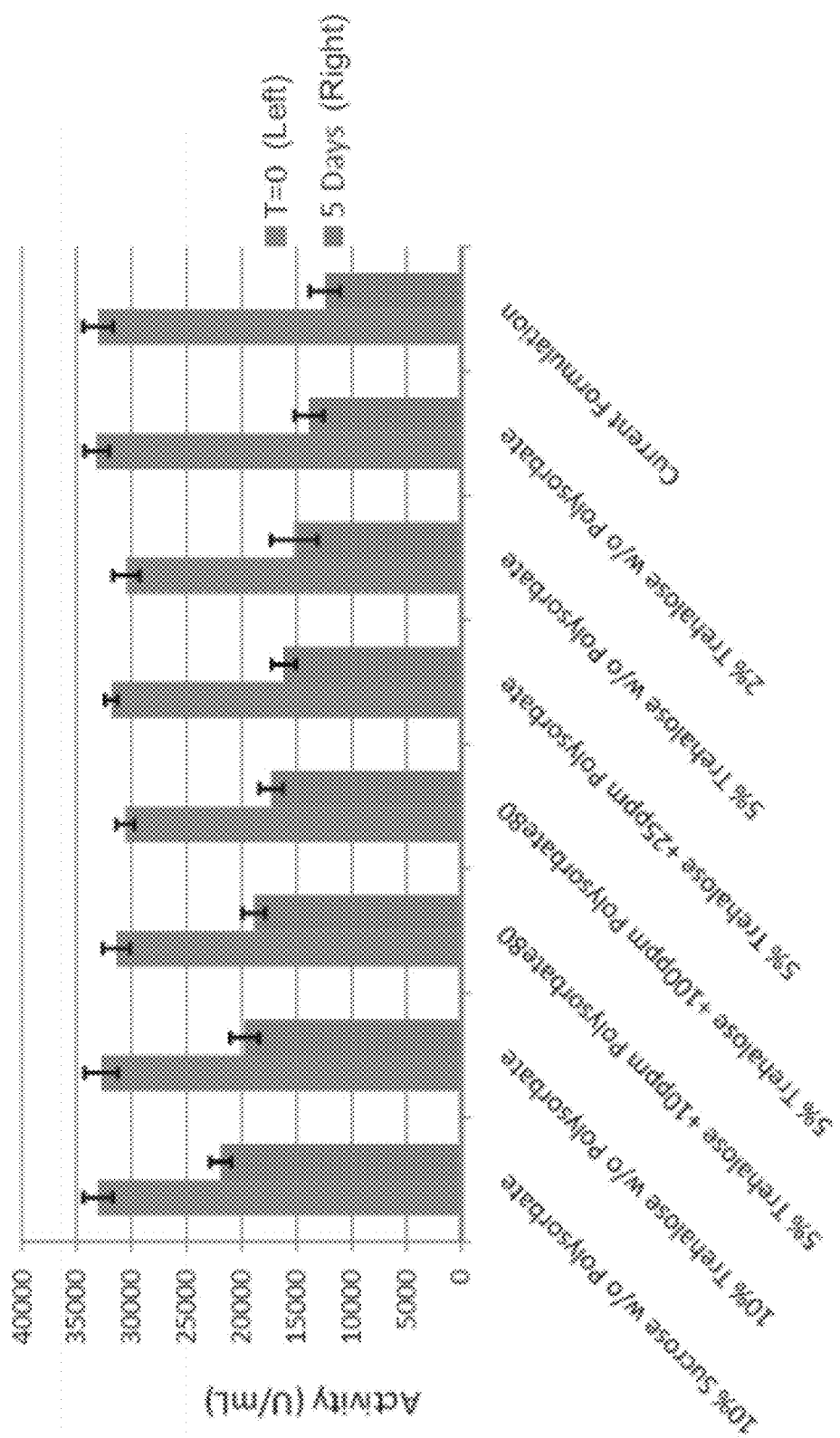

FIG. 23. rFurin stability in trehalose after 5 days of incubation at 37° C. analyzed by the furin activity assay. The effects of varied amounts of trehalose and polysorbate 80 on rfurin stability at 37° C. are examined using the furin activity assay. First, all samples were spiked with HEPES and acetic acid (final concentrations: HEPES—50 mM, acetic acid—50 mM, pH 6.0) then, either 10% sucrose or various amounts of trehalose and/or polysorbate 80 were added. A rfurin sample in the control formulation is also included. The data are sorted from the highest to lowest activity values after 5 days of incubation at 37° C. (right bar in each pair). The left bar in each pair depicts furin activity values at time zero. Error bars are ±1 standard deviation; n=4.

Figure 24:
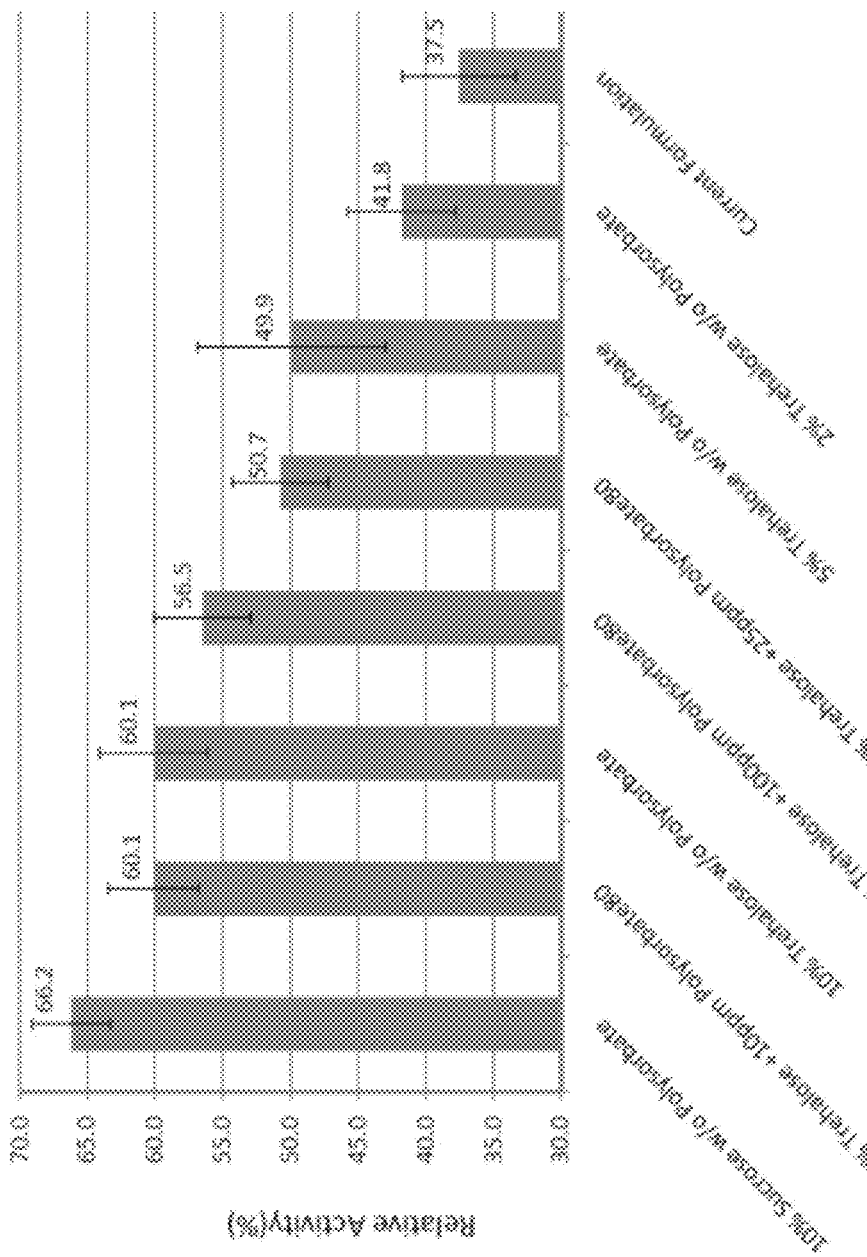

FIG. 24. rFurin activity in trehalose after 5 days of incubation at 37° C. The same samples as in FIG. 23 are displayed after recalculation to show what percentage of each sample's initial activity remained after five days of incubation at 37° C. A rfurin sample in the control formulation is also included. Error bars are ±1 standard deviation; n=4.

Figure 25:
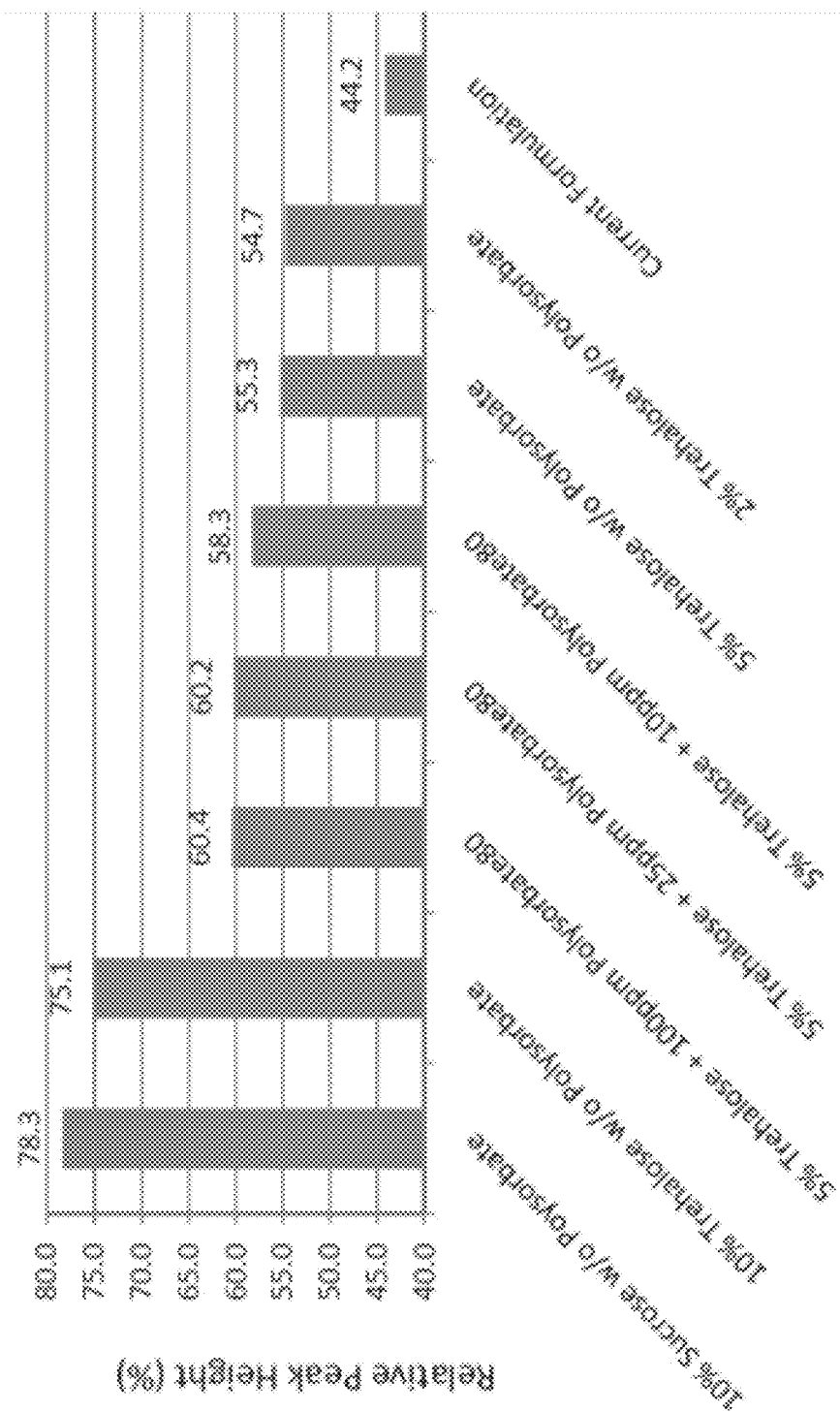

FIG. 25. rFurin stability in trehalose after 5 days of incubation at 37° C. analyzed using SEC. The same samples as in FIG. 24. The graph shows what percentage of each sample's initial rfurin peak remained after five days of incubation at 37° C. A rfurin sample in the control formulation is also included.

Figure 26:
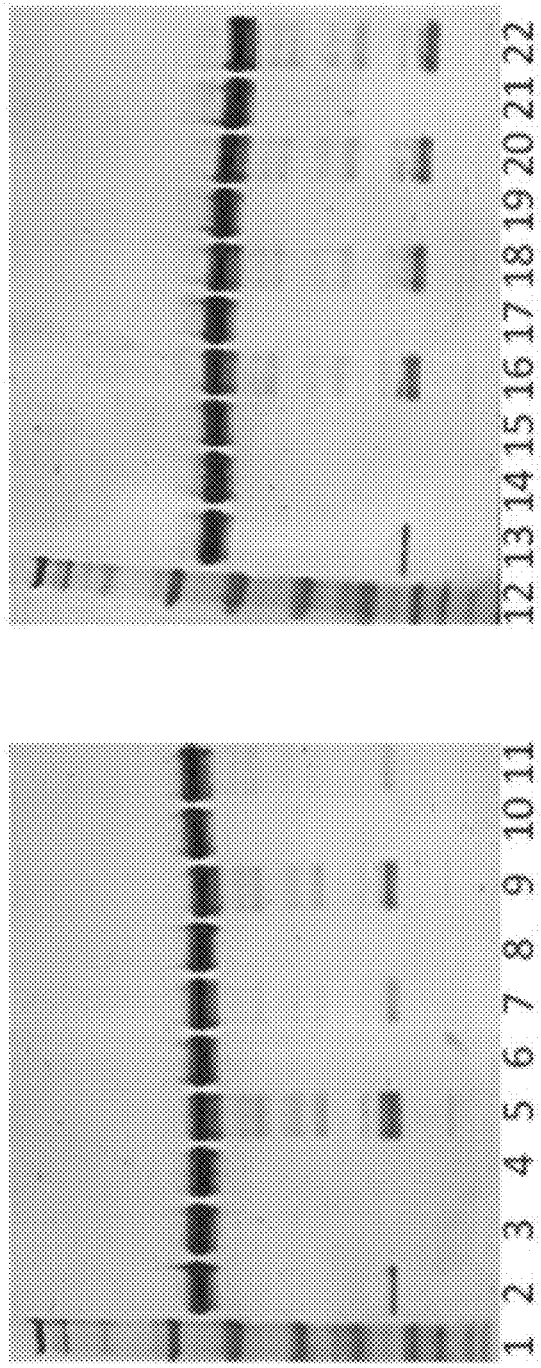

FIG. 26. rFurin stability in trehalose after 5 days of incubation at 35° C. analyzed using Western Blotting. The same samples as in FIG. 24. The samples are paired: first sample—time zero, second sample—incubated at 37° C. for 5 days. Lanes: (1) MWM marker; (2) furin reference, (3) control; (4) control formulation, T=0; (5) control formulation, 5 days; (6) 10% sucrose, T=0; (7) 10% sucrose, 5 days; (8) 2% trehalose, T=0; (9) 2% trehalose, 5 days; (10) 10% trehalose, T=0; (11) 10% trehalose, 5 days; (12) MWM marker; (13) furin reference; (14) control; (15) 5% trehalose, T=0; (16) 5% trehalose, 5 days; (17) 5% trehalose, +10 ppm Tween80, T=0; (18) 5% trehalose, +10 ppm Tween80, 5 days; (19) 5% trehalose, +25 ppm Tween80, T=0; (20) 5% trehalose, +25 ppm Tween80, 5 days; (21) 5% trehalose, +100 ppm Tween80, T=0; and (22) 5% trehalose, +100 ppm Tween80, 5 days.

Figure 27:
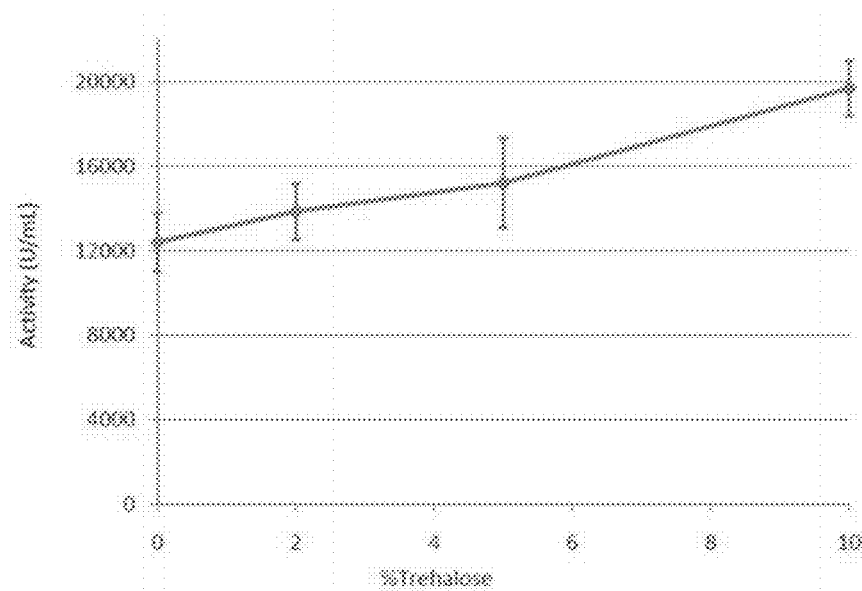

FIG. 27. Effect of the trehalose content on rfurin activity tested after 5 days of incubation at 37° C. The same experiment as in FIG. 24. First, all samples were spiked with HEPES and acetic acid (final concentrations: HEPES—50 mM, acetic acid—50 mM, pH 6.0) then, various amounts of trehalose were added. furin activity after five days of incubation at 37° C. is plotted against the percentage of trehalose added to the samples. Error bars are ±1 standard deviation; n=4.

Figure 28:
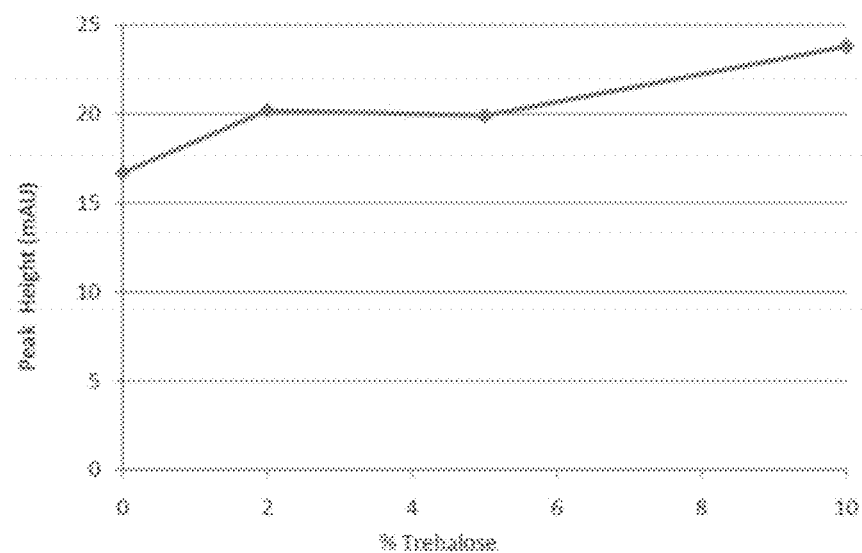

FIG. 28. Effect of the trehalose content on rfurin stability at 37° C. analyzed using SEC after 5 days of incubation. The same experiment as in FIG. 27. rFurin peak heights after five days of incubation at 37° C. are plotted against the percentage of trehalose added to the samples.

Figure 29:
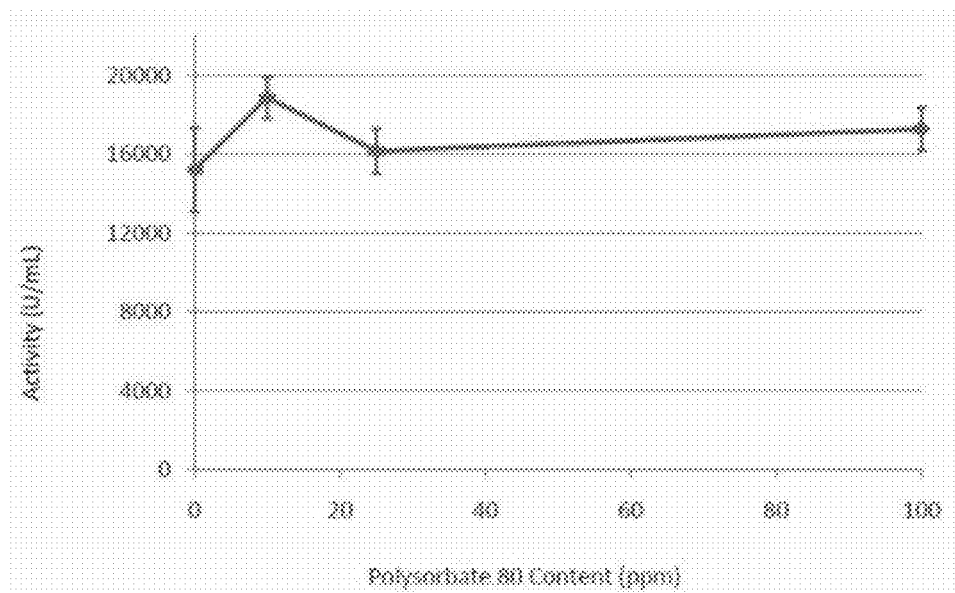

FIG. 29. Effect of polysorbate 80 content on rfurin activity tested after 5 days of incubation at 37° C. The same experiment as in FIG. 24. First, all samples were spiked with HEPES, acetic acid (final concentrations: HEPES—50 mM, acetic acid—50 mM, pH 6.0), and 5% trehalose then, various amounts of polysorbate 80 were added. furin activity after five days of incubation at 37° C. is plotted against the amount of polysorbate 80 added to the samples. Error bars are ±1 standard deviation; n=4.

Figure 30:
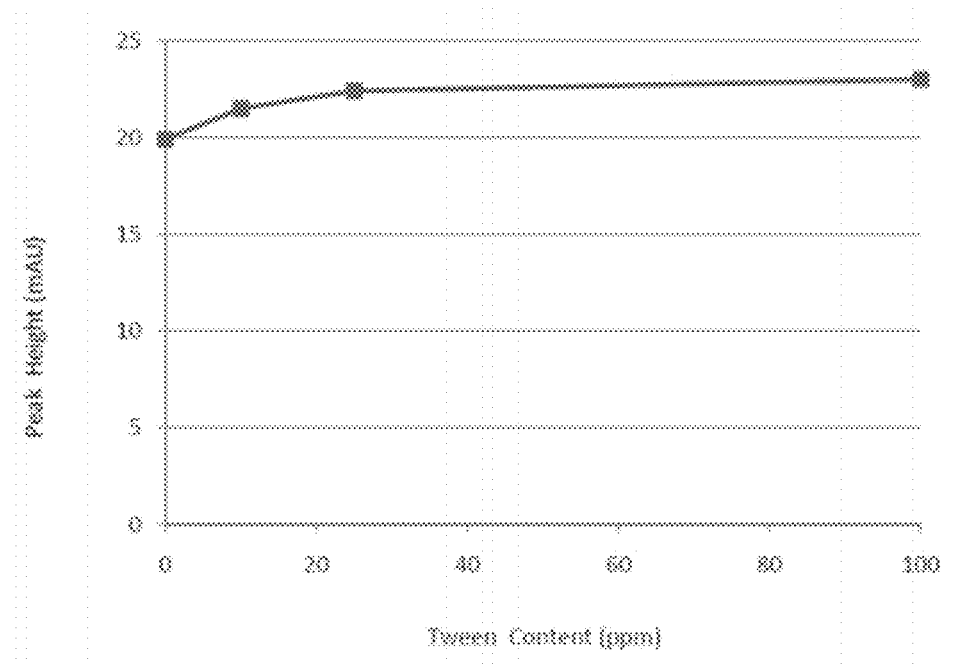

FIG. 30. Effect of Polysorbate 80 content on rfurin stability at 37° C. analyzed using SEC after 5 days of incubation. The same samples as in FIG. 29. rFurin peak heights after five days of incubation at 37° C. are plotted against the amount of polysorbate 80 added to the samples.

Figure 31:
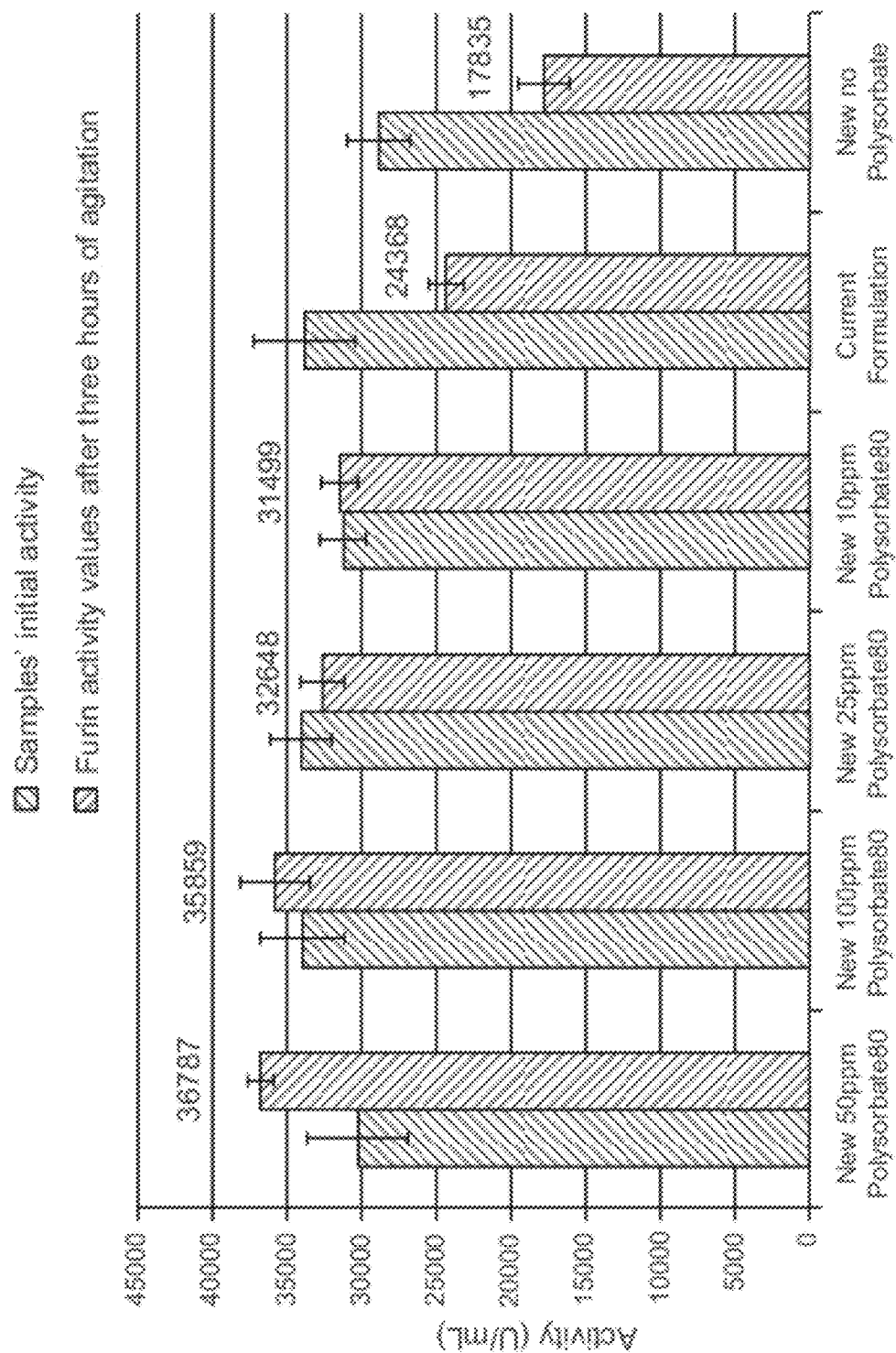

FIG. 31. rFurin in the highly stabilized formulation—agitation study analyzed using the furin activity assay. The rfurin samples in the highly stabilized formulation were spiked with various amount of polysorbate 80. The graph shows furin activity values before and after three hours of agitation. The data are sorted from the highest to the lowest activity. Error bars are ±1 standard deviation; n=4. Left bars in each pair show activity at time 0, right bars in each pair show activity after agitation.

Figure 32:
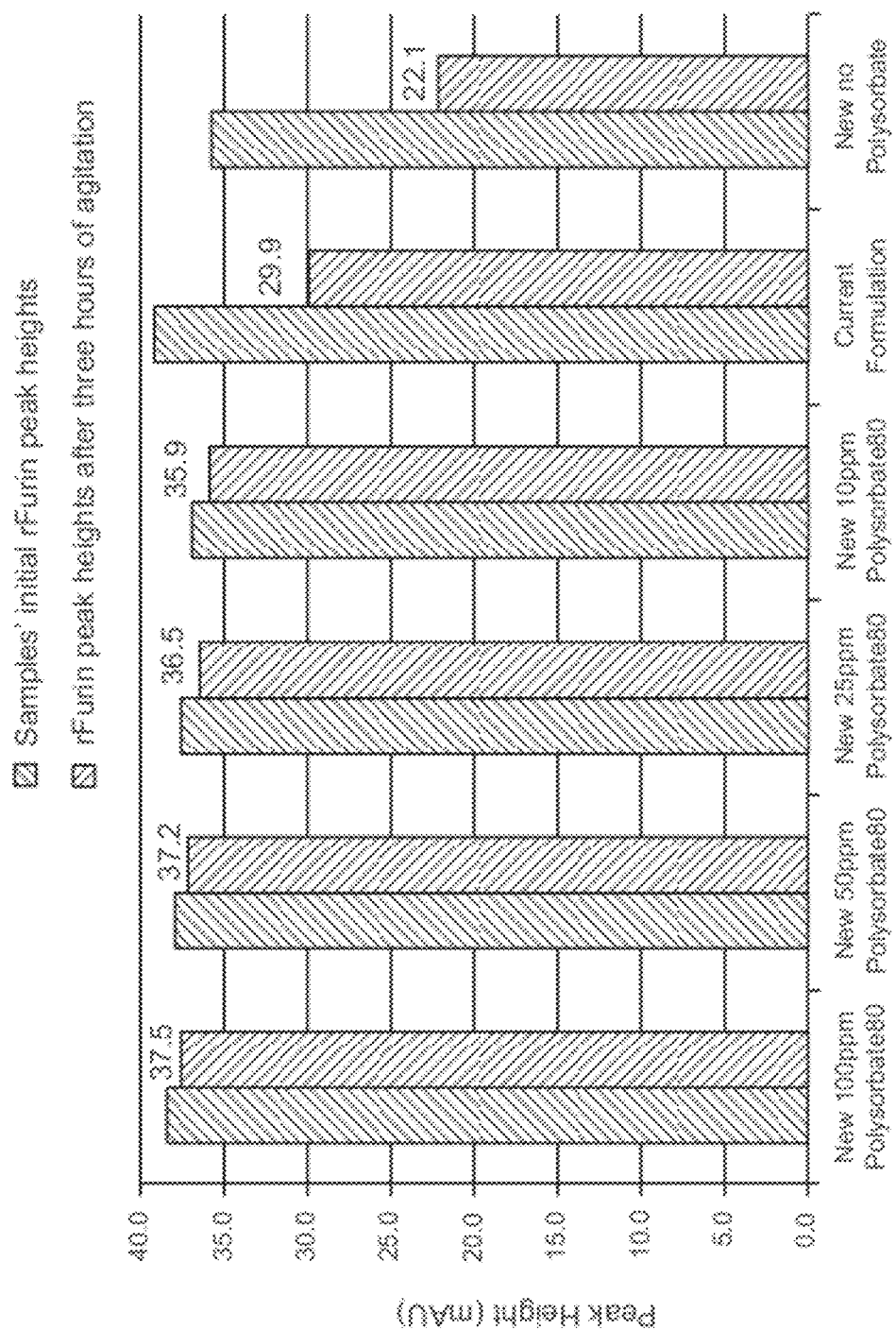

FIG. 32. rFurin in the highly stabilized formulation—agitation study analyzed using SEC. The same experiment as in FIG. 31. The graph shows rfurin peak heights before and after three hours of agitation. The data are sorted from the highest to the lowest. Left bars in each pair show activity at time 0, right bars in each pair show activity after agitation.

Figure 33:
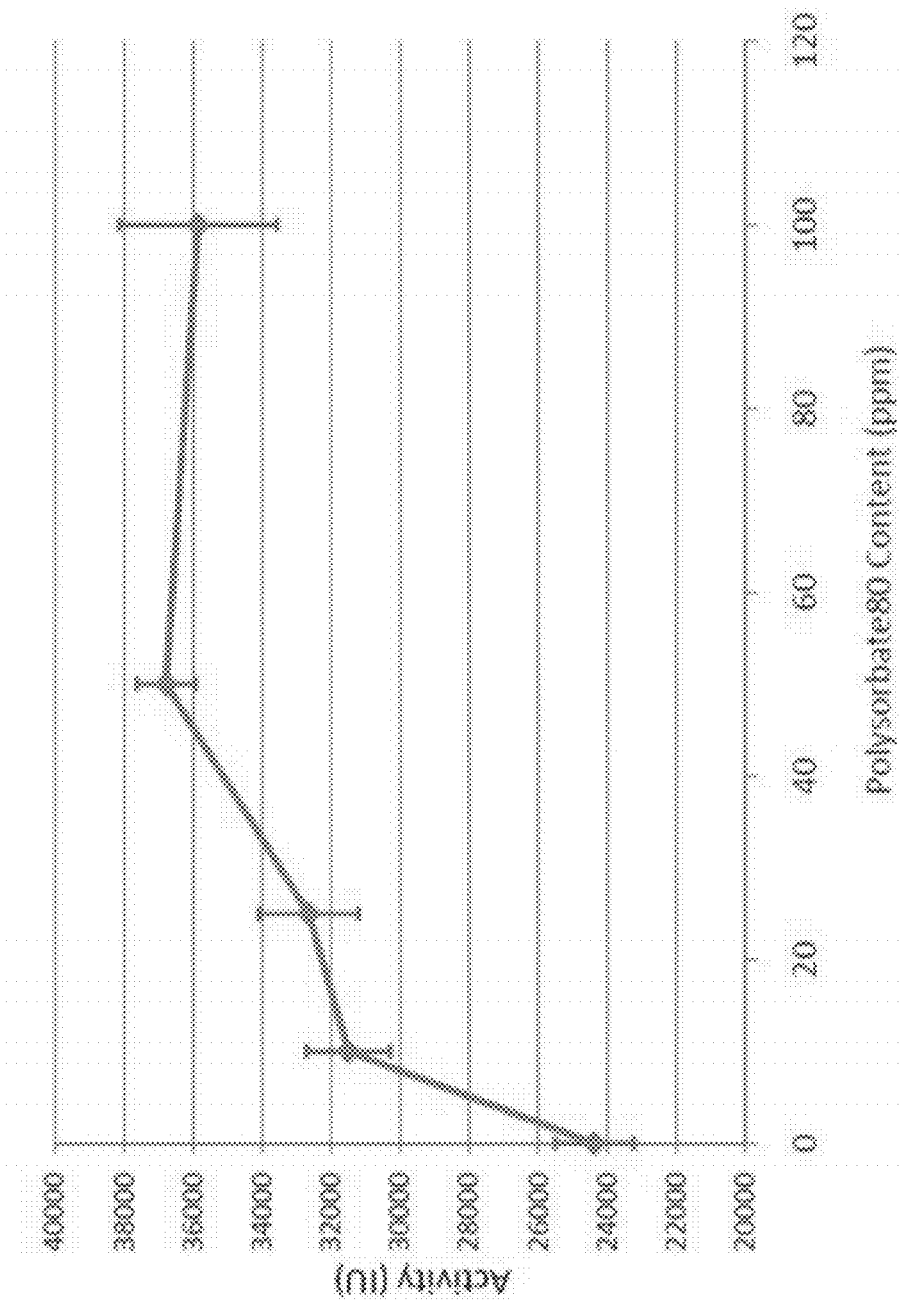

FIG. 33. rFurin in the highly stabilized formulation—effects of polysorbate content in an agitation study analyzed using the furin activity assay. The same samples as in FIG. 32. furin activity after three hours of agitation is plotted against the content of polysorbate 80. Error bars are ±1 standard deviation; n=4.

Figure 34:
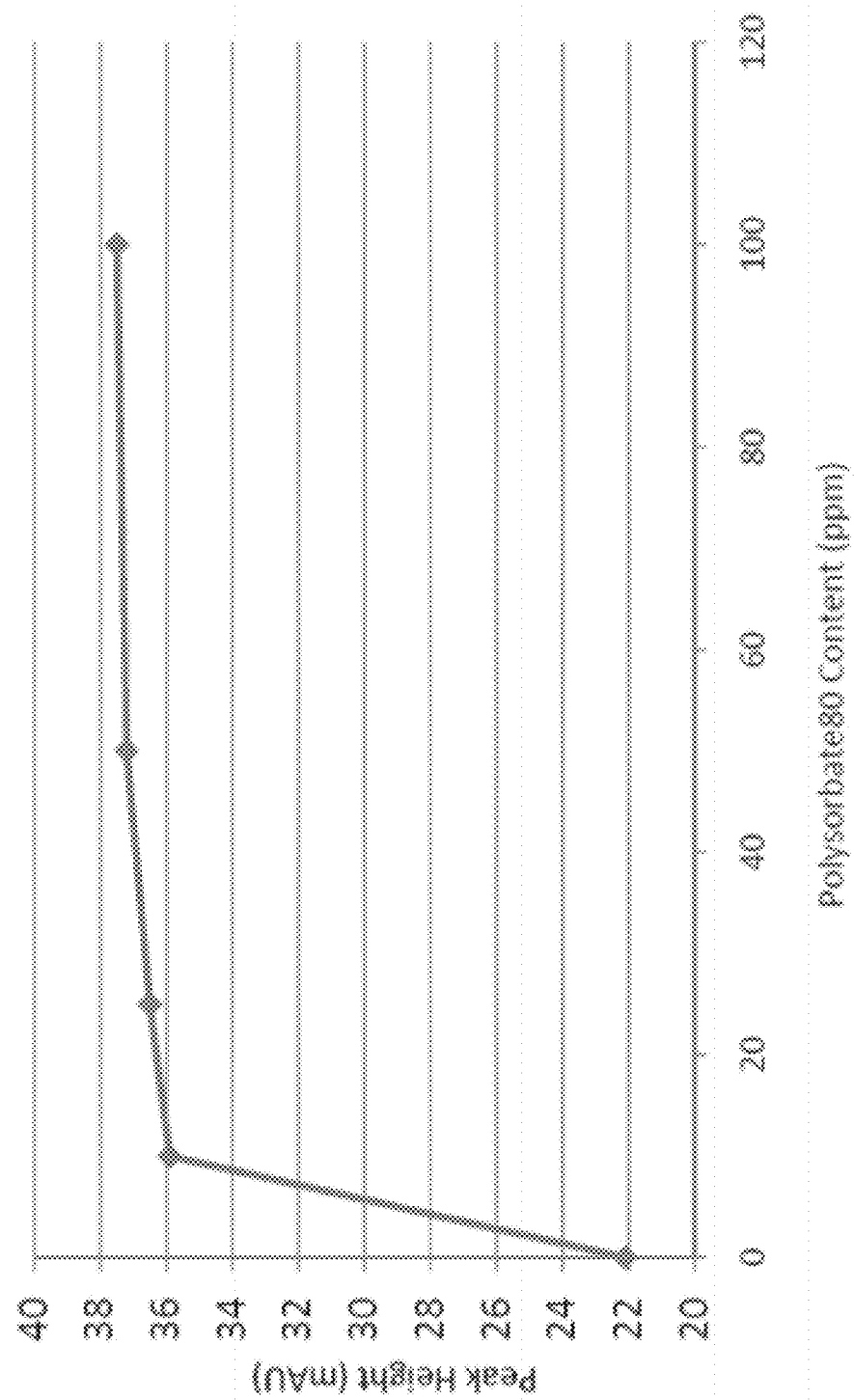

FIG. 34. rFurin in the highly stabilized formulation—effect of polysorbate 80 in agitation study analyzed using SEC.

The same samples as in FIG. 32. rFurin peak heights after three hours of agitation are plotted against the content of polysorbate 80.

Figure 35:
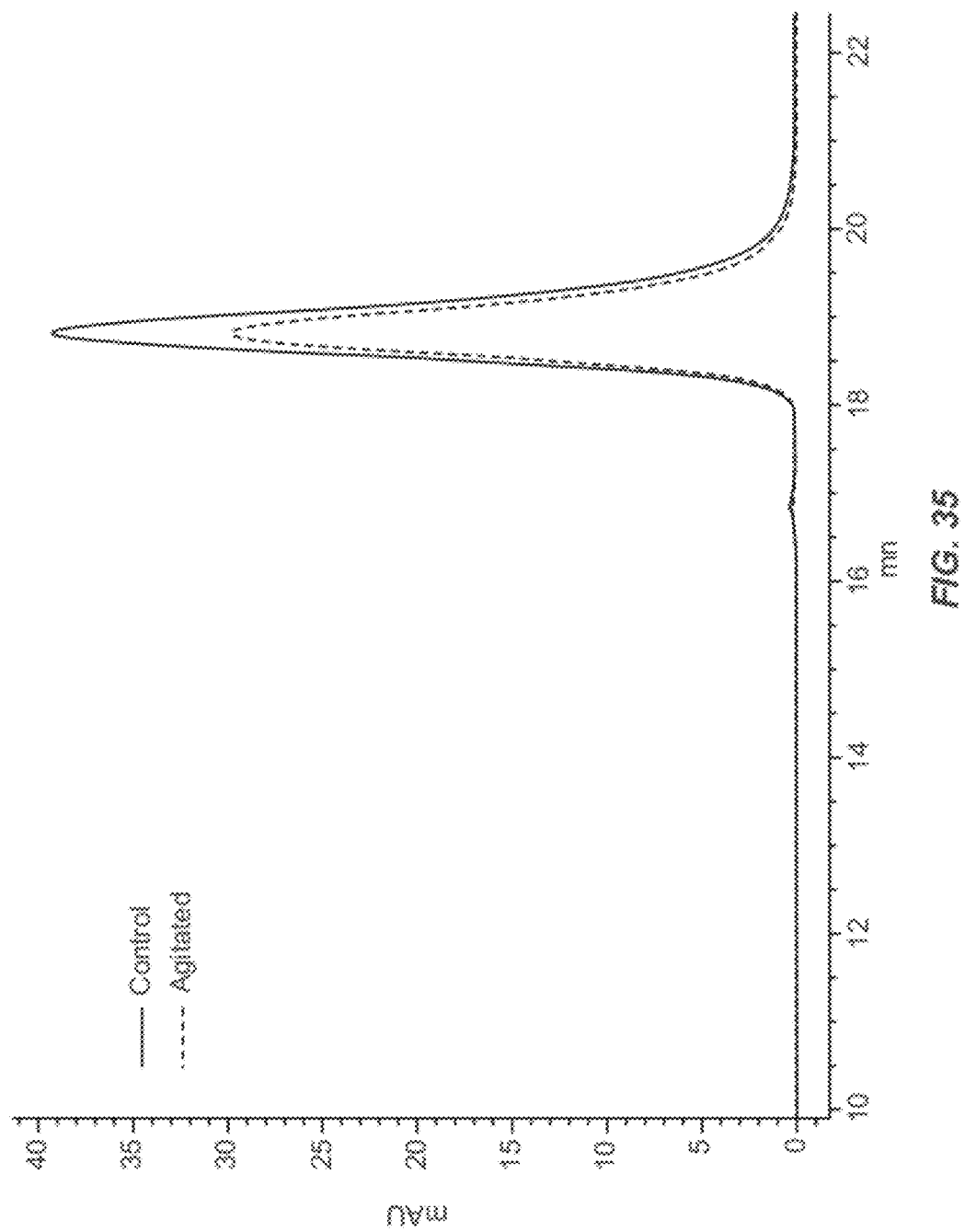

FIG. 35. rFurin in the control formulation—agitation study analyzed using SEC. The chromatogram shows an overlay of SEC absorption profiles at 280 nm comparing rfurin samples in the control formulation before and after three hours of agitation. The rfurin peak of the agitated sample is significantly smaller than the control sample. The absence of high molecular mass peaks in the agitated sample is observed (see paragraph 3.5.1 for explanation).

Figure 36:
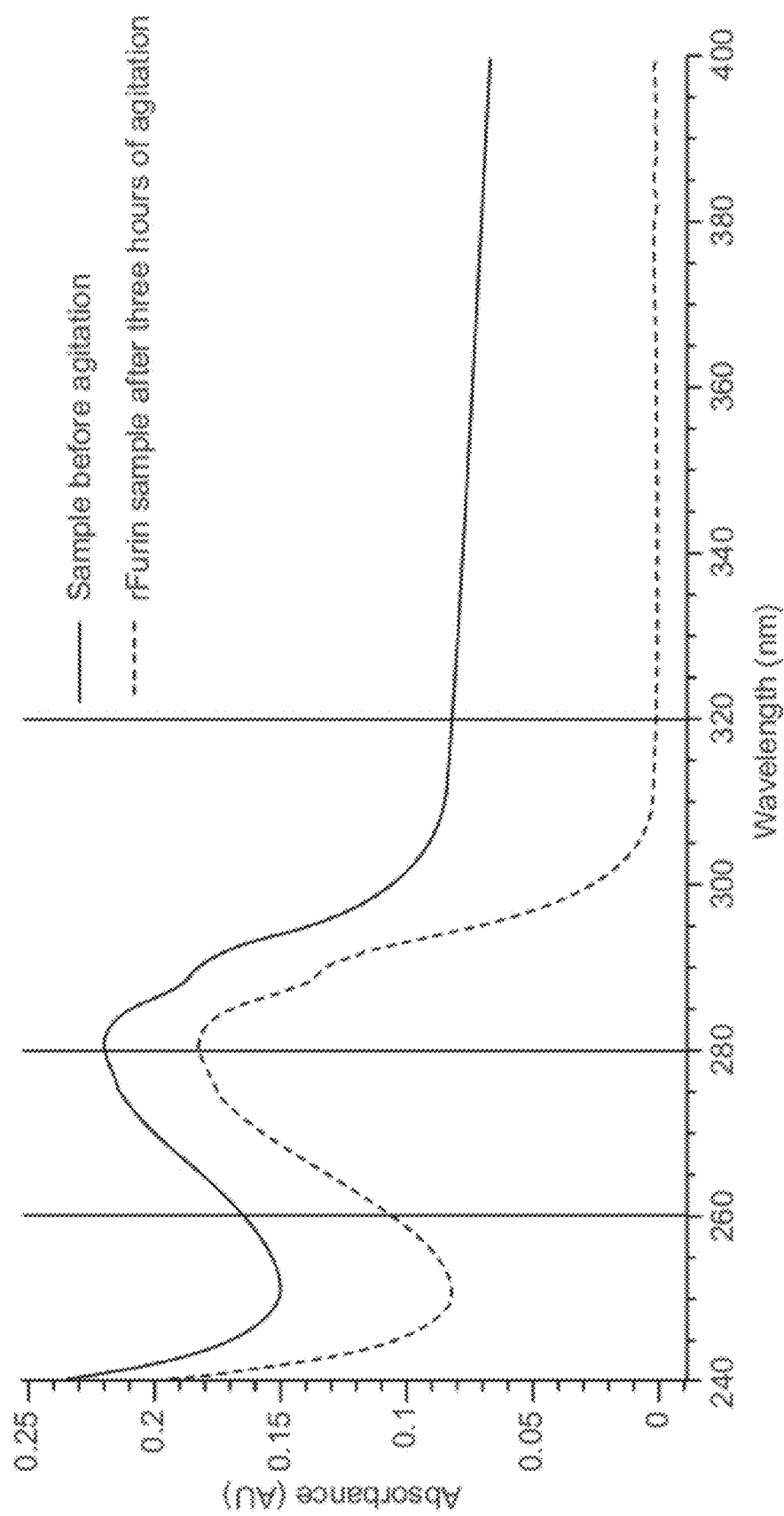

FIG. 36. UV spectra of rfurin in the control formulation (the same samples as in FIG. 35). The UV spectrum of the rfurin sample after three hours of agitation shows a slanted and extremely elevated profile compared to the sample before agitation, which indicates the presence of a significant level of aggregates in the agitated sample.

Figure 37:
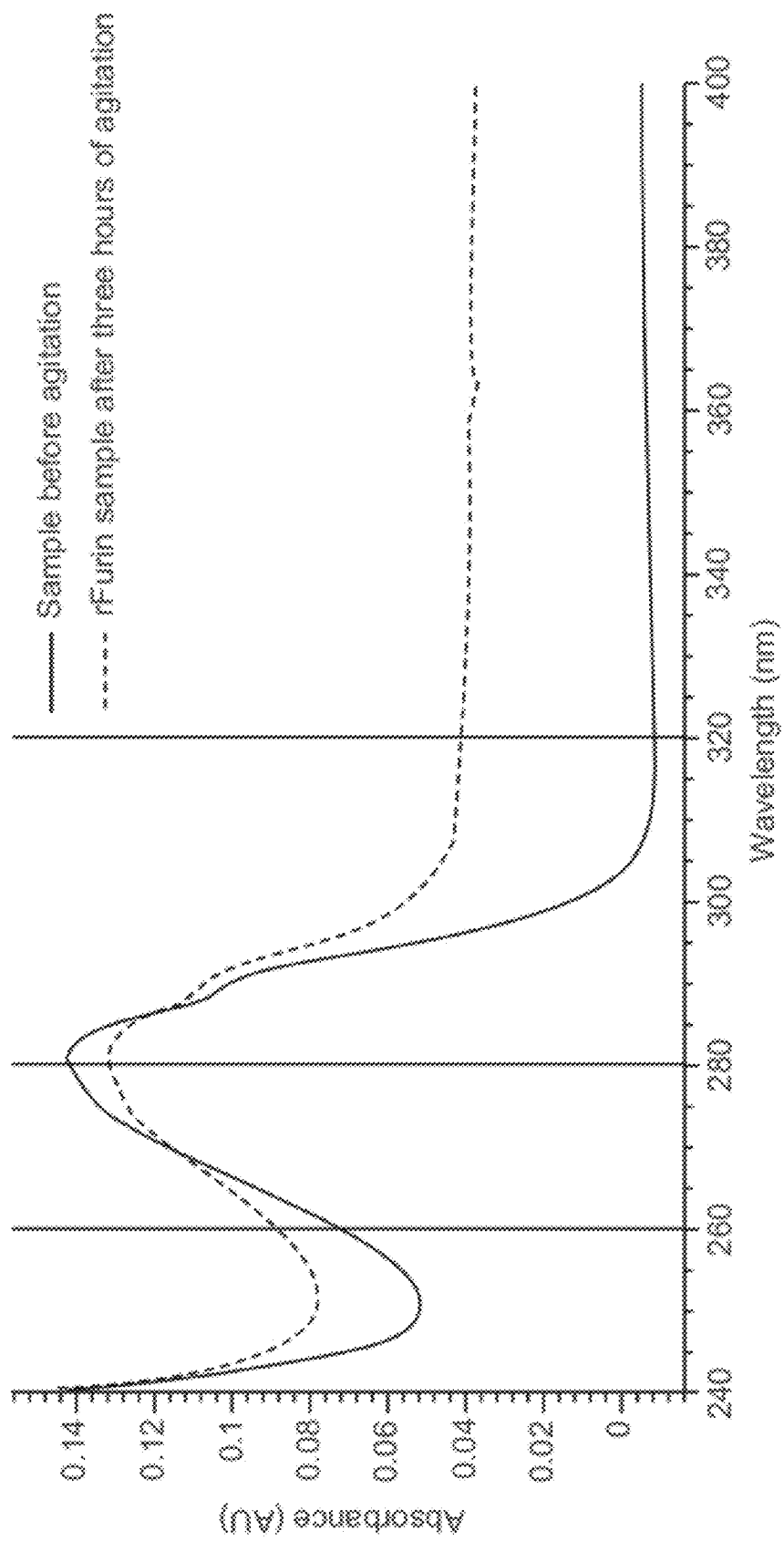

FIG. 37. UV spectra of the rfurin samples in the highly stabilized formulation without polysorbate 80. The UV spectrum of the rfurin sample after three hours of agitation shows an elevated profile compared to the sample before agitation, which indicates the presence of significant level of aggregates in the agitated sample.

Figure 38:
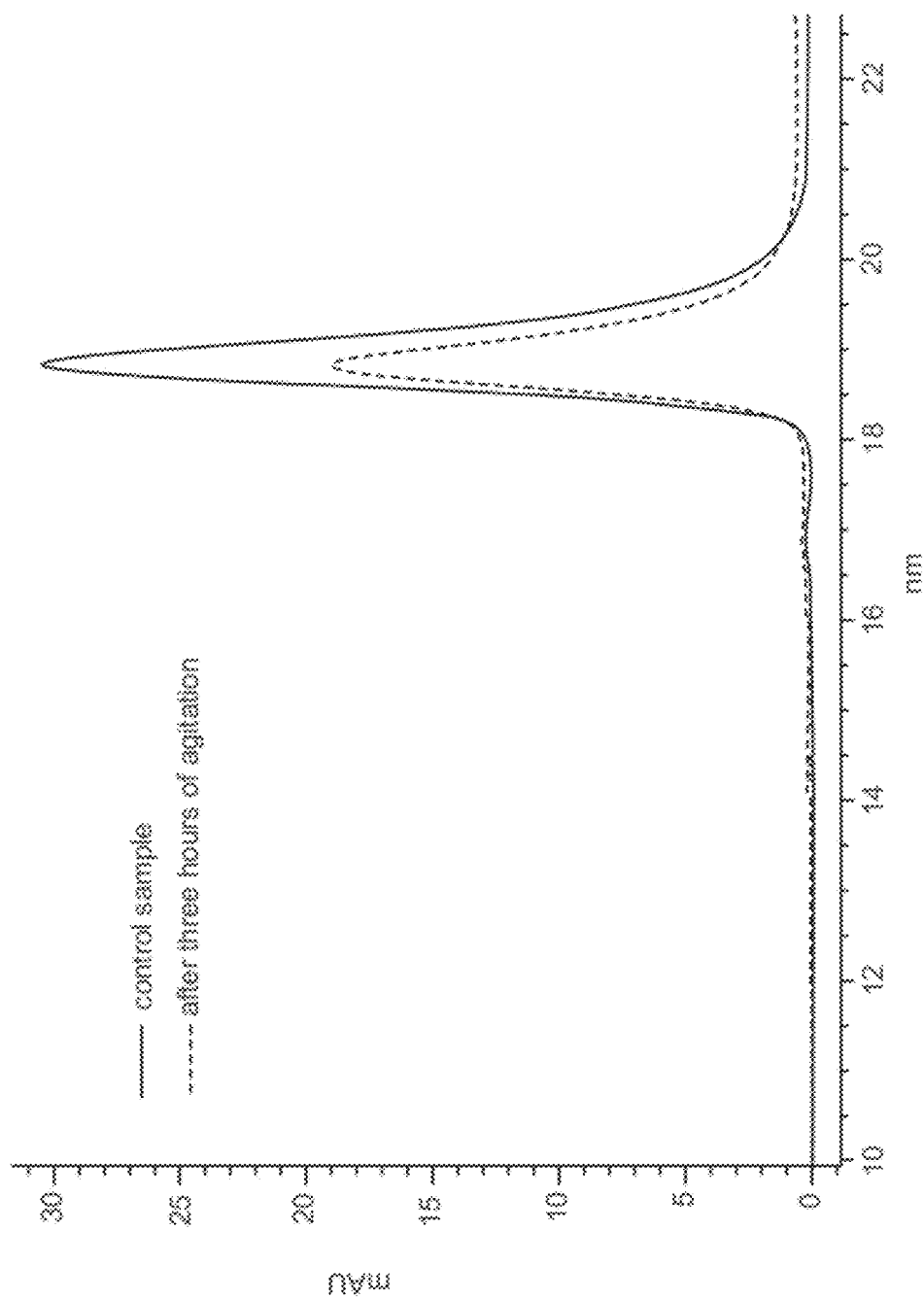

FIG. 38. rFurin in the highly stabilized Formulation without polysorbate 80—an agitation study analyzed using SEC. The chromatogram shows an overlay of SEC absorption profiles at 280 nm comparing rfurin samples in the highly stabilized formulation without polysorbate 80 before and after three hours of agitation. The rfurin peak of the agitated sample is significantly smaller than the control sample. The absence of high molecular mass peaks is observed.

Figure 39:
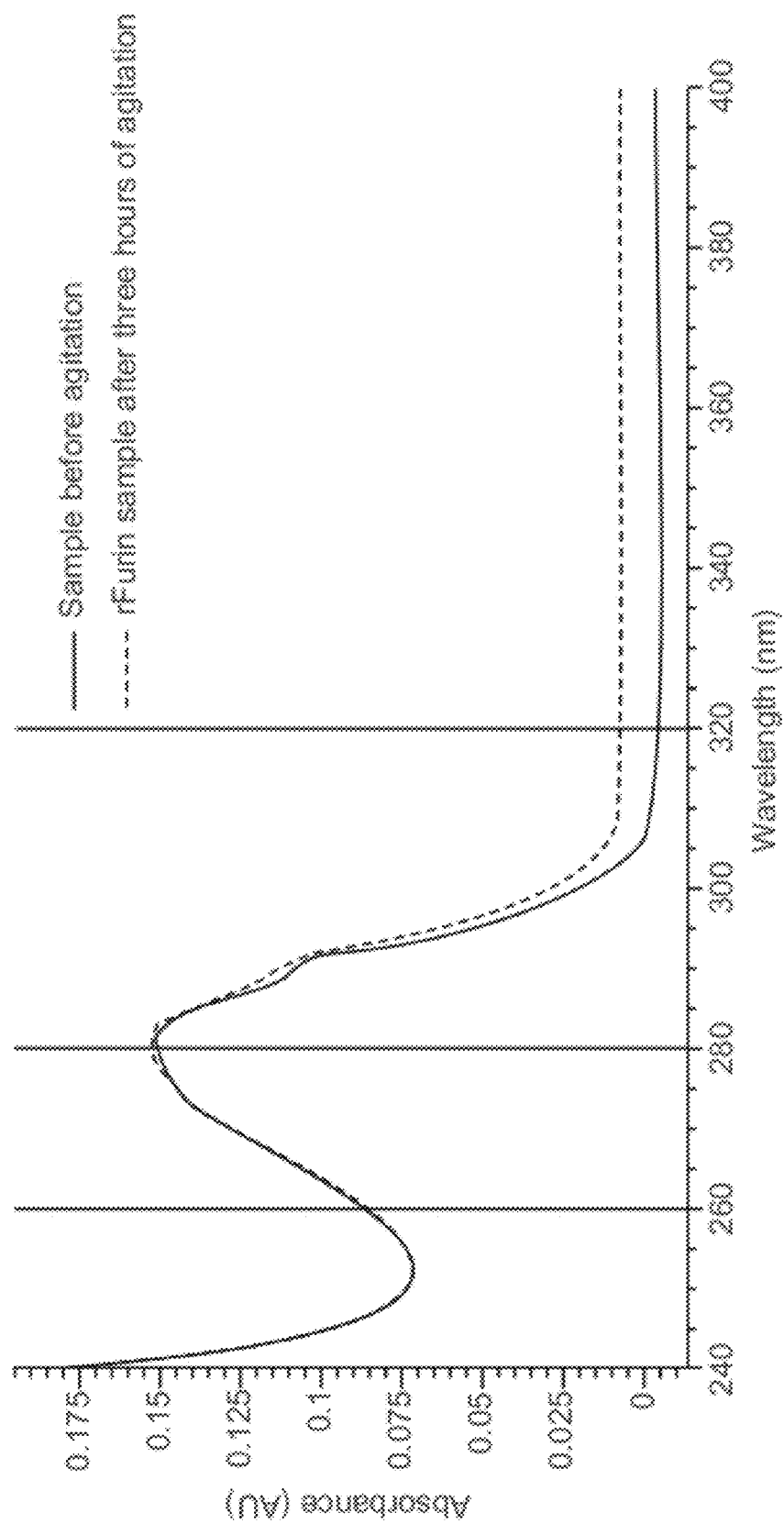

FIG. 39. UV spectra of the rfurin samples in the highly stabilized formulation containing 10 ppm polysorbate 80. The UV spectrum of the rfurin sample after three hours of agitation shows a slightly elevated profile compared to the sample before agitation, which indicates the presence of aggregates in the agitated sample. The 'agitated' spectra is closer to the 'before agitated' spectra, relative to those seen in samples without polysorbate (FIGS. 36 and 37), which indicated that that the level of aggregation is less than that seen in samples without polysorbate.

Figure 40:
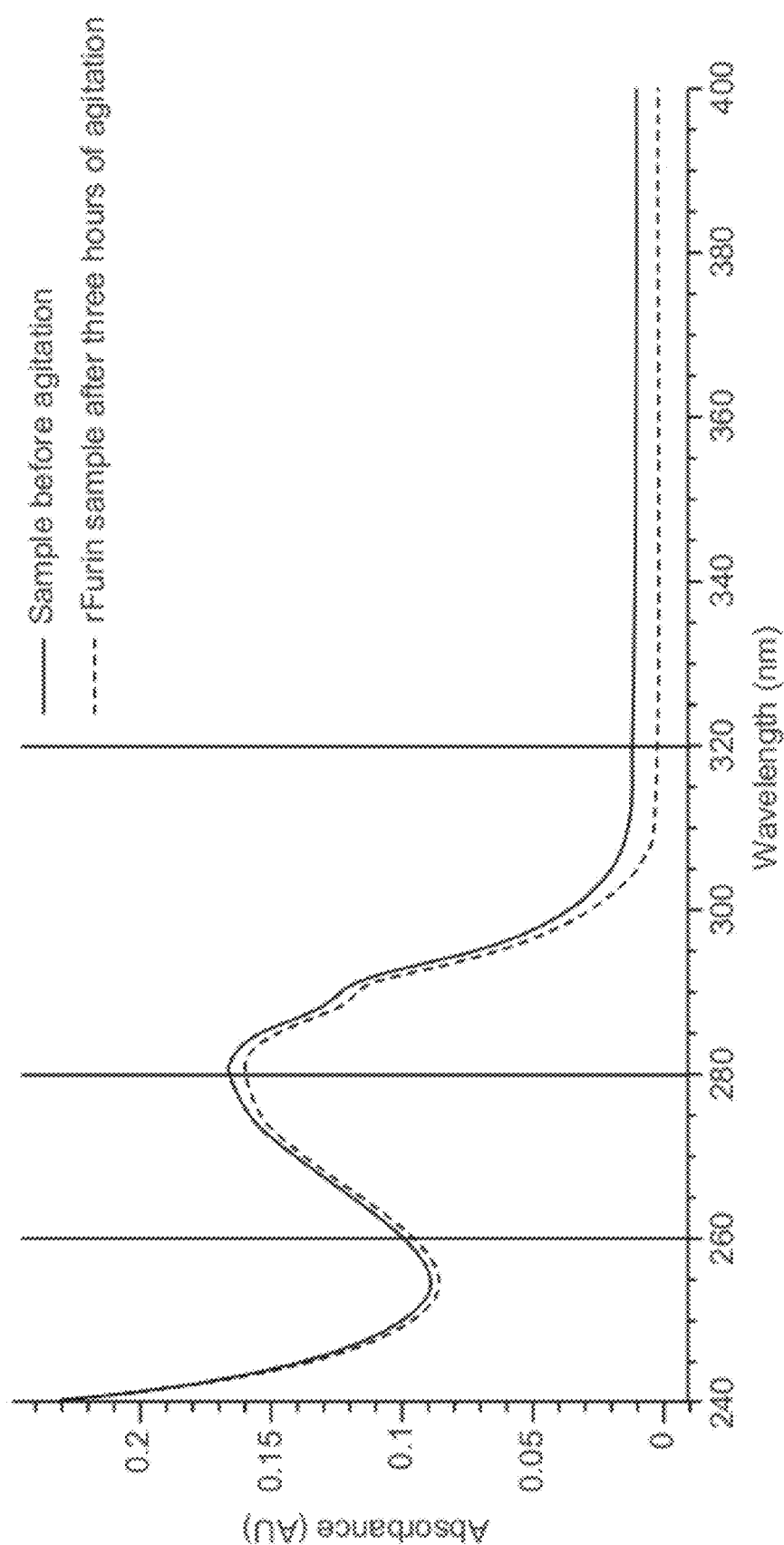

FIG. 40. UV spectra of the rfurin samples in the highly stabilized formulation containing 25 ppm polysorbate 80. The UV spectrum of the rfurin sample after three hours of agitation shows a slightly elevated profile compared to the sample before agitation, which indicates presence of a small amount of aggregates in the agitated sample.

Figure 41:
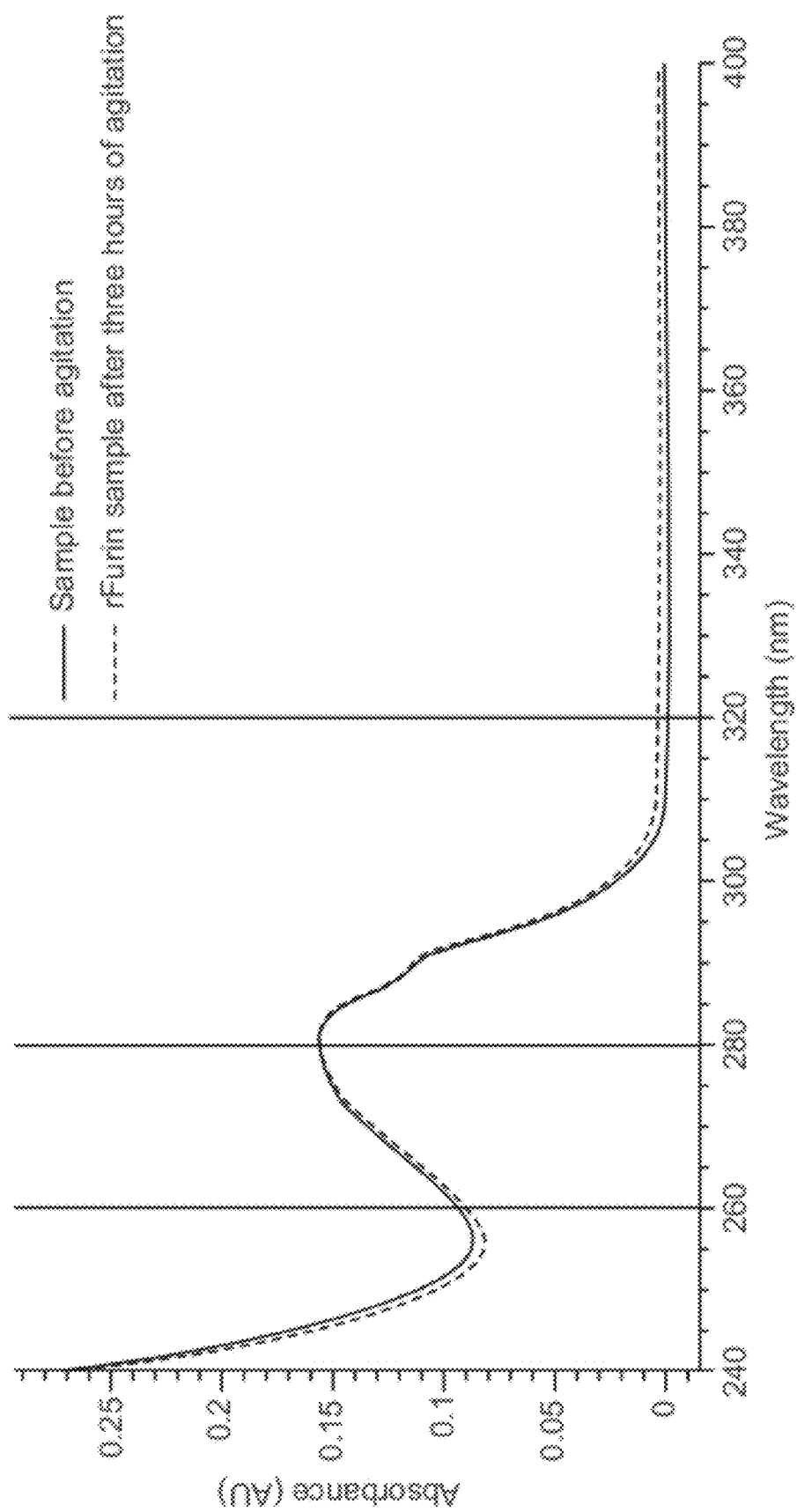

FIG. 41. UV spectra of the rfurin samples in the highly stabilized formulation containing 50 ppm polysorbate 80. The UV spectrum of the rfurin sample after three hours of agitation shows a very similar profile to the sample before agitation. Neither spectra is slanted or elevated, which indicates that neither sample contains significant amounts of large aggregates.

Figure 42:
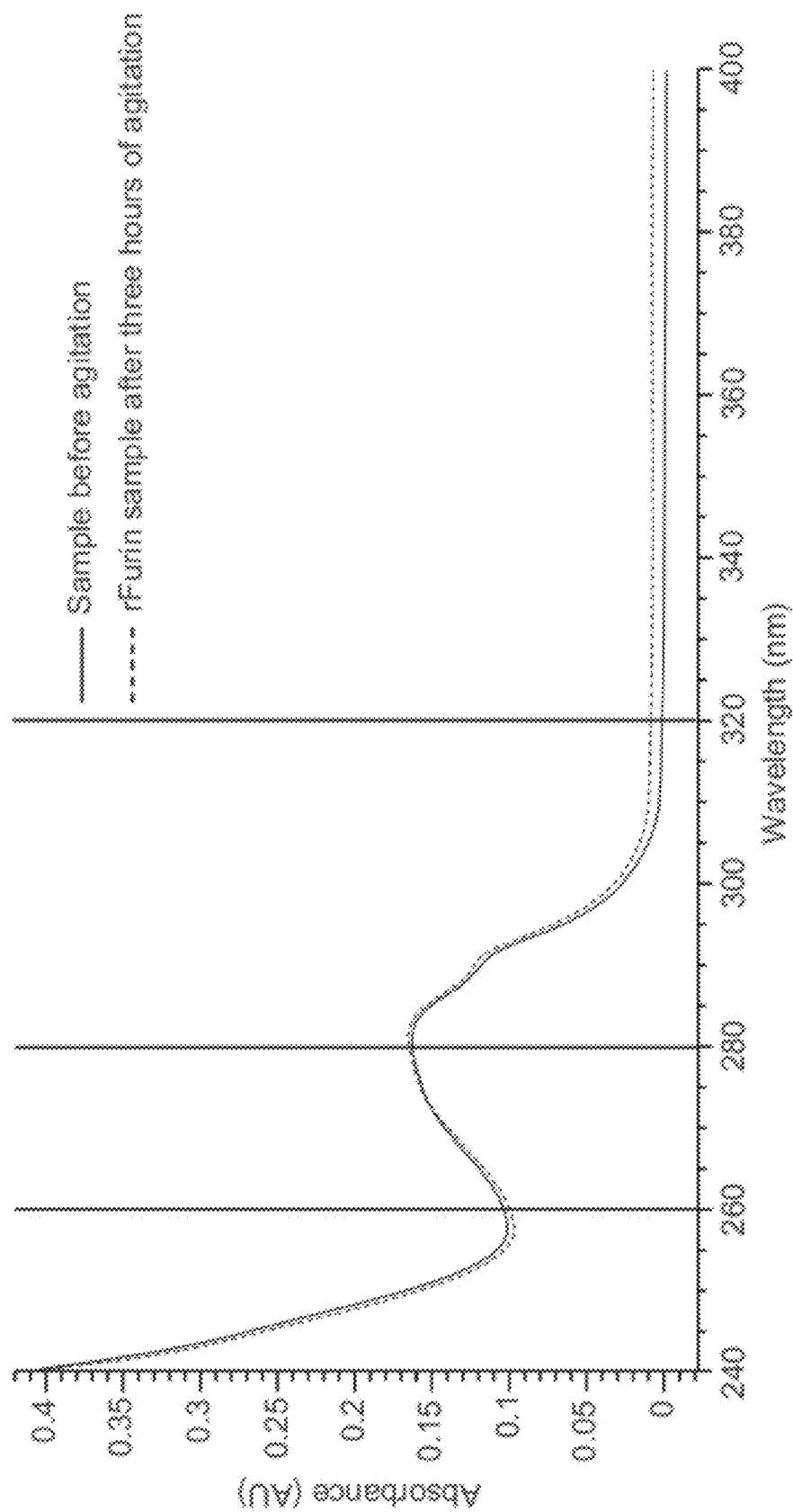

FIG. 42. UV spectra of the rfurin samples in the highly stabilized formulation containing 100 ppm polysorbate 80. The UV spectrum of the rfurin sample after three hours of agitation shows a very similar profile to the sample before agitation. Neither spectra is slanted or elevated, which indicates that neither sample contains significant amounts of large aggregates.

Figure 43:
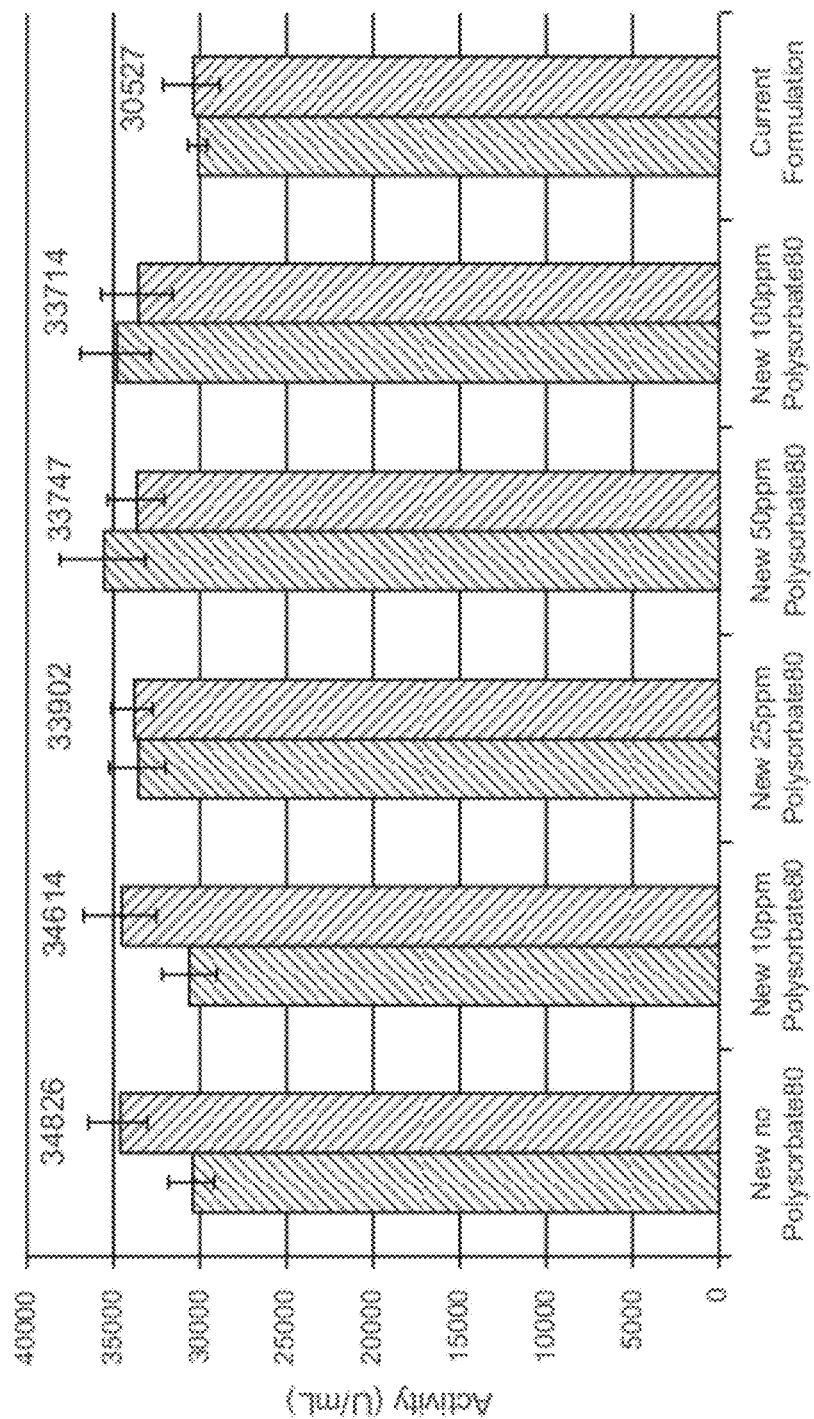

FIG. 43. rFurin in the highly stabilized Formulation—a freeze/thaw study analyzed using the furin activity assay. rFurin samples in the highly stabilized formulation were spiked with different amounts of polysorbate 80. The data show rfurin activity in the samples before and after 5 freeze/thaw cycles. The data are sorted from the highest to the lowest. Error bars are ±1 standard deviation; n=4.

Figure 44:
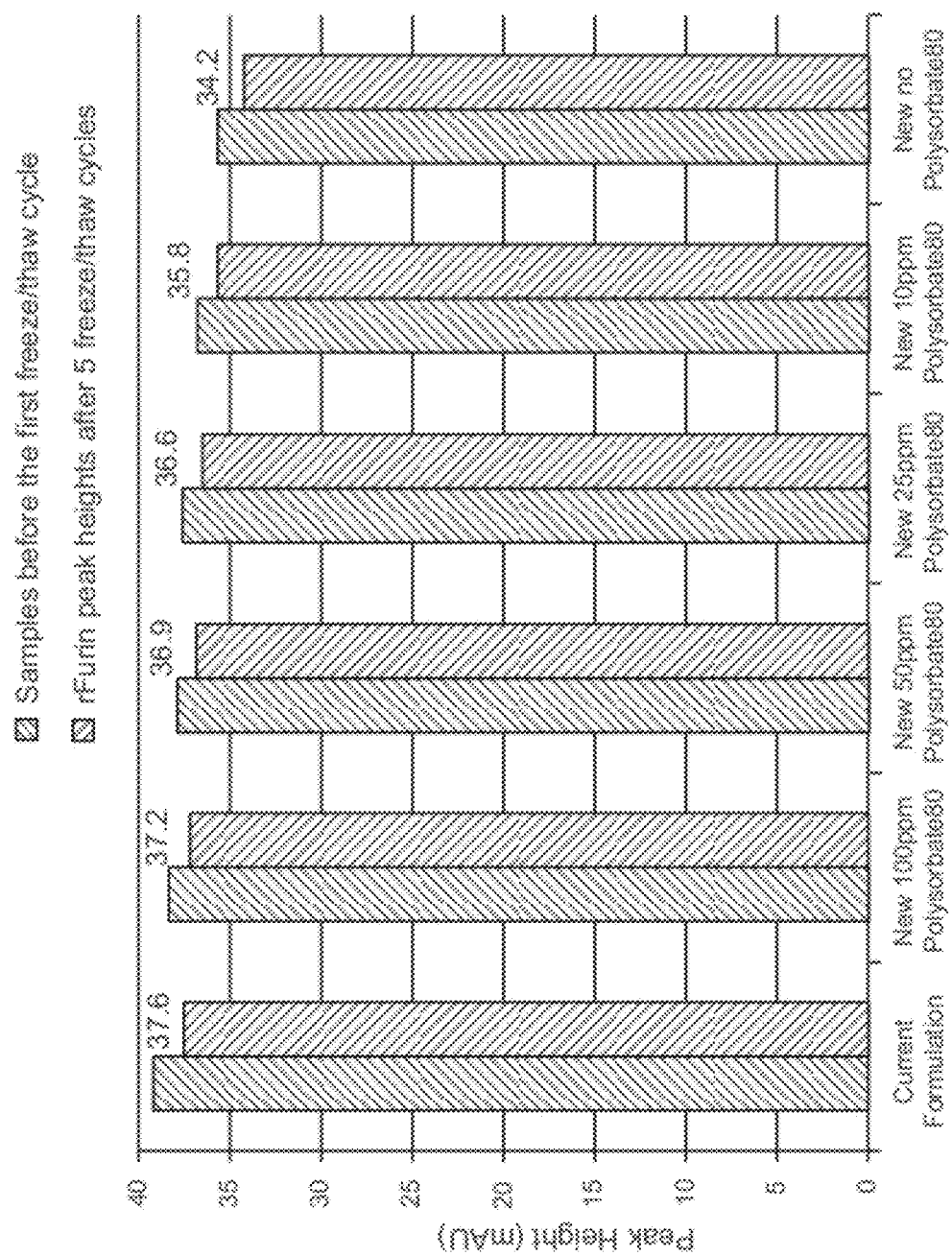

FIG. 44. rFurin in the highly stabilized formulation—a freeze/thaw study analyzed using SEC. The same samples as in FIG. 43. The data show the rfurin peak heights before and after 5 freeze/thaw cycles. The data are sorted from the highest to the lowest.

Figure 45:
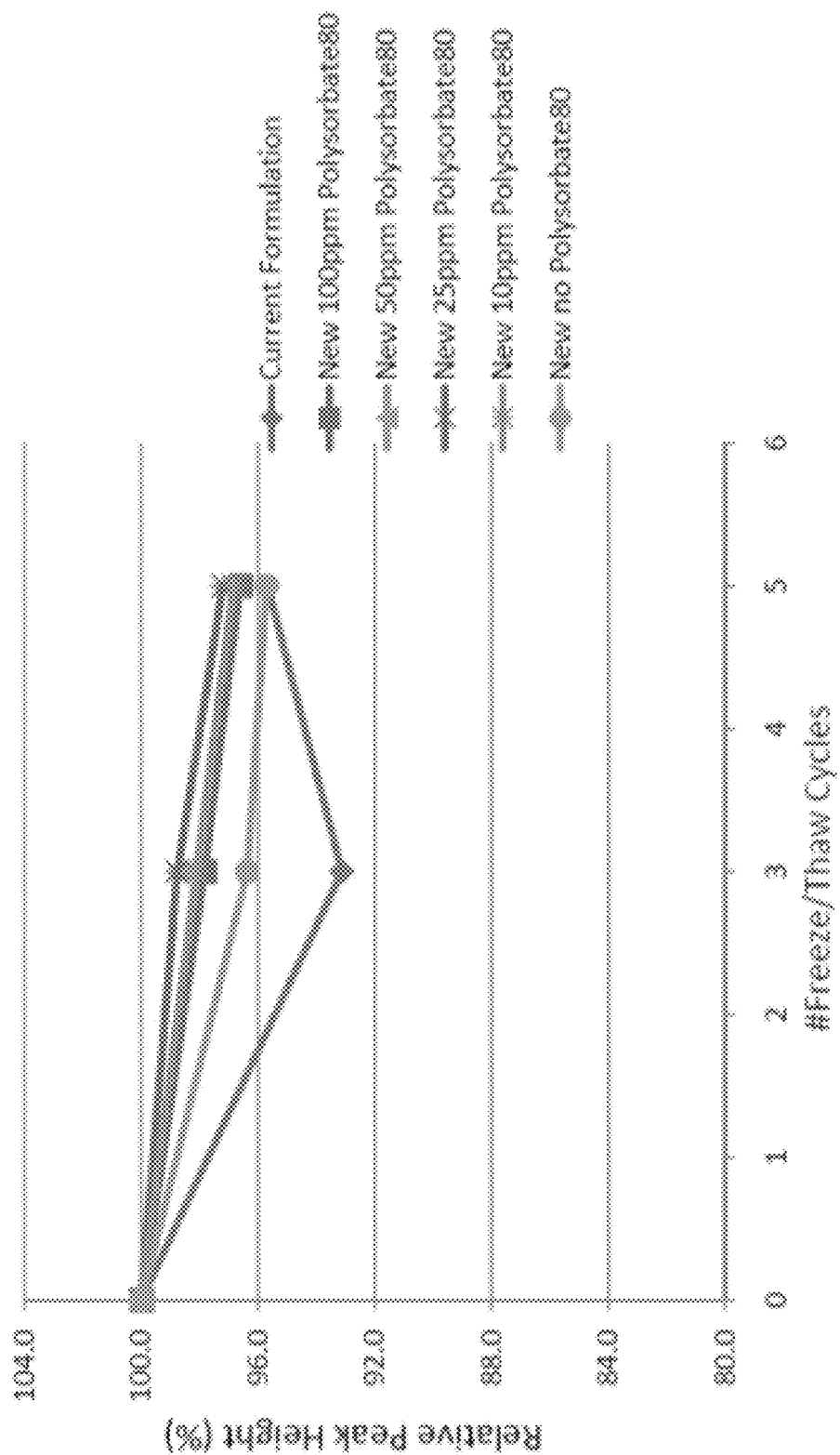

FIG. 45. rFurin in the highly stabilized Formulation—a freeze/thaw study analyzed using SEC. The same samples as in FIG. 44. The relative peak heights of rfurin are plotted against the number of freeze/thaw cycles. The relative peak heights were calculated as the percentages of the rfurin peak heights before the first freeze/thaw cycle.

Figure 46:
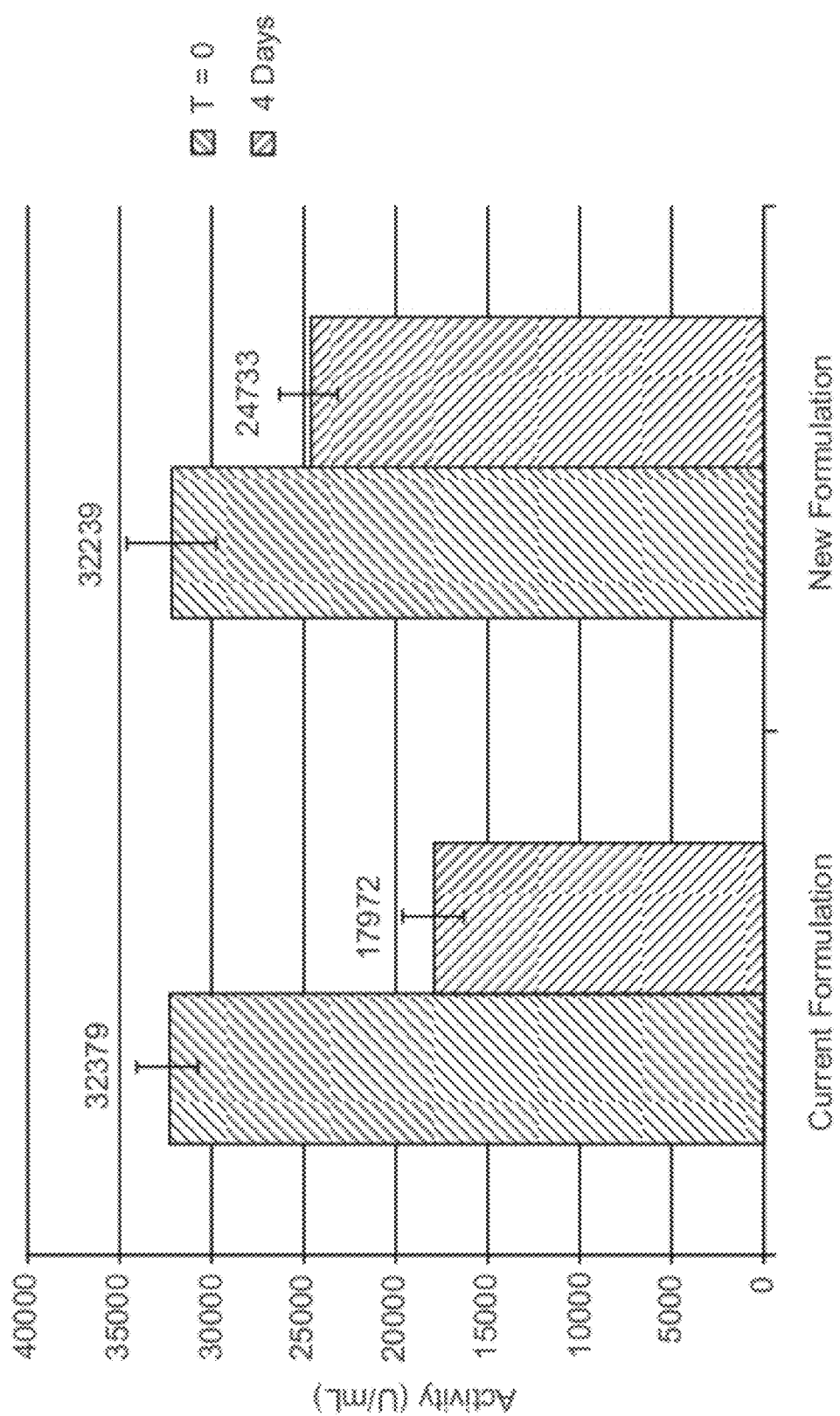

FIG. 46. rFurin stability in the highly stabilized formulation at 37° C. analyzed using the furin activity assay. rFurin samples in either the control formulation or in the highly stabilized formulation were incubated at 37° C. for 4 days. Error bars are ±1 standard deviation; n=4.

Figure 47:
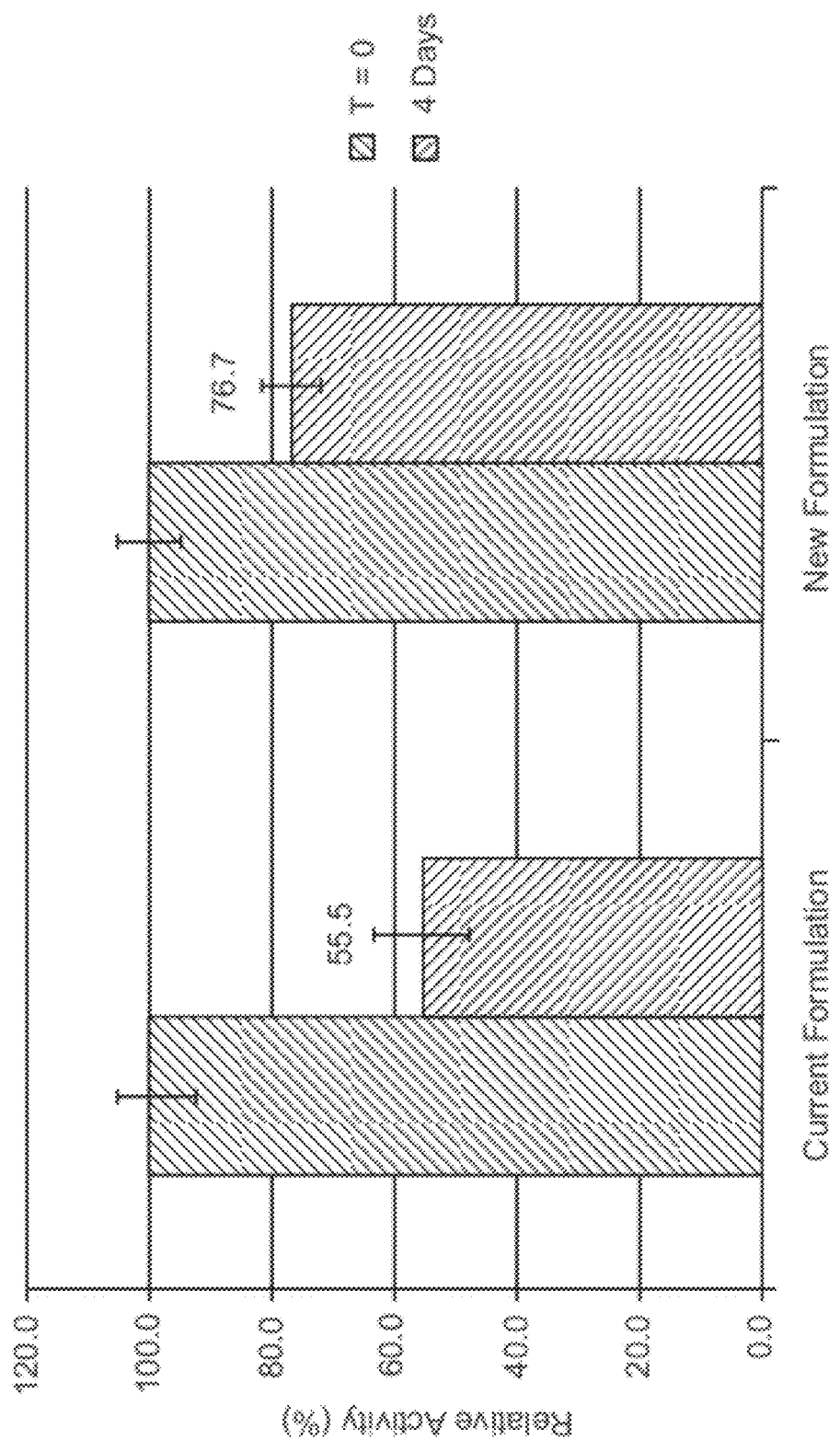

FIG. 47. rFurin stability in the highly stabilized formulation at 37° C. analyzed using the furin activity assay. The same samples as in FIG. 46 recalculated. The relative activity of each sample was calculated as the percentage of its initial activity. Error bars are ±1 standard deviation; n=4.

Figure 48:
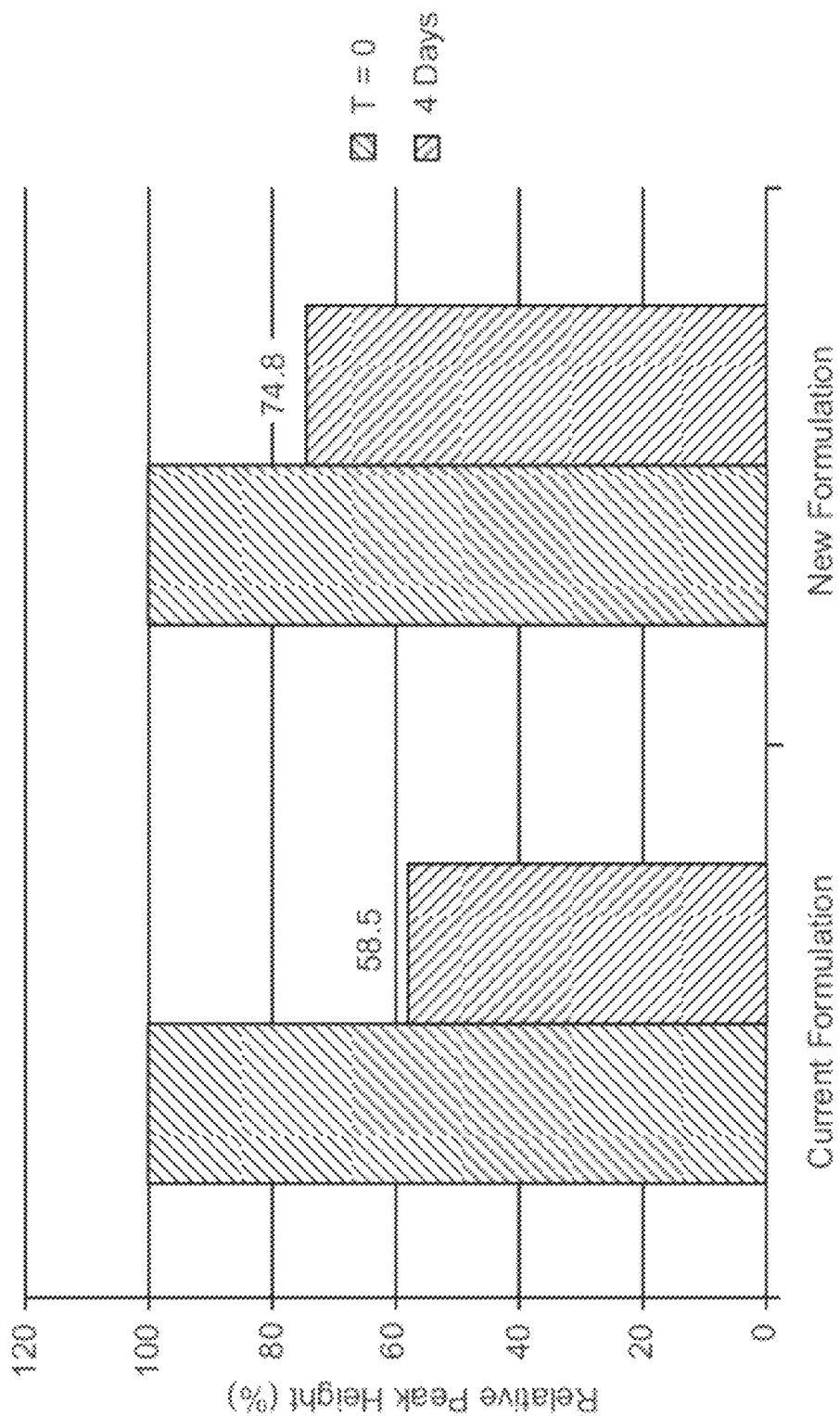

FIG. 48. rFurin stability in the highly stabilized formulation at 37° C. analyzed using SEC. The same samples as in FIG. 46. The relative peak height of rfurin for every sample was calculated as the percentage of its initial peak height. Error bars are ±1 standard deviation; n=4.

Figure 49A:
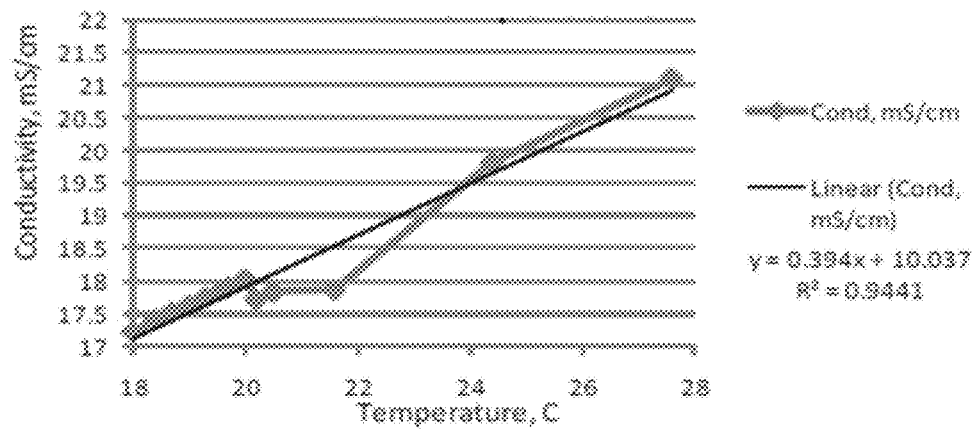
Figure 49B:
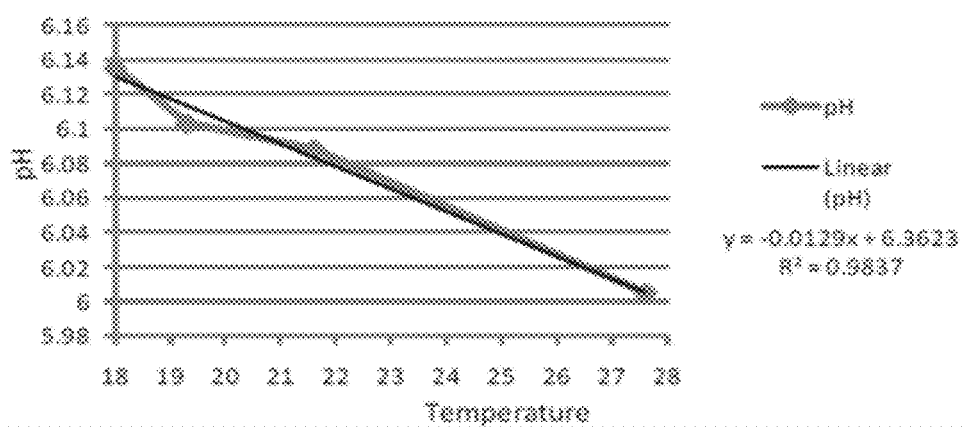

FIG. 49. Effect of temperature on the pH (B) and conductivity (A) of the highly stabilized formulation stock buffer (500 mM HEPES, 400 mM acetic acid, 1 mM $CaCl_2$, pH 6.0).

DETAILED DESCRIPTION OF THE INVENTION

I. Introduction

The present disclosure is based in part on the discovery that aqueous furin compositions can be stabilized against various chemical and mechanical stresses by the addition of sugars, sugar alcohols, and non-ionic surfactants. The aqueous furin compositions described herein are significantly more stable when stored at or above room temperature, as well as when subjected to mechanical stress, as compared to similar furin compositions lacking sugars, sugar alcohols, and non-ionic surfactants. The present disclosure is also based in part on the discovery that the addition of non-ionic surfactants to furin dilution buffers enables a greater recovery of furin activity when the enzyme is diluted to lower concentrations used during the manufacture of various recombinant biologics, such as VWF.

Advantageously, the studies described herein demonstrate that the addition of sugar or sugar alcohols to a furin composition enhances the stability of the composition when stored over a period of time. For example, it is shown herein that the inclusion of as little as 2% sugar or sugar alcohol in an aqueous furin formulation can increase the stability of the composition by greater than 10%. It is further shown that inclusion of 10% sugar or sugar alcohol in an aqueous furin formulation can increase the stability of the composition by greater than 75%.

Advantageously, the studies described herein also demonstrate that the addition of non-ionic surfactant to a furin composition enhances the stability of the composition when subjected to mechanical stress. For example, it is shown herein that the inclusion of as little as 10 ppm of non-ionic surfactant in an aqueous furin formulation can increase the stability of the composition by greater than 75%.

Advantageously, the studies described herein also demonstrate that the inclusion of non-ionic surfactant to a furin dilution buffer increases the recovery of furin activity after dilution. For example, it is shown herein that the inclusion of 75 ppm of non-ionic surfactant in a furin dilution buffer increases the recovery of furin activity after dilution by 3- to 4-fold.

Accordingly, the present disclosure provides compositions of highly stabilized furin formulations. Although the majority of the discussion herein is in terms of highly stabilized formulations of recombinant furin (rfurin), it will be appreciated that any furin protein, including furin isolated from a subject or any derivatives or mutants of furin, can be included in the formulations of the present invention.

In one aspect, the present disclosure provides highly stabilized furin formulations that show improved stability over control formulations when assayed after subjecting the formulation to one or more stressors, including without limitation exposure of the formulations to a range of temperatures, to several freeze/thaw cycles, and/or to agitation. Improved stability is generally assessed by level of furin activity—for example, after storage at higher than ambient room temperature, a highly stabilized furin formulation will show a higher level of activity than a control formulation stored under identical conditions as compared to the activity of each prior to storage (i.e., at time=0). Methods for assessing the stability of a furin formulation are described herein.

In further aspects, the present disclosure provides methods for forming highly stabilized furin formulations of the present invention. Such methods include methods for stabilizing a formulation of furin for storage, including frozen storage, storage at ambient room temperature or above, or lyophilization.

In yet other aspects, the present disclosure provides methods for diluting concentrated furin solutions that result in increased retention of furin activity after dilution. As compared to furin compositions diluted with solutions lacking non-ionic surfactant, aqueous compositions of furin diluted according to the methods provided herein retain 3- to 4-times more enzymatic activity.

II. Definitions

As used herein, the term "furin" refers to any protein or polypeptide with furin activity, particularly the ability to cleave the peptide bond between residues Arg-763 and Ser-764 of the pro-von Willebrand Factor (pro-VWF) polypeptide. In an exemplary embodiment, furin refers to a polypeptide comprising an amino acid sequence identical or highly identical to that of NP_002560.1 (human furin preproprotein). In an exemplary embodiment, furin refers to a polypeptide comprising an amino acid sequence identical or highly identical to amino acids 25-794 of NP_002560.1 (human furin proprotein). In an exemplary embodiment, furin refers to a polypeptide comprising an amino acid sequence identical or highly identical to amino acids 108-794 of NP_002560.1 (human mature furin protein). As used herein, furin polypeptides also include natural variants of furin with VWF cleaving activity, as well as modified furin constructs with VWF cleaving activity. As used herein, furin encompasses any natural variants, alternative sequences, isoforms or mutant proteins that retain some basal activity (for example, at least 1%, 5%, 10%, 20%, 30%, 40%, 50%, 60%, 70%, 80%, 90%, 95%, 96%, 97%, 98%, 99%, or more activity as compared to the activity of wild-type furin). Examples of furin mutations found in the human population include, without limitation, A43E, A43G, A43V, R50W, Y64C, L77P, R81C, E97A, E97V, V109M, V109L, R130W, A139V, P169T, N245S, E271K, Q339R, N407S, E457Q, R464W, K469R, S524Y, T536S, L570F, D624N, A642T, S685P, V728I, V735I, R745Q, P772L, and A793T. Furin polypeptides also include polypeptides containing post-translational modification. For example, it has been shown that furin is phosphorylated at residues S773 and S775 and predicted that furin is glycosylated at residues N387, N440, and N553.

In the context of the present disclosure, furin proteins include recombinant furin polypeptides as well as native furin polypeptides isolated from a source material (e.g., tissue or blood). Furin polypeptides (recombinant and source purified) may be derived from any suitable organism, for example, a mammal such as a primate, human, monkey, rabbit, pig, rodent, mouse, rat, hamster, gerbil, canine, feline, and biologically active derivatives thereof. Mutant and variant furin polypeptides having VWF cleaving activity are also embraced, as are functional fragments, and fusion proteins comprising furin polypeptides. Furthermore, the furin polypeptides described herein may further comprise tags that facilitate purification, detection, or both. The furin polypeptides described herein may further be modified with a therapeutic moiety or a moiety suitable for imaging in vitro or in vivo.

Proteolytically active recombinant furin may be prepared by expression in cell culture (e.g., mammalian cell culture). Non-limiting examples of expression and purification methods for preparing recombinant furin are described in WO 1991/06314, WO 1992/09698, U.S. Pat. Nos. 6,210,929 and 6,596,526, as well as in U.S. Patent Application Publication Nos. 2009/0181423 and 2009/0304669, the contents of which are hereby incorporated by reference in their entireties for all purposes.

As used herein, "activity" refers to a functional activity or activities of furin or portion thereof associated with a full-length (complete) protein. Functional activities include, but are not limited to, biological activity, including participation in the proteolytic maturation of proprotein substrates and cleavage of test substrates such as Boc-Arg-Val-Arg-Arg-AMC (SEQ ID NO:1; AMC=7-amino-4-methoxy coumarin). Substrates for furin include von Willebrand factor, proparathyroid hormone, transforming growth factor beta 1 precursor, proalbumin, pro-beta-secretase, membrane type-1 matrix metalloproteinase, and the beta subunit of pro-nerve growth factor. In one embodiment, one Unit (U) of furin activity is defined as the amount of furin that releases 1 pmol of AMC from Boc-Arg-Val-Arg-Arg-AMC (SEQ ID NO:1) per minute.

As used herein, the term "stability" (such as furin stability or furin formulation stability) is used in a structural context, e.g., relating to the structural integrity of a protein, or in a functional context, e.g., relating to a protein's ability to retain its function and/or activity over time. As will be appreciated, the protein under discussion may be contained within a formulation in accordance with the methods and compositions described herein, and the stability of that protein refers to its stability in that formulation. In one embodiment, the stability of a furin composition is determined by measuring the furin activity of the composition. For example, by using a detectable furin substrate such as Boc-Arg-Val-Arg-Arg-AMC (SEQ ID NO:1; e.g., ALX-260-040-M001 sold by Enzo Life Sciences), for example, in an assay as described in Malloy SS, et al., J Biol Chem. 1992 Aug. 15; 267(23):16396-402, the content of which is hereby incorporated herein by reference in its entirety for all purposes. In one embodiment, the stability of furin composition formulated with sugar, sugar alcohol, and/or non-ionic surfactant, as described herein, is compared to a furin composition formulated without the sugar, sugar alcohol, and/or non-ionic surfactant.

As used herein, a "storage stable" aqueous furin composition refers to a furin polypeptide solution (e.g., a rfurin polypeptide solution) that has been formulated to increase the stability of the protein in solution, for example by at least 10%, over a given storage time. In the context of the present disclosure, a furin polypeptide solution (e.g., a rfurin polypeptide solution) can be made "storage stable" by the addition of a sugar, sugar alcohol, or non-ionic surfactant as a stabilizing agent. In some embodiments, the stability of the furin polypeptide in any given formulation can be measured, for example, by monitoring the formation of aggregates, loss of bulk enzymatic activity, or formation of degradation products, over a period of time. The absolute stability of a formulation, and the stabilizing effects of the sugar, sugar alcohol, or non-ionic surfactant, will vary dependent upon the particular composition being stabilized. In one embodiment, the stability of a furin composition is determined by measuring the furin activity of the composition. For example, by using a detectable furin substrate such as Boc-Arg-Val-Arg-Arg-AMC (SEQ ID NO:1; e.g., ALX-260-040-M001 sold by Enzo Life Sciences), in an assay, for example, as described in Malloy SS, et al., J Biol Chem. 1992 Aug. 15; 267(23):16396-402, the content of which is hereby incorporated by reference in its entirety for all purposes. In one embodiment, the stability of furin composition formulated with sugar, sugar alcohol, and/or non-ionic surfactant, as described herein, is compared to a furin composition formulated without the sugar, sugar alcohol, and/or non-ionic surfactant.

As used herein, "shelf-life" refers to the period of time a formulation maintains a predetermined level of stability at a predetermined temperature. In particular embodiments, the predetermined temperature refers to frozen (e.g., −80° C., −25° C., 0° C.), refrigerated (e.g., 0° to 10° C.), or room temperature (e.g., 18° C. to 32° C.) storage.

As used herein, the term "time of stability" refers to the length of time a formulation is considered stable. For example, the time of stability for a formulation may refer to the length of time for which the level of protein aggregation and/or degradation in the formulation remains below a certain threshold (e.g., 1%, 2%, 3%, 4%, 5%, 6%, 7%, 8%, 9%, 10%, 11%, 12%, 13%, 14%, 15%, 16%, 17%, 18%, 19%, 20%, etc.), and/or the length of time a formulation maintains biological activity above a certain threshold (e.g., 100%, 95%, 90%, 85%, 80%, 75%, 70%, 65%, 60%, 55%, 50%, etc.) of the amount of activity present in the formulation at the start of the storage period.

In the context of the present disclosure, a storage stable aqueous composition of a furin polypeptide (e.g., rfurin polypeptide) formulated with a sugar, sugar alcohol, and/or non-ionic surfactant will have a longer time of stability than a composition of the same furin polypeptide formulated without the sugar, sugar alcohol, and/or non-ionic surfactant. In some embodiments, a storage stable aqueous composition of a furin polypeptide, will have a time of stability that is, for example, at least 10% greater than the time of stability for the same composition formulated in the absence of the sugar, sugar alcohol, and/or non-ionic surfactant, or at least 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190% greater, or at least 2 times greater, or at least 2.5 times, 3.0 times, 3.5 times, 4.0 times, 4.5 times, 5.0 times, 5.5 times, 6.0 times, 6.5 times, 7.0 times, 7.5 times, 8.0 times, 8.5 times, 9.0 times, 9.5 times, 10 times, or more times greater than the time of stability for the same composition formulated in the absence of the sugar, sugar alcohol, and/or non-ionic surfactant.

As used herein, "storage" means that a formulation is not immediately administered to a subject or utilized in a production process once prepared, but is kept for a period of time under particular conditions (e.g. particular temperature) prior to use. For example, a furin formulation can be kept for days, weeks, months or years, prior to administration to a subject under varied temperatures such as frozen (e.g., −80° C., −25° C., 0° C.), refrigerated (e.g., 0° to 10° C.), or room temperature (e.g., 18° C. to 32° C.). As will be appreciated, such formulations may be liquid or lyophilized formulations.

As used herein, the term "about" denotes an approximate range of plus or minus 10% from a specified value. For instance, the language "about 20%" encompasses a range of 18-22%.

As used herein, when referring to a concentration of an individual component of a composition, the phrases "no more than X" and "from 0 to X" are equivalent and refer to any concentration between and including 0 and X. For example, the phrases "a concentration of no more than 2%" and "a concentration of from 0% to 2%" are equivalent and include 0%, 1%, and 2%.

As used herein, when referring to a concentration of an individual component of a composition, the phrases "no less than X" refers to any concentration X or higher. For example, the phrase "a concentration of no less than 98%" includes 98%, 99%, and 100%.

As used herein, when referring to a concentration of an individual component of a composition, the phrases "between X and Y" and "from X to X" are equivalent and refer to any concentration between and including X and Y. For example, the phrases "a concentration of between 49% and 51%" and "a concentration of from 49% to 51%" are equivalent and include 49%, 50%, and 51%.

As used herein, a "sugar" refers to monosaccharides having the general formula $C_xH_{2y}O_y$ (linear) or $C_xH_{(2y-1)}O_y$ (cyclic), and disaccharides consisting of two monosaccharide units formed through a dehydration reaction. Monosaccharides can be classified by the number of carbon atoms they contain: diose (2), triose (3), tetrose (4), pentose (5), hexose (6), heptose (7), etc. Accordingly, as used herein, a C(X) sugar refers to a sugar containing X-number of carbon molecules. For example, a C(5) sugar refers to a pentose sugar, while a C(6) sugar refers to a hexose sugar. Non-limiting examples of sugars that may be used in the formulations provided herein include: diose sugar glycolaldehyde, triose sugars glyceraldehyde and dihydroxyacetone; tetrose sugars erythrose, threose, and erythrulose; pentose sugars arabinose, lyxose, ribose, xylose, ribulose, and xylulose; hexose sugars allose, altrose, glucose, mannose, gulose, idose, galactose, talose, psicose, fructose, sorbose, and tagatose; heptose sugars sedoheptulose, mannoheptulose, and L-glycero-D-manno-heptose; and all possible combinations of disaccharide sugars formed thereform, including without limitation sucrose, lactulose, lactose, maltose, trehalose, cellobiose, kojibiose, nigerose, isomaltose, β,β-trehalose, α,β-trehalose, sophorose, laminaribiose, gentiobiose, turanose, maltulose, palatinose, gentiobiulose, mannobiose, melibiose, melibiulose, rutinose, rutinulose, and xylobiose.

As used herein, a "sugar alcohol" refers to a hydrogenated form of a mono- or disaccharide, whose carbonyl group has been reduced to form a primary or secondary hydroxyl. In one embodiment, the sugar alcohol has between about 4 and about 8 carbon atoms. Non-limiting examples of sugar alcohols that may be used in formulations provided herein include glycol, glycerol, erythritol, threitol, ribitol, fucitol, iditol, volmitol, isomalt, maltitol, lactitol, mannitol, sorbitol, inositol, galactitol, dulcitol, xylitol, and arabitol.

As used herein, a "pharmaceutically acceptable salt" refers to a salt that is safe for administration to a subject (e.g., a human) in a drug formulation. The selection and use of pharmaceutically acceptable salts is well known in the art, for example, see Stahl and Wermuth, *Pharmaceutical Salts Properties, Selection, and Use*, 2nd Revised edition, Wiley, Hoboken, N.J. In certain embodiments, the pharmaceutically acceptable salt is sodium chloride, potassium chloride, or a combination thereof.

As used herein, the term "non-ionic surfactant" refers to a surface active agent that is non-ionized under physiologically relevant conditions. Non-limiting examples of non-ionic surfactants useful for the stabilized aqueous furin compositions provided herein include: non-ionic water soluble mono-, di-, and tri-glycerides (e.g., propylene glycol dicarpylate/dicaprate (e.g. MIGLYOL® 840), medium chain mono- and diglycerides (e.g. CAPMUL® and IMWITOR® 72), medium-chain triglycerides (e.g. caprylic and capric triglycerides such as LAVRAFAC, MIGLYOL® 810 or 812, CRODAMOL® GTCC-PN, and SOFTISON 378), long chain monoglycerides (e.g. glyceryl monooleates such as PECEOL®, and glyceryl monolinoleates such as MAISINE®), polyoxyl castor oil (e.g. macrogolglycerol ricinoleate, macrogolglycerol hydroxystearate, macrogol cetostearyl ether)); non-ionic water soluble mono- and di-fatty acid esters of polyethyelene glycol; non-ionic water soluble sorbitan fatty acid esters (e.g., sorbitan monolaurates such as polyoxyethylene (20) sorbitan monolaurate (TWEEN 20) and sorbitan monolaurate (SPAN 20); sorbitan monopalmitates such as polyoxyethylene (20) sorbitan monopalmitates (TWEEN 40) and sorbitan monopalmitate (SPAN 40); sorbitan monostearates such as polyoxyethylene (20) sorbitan monostearate (TWEEN 60) and sorbitan monostearate (SPAN 60); sorbitan monooleates such as polyoxyethylene (20) sorbitan monooleate (TWEEN 80) and sorbitan monooleate (SPAN 80); sorbitane trioleates such as sorbitane trioleate (SPAN 85); and sorbitan tristearates such as sorbitan tristearate (SPAN65)); polyglycolyzed glycerides (e.g., lauroyl macrogol-6 glycerides (Labrafil® M2130CS); d-α-tocopheryl polyethyleneglycol 1000 succinate (TPGS), poyethyleneglycol 660 12-hydroxystearate (SOLUTOL® HS 15), polyoxyl oleate and stearate (e.g. PEG 400 monostearate and PEG 1750 monostearate)); non-ionic water soluble triblock copolymers (e.g. poly(ethyleneoxide)/poly-(propyleneoxide)/poly(ethyleneoxide) triblock copolymers such as methyl-oxirane polymer with oxirane BHT (PLURONIC® F-127)).

In one embodiment, storage stable compositions of furin (e.g., rfurin) are provided which contain a non-ionic surfactant selected from a non-ionic water soluble monoglyceride, a non-ionic water soluble diglyceride, a non-ionic water soluble triglyceride, a non-ionic water soluble monofatty acid esters of polyethyelene glycol, a non-ionic water soluble difatty acid esters of polyethyelene glycol, a non-ionic water soluble sorbitan fatty acid ester, a non-ionic polyglycolyzed glyceride, a non-ionic water soluble triblock copolymer, and a combination thereof.

As used herein, the term "biologically active derivative," when used in the context of furin polypeptide, also embraces polypeptides obtained via recombinant DNA technology. This may include any method known in the art for (i) the production of recombinant DNA by genetic engineering, e.g., via reverse transcription of RNA and/or amplification of DNA, (ii) introducing recombinant DNA into prokaryotic or eukaryotic cells by transfection, e.g., via electroporation or microinjection, (iii) cultivating said transformed cells, e.g., in a continuous or batch-wise manner, (iv) expressing furin protein, e.g., constitutively or upon induction, and (v) isolating said furin protein, e.g., from the culture medium or by harvesting the transformed cells, in order to (vi) obtain substantially purified recombinant furin protein, e.g., via ion exchange chromatography, size exclusion chromatography, affinity chromatography, hydrophobic interaction chromatography, and the like. The term "biologically active derivative" includes also chimeric molecules such as e.g., a furin protein, or functional fragment thereof, in combination with a second polypeptide, e.g., an immunoglobulin Fc domain or an albumin domain, in order to improve the biological/pharmacological properties such as e.g., half life of the furin protein in the circulation system of a mammal, particularly a human.

As used herein and in the appended claims, the singular forms "a," "an," and "the" include plural referents unless the context clearly dictates otherwise. Thus, for example, reference to "a buffering agent" refers to one agent or mixtures of such agents, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, compositions, formulations and methodologies which are described in the publication and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

As used herein, "BDS" refers to "Bulk Drug Substance."

III. Stabilized Aqueous Compositions of Recombinant Furin

In one aspect, the present disclosure provides stabilized aqueous formulations of furin, e.g., rfurin. The following embodiments are based in part on the discovery that inclusion of a sugar, sugar alcohol, and/or non-ionic surfactant stabilizes aqueous furin compositions, as compared to compositions lacking the sugar, sugar alcohol, and/or non-ionic surfactant.

As will be recognized by one of skill in the art, furin compositions (e.g., rfurin compositions) formulated according to the embodiments provided herein may contain, in addition to the components explicitly disclosed, counter ions contributed by the inclusion of solution components or pH modifying agents, for example, sodium or potassium contributed from an acetate salt, sodium hydroxide, or potassium hydroxide or chloride contributed by calcium chloride or hydrochloric acid. In the context of the present disclosure, a storage stable furin composition (e.g., rfurin) consisting of or consisting essentially of a given formulation may further comprise one or more counter ion, as necessitated by the formulation process at a particular pH.

In one embodiment, a storage stable furin composition (e.g., rfurin composition) provided herein will be stabilized at room temperature (i.e., between 18° C. and 32° C.) for a period of time. For example, in one embodiment, a storage stable, aqueous immunoglobulin composition will be stable when stored at room temperature for at least 4 days. In other embodiments, the composition will be stabile at room temperature for at least 1, 2, 3, 4, 5, 6, 7, 8, 9, 10, 11, 12, 13, 14, 21, 28, or more days. In other embodiments, the composition will be stable for at least 1 month. In yet other embodiments, the composition will be stable for at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or more months. In certain embodiments, room temperature refers to between 20° C. and 30° C., between 21° C. and 29° C., between 22° C. and 28° C., between 23° C. and 27° C., between 24° C. and 26° C., or about 25° C. In a specific embodiment, the composition will be stable for an extended period of time when stored at a temperature between 20° C. and 25° C.

In one embodiment, a storage stable furin composition (e.g., rfurin composition) provided herein will be stabilized at refrigerated temperature (i.e., between 2° C. and 10° C.) for a period of time. For example, in one embodiment, a storage stable, aqueous immunoglobulin composition will be stable when stored at refrigerated temperature for at least 4 days. In other embodiments, the composition will be stabile at refrigerated temperature for at least 1, 2, 3, 4, 5, 6, 7, 8, 9, 10, 11, 12, 13, 14, 21, 28, or more days. In other embodiments, the composition will be stable for at least 1 month. In yet other embodiments, the composition will be stable for at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or more months. In a specific embodiment, the composition will be stable for an extended period of time when stored at a temperature between 2° C. and 8° C.

In one embodiment, a storage stable furin composition (e.g., rfurin composition) provided herein will be stabilized at elevated temperature (i.e., between 32° C. and 42° C.) for a period of time. For example, in one embodiment, a storage stable, aqueous immunoglobulin composition will be stable when stored at elevated temperature for at least 4 days. In other embodiments, the composition will be stabile at elevated temperature for at least 1, 2, 3, 4, 5, 6, 7, 8, 9, 10, 11, 12, 13, 14, 21, 28, or more days. In other embodiments, the composition will be stable for at least 1 month. In yet other embodiments, the composition will be stable for at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or more months. In a specific embodiment, the composition will be stable for an extended period of time when stored at a temperature between 35° C. and 40° C.

In one embodiment, a stored furin composition is considered storage stable as long as the composition maintains at least 40% of the furin activity present at the start of the storage period (e.g., at time=0). In another embodiment, a stored composition is considered stable as long as the composition maintains at least 45%, 50%, 55%, 60%, 65%, 70%, 75%, 80%, 85%, 90%, 95% or more of the furin activity present at the start of the storage period (e.g., at time=0). In one embodiment, furin activity is measures in an assay as described in Malloy S S, et al., J Biol Chem. 1992 Aug. 15; 267(23): 16396-402.

In one embodiment, a furin composition is considered to have been stabilized by the addition of a stabilizing agent (e.g., a sugar, sugar alcohol, or non-ionic surfactant) when the composition contains at least 10% more furin activity after storage for a period of time, as compared to a furin composition not containing the stabilizing agent or containing a lower amount of the stabilizing agent. In other embodiments, a furin composition is considered to have been stabilized by the addition of a stabilizing agent (e.g., a sugar, sugar alcohol, or non-ionic surfactant) when the composition contains at least 15%, 20%, 25%, 30%, 35%, 40%, 45%, 50%, 55%, 60%, 65%, 70%, 75%, 80%, 85%, 90%, 95%, 100%, or a greater percentage more furin activity after storage for a period of time, as compared to a furin composition not containing the stabilizing agent or containing a lower amount of the stabilizing agent.

In one embodiment, a stored furin composition is considered stable as long as the percentage of furin present in an aggregated state remains no more than 50%. In other embodiments, a stored furin composition is considered stable as long as the percentage of furin present in an aggregated state remains no more than 45%, 40%, 35%, 30%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1%, or less.

In one embodiment, a furin composition is considered to have been stabilized by the addition of a stabilizing agent (e.g., a sugar, sugar alcohol, or non-ionic surfactant) when the composition contains at least 10% less furin present in an aggregated state after storage for a period of time, as compared to a furin composition not containing the stabilizing agent or containing a lower amount of the stabilizing agent. In other embodiments, a furin composition is considered to have been stabilized by the addition of a stabilizing agent (e.g., a sugar, sugar alcohol, or non-ionic surfactant) when the composition contains at least 15%, 20%, 25%, 30%, 35%, 40%, 45%, 50%, 55%, 60%, 65%, 70%, 75%, 80%, 85%, 90%, 95%, 100%, or a greater percentage less furin present in an aggregated state after storage for a period of time, as compared to a furin composition not containing the stabilizing agent or containing a lower amount of the stabilizing agent.

In one embodiment, a stored furin composition is considered stable as long as the composition maintains at least 40% of the starting furin activity (e.g., at time=0) after being subjected to mechanical stress. In another embodiment, a stored composition is considered stable as long as the composition maintains 45%, 50%, 55%, 60%, 65%, 70%, 75%, 80%, 85%, 90%, 95% or more of the starting furin activity (e.g., at time=0) after being subjected to mechanical stress. In a specific embodiment, the mechanical stress is agitation (e.g., shaking).

In one embodiment, a furin composition is considered to have been stabilized by the addition of a stabilizing agent (e.g., a sugar, sugar alcohol, or non-ionic surfactant) when the composition contains at least 10% more furin activity after being subjected to mechanical stress, as compared to a furin composition not containing the stabilizing agent or containing a lower amount of the stabilizing agent. In other embodiments, a furin composition is considered to have been stabilized by the addition of a stabilizing agent (e.g., a sugar, sugar alcohol, or non-ionic surfactant) when the composition contains at least 15%, 20%, 25%, 30%, 35%, 40%, 45%, 50%, 55%, 60%, 65%, 70%, 75%, 80%, 85%, 90%, 95%, 100%, or a greater percentage more furin activity after being subjected to mechanical stress, as compared to a furin composition not containing the stabilizing agent or containing a lower amount of the stabilizing agent. In a specific embodiment, the mechanical stress is agitation (e.g., shaking).

In one embodiment, a stored furin composition is considered stable as long as the percentage of furin present in an aggregated state remains no more than 50% after being subjected to mechanical stress. In other embodiments, a stored furin composition is considered stable as long as the percentage of furin present in an aggregated state remains no more than 45%, 40%, 35%, 30%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1%, or less after being subjected to mechanical stress. In a specific embodiment, the mechanical stress is agitation (e.g., shaking).

In one embodiment, a furin composition is considered to have been stabilized by the addition of a stabilizing agent (e.g., a sugar, sugar alcohol, or non-ionic surfactant) when the composition contains at least 10% less furin present in an aggregated state after being subjected to mechanical stress, as compared to a furin composition not containing the stabilizing agent or containing a lower amount of the stabilizing agent. In other embodiments, a furin composition is considered to have been stabilized by the addition of a stabilizing agent (e.g., a sugar, sugar alcohol, or non-ionic surfactant) when the composition contains at least 15%, 20%, 25%, 30%, 35%, 40%, 45%, 50%, 55%, 60%, 65%, 70%, 75%, 80%, 85%, 90%, 95%, 100%, or a greater percentage less furin present in an aggregated state after being subjected to mechanical stress, as compared to a furin composition not containing the stabilizing agent or containing a lower amount of the stabilizing agent. In a specific embodiment, the mechanical stress is agitation (e.g., shaking).

While the furin (e.g., rfurin) formulations described in this application can be lyophilized and reconstituted in the indicated concentrations, it will be appreciated that these preparations can also be reconstituted in more dilute form. For example, a preparation according the present disclosure which is lyophilized and/or normally reconstituted in 2 mL of solution can also be reconstituted in a larger volume of diluent, such as 5 mL. Likewise, lyophilized furin (e.g., rfurin) formulations can also be reconstituted in more concentrated form. For example, a preparation according the present disclosure which is lyophilized and/or normally reconstituted in 2 ml of solution can also be reconstituted in a smaller volume, such as 1 mL.

Advantageously, in one aspect, the highly stabilized furin (e.g., rfurin) formulations of the present invention are combined with a diluent that confers increased furin recovery when the resultant composition is used in a production method, for example, in the maturation of rVWF (also referred to herein as an "rVWF maturation method"). Maturation of pro-von Willebrand factor (vWF) to its active form requires proteolytic processing after a pair of dibasic amino acids (-Lys-Arg-) at residue 763. It has been shown that vWF is preferentially processed by the paired dibasic amino acid-cleaving enzyme furin. Production processes for vWF thus include the use of furin, preferably in a highly stabilized formulation. In a further aspect, the highly stabilized formulation in this diluent increases furin activity recovery in the rVWF maturation step by three to four times compared to control formulations placed in control diluents.

In certain aspects, the highly stabilized formulations of the invention have a shelf life of at least 6 months. As will be appreciated, this shelf life may be at frozen temperatures (i.e., −80° C., −25° C., 0° C.), refrigerated (0° C. to 10° C.), or room temperature (20° C. to 32° C.) in liquid or lyophilized form. In further aspects, the highly stabilized formulations of the invention have a shelf life of at least 12, 18, 24, 30, 36, 42, 48, 54, or 60 months.

In further aspects and in accordance with the above, shelf life is determined by a percent activity remaining after storage at any of the above temperatures for any of the above periods of time. In certain embodiments, shelf life means that the formulation retains at least 10%, 15%, 20%, 25%, 30%, 35%, 40%, 45%, 50%, 55%, 60%, 65%, 70%, 75%, 80%, 85%, 90%, 95%, 96%, 97%, 98%, 99%, 100% of furin activity as measured by any of the assays described herein or known in the art as compared to activity prior to storage for any of the above amounts of time at any of the above temperatures.

In one aspect, a highly stabilized formulation of furin (e.g. rfurin) in accordance with the present disclosure includes: (a) 8,000 U/mL-57,000 U/mL furin (e.g., rfurin); (b) 190 mM sodium chloride; (c) 0.92 mM calcium chloride; (d) 10% w/w trehalose dihydrate; (e) 75 ppm polysorbate 80; (f) 45 mM acetic acid; and (g) 46 mM HEPES.

In certain aspects, highly stabilized formulations of the present disclosure include the following components: 47 mM HEPES, 46 mM acetic acid, 195 mM sodium chloride, 0.094 mM calcium chloride, 0.0075% polysorbate 80, 10% w/w trehalose dihydrate, pH 6.0.

In further aspects, highly stabilized formulations of furin, including rfurin, in accordance with the present disclosure include (a) about 5,500 U/mL to 55,000 U/mL; 6,000 U/mL to 50,000 U/mL; 6,500 U/mL to 45,000 U/mL; 7,000 U/mL to 40,000 U/mL; 7,500 U/mL to 35,000 U/mL; 8,000 U/mL to 30,000 U/mL; 8,500 U/mL to 25,000 U/mL; 9,000 U/mL to 20,000 U/mL; 9,500 U/mL to 15,000 U/mL; or 10,000 U/mL furin; (b) about 100 mM to 300 mM, 110 mM to 280 mM, 120 mM to 260 mM, 130 mM to 240 mM, 140 mM to 220 mM, 150 mM to 200 mM, or 160 mM to 180 mM sodium chloride; (c) about 0.5 mM to 9 mM, 1 mM to 8 mM, 1.5 mM to 7 mM, 2 mM to 6 mM, 2.5 mM to 5 mM, or 3 mM to 4.5 mM calcium chloride; (d) about 0.5% to 19%, 1% to 18%, 1.5% to 17%, 2.0% to 16%, 2.5% to 15%, 3.0% to 14%, 3.5% to 13%, 4.0% to 12%, 4.5% to 11%, 5.0% to 10%, 5.5% to 9%, or 6.0% to 8% trehalose dihydrate; (e) about 0.5 ppm to 140 ppm, 1.0 ppm to 130 ppm, 10 ppm to 120 ppm, 20 ppm to 110 ppm, 30 ppm to 100 ppm, 40 ppm to 95 ppm, 50 ppm to 90 ppm, 55 ppm to 85 ppm, 60 ppm to 80 ppm, or 70 ppm to 75 ppm polysorbate 80; (f) about 25 mM to 90 mM, 30 mM to 80 mM, 35 mM to 70 mM, 40 mM to 60 mM, or 45 mM to 50 mM acetic acid, and (g) 15 mM to 95 mM, 20 mM to 90 mM, 25 mM to 85 mM, 30 mM to 80 mM, 35 mM to 75 mM, 40 mM to 70 mM, 45 mM to 65 mM, or 50 mM to 60 mM HEPES.

In one aspect, the present disclosure provides a stabilized aqueous furin composition (e.g., rfurin) comprising: furin (e.g., rfurin), from 2% to 20% sugar or sugar alcohol, from 10 ppm to 200 ppm non-ionic surfactant, from 50 mM to 500 mM of a pharmaceutically acceptable salt, from 0.5 mM to 10 mM calcium, a buffering agent, and a pH from 5.5 to 7.5. In a specific embodiment, the sugar is a pentose or hexose sugar.

In one embodiment, a stabilized aqueous furin composition (e.g., rfurin) comprises: furin (e.g., rfurin), from 100 mM to 300 mM of a pharmaceutically acceptable salt; from 0.5 mM to 2 mM calcium; from 2% to 20% of a sugar or sugar alcohol; from 100 to 200 ppm of a non-ionic surfactant; from 10 to 200 mM buffering agent; and a pH from 5.5 to 7.5. In a specific embodiment, the sugar is a pentose or hexose sugar.

In a specific embodiment, highly stabilized formulations of the invention include the following components: 47 mM HEPES, 46 mM acetic acid, 195 mM sodium chloride, 0.094 mM calcium chloride, 0.0075% polysorbate 80, 10% w/w trehalose dihydrate, pH 6.0.

In another specific embodiment, a highly stabilized formulation of furin (e.g., rfurin) in accordance with the present invention includes: (a) 8,000-57,000 U/mL rfurin; (b) 190 mM sodium chloride; (c) 0.92 mM calcium chloride; (d) 10% w/w trehalose dihydrate; (e) 75 ppm polysorbate 80; (f) 45 mM acetic acid; and (g) 46 mM HEPES.

A. Stabilizing Agents

Advantageously, it was found that the inclusion of sugars, sugar alcohols, and non-ionic surfactants stabilizes aqueous furin (e.g., rfurin) compositions. These effects are demonstrated in the examples provided herein. For example, the addition of these agents increases furin activity retention upon liquid storage, reduces aggregation of furin polypeptides upon liquid storage, reduces the degradation of furin polypeptides upon liquid storage, reduces the loss of furin activity upon agitation of an aqueous furin composition, and reduces aggregation caused by agitation of an aqueous furin composition.

Accordingly, in one embodiment, the present disclosure provides an aqueous furin composition (e.g., a rfurin composition) comprising from 2% to 20% sugar or sugar alcohol and from 10 ppm to 200 ppm non-ionic surfactant. In another embodiment, the composition comprises from 2% to 10% sugar or sugar alcohol and from 10 ppm to 100 ppm non-ionic surfactant. In another embodiment, the composition comprises 10±2% sugar or sugar alcohol and 75±25 ppm non-ionic surfactant. In a specific embodiment, the composition comprises 10% sugar or sugar alcohol and 75 ppm non-ionic surfactant. In yet other embodiments, the composition comprises a combination of sugar or sugar alcohol and non-ionic surfactant selected from variations 1 to 6035 found in Table 1 to Table 9.

TABLE 1

Exemplary embodiments for the combination of sugar or sugar alcohol and non-ionic surfactant concentrations useful for the stabilization of furin (e.g., rfurin) compositions.

| | | Sugar or Sugar Alcohol (%) | | | | | | | |
|---|---|---|---|---|---|---|---|---|---|
| | | 2%-20% | 2%-17.5% | 2%-15% | 2%-12.5% | 2%-10% | 2%-9% | 2%-8% | 2%-7% |
| Non-Ionic Surfactant (ppm) | 10-200 | Var. 1 | Var. 86 | Var. 171 | Var. 256 | Var. 341 | Var. 426 | Var. 511 | Var. 596 |
| | 10-175 | Var. 2 | Var. 87 | Var. 172 | Var. 257 | Var. 342 | Var. 427 | Var. 512 | Var. 597 |
| | 10-150 | Var. 3 | Var. 88 | Var. 173 | Var. 258 | Var. 343 | Var. 428 | Var. 513 | Var. 598 |
| | 10-125 | Var. 4 | Var. 89 | Var. 174 | Var. 259 | Var. 344 | Var. 429 | Var. 514 | Var. 599 |
| | 10-100 | Var. 5 | Var. 90 | Var. 175 | Var. 260 | Var. 345 | Var. 430 | Var. 515 | Var. 600 |
| | 10-90 | Var. 6 | Var. 91 | Var. 176 | Var. 261 | Var. 346 | Var. 431 | Var. 516 | Var. 601 |
| | 10-80 | Var. 7 | Var. 92 | Var. 177 | Var. 262 | Var. 347 | Var. 432 | Var. 517 | Var. 602 |
| | 10-75 | Var. 8 | Var. 93 | Var. 178 | Var. 263 | Var. 348 | Var. 433 | Var. 518 | Var. 603 |
| | 10-70 | Var. 9 | Var. 94 | Var. 179 | Var. 264 | Var. 349 | Var. 434 | Var. 519 | Var. 604 |
| | 10-60 | Var. 10 | Var. 95 | Var. 180 | Var. 265 | Var. 350 | Var. 435 | Var. 520 | Var. 605 |
| | 10-50 | Var. 11 | Var. 96 | Var. 181 | Var. 266 | Var. 351 | Var. 436 | Var. 521 | Var. 606 |
| | 10-25 | Var. 12 | Var. 97 | Var. 182 | Var. 267 | Var. 352 | Var. 437 | Var. 522 | Var. 607 |
| | 25-200 | Var. 13 | Var. 98 | Var. 183 | Var. 268 | Var. 353 | Var. 438 | Var. 523 | Var. 608 |
| | 25-175 | Var. 14 | Var. 99 | Var. 184 | Var. 269 | Var. 354 | Var. 439 | Var. 524 | Var. 609 |
| | 25-150 | Var. 15 | Var. 100 | Var. 185 | Var. 270 | Var. 355 | Var. 440 | Var. 525 | Var. 610 |
| | 25-125 | Var. 16 | Var. 101 | Var. 186 | Var. 271 | Var. 356 | Var. 441 | Var. 526 | Var. 611 |
| | 25-100 | Var. 17 | Var. 102 | Var. 187 | Var. 272 | Var. 357 | Var. 442 | Var. 527 | Var. 612 |
| | 25-90 | Var. 18 | Var. 103 | Var. 188 | Var. 273 | Var. 358 | Var. 443 | Var. 528 | Var. 613 |
| | 25-80 | Var. 19 | Var. 104 | Var. 189 | Var. 274 | Var. 359 | Var. 444 | Var. 529 | Var. 614 |
| | 25-70 | Var. 20 | Var. 105 | Var. 190 | Var. 275 | Var. 360 | Var. 445 | Var. 530 | Var. 615 |
| | 25-60 | Var. 21 | Var. 106 | Var. 191 | Var. 276 | Var. 361 | Var. 446 | Var. 531 | Var. 616 |
| | 25-50 | Var. 22 | Var. 107 | Var. 192 | Var. 277 | Var. 362 | Var. 447 | Var. 532 | Var. 617 |
| | 50-200 | Var. 23 | Var. 108 | Var. 193 | Var. 278 | Var. 363 | Var. 448 | Var. 533 | Var. 618 |
| | 50-175 | Var. 24 | Var. 109 | Var. 194 | Var. 279 | Var. 364 | Var. 449 | Var. 534 | Var. 619 |
| | 50-150 | Var. 25 | Var. 110 | Var. 195 | Var. 280 | Var. 365 | Var. 450 | Var. 535 | Var. 620 |
| | 50-125 | Var. 26 | Var. 111 | Var. 196 | Var. 281 | Var. 366 | Var. 451 | Var. 536 | Var. 621 |
| | 50-90 | Var. 27 | Var. 112 | Var. 197 | Var. 282 | Var. 367 | Var. 452 | Var. 537 | Var. 622 |
| | 50-80 | Var. 28 | Var. 113 | Var. 198 | Var. 283 | Var. 368 | Var. 453 | Var. 538 | Var. 623 |
| | 75-200 | Var. 29 | Var. 114 | Var. 199 | Var. 284 | Var. 369 | Var. 454 | Var. 539 | Var. 624 |
| | 75-175 | Var. 30 | Var. 115 | Var. 200 | Var. 285 | Var. 370 | Var. 455 | Var. 540 | Var. 625 |
| | 75-150 | Var. 31 | Var. 116 | Var. 201 | Var. 286 | Var. 371 | Var. 456 | Var. 541 | Var. 626 |
| | 100-200 | Var. 32 | Var. 117 | Var. 202 | Var. 287 | Var. 372 | Var. 457 | Var. 542 | Var. 627 |
| | 100-175 | Var. 33 | Var. 118 | Var. 203 | Var. 288 | Var. 373 | Var. 458 | Var. 543 | Var. 628 |
| | 50 ± 25 | Var. 34 | Var. 119 | Var. 204 | Var. 289 | Var. 374 | Var. 459 | Var. 544 | Var. 629 |
| | 60 ± 25 | Var. 35 | Var. 120 | Var. 205 | Var. 290 | Var. 375 | Var. 460 | Var. 545 | Var. 630 |
| | 70 ± 25 | Var. 36 | Var. 121 | Var. 206 | Var. 291 | Var. 376 | Var. 461 | Var. 546 | Var. 631 |
| | 75 ± 25 | Var. 37 | Var. 122 | Var. 207 | Var. 292 | Var. 377 | Var. 462 | Var. 547 | Var. 632 |
| | 80 ± 25 | Var. 38 | Var. 123 | Var. 208 | Var. 293 | Var. 378 | Var. 463 | Var. 548 | Var. 633 |
| | 90 ± 25 | Var. 39 | Var. 124 | Var. 209 | Var. 294 | Var. 379 | Var. 464 | Var. 549 | Var. 634 |
| | 100 ± 25 | Var. 40 | Var. 125 | Var. 210 | Var. 295 | Var. 380 | Var. 465 | Var. 550 | Var. 635 |
| | 125 ± 25 | Var. 41 | Var. 126 | Var. 211 | Var. 296 | Var. 381 | Var. 466 | Var. 551 | Var. 636 |
| | 150 ± 25 | Var. 42 | Var. 127 | Var. 212 | Var. 297 | Var. 382 | Var. 467 | Var. 552 | Var. 637 |
| | 175 ± 25 | Var. 43 | Var. 128 | Var. 213 | Var. 298 | Var. 383 | Var. 468 | Var. 553 | Var. 638 |
| | 30 ± 10 | Var. 44 | Var. 129 | Var. 214 | Var. 299 | Var. 384 | Var. 469 | Var. 554 | Var. 639 |
| | 40 ± 10 | Var. 45 | Var. 130 | Var. 215 | Var. 300 | Var. 385 | Var. 470 | Var. 555 | Var. 640 |
| | 50 ± 10 | Var. 46 | Var. 131 | Var. 216 | Var. 301 | Var. 386 | Var. 471 | Var. 556 | Var. 641 |
| | 60 ± 10 | Var. 47 | Var. 132 | Var. 217 | Var. 302 | Var. 387 | Var. 472 | Var. 557 | Var. 642 |
| | 70 ± 10 | Var. 48 | Var. 133 | Var. 218 | Var. 303 | Var. 388 | Var. 473 | Var. 558 | Var. 643 |
| | 75 ± 10 | Var. 49 | Var. 134 | Var. 219 | Var. 304 | Var. 389 | Var. 474 | Var. 559 | Var. 644 |
| | 80 ± 10 | Var. 50 | Var. 135 | Var. 220 | Var. 305 | Var. 390 | Var. 475 | Var. 560 | Var. 645 |
| | 90 ± 10 | Var. 51 | Var. 136 | Var. 221 | Var. 306 | Var. 391 | Var. 476 | Var. 561 | Var. 646 |
| | 100 ± 10 | Var. 52 | Var. 137 | Var. 222 | Var. 307 | Var. 392 | Var. 477 | Var. 562 | Var. 647 |
| | 110 ± 10 | Var. 53 | Var. 138 | Var. 223 | Var. 308 | Var. 393 | Var. 478 | Var. 563 | Var. 648 |
| | 120 ± 10 | Var. 54 | Var. 139 | Var. 224 | Var. 309 | Var. 394 | Var. 479 | Var. 564 | Var. 649 |
| | 125 ± 10 | Var. 55 | Var. 140 | Var. 225 | Var. 310 | Var. 395 | Var. 480 | Var. 565 | Var. 650 |
| | 130 ± 10 | Var. 56 | Var. 141 | Var. 226 | Var. 311 | Var. 396 | Var. 481 | Var. 566 | Var. 651 |
| | 140 ± 10 | Var. 57 | Var. 142 | Var. 227 | Var. 312 | Var. 397 | Var. 482 | Var. 567 | Var. 652 |
| | 150 ± 10 | Var. 58 | Var. 143 | Var. 228 | Var. 313 | Var. 398 | Var. 483 | Var. 568 | Var. 653 |

TABLE 1-continued Exemplary embodiments for the combination of sugar or sugar alcohol and non-ionic surfactant conc TABLE 2-continued Exemplary embodiments for the combination of sugar or sugar alcohol and non-ionic surfactant concentrations useful for the stabilization of furin (e.g., rfurin) compositions.

| | | Sugar or Sugar Alcohol (%) | | | | | | |
|---|---|---|---|---|---|---|---|---|
| | | 5%-20% | 5%-17.5% | 5%-15% | 5%-12.5% | 5%-10% | 7.5%-20% | 7.5%-7.5% | 7.5%-15% |
| | 100-175 | Var. 713 | Var. 798 | Var. 883 | Var. 968 | Var. 1053 | Var. 1138 | Var. 1223 | Var. 1308 |
| | 50 ± 25 | Var. 714 | Var. 799 | Var. 884 | Var. 969 | Var. 1054 | Var. 1139 | Var. 1224 | Var. 1309 |
| | 60 ± 25 | Var. 715 | Var. 800 | Var. 885 | Var. 970 | Var. 1055 | Var. 1140 | Var. 1225 | Var. 1310 |
| | 70 ± 25 | Var. 716 | Var. 801 | Var. 886 | Var. 971 | Var. 1056 | Var. 1141 | Var. 1226 | Var. 1311 |
| | 75 ± 25 | Var. 717 | Var. 802 | Var. 887 | Var. 972 | Var. 1057 | Var. 1142 | Var. 1227 | Var. 1312 |
| | 80 ± 25 | Var. 718 | Var. 803 | Var. 888 | Var. 973 | Var. 1058 | Var. 1143 | Var. 1228 | Var. 1313 |
| | 90 ± 25 | Var. 719 | Var. 804 | Var. 889 | Var. 974 | Var. 1059 | Var. 1144 | Var. 1229 | Var. 1314 |
| | 100 ± 25 | Var. 720 | Var. 805 | Var. 890 | Var. 975 | Var. 1060 | Var. 1145 | Var. 1230 | Var. 1315 |
| | 125 ± 25 | Var. 721 | Var. 806 | Var. 891 | Var. 976 | Var. 1061 | Var. 1146 | Var. 1231 | Var. 1316 |
| | 150 ± 25 | Var. 722 | Var. 807 | Var. 892 | Var. 977 | Var. 1062 | Var. 1147 | Var. 1232 | Var. 1317 |
| | 175 ± 25 | Var. 723 | Var. 808 | Var. 893 | Var. 978 | Var. 1063 | Var. 1148 | Var. 1233 | Var. 1318 |
| | 30 ± 10 | Var. 724 | Var. 809 | Var. 894 | Var. 979 | Var. 1064 | Var. 1149 | Var. 1234 | Var. 1319 |
| | 40 ± 10 | Var. 725 | Var. 810 | Var. 895 | Var. 980 | Var. 1065 | Var. 1150 | Var. 1235 | Var. 1320 |
| | 50 ± 10 | Var. 726 | Var. 811 | Var. 896 | Var. 981 | Var. 1066 | Var. 1151 | Var. 1236 | Var. 1321 |
| | 60 ± 10 | Var. 727 | Var. 812 | Var. 897 | Var. 982 | Var. 1067 | Var. 1152 | Var. 1237 | Var. 1322 |
| | 70 ± 10 | Var. 728 | Var. 813 | Var. 898 | Var. 983 | Var. 1068 | Var. 1153 | Var. 1238 | Var. 1323 |
| | 75 ± 10 | Var. 729 | Var. 814 | Var. 899 | Var. 984 | Var. 1069 | Var. 1154 | Var. 1239 | Var. 1324 |
| | 80 ± 10 | Var. 730 | Var. 815 | Var. 900 | Var. 985 | Var. 1070 | Var. 1155 | Var. 1240 | Var. 1325 |
| | 90 ± 10 | Var. 731 | Var. 816 | Var. 901 | Var. 986 | Var. 1071 | Var. 1156 | Var. 1241 | Var. 1326 |
| | 100 ± 10 | Var. 732 | Var. 817 | Var. 902 | Var. 987 | Var. 1072 | Var. 1157 | Var. 1242 | Var. 1327 |
| | 110 ± 10 | Var. 733 | Var. 818 | Var. 903 | Var. 988 | Var. 1073 | Var. 1158 | Var. 1243 | Var. 1328 |
| | 120 ± 10 | Var. 734 | Var. 819 | Var. 904 | Var. 989 | Var. 1074 | Var. 1159 | Var. 1244 | Var. 1329 |
| | 125 ± 10 | Var. 735 | Var. 820 | Var. 905 | Var. 990 | Var. 1075 | Var. 1160 | Var. 1245 | Var. 1330 |
| | 130 ± 10 | Var. 736 | Var. 821 | Var. 906 | Var. 991 | Var. 1076 | Var. 1161 | Var. 1246 | Var. 1331 |
| | 140 ± 10 | Var. 737 | Var. 822 | Var. 907 | Var. 992 | Var. 1077 | Var. 1162 | Var. 1247 | Var. 1332 |
| | 150 ± 10 | Var. 738 | Var. 823 | Var. 908 | Var. 993 | Var. 1078 | Var. 1163 | Var. 1248 | Var. 1333 |
| | 160 ± 10 | Var. 739 | Var. 824 | Var. 909 | Var. 994 | Var. 1079 | Var. 1164 | Var. 1249 | Var. 1334 |
| | 170 ± 10 | Var. 740 | Var. 825 | Var. 910 | Var. 995 | Var. 1080 | Var. 1165 | Var. 1250 | Var. 1335 |
| | 175 ± 10 | Var. 741 | Var. 826 | Var. 911 | Var. 996 | Var. 1081 | Var. 1166 | Var. 1251 | Var. 1336 |
| | 180 ± 10 | Var. 742 | Var. 827 | Var. 912 | Var. 997 | Var. 1082 | Var. 1167 | Var. 1252 | Var. 1337 |
| | 190 ± 10 | Var. 743 | Var. 828 | Var. 913 | Var. 998 | Var. 1083 | Var. 1168 | Var. 1253 | Var. 1338 |
| | 25 | Var. 744 | Var. 829 | Var. 914 | Var. 999 | Var. 1084 | Var. 1169 | Var. 1254 | Var. 1339 |
| | 30 | Var. 745 | Var. 830 | Var. 915 | Var. 1000 | Var. 1085 | Var. 1170 | Var. 1255 | Var. 1340 |
| | 40 | Var. 746 | Var. 831 | Var. 916 | Var. 1001 | Var. 1086 | Var. 1171 | Var. 1256 | Var. 1341 |
| | 50 | Var. 747 | Var. 832 | Var. 917 | Var. 1002 | Var. 1087 | Var. 1172 | Var. 1257 | Var. 1342 |
| | 60 | Var. 748 | Var. 833 | Var. 918 | Var. 1003 | Var. 1088 | Var. 1173 | Var. 1258 | Var. 1343 |
| | 70 | Var. 749 | Var. 834 | Var. 919 | Var. 1004 | Var. 1089 | Var. 1174 | Var. 1259 | Var. 1344 |
| | 75 | Var. 750 | Var. 835 | Var. 920 | Var. 1005 | Var. 1090 | Var. 1175 | Var. 1260 | Var. 1345 |
| | 80 | Var. 751 | Var. 836 | Var. 921 | Var. 1006 | Var. 1091 | Var. 1176 | Var. 1261 | Var. 1346 |
| | 90 | Var. 752 | Var. 837 | Var. 922 | Var. 1007 | Var. 1092 | Var. 1177 | Var. 1262 | Var. 1347 |
| | 100 | Var. 753 | Var. 838 | Var. 923 | Var. 1008 | Var. 1093 | Var. 1178 | Var. 1263 | Var. 1348 |
| | 110 | Var. 754 | Var. 839 | Var. 924 | Var. 1009 | Var. 1094 | Var. 1179 | Var. 1264 | Var. 1349 |
| | 120 | Var. 755 | Var. 840 | Var. 925 | Var. 1010 | Var. 1095 | Var. 1180 | Var. 1265 | Var. 1350 |
| | 125 | Var. 756 | Var. 841 | Var. 926 | Var. 1011 | Var. 1096 | Var. 1181 | Var. 1266 | Var. 1351 |
| | 130 | Var. 757 | Var. 842 | Var. 927 | Var. 1012 | Var. 1097 | Var. 1182 | Var. 1267 | Var. 1352 |
| | 140 | Var. 758 | Var. 843 | Var. 928 | Var. 1013 | Var. 1098 | Var. 1183 | Var. 1268 | Var. 1353 |
| | 150 | Var. 759 | Var. 844 | Var. 929 | Var. 1014 | Var. 1099 | Var. 1184 | Var. 1269 | Var. 1354 |
| | 160 | Var. 760 | Var. 845 | Var. 930 | Var. 1015 | Var. 1100 | Var. 1185 | Var. 1270 | Var. 1355 |
| | 170 | Var. 761 | Var. 846 | Var. 931 | Var. 1016 | Var. 1101 | Var. 1186 | Var. 1271 | Var. 1356 |
| | 175 | Var. 762 | Var. 847 | Var. 932 | Var. 1017 | Var. 1102 | Var. 1187 | Var. 1272 | Var. 1357 |
| | 180 | Var. 763 | Var. 848 | Var. 933 | Var. 1018 | Var. 1103 | Var. 1188 | Var. 1273 | Var. 1358 |
| | 190 | Var. 764 | Var. 849 | Var. 934 | Var. 1019 | Var. 1104 | Var. 1189 | Var. 1274 | Var. 1359 |
| | 200 | Var. 765 | Var. 850 | Var. 935 | Var. 1020 | Var. 1105 | Var. 1190 | Var. 1275 | Var. 1360 |

Var. = Variation

TABLE 3

Exemplary embodiments for the combination of sugar or sugar alcohol and non-ionic surfactant concentrations useful for the stabilization of furin (e.g., rfurin) compositions.

| | | Sugar or Sugar Alcohol (%) | | | | | | | |
|---|---|---|---|---|---|---|---|---|---|
| | | 7.5%-12.5% | 10%-20% | 10%-17.5% | 10%-15% | 4 ± 2% | 5 ± 2% | 6 ± 2% | 7 ± 2% |
| Non-Ionic Surfactant (ppm) | 10-200 | Var. 1361 | Var. 1446 | Var. 1531 | Var. 1616 | Var. 1701 | Var. 1786 | Var. 1871 | Var. 1956 |
| | 10-175 | Var. 1362 | Var. 1447 | Var. 1532 | Var. 1617 | Var. 1702 | Var. 1787 | Var. 1872 | Var. 1957 |
| | 10-150 | Var. 1363 | Var. 1448 | Var. 1533 | Var. 1618 | Var. 1703 | Var. 1788 | Var. 1873 | Var. 1958 |
| | 10-125 | Var. 1364 | Var. 1449 | Var. 1534 | Var. 1619 | Var. 1704 | Var. 1789 | Var. 1874 | Var. 1959 |
| | 10-100 | Var. 1365 | Var. 1450 | Var. 1535 | Var. 1620 | Var. 1705 | Var. 1790 | Var. 1875 | Var. 1960 |
| | 10-90 | Var. 1366 | Var. 1451 | Var. 1536 | Var. 1621 | Var. 1706 | Var. 1791 | Var. 1876 | Var. 1961 |

TABLE 3-continued

Exemplary embodiments for the combination of sugar or sugar alcohol and non-ionic surfactant concentrations useful for the stabilization of furin (e.g., rfurin) compositions.

| | Sugar or Sugar Alcohol (%) | | | | | | | |
|---|---|---|---|---|---|---|---|---|
| |

TABLE 3-continued

Exemplary embodiments for the combination of sugar or sugar alcohol and non-ionic surfactant concentrations useful for the stabilization of furin (e.g., rfurin) compositions.

| | | Sugar or Sugar Alcohol (%) | | | | | | |
|---|---|---|---|---|---|---|---|---|

TABLE 4-continued

Exemplary embodiments for the combination of sugar or sugar alcohol and non-ionic surfactant concentrations useful for the stabilization of furin (e TABLE 5-continued Exemplary embodiments for the combination of sugar or sugar alcohol and non-ionic surfactant concentrations useful for the stabilization of furin (e.g., rfurin) compositions.

| | Sugar or Sugar Alcohol (%) | | | | | | | |
|---|---|---|---|---|---|---|---|---|
| | 16 ± 2% | 17 ± 2% | 18 ± 2% | 3 ± 1% | 4 ± 1% | 5 ± 1% | 6 ± 1% | 7 ± 1% |
| 50-80 | Var. 2748 | Var. 2833 | Var. 2918 | Var. 3003 | Var. 3088 | Var. 3173 | Var. 3258 | Var. 3343 |
| 75-200 | Var. 2749 | Var. 2834 | Var. 2919 | Var. 3004 | Var. 3089 | Var. 3174 | Var. 3259 | Var. 3344 |
| 75-175 | Var. 2750 | Var. 2835 | Var. 2920 | Var. 3005 | Var. 3090 | Var. 3175 | Var. 3260 | Var. 3345 |
| 75-150 | Var. 2751 | Var. 2836 | Var. 2921 | Var. 3006 | Var. 3091 | Var. 3176 | Var. 3261 | Var. 3346 |
| 100-200 | Var. 2752 | Var. 2837 | Var. 2922 | Var. 3007 | Var. 3092 | Var. 3177 | Var. 3262 | Var. 3347 |
| 100-175 | Var. 2753 | Var. 2838 | Var. 2923 | Var. 3008 | Var. 3093 | Var. 3178 | Var. 3263 | Var. 3348 |
| 50 ± 25 | Var. 2754 | Var. 2839 | Var. 2924 | Var. 3009 | Var. 3094 | Var. 3179 | Var. 3264 | Var. 3349 |
| 60 ± 25 | Var. 2755 | Var. 2840 | Var. 2925 | Var. 3010 | Var. 3095 | Var. 3180 | Var. 3265 | Var. 3350 |
| 70 ± 25 | Var. 2756 | Var. 2841 | Var. 2926 | Var. 3011 | Var. 3096 | Var. 3181 | Var. 3266 | Var. 3351 |
| 75 ± 25 | Var. 2757 | Var. 2842 | Var. 2927 | Var. 3012 | Var. 3097 | Var. 3182 | Var. 3267 | Var. 3352 |
| 80 ± 25 | Var. 2758 | Var. 2843 | Var. 2928 | Var. 3013 | Var. 3098 | Var. 3183 | Var. 3268 | Var. 3353 |
| 90 ± 25 | Var. 2759 | Var. 2844 | Var. 2929 | Var. 3014 | Var. 3099 | Var. 3184 | Var. 3269 | Var. 3354 |
| 100 ± 25 | Var. 2760 | Var. 2845 | Var. 2930 | Var. 3015 | Var. 3100 | Var. 3185 | Var. 3270 | Var. 3355 |
| 125 ± 25 | Var. 2761 | Var. 2846 | Var. 2931 | Var. 3016 | Var. 3101 | Var. 3186 | Var. 3271 | Var. 3356 |
| 150 ± 25 | Var. 2762 | Var. 2847 | Var. 2932 | Var. 3017 | Var. 3102 | Var. 3187 | Var. 3272 | Var. 3357 |
| 175 ± 25 | Var. 2763 | Var. 2848 | Var. 2933 | Var. 3018 | Var. 3103 | Var. 3188 | Var. 3273 | Var. 3358 |
| 30 ± 10 | Var. 2764 | Var. 2849 | Var. 2934 | Var. 3019 | Var. 3104 | Var. 3189 | Var. 3274 | Var. 3359 |
| 40 ± 10 | Var. 2765 | Var. 2850 | Var. 2935 | Var. 3020 | Var. 3105 | Var. 3190 | Var. 3275 | Var. 3360 |
| 50 ± 10 | Var. 2766 | Var. 2851 | Var. 2936 | Var. 3021 | Var. 3106 | Var. 3191 | Var. 3276 | Var. 3361 |
| 60 ± 10 | Var. 2767 | Var. 2852 | Var. 2937 | Var. 3022 | Var. 3107 | Var. 3192 | Var. 3277 | Var. 3362 |
| 70 ± 10 | Var. 2768 | Var. 2853 | Var. 2938 | Var. 3023 | Var. 3108 | Var. 3193 | Var. 3278 | Var. 3363 |
| 75 ± 10 | Var. 2769 | Var. 2854 | Var. 2939 | Var. 3024 | Var. 3109 | Var. 3194 | Var. 3279 | Var. 3364 |
| 80 ± 10 | Var. 2770 | Var. 2855 | Var. 2940 | Var. 3025 | Var. 3110 | Var. 3195 | Var. 3280 | Var. 3365 |
| 90 ± 10 | Var. 2771 | Var. 2856 | Var. 2941 | Var. 3026 | Var. 3111 | Var. 3196 | Var. 3281 | Var. 3366 |
| 100 ± 10 | Var. 2772 | Var. 2857 | Var. 2942 | Var. 3027 | Var. 3112 | Var. 3197 | Var. 3282 | Var. 3367 |
| 110 ± 10 | Var. 2773 | Var. 2858 | Var. 2943 | Var. 3028 | Var. 3113 | Var. 3198 | Var. 3283 | Var. 3368 |
| 120 ± 10 | Var. 2774 | Var. 2859 | Var. 2944 | Var. 3029 | Var. 3114 | Var. 3199 | Var. 3284 | Var. 3369 |
| 125 ± 10 | Var. 2775 | Var. 2860 | Var. 2945 | Var. 3030 | Var. 3115 | Var. 3200 | Var. 3285 | Var. 3370 |
| 130 ± 10 | Var. 2776 | Var. 2861 | Var. 2946 | Var. 3031 | Var. 3116 | Var. 3201 | Var. 3286 | Var. 3371 |
| 140 ± 10 | Var. 2777 | Var. 2862 | Var. 2947 | Var. 3032 | Var. 3117 | Var. 3202 | Var. 3287 | Var. 3372 |
| 150 ± 10 | Var. 2778 | Var. 2863 | Var. 2948 | Var. 3033 | Var. 3118 | Var. 3203 | Var. 3288 | Var. 3373 |
| 160 ± 10 | Var. 2779 | Var. 2864 | Var. 2949 | Var. 3034 | Var. 3119 | Var. 3204 | Var. 3289 | Var. 3374 |
| 170 ± 10 | Var. 2780 | Var. 2865 | Var. 2950 | Var. 3035 | Var. 3120 | Var. 3205 | Var. 3290 | Var. 3375 |
| 175 ± 10 | Var. 2781 | Var. 2866 | Var. 2951 | Var. 3036 | Var. 3121 | Var. 3206 | Var. 3291 | Var. 3376 |
| 180 ± 10 | Var. 2782 | Var. 2867 | Var. 2952 | Var. 3037 | Var. 3122 | Var. 3207 | Var. 3292 | Var. 3377 |
| 190 ± 10 | Var. 2783 | Var. 2868 | Var. 2953 | Var. 3038 | Var. 3123 | Var. 3208 | Var. 3293 | Var. 3378 |
| 25 | Var. 2784 | Var. 2869 | Var. 2954 | Var. 3039 | Var. 3124 | Var. 3209 | Var. 3294 | Var. 3379 |
| 30 | Var. 2785 | Var. 2870 | Var. 2955 | Var. 3040 | Var. 3125 | Var. 3210 | Var. 3295 | Var. 3380 |
| 40 | Var. 2786 | Var. 2871 | Var. 2956 | Var. 3041 | Var. 3126 | Var. 3211 | Var. 3296 | Var. 3381 |
| 50 | Var. 2787 | Var. 2872 | Var. 2957 | Var. 3042 | Var. 3127 | Var. 3212 | Var. 3297 | Var. 3382 |
| 60 | Var. 2788 | Var. 2873 | Var. 2958 | Var. 3043 | Var. 3128 | Var. 3213 | Var. 3298 | Var. 3383 |
| 70 | Var. 2789 | Var. 2874 | Var. 2959 | Var. 3044 | Var. 3129 | Var. 3214 | Var. 3299 | Var. 3384 |
| 75 | Var. 2790 | Var. 2875 | Var. 2960 | Var. 3045 | Var. 3130 | Var. 3215 | Var. 3300 | Var. 3385 |
| 80 | Var. 2791 | Var. 2876 | Var. 2961 | Var. 3046 | Var. 3131 | Var. 3216 | Var. 3301 | Var. 3386 |
| 90 | Var. 2792 | Var. 2877 | Var. 2962 | Var. 3047 | Var. 3132 | Var. 3217 | Var. 3302 | Var. 3387 |
| 100 | Var. 2793 | Var. 2878 | Var. 2963 | Var. 3048 | Var. 3133 | Var. 3218 | Var. 3303 | Var. 3388 |
| 110 | Var. 2794 | Var. 2879 | Var. 2964 | Var. 3049 | Var. 3134 | Var. 3219 | Var. 3304 | Var. 3389 |
| 120 | Var. 2795 | Var. 2880 | Var. 2965 | Var. 3050 | Var. 3135 | Var. 3220 | Var. 3305 | Var. 3390 |
| 125 | Var. 2796 | Var. 2881 | Var. 2966 | Var. 3051 | Var. 3136 | Var. 3221 | Var. 3306 | Var. 3391 |
| 130 | Var. 2797 | Var. 2882 | Var. 2967 | Var. 3052 | Var. 3137 | Var. 3222 | Var. 3307 | Var. 3392 |
| 140 | Var. 2798 | Var. 2883 | Var. 2968 | Var. 3053 | Var. 3138 | Var. 3223 | Var. 3308 | Var. 3393 |
| 150 | Var. 2799 | Var. 2884 | Var. 2969 | Var. 3054 | Var. 3139 | Var. 3224 | Var. 3309 | Var. 3394 |
| 160 | Var. 2800 | Var. 2885 | Var. 2970 | Var. 3055 | Var. 3140 | Var. 3225 | Var. 3310 | Var. 3395 |
| 170 | Var. 2801 | Var. 2886 | Var. 2971 | Var. 3056 | Var. 3141 | Var. 3226 | Var. 3311 | Var. 3396 |
| 175 | Var. 2802 | Var. 2887 | Var. 2972 | Var. 3057 | Var. 3142 | Var. 3227 | Var. 3312 | Var. 3397 |
| 180 | Var. 2803 | Var. 2888 | Var. 2973 | Var. 3058 | Var. 3143 | Var. 3228 | Var. 3313 | Var. 3398 |
| 190 | Var. 2804 | Var. 2889 | Var. 2974 | Var. 3059 | Var. 3144 | Var. 3229 | Var. 3314 | Var. 3399 |
| 200 | Var. 2805 | Var. 2890 | Var. 2975 | Var. 3060 | Var. 3145 | Var. 3230 | Var. 3315 | Var. 3400 |

Var. = Variation

TABLE 6

Exemplary embodiments for the combination of sugar or sugar alcohol and non-ionic surfactant concentrations useful for the stabilization of furin (e.g., rfurin) compositions.

| | | Sugar or Sugar Alcohol (%) | | | | | | | |
|---|---|---|---|---|---|---|---|---|---|
| | | 8 ± 1% | 9 ± 1% | 10 ± 1% | 11 ± 1% | 12 ± 1% | 13 ± 1% | 14 ± 1% | 15 ± 1% |
| Non-Ionic | 10-200 | Var. 3401 | Var. 3486 | Var. 3571 | Var. 3656 | Var. 3741 | Var. 3826 | Var. 3911 | Var. 3996 |
| Surfactant | 10-175 | Var. 3402 | Var. 3487 | Var. 3572 | Var. 3657 | Var. 3742 | Var. 3827 | Var. 3912 | Var. 3997 |
| (ppm) | 10-150 | Var. 3403 | Var. 3488 | Var. 3573 | Var. 3658 | Var. 3743 | Var. 3828 | Var. 3913 | Var. 3998 |
| | 10-125 | Var. 3404 | Var. 3489 | Var. 3574 | Var. 3659 | Var. 3744 | Var. 3829 | Var. 3914 | Var. 3999 |
| | 10-100 | Var. 3405 | Var. 3490 | Var. 3575 | Var. 3660 | Var. 3745 | Var. 3830 | Var. 3915 | Var. 4000 |
| | 10-90 | Var. 3406 | Var. 3491 | Var. 3576 | Var. 3661 | Var. 3746 | Var. 3831 | Var. 3916 | Var. 4001 |
| | 10-80 | Var. 3407 | Var. 3492 | Var. 3577 | Var. 3662 | Var. 3747 | Var. 3832 | Var. 3917 | Var. 4002 |
| | 10-75 | Var. 3408 | Var. 3493 | Var. 3578 | Var. 3663 | Var. 3748 | Var. 3833 | Var. 3918 | Var. 4003 |
| | 10-70 | Var. 3409 | Var. 3494 | Var. 3579 | Var. 3664 | Var. 3749 | Var. 3834 | Var. 3919 | Var. 4004 |
| | 10-60 | Var. 3410 | Var. 3495 | Var. 3580 | Var. 3665 | Var. 3750 | Var. 3835 | Var. 3920 | Var. 4005 |
| | 10-50 | Var. 3411 | Var. 3496 | Var. 3581 | Var. 3666 | Var. 3751 | Var. 3836 | Var. 3921 | Var. 4006 |
| | 10-25 | Var. 3412 | Var. 3497 | Var. 3582 | Var. 3667 | Var. 3752 | Var. 3837 | Var. 3922 | Var. 4007 |
| | 25-200 | Var. 3413 | Var. 3498 | Var. 3583 | Var. 3668 | Var. 3753 | Var. 3838 | Var. 3923 | Var. 4008 |
| | 25-175 | Var. 3414 | Var. 3499 | Var. 3584 | Var. 3669 | Var. 3754 | Var. 3839 | Var. 3924 | Var. 4009 |
| | 25-150 | Var. 3415 | Var. 3500 | Var. 3585 | Var. 3670 | Var. 3755 | Var. 3840 | Var. 3925 | Var. 4010 |
| | 25-125 | Var. 3416 | Var. 3501 | Var. 3586 | Var. 3671 | Var. 3756 | Var. 3841 | Var. 3926 | Var. 4011 |
| | 25-100 | Var. 3417 | Var. 3502 | Var. 3587 | Var. 3672 | Var. 3757 | Var. 3842 | Var. 3927 | Var. 4012 |
| | 25-90 | Var. 3418 | Var. 3503 | Var. 3588 | Var. 3673 | Var. 3758 | Var. 3843 | Var. 3928 | Var. 4013 |
| | 25-80 | Var. 3419 | Var. 3504 | Var. 3589 | Var. 3674 | Var. 3759 | Var. 3844 | Var. 3929 | Var. 4014 |
| | 25-70 | Var. 3420 | Var. 3505 | Var. 3590 | Var. 3675 | Var. 3760 | Var. 3845 | Var. 3930 | Var. 4015 |
| | 25-60 | Var. 3421 | Var. 3506 | Var. 3591 | Var. 3676 | Var. 3761 | Var. 3846 | Var. 3931 | Var. 4016 |
| | 25-50 | Var. 3422 | Var. 3507 | Var. 3592 | Var. 3677 | Var. 3762 | Var. 3847 | Var. 3932 | Var. 4017 |
| | 50-200 | Var. 3423 | Var. 3508 | Var. 3593 | Var. 3678 | Var. 3763 | Var. 3848 | Var. 3933 | Var. 4018 |
| | 50-175 | Var. 3424 | Var. 3509 | Var. 3594 | Var. 3679 | Var. 3764 | Var. 3849 | Var. 3934 | Var. 4019 |
| | 50-150 | Var. 3425 | Var. 3510 | Var. 3595 | Var. 3680 | Var. 3765 | Var. 3850 | Var. 3935 | Var. 4020 |
| | 50-125 | Var. 3426 | Var. 3511 | Var. 3596 | Var. 3681 | Var. 3766 | Var. 3851 | Var. 3936 | Var. 4021 |
| | 50-90 | Var. 3427 | Var. 3512 | Var. 3597 | Var. 3682 | Var. 3767 | Var. 3852 | Var. 3937 | Var. 4022 |
| | 50-80 | Var. 3428 | Var. 3513 | Var. 3598 | Var. 3683 | Var. 3768 | Var. 3853 | Var. 3938 | Var. 4023 |
| | 75-200 | Var. 3429 | Var. 3514 | Var. 3599 | Var. 3684 | Var. 3769 | Var. 3854 | Var. 3939 | Var. 4024 |
| | 75-175 | Var. 3430 | Var. 3515 | Var. 3600 | Var. 3685 | Var. 3770 | Var. 3855 | Var. 3940 | Var. 4025 |
| | 75-150 | Var. 3431 | Var. 3516 | Var. 3601 | Var. 3686 | Var. 3771 | Var. 3856 | Var. 3941 | Var. 4026 |
| | 100-200 | Var. 3432 | Var. 3517 | Var. 3602 | Var. 3687 | Var. 3772 | Var. 3857 | Var. 3942 | Var. 4027 |
| | 100-175 | Var. 3433 | Var. 3518 | Var. 3603 | Var. 3688 | Var. 3773 | Var. 3858 | Var. 3943 | Var. 4028 |
| | 50 ± 25 | Var. 3434 | Var. 3519 | Var. 3604 | Var. 3689 | Var. 3774 | Var. 3859 | Var. 3944 | Var. 4029 |
| | 60 ± 25 | Var. 3435 | Var. 3520 | Var. 3605 | Var. 3690 | Var. 3775 | Var. 3860 | Var. 3945 | Var. 4030 |
| | 70 ± 25 | Var. 3436 | Var. 3521 | Var. 3606 | Var. 3691 | Var. 3776 | Var. 3861 | Var. 3946 | Var. 4031 |
| | 75 ± 25 | Var. 3437 | Var. 3522 | Var. 3607 | Var. 3692 | Var. 3777 | Var. 3862 | Var. 3947 | Var. 4032 |
| | 80 ± 25 | Var. 3438 | Var. 3523 | Var. 3608 | Var. 3693 | Var. 3778 | Var. 3863 | Var. 3948 | Var. 4033 |
| | 90 ± 25 | Var. 3439 | Var. 3524 | Var. 3609 | Var. 3694 | Var. 3779 | Var. 3864 | Var. 3949 | Var. 4034 |
| | 100 ± 25 | Var. 3440 | Var. 3525 | Var. 3610 | Var. 3695 | Var. 3780 | Var. 3865 | Var. 3950 | Var. 4035 |
| | 125 ± 25 | Var. 3441 | Var. 3526 | Var. 3611 | Var. 3696 | Var. 3781 | Var. 3866 | Var. 3951 | Var. 4036 |
| | 150 ± 25 | Var. 3442 | Var. 3527 | Var. 3612 | Var. 3697 | Var. 3782 | Var. 3867 | Var. 3952 | Var. 4037 |
| | 175 ± 25 | Var. 3443 | Var. 3528 | Var. 3613 | Var. 3698 | Var. 3783 | Var. 3868 | Var. 3953 | Var. 4038 |
| | 30 ± 10 | Var. 3444 | Var. 3529 | Var. 3614 | Var. 3699 | Var. 3784 | Var. 3869 | Var. 3954 | Var. 4039 |
| | 40 ± 10 | Var. 3445 | Var. 3530 | Var. 3615 | Var. 3700 | Var. 3785 | Var. 3870 | Var. 3955 | Var. 4040 |
| | 50 ± 10 | Var. 3446 | Var. 3531 | Var. 3616 | Var. 3701 | Var. 3786 | Var. 3871 | Var. 3956 | Var. 4041 |
| | 60 ± 10 | Var. 3447 | Var. 3532 | Var. 3617 | Var. 3702 | Var. 3787 | Var. 3872 | Var. 3957 | Var. 4042 |
| | 70 ± 10 | Var. 3448 | Var. 3533 | Var. 3618 | Var. 3703 | Var. 3788 | Var. 3873 | Var. 3958 | Var. 4043 |
| | 75 ± 10 | Var. 3449 | Var. 3534 | Var. 3619 | Var. 3704 | Var. 3789 | Var. 3874 | Var. 3959 | Var. 4044 |
| | 80 ± 10 | Var. 3450 | Var. 3535 | Var. 3620 | Var. 3705 | Var. 3790 | Var. 3875 | Var. 3960 | Var. 4045 |
| | 90 ± 10 | Var. 3451 | Var. 3536 | Var. 3621 | Var. 3706 | Var. 3791 | Var. 3876 | Var. 3961 | Var. 4046 |
| | 100 ± 10 | Var. 3452 | Var. 3537 | Var. 3622 | Var. 3707 | Var. 3792 | Var. 3877 | Var. 3962 | Var. 4047 |
| | 110 ± 10 | Var. 3453 | Var. 3538 | Var. 3623 | Var. 3708 | Var. 3793 | Var. 3878 | Var. 3963 | Var. 4048 |
| | 120 ± 10 | Var. 3454 | Var. 3539 | Var. 3624 | Var. 3709 | Var. 3794 | Var. 3879 | Var. 3964 | Var. 4049 |
| | 125 ± 10 | Var. 3455 | Var. 3540 | Var. 3625 | Var. 3710 | Var. 3795 | Var. 3880 | Var. 3965 | Var. 4050 |
| | 130 ± 10 | Var. 3456 | Var. 3541 | Var. 3626 | Var. 3711 | Var. 3796 | Var. 3881 | Var. 3966 | Var. 4051 |
| | 140 ± 10 | Var. 3457 | Var. 3542 | Var. 3627 | Var. 3712 | Var. 3797 | Var. 3882 | Var. 3967 | Var. 4052 |
| | 150 ± 10 | Var. 3458 | Var. 3543 | Var. 3628 | Var. 3713 | Var. 3798 | Var. 3883 | Var. 3968 | Var. 4053 |
| | 160 ± 10 | Var. 3459 | Var. 3544 | Var. 3629 | Var. 3714 | Var. 3799 | Var. 3884 | Var. 3969 | Var. 4054 |
| | 170 ± 10 | Var. 3460 | Var. 3545 | Var. 3630 | Var. 3715 | Var. 3800 | Var. 3885 | Var. 3970 | Var. 4055 |
| | 175 ± 10 | Var. 3461 | Var. 3546 | Var. 3631 | Var. 3716 | Var. 3801 | Var. 3886 | Var. 3971 | Var. 4056 |
| | 180 ± 10 | Var. 3462 | Var. 3547 | Var. 3632 | Var. 3717 | Var. 3802 | Var. 3887 | Var. 3972 | Var. 4057 |
| | 190 ± 10 | Var. 3463 | Var. 3548 | Var. 3633 | Var. 3718 | Var. 3803 | Var. 3888 | Var. 3973 | Var. 4058 |
| | 25 | Var. 3464 | Var. 3549 | Var. 3634 | Var. 3719 | Var. 3804 | Var. 3889 | Var. 3974 | Var. 4059 |
| | 30 | Var. 3465 | Var. 3550 | Var. 3635 | Var. 3720 | Var. 3805 | Var. 3890 | Var. 3975 | Var. 4060 |
| | 40 | Var. 3466 | Var. 3551 | Var. 3636 | Var. 3721 | Var. 3806 | Var. 3891 | Var. 3976 | Var. 4061 |
| | 50 | Var. 3467 | Var. 3552 | Var. 3637 | Var. 3722 | Var. 3807 | Var. 3892 | Var. 3977 | Var. 4062 |
| | 60 | Var. 3468 | Var. 3553 | Var. 3638 | Var. 3723 | Var. 3808 | Var. 3893 | Var. 3978 | Var. 4063 |
| | 70 | Var. 3469 | Var. 3554 | Var. 3639 | Var. 3724 | Var. 3809 | Var. 3894 | Var. 3979 | Var. 4064 |
| | 75 | Var. 3470 | Var. 3555 | Var. 3640 | Var. 3725 | Var. 3810 | Var. 3895 | Var. 3980 | Var. 4065 |
| | 80 | Var. 3471 | Var. 3556 | Var. 3641 | Var. 3726 | Var. 3811 | Var. 3896 | Var. 3981 | Var. 4066 |
| | 90 | Var. 3472 | Var. 3557 | Var. 3642 | Var. 3727 | Var. 3812 | Var. 3897 | Var. 3982 | Var. 4067 |
| | 100 | Var. 3473 | Var. 3558 | Var. 3643 | Var. 3728 | Var. 3813 | Var. 3898 | Var. 3983 | Var. 4068 |

TABLE 6-continued

Exemplary embodiments for the combination of sugar or sugar alcohol and non-ionic surfactant concentrations useful for the stabilization of furin (e.g., rfurin) compositions.

| | | Sugar or Sugar Alcohol (%) | | | | | | |
|---|---|---|

TABLE 7-continued

Exemplary embodiments for the combination of sugar or sugar alcohol and non-ionic surfactant concentrations useful for the stabilization of furin (e.g., rfurin) compositions.

| | | Sugar or Sugar Alcohol (%) | | | | | | |
|---|---|---|---|---|---|---|---|---|
| | | 16 ± 1% | 17 ± 1% | 18 ± 1% | 19 ± 1% | 2% | 3% | 4% | 5% |
| | 70 ± 10 | Var. 4128 | Var. 4213 | Var. 4298 | Var. 4383 | Var. 4468 | Var. 4553 | Var. 4638 | Var. 4723 |
| | 75 ± 10 | Var. 4129 | Var. 4214 | Var. 4299 | Var. 4384 | Var. 4469 | Var. 4554 | Var. 4639 | Var. 4724 |
| | 80 ± 10 | Var. 4130 | Var. 4215 | Var. 4300 | Var. 4385 | Var. 4470 | Var. 4555 | Var. 4640 | Var. 4725 |
| | 90 ± 10 | Var. 4131 | Var. 4216 | Var. 4301 | Var. 4386 | Var. 4471 | Var. 4556 | Var. 4641 | Var. 4726 |
| | 100 ± 10 | Var. 4132 | Var. 4217 | Var. 4302 | Var. 4387 | Var. 4472 | Var. 4557 | Var. 4642 | Var. 4727 |
| | 110 ± 10 | Var. 4133 | Var. 4218 | Var. 4303 | Var. 4338 | Var. 4473 | Var. 4558 | Var. 4643 | Var. 4728 |
| | 120-10 | Var. 4134 | Var. 4219 | Var. 4304 | Var. 4389 | Var. 4474 | Var. 4559 | Var. 4644 | Var. 4729 |
| | 125 ± 10 | Var. 4135 | Var. 4220 | Var. 4305 | Var. 4390 | Var. 4475 | Var. 4560 | Var. 4645 | Var. 4730 |
| | 130 ± 10 | Var. 4136 | Var. 4221 | Var. 4306 | Var. 4391 | Var. 4476 | Var. 4561 | Var. 4646 | Var. 4731 |
| | 140 ± 10 | Var. 4137 | Var. 4222 | Var. 4307 | Var. 4392 | Var. 4477 | Var. 4562 | Var. 4647 | Var. 4732 |
| | 150 ± 10 | Var. 4138 | Var. 4223 | Var. 4308 | Var. 4393 | Var. 4478 | Var. 4563 | Var. 4648 | Var. 4733 |
| | 160 ± 10 | Var. 4139 | Var. 4224 | Var. 4309 | Var. 4394 | Var. 4479 | Var. 4564 | Var. 4649 | Var. 4734 |
| | 170 ± 10 | Var. 4140 | Var. 4225 | Var. 4310 | Var. 4395 | Var. 4480 | Var. 4565 | Var. 4650 | Var. 4735 |
| | 175 ± 10 | Var. 4141 | Var. 4226 | Var. 4311 | Var. 4396 | Var. 4481 | Var. 4566 | Var. 4651 | Var. 4736 |
| | 180 ± 10 | Var. 4142 | Var. 4227 | Var. 4312 | Var. 4397 | Var. 4482 | Var. 4567 | Var. 4652 | Var. 4737 |
| | 190 ± 10 | Var. 4143 | Var. 4228 | Var. 4313 | Var. 4398 | Var. 4483 | Var. 4568 | Var. 4653 | Var. 4738 |
| | 25 | Var. 4144 | Var. 4229 | Var. 4314 | Var. 4399 | Var. 4484 | Var. 4569 | Var. 4654 | Var. 4739 |
| | 30 | Var. 4145 | Var. 4230 | Var. 4315 | Var. 4400 | Var. 4485 | Var. 4570 | Var. 4655 | Var. 4740 |
| | 40 | Var. 4146 | Var. 4231 | Var. 4316 | Var. 4401 | Var. 4486 | Var. 4571 | Var. 4656 | Var. 4741 |
| | 50 | Var. 4147 | Var. 4232 | Var. 4317 | Var. 4402 | Var. 4487 | Var. 4572 | Var. 4657 | Var. 4742 |
| | 60 | Var. 4148 | Var. 4233 | Var. 4318 | Var. 4403 | Var. 4488 | Var. 4573 | Var. 4658 | Var. 4743 |
| | 70 | Var. 4149 | Var. 4234 | Var. 4319 | Var. 4404 | Var. 4489 | Var. 4574 | Var. 4659 | Var. 4744 |
| | 75 | Var. 4150 | Var. 4235 | Var. 4320 | Var. 4405 | Var. 4490 | Var. 4575 | Var. 4660 | Var. 4745 |
| | 80 | Var. 4151 | Var. 4236 | Var. 4321 | Var. 4406 | Var. 4491 | Var. 4576 | Var. 4661 | Var. 4746 |
| | 90 | Var. 4152 | Var. 4237 | Var. 4322 | Var. 4407 | Var. 4492 | Var. 4577 | Var. 4662 | Var. 4747 |
| | 100 | Var. 4153 | Var. 4238 | Var. 4323 | Var. 4408 | Var. 4493 | Var. 4578 | Var. 4663 | Var. 4748 |
| | 110 | Var. 4154 | Var. 4239 | Var. 4324 | Var. 4409 | Var. 4494 | Var. 4579 | Var. 4664 | Var. 4749 |
| | 120 | Var. 4155 | Var. 4240 | Var. 4325 | Var. 4410 | Var. 4495 | Var. 4580 | Var. 4665 | Var. 4750 |
| | 125 | Var. 4156 | Var. 4241 | Var. 4326 | Var. 4411 | Var. 4496 | Var. 4581 | Var. 4666 | Var. 4751 |
| | 130 | Var. 4157 | Var. 4242 | Var. 4327 | Var. 4412 | Var. 4497 | Var. 4582 | Var. 4667 | Var. 4752 |
| | 140 | Var. 4158 | Var. 4243 | Var. 4328 | Var. 4413 | Var. 4498 | Var. 4583 | Var. 4668 | Var. 4753 |
| | 150 | Var. 4159 | Var. 4244 | Var. 4329 | Var. 4414 | Var. 4499 | Var. 4584 | Var. 4669 | Var. 4754 |
| | 160 | Var. 4160 | Var. 4245 | Var. 4330 | Var. 4415 | Var. 4500 | Var. 4585 | Var. 4670 | Var. 4755 |
| | 170 | Var. 4161 | Var. 4246 | Var. 4331 | Var. 4416 | Var. 4501 | Var. 4586 | Var. 4671 | Var. 4756 |
| | 175 | Var. 4162 | Var. 4247 | Var. 4332 | Var. 4417 | Var. 4502 | Var. 4587 | Var. 4672 | Var. 4757 |
| | 180 | Var. 4163 | Var. 4248 | Var. 4333 | Var. 4418 | Var. 4503 | Var. 4588 | Var. 4673 | Var. 4758 |
| | 190 | Var. 4164 | Var. 4249 | Var. 4334 | Var. 4419 | Var. 4504 | Var. 4589 | Var. 4674 | Var. 4759 |
| | 200 | Var. 4165 | Var. 4250 | Var. 4335 | Var. 4420 | Var. 4505 | Var. 4590 | Var. 4675 | Var. 4760 |

Var. = Variation

TABLE 8

Exemplary embodiments for the combination of sugar or sugar alcohol and non-ionic surfactant concentrations useful for the stabilization of furin (e.g., rfurin) compositions.

| | | Sugar or Sugar Alcohol (%) | | | | | | |
|---|---|---|---|---|---|---|---|---|
| | | 6% | 7% | 8% | 9% | 10% | 11% | 12% | 13% |
| Non-Ionic | 10-200 | Var. 4761 | Var. 4846 | Var. 4931 | Var. 5016 | Var. 5101 | Var. 5186 | Var. 5271 | Var. 5356 |
| Surfactant | 10-175 | Var. 4762 | Var. 4847 | Var. 4932 | Var. 5017 | Var. 5102 | Var. 5187 | Var. 5272 | Var. 5357 |
| (ppm) | 10-150 | Var. 4763 | Var. 4848 | Var. 4933 | Var. 5018 | Var. 5103 | Var. 5188 | Var. 5273 | Var. 5358 |
| | 10-125 | Var. 4764 | Var. 4849 | Var. 4934 | Var. 5019 | Var. 5104 | Var. 5189 | Var. 5274 | Var. 5359 |
| | 10-100 | Var. 4765 | Var. 4850 | Var. 4935 | Var. 5020 | Var. 5105 | Var. 5190 | Var. 5275 | Var. 5360 |
| | 10-90 | Var. 4766 | Var. 4851 | Var. 4936 | Var. 5021 | Var. 5106 | Var. 5191 | Var. 5276 | Var. 5361 |
| | 10-80 | Var. 4767 | Var. 4852 | Var. 4937 | Var. 5022 | Var. 5107 | Var. 5192 | Var. 5277 | Var. 5362 |
| | 10-75 | Var. 4768 | Var. 4853 | Var. 4938 | Var. 5023 | Var. 5108 | Var. 5193 | Var. 5278 | Var. 5363 |
| | 10-70 | Var. 4769 | Var. 4854 | Var. 4939 | Var. 5024 | Var. 5109 | Var. 5194 | Var. 5279 | Var. 5364 |
| | 10-60 | Var. 4770 | Var. 4855 | Var. 4940 | Var. 5025 | Var. 5110 | Var. 5195 | Var. 5280 | Var. 5365 |
| | 10-50 | Var. 4771 | Var. 4856 | Var. 4941 | Var. 5026 | Var. 5111 | Var. 5196 | Var. 5281 | Var. 5366 |
| | 10-25 | Var. 4772 | Var. 4857 | Var. 4942 | Var. 5027 | Var. 5112 | Var. 5197 | Var. 5282 | Var. 5367 |
| | 25-200 | Var. 4773 | Var. 4858 | Var. 4943 | Var. 5028 | Var. 5113 | Var. 5198 | Var. 5283 | Var. 5368 |
| | 25-175 | Var. 4774 | Var. 4859 | Var. 4944 | Var. 5029 | Var. 5114 | Var. 5199 | Var. 5284 | Var. 5369 |
| | 25-150 | Var. 4775 | Var. 4860 | Var. 4945 | Var. 5030 | Var. 5115 | Var. 5200 | Var. 5285 | Var. 5370 |
| | 25-125 | Var. 4776 | Var. 4861 | Var. 4946 | Var. 5031 | Var. 5116 | Var. 5201 | Var. 5286 | Var. 5371 |
| | 25-100 | Var. 4777 | Var. 4862 | Var. 4947 | Var. 5032 | Var. 5117 | Var. 5202 | Var. 5287 | Var. 5372 |
| | 25-90 | Var. 4778 | Var. 4863 | Var. 4948 | Var. 5033 | Var. 5118 | Var. 5203 | Var. 5288 | Var. 5373 |
| | 25-80 | Var. 4779 | Var. 4864 | Var. 4949 | Var. 5034 | Var. 5119 | Var. 5204 | Var. 5289 | Var. 5374 |
| | 25-70 | Var. 4780 | Var. 4865 | Var. 4950 | Var. 5035 | Var. 5120 | Var. 5205 | Var. 5290 | Var. 5375 |
| | 25-60 | Var. 4781 | Var. 4866 | Var. 4951 | Var. 5036 | Var. 5121 | Var. 5206 | Var. 5291 | Var. 5376 |

TABLE 8-continued

Exemplary embodiments for the combination of sugar or sugar alcohol and non-ionic surfactant concentrations useful for the stabilization of furin (e.g., rfurin) compositions.

| | Sugar or Sugar Alcohol (%) | | | | | | | |
|---|---|---|---|---|---|---|---|---|
| | 6% | 7% | 8% | 9% | 10% | 11% | 12% | 13% |
| 25-50 | Var. 4782 | Var. 4867 | Var. 4952 | Var. 5037 | Var. 5122 | Var. 5207 | Var. 5292 | Var. 5377 |
| 50-200 | Var. 4783 | Var. 4868 | Var. 4953 | Var. 5038 | Var. 5123 | Var. 5208 | Var. 5293 | Var. 5378 |
| 50-175 | Var. 4784 | Var. 4869 | Var. 4954 | Var. 5039 | Var. 5124 | Var. 5209 | Var. 5294 | Var. 5379 |
| 50-150 | Var. 4785 | Var. 4870 | Var. 4955 | Var. 5040 | Var. 5125 | Var. 5210 | Var. 5295 | Var. 5380 |
| 50-125 | Var. 4786 | Var. 4871 | Var. 4956 | Var. 5041 | Var. 5126 | Var. 5211 | Var. 5296 | Var. 5381 |
| 50-90 | Var. 4787 | Var. 4872 | Var. 4957 | Var. 5042 | Var. 5127 | Var. 5212 | Var. 5297 | Var. 5382 |
| 50-80 | Var. 4788 | Var. 4873 | Var. 4958 | Var. 5043 | Var. 5128 | Var. 5213 | Var. 5298 | Var. 5383 |
| 75-200 | Var. 4789 | Var. 4874 | Var. 4959 | Var. 5044 | Var. 5129 | Var. 5214 | Var. 5299 | Var. 5384 |
| 75-175 | Var. 4790 | Var. 4875 | Var. 4960 | Var. 5045 | Var. 5130 | Var. 5215 | Var. 5300 | Var. 5385 |
| 75-150 | Var. 4791 | Var. 4876 | Var. 4961 | Var. 5046 | Var. 5131 | Var. 5216 | Var. 5301 | Var. 5386 |
| 100-200 | Var. 4792 | Var. 4877 | Var. 4962 | Var. 5047 | Var. 5132 | Var. 5217 | Var. 5302 | Var. 5387 |
| 100-175 | Var. 4793 | Var. 4878 | Var. 4963 | Var. 5048 | Var. 5133 | Var. 5218 | Var. 5303 | Var. 5388 |
| 50 ± 25 | Var. 4794 | Var. 4879 | Var. 4964 | Var. 5049 | Var. 5134 | Var. 5219 | Var. 5304 | Var. 5389 |
| 60 ± 25 | Var. 4795 | Var. 4880 | Var. 4965 | Var. 5050 | Var. 5135 | Var. 5220 | Var. 5305 | Var. 5390 |
| 70 ± 25 | Var. 4796 | Var. 4881 | Var. 4966 | Var. 5051 | Var. 5136 | Var. 5221 | Var. 5306 | Var. 5391 |
| 75 ± 25 | Var. 4797 | Var. 4882 | Var. 4967 | Var. 5052 | Var. 5137 | Var. 5222 | Var. 5307 | Var. 5392 |
| 80 ± 25 | Var. 4798 | Var. 4883 | Var. 4968 | Var. 5053 | Var. 5138 | Var. 5223 | Var. 5308 | Var. 5393 |
| 90 ± 25 | Var. 4799 | Var. 4884 | Var. 4969 | Var. 5054 | Var. 5139 | Var. 5224 | Var. 5309 | Var. 5394 |
| 100 ± 25 | Var. 4800 | Var. 4885 | Var. 4970 | Var. 5055 | Var. 5140 | Var. 5225 | Var. 5310 | Var. 5395 |
| 125 ± 25 | Var. 4801 | Var. 4886 | Var. 4971 | Var. 5056 | Var. 5141 | Var. 5226 | Var. 5311 | Var. 5396 |
| 150 ± 25 | Var. 4802 | Var. 4887 | Var. 4972 | Var. 5057 | Var. 5142 | Var. 5227 | Var. 5312 | Var. 5397 |
| 175 ± 25 | Var. 4803 | Var. 4888 | Var. 4973 | Var. 5058 | Var. 5143 | Var. 5228 | Var. 5313 | Var. 5398 |
| 30 ± 10 | Var. 4804 | Var. 4889 | Var. 4974 | Var. 5059 | Var. 5144 | Var. 5229 | Var. 5314 | Var. 5399 |
| 40 ± 10 | Var. 4805 | Var. 4890 | Var. 4975 | Var. 5060 | Var. 5145 | Var. 5230 | Var. 5315 | Var. 5400 |
| 50 ± 10 | Var. 4806 | Var. 4891 | Var. 4976 | Var. 5061 | Var. 5146 | Var. 5231 | Var. 5316 | Var. 5401 |
| 60 ± 10 | Var. 4807 | Var. 4892 | Var. 4977 | Var. 5062 | Var. 5147 | Var. 5232 | Var. 5317 | Var. 5402 |
| 70 ± 10 | Var. 4808 | Var. 4893 | Var. 4978 | Var. 5063 | Var. 5148 | Var. 5233 | Var. 5318 | Var. 5403 |
| 75 ± 10 | Var. 4809 | Var. 4894 | Var. 4979 | Var. 5064 | Var. 5149 | Var. 5234 | Var. 5319 | Var. 5404 |
| 80 ± 10 | Var. 4810 | Var. 4895 | Var. 4980 | Var. 5065 | Var. 5150 | Var. 5235 | Var. 5320 | Var. 5405 |
| 90 ± 10 | Var. 4811 | Var. 4896 | Var. 4981 | Var. 5066 | Var. 5151 | Var. 5236 | Var. 5321 | Var. 5406 |
| 100 ± 10 | Var. 4812 | Var. 4897 | Var. 4982 | Var. 5067 | Var. 5152 | Var. 5237 | Var. 5322 | Var. 5407 |
| 110 ± 10 | Var. 4813 | Var. 4898 | Var. 4983 | Var. 5068 | Var. 5153 | Var. 5238 | Var. 5323 | Var. 5408 |
| 120 ± 10 | Var. 4814 | Var. 4899 | Var. 4984 | Var. 5069 | Var. 5154 | Var. 5239 | Var. 5324 | Var. 5409 |
| 125 ± 10 | Var. 4815 | Var. 4900 | Var. 4985 | Var. 5070 | Var. 5155 | Var. 5240 | Var. 5325 | Var. 5410 |
| 130 ± 10 | Var. 4816 | Var. 4901 | Var. 4986 | Var. 5071 | Var. 5156 | Var. 5241 | Var. 5326 | Var. 5411 |
| 140 ± 10 | Var. 4817 | Var. 4902 | Var. 4987 | Var. 5072 | Var. 5157 | Var. 5242 | Var. 5327 | Var. 5412 |
| 150 ± 10 | Var. 4818 | Var. 4903 | Var. 4988 | Var. 5073 | Var. 5158 | Var. 5243 | Var. 5328 | Var. 5413 |
| 160 ± 10 | Var. 4819 | Var. 4904 | Var. 4989 | Var. 5074 | Var. 5159 | Var. 5244 | Var. 5329 | Var. 5414 |
| 170 ± 10 | Var. 4820 | Var. 4905 | Var. 4990 | Var. 5075 | Var. 5160 | Var. 5245 | Var. 5330 | Var. 5415 |
| 175 ± 10 | Var. 4821 | Var. 4906 | Var. 4991 | Var. 5076 | Var. 5161 | Var. 5246 | Var. 5331 | Var. 5416 |
| 180 ± 10 | Var. 4822 | Var. 4907 | Var. 4992 | Var. 5077 | Var. 5162 | Var. 5247 | Var. 5332 | Var. 5417 |
| 190 ± 10 | Var. 4823 | Var. 4908 | Var. 4993 | Var. 5078 | Var. 5163 | Var. 5248 | Var. 5333 | Var. 5418 |
| 25 | Var. 4824 | Var. 4909 | Var. 4994 | Var. 5079 | Var. 5164 | Var. 5249 | Var. 5334 | Var. 5419 |
| 30 | Var. 4825 | Var. 4910 | Var. 4995 | Var. 5080 | Var. 5165 | Var. 5250 | Var. 5335 | Var. 5420 |
| 40 | Var. 4826 | Var. 4911 | Var. 4996 | Var. 5081 | Var. 5166 | Var. 5251 | Var. 5336 | Var. 5421 |
| 50 | Var. 4827 | Var. 4912 | Var. 4997 | Var. 5082 | Var. 5167 | Var. 5252 | Var. 5337 | Var. 5422 |
| 60 | Var. 4828 | Var. 4913 | Var. 4998 | Var. 5083 | Var. 5168 | Var. 5253 | Var. 5338 | Var. 5423 |
| 70 | Var. 4829 | Var. 4914 | Var. 4999 | Var. 5084 | Var. 5169 | Var. 5254 | Var. 5339 | Var. 5424 |
| 75 | Var. 4830 | Var. 4915 | Var. 5000 | Var. 5085 | Var. 5170 | Var. 5255 | Var. 5340 | Var. 5425 |
| 80 | Var. 4831 | Var. 4916 | Var. 5001 | Var. 5086 | Var. 5171 | Var. 5256 | Var. 5341 | Var. 5426 |
| 90 | Var. 4832 | Var. 4917 | Var. 5002 | Var. 5087 | Var. 5172 | Var. 5257 | Var. 5342 | Var. 5427 |
| 100 | Var. 4833 | Var. 4918 | Var. 5003 | Var. 5088 | Var. 5173 | Var. 5258 | Var. 5343 | Var. 5428 |
| 110 | Var. 4834 | Var. 4919 | Var. 5004 | Var. 5089 | Var. 5174 | Var. 5259 | Var. 5344 | Var. 5429 |
| 120 | Var. 4835 | Var. 4920 | Var. 5005 | Var. 5090 | Var. 5175 | Var. 5260 | Var. 5345 | Var. 5430 |
| 125 | Var. 4836 | Var. 4921 | Var. 5006 | Var. 5091 | Var. 5176 | Var. 5261 | Var. 5346 | Var. 5431 |
| 130 | Var. 4837 | Var. 4922 | Var. 5007 | Var. 5092 | Var. 5177 | Var. 5262 | Var. 5347 | Var. 5432 |
| 140 | Var. 4838 | Var. 4923 | Var. 5008 | Var. 5093 | Var. 5178 | Var. 5263 | Var. 5348 | Var. 5433 |
| 150 | Var. 4839 | Var. 4924 | Var. 5009 | Var. 5094 | Var. 5179 | Var. 5264 | Var. 5349 | Var. 5434 |
| 160 | Var. 4840 | Var. 4925 | Var. 5010 | Var. 5095 | Var. 5180 | Var. 5265 | Var. 5350 | Var. 5435 |
| 170 | Var. 4841 | Var. 4926 | Var. 5011 | Var. 5096 | Var. 5181 | Var. 5266 | Var. 5351 | Var. 5436 |
| 175 | Var. 4842 | Var. 4927 | Var. 5012 | Var. 5097 | Var. 5182 | Var. 5267 | Var. 5352 | Var. 5437 |
| 180 | Var. 4843 | Var. 4928 | Var. 5013 | Var. 5098 | Var. 5183 | Var. 5268 | Var. 5353 | Var. 5438 |
| 190 | Var. 4844 | Var. 4929 | Var. 5014 | Var. 5099 | Var. 5184 | Var. 5269 | Var. 5354 | Var. 5439 |
| 200 | Var. 4845 | Var. 4930 | Var. 5015 | Var. 5100 | Var. 5185 | Var. 5270 | Var. 5355 | Var. 5440 |

Var. = Variation

TABLE 9

Exemplary embodiments for the combination of sugar or sugar alcohol and non-ionic surfactant concentrations useful for the stabilization of furin (e.g., rfurin) compositions.

| | | Sugar or Sugar Alcohol (%) | | | | | | |
|---|---|---|---|---|---|---|---|---|
| | | 14% | 15% | 16% | 17% | 18% | 19% | 20% |
| Non-Ionic Surfactant (ppm) | 10-200 | Var. 5441 | Var. 5526 | Var. 5611 | Var. 5696 | Var. 5781 | Var. 5866 | Var. 5951 |
| | 10-175 | Var. 5442 | Var. 5527 | Var. 5612 | Var. 5697 | Var. 5782 | Var. 5867 | Var. 5952 |
| | 10-150 | Var. 5443 | Var. 5528 | Var. 5613 | Var. 5698 | Var. 5783 | Var. 5868 | Var. 5953 |
| | 10-125 | Var. 5444 | Var. 5529 | Var. 5614 | Var. 5699 | Var. 5784 | Var. 5869 | Var. 5954 |
| | 10-100 | Var. 5445 | Var. 5530 | Var. 5615 | Var. 5700 | Var. 5785 | Var. 5870 | Var. 5955 |
| | 10-90 | Var. 5446 | Var. 5531 | Var. 5616 | Var. 5701 | Var. 5786 | Var. 5871 | Var. 5956 |
| | 10-80 | Var. 5447 | Var. 5532 | Var. 5617 | Var. 5702 | Var. 5787 | Var. 5872 | Var. 5957 |
| | 10-75 | Var. 5448 | Var. 5533 | Var. 5618 | Var. 5703 | Var. 5788 | Var. 5873 | Var. 5958 |
| | 10-70 | Var. 5449 | Var. 5534 | Var. 5619 | Var. 5704 | Var. 5789 | Var. 5874 | Var. 5959 |
| | 10-60 | Var. 5450 | Var. 5535 | Var. 5620 | Var. 5705 | Var. 5790 | Var. 5875 | Var. 5960 |
| | 10-50 | Var. 5451 | Var. 5536 | Var. 5621 | Var. 5706 | Var. 5791 | Var. 5876 | Var. 5961 |
| | 10-25 | Var. 5452 | Var. 5537 | Var. 5622 | Var. 5707 | Var. 5792 | Var. 5877 | Var. 5962 |
| | 25-200 | Var. 5453 | Var. 5538 | Var. 5623 | Var. 5708 | Var. 5793 | Var. 5878 | Var. 5963 |
| | 25-175 | Var. 5454 | Var. 5539 | Var. 5624 | Var. 5709 | Var. 5794 | Var. 5879 | Var. 5964 |
| | 25-150 | Var. 5455 | Var. 5540 | Var. 5625 | Var. 5710 | Var. 5795 | Var. 5880 | Var. 5965 |
| | 25-125 | Var. 5456 | Var. 5541 | Var. 5626 | Var. 5711 | Var. 5796 | Var. 5881 | Var. 5966 |
| | 25-100 | Var. 5457 | Var. 5542 | Var. 5627 | Var. 5712 | Var. 5797 | Var. 5882 | Var. 5967 |
| | 25-90 | Var. 5458 | Var. 5543 | Var. 5628 | Var. 5713 | Var. 5798 | Var. 5883 | Var. 5968 |
| | 25-80 | Var. 5459 | Var. 5544 | Var. 5629 | Var. 5714 | Var. 5799 | Var. 5884 | Var. 5969 |
| | 25-70 | Var. 5460 | Var. 5545 | Var. 5630 | Var. 5715 | Var. 5800 | Var. 5885 | Var. 5970 |
| | 25-60 | Var. 5461 | Var. 5546 | Var. 5631 | Var. 5716 | Var. 5801 | Var. 5886 | Var. 5971 |
| | 25-50 | Var. 5462 | Var. 5547 | Var. 5632 | Var. 5717 | Var. 5802 | Var. 5887 | Var. 5972 |
| | 50-200 | Var. 5463 | Var. 5548 | Var. 5633 | Var. 5718 | Var. 5803 | Var. 5888 | Var. 5973 |
| | 50-175 | Var. 5464 | Var. 5549 | Var. 5634 | Var. 5719 | Var. 5804 | Var. 5889 | Var. 5974 |
| | 50-150 | Var. 5465 | Var. 5550 | Var. 5635 | Var. 5720 | Var. 5805 | Var. 5890 | Var. 5975 |
| | 50-125 | Var. 5466 | Var. 5551 | Var. 5636 | Var. 5721 | Var. 5806 | Var. 5891 | Var. 5976 |
| | 50-90 | Var. 5467 | Var. 5552 | Var. 5637 | Var. 5722 | Var. 5807 | Var. 5892 | Var. 5977 |
| | 50-80 | Var. 5468 | Var. 5553 | Var. 5638 | Var. 5723 | Var. 5808 | Var. 5893 | Var. 5978 |
| | 75-200 | Var. 5469 | Var. 5554 | Var. 5639 | Var. 5724 | Var. 5809 | Var. 5894 | Var. 5979 |
| | 75-175 | Var. 5470 | Var. 5555 | Var. 5640 | Var. 5725 | Var. 5810 | Var. 5895 | Var. 5980 |
| | 75-150 | Var. 5471 | Var. 5556 | Var. 5641 | Var. 5726 | Var. 5811 | Var. 5896 | Var. 5981 |
| | 100-200 | Var. 5472 | Var. 5557 | Var. 5642 | Var. 5727 | Var. 5812 | Var. 5897 | Var. 5982 |
| | 100-175 | Var. 5473 | Var. 5558 | Var. 5643 | Var. 5728 | Var. 5813 | Var. 5898 | Var. 5983 |
| | 50 ± 25 | Var. 5474 | Var. 5559 | Var. 5644 | Var. 5729 | Var. 5814 | Var. 5899 | Var. 5984 |
| | 60 ± 25 | Var. 5475 | Var. 5560 | Var. 5645 | Var. 5730 | Var. 5815 | Var. 5900 | Var. 5985 |
| | 70 ± 25 | Var. 5476 | Var. 5561 | Var. 5646 | Var. 5731 | Var. 5816 | Var. 5901 | Var. 5986 |
| | 75 ± 25 | Var. 5477 | Var. 5562 | Var. 5647 | Var. 5732 | Var. 5817 | Var. 5902 | Var. 5987 |
| | 80 ± 25 | Var. 5478 | Var. 5563 | Var. 5648 | Var. 5733 | Var. 5818 | Var. 5903 | Var. 5988 |
| | 90 ± 25 | Var. 5479 | Var. 5564 | Var. 5649 | Var. 5734 | Var. 5819 | Var. 5904 | Var. 5989 |
| | 100 ± 25 | Var. 5480 | Var. 5565 | Var. 5650 | Var. 5735 | Var. 5820 | Var. 5905 | Var. 5990 |
| | 125 ± 25 | Var. 5481 | Var. 5566 | Var. 5651 | Var. 5736 | Var. 5821 | Var. 5906 | Var. 5991 |
| | 150 ± 25 | Var. 5482 | Var. 5567 | Var. 5652 | Var. 5737 | Var. 5822 | Var. 5907 | Var. 5992 |
| | 175 ± 25 | Var. 5483 | Var. 5568 | Var. 5653 | Var. 5738 | Var. 5823 | Var. 5908 | Var. 5993 |
| | 30 ± 10 | Var. 5484 | Var. 5569 | Var. 5654 | Var. 5739 | Var. 5824 | Var. 5909 | Var. 5994 |
| | 40 ± 10 | Var. 5485 | Var. 5570 | Var. 5655 | Var. 5740 | Var. 5825 | Var. 5910 | Var. 5995 |
| | 50 ± 10 | Var. 5486 | Var. 5571 | Var. 5656 | Var. 5741 | Var. 5826 | Var. 5911 | Var. 5996 |
| | 60 ± 10 | Var. 5487 | Var. 5572 | Var. 5657 | Var. 5742 | Var. 5827 | Var. 5912 | Var. 5997 |
| | 70 ± 10 | Var. 5488 | Var. 5573 | Var. 5658 | Var. 5743 | Var. 5828 | Var. 5913 | Var. 5998 |
| | 75 ± 10 | Var. 5489 | Var. 5574 | Var. 5659 | Var. 5744 | Var. 5829 | Var. 5914 | Var. 5999 |
| | 80 ± 10 | Var. 5490 | Var. 5575 | Var. 5660 | Var. 5745 | Var. 5830 | Var. 5915 | Var. 6000 |
| | 90 ± 10 | Var. 5491 | Var. 5576 | Var. 5661 | Var. 5746 | Var. 5831 | Var. 5916 | Var. 6001 |
| | 100 ± 10 | Var. 5492 | Var. 5577 | Var. 5662 | Var. 5747 | Var. 5832 | Var. 5917 | Var. 6002 |
| | 110 ± 10 | Var. 5493 | Var. 5578 | Var. 5663 | Var. 5748 | Var. 5833 | Var. 5918 | Var. 6003 |
| | 120 ± 10 | Var. 5494 | Var. 5579 | Var. 5664 | Var. 5749 | Var. 5834 | Var. 5919 | Var. 6004 |
| | 125 ± 10 | Var. 5495 | Var. 5580 | Var. 5665 | Var. 5750 | Var. 5835 | Var. 5920 | Var. 6005 |
| | 130 ± 10 | Var. 5496 | Var. 5581 | Var. 5666 | Var. 5751 | Var. 5836 | Var. 5921 | Var. 6006 |
| | 140 ± 10 | Var. 5497 | Var. 5582 | Var. 5667 | Var. 5752 | Var. 5837 | Var. 5922 | Var. 6007 |
| | 150 ± 10 | Var. 5498 | Var. 5583 | Var. 5668 | Var. 5753 | Var. 5838 | Var. 5923 | Var. 6008 |
| | 160 ± 10 | Var. 5499 | Var. 5584 | Var. 5669 | Var. 5754 | Var. 5839 | Var. 5924 | Var. 6009 |
| | 170 ± 10 | Var. 5500 | Var. 5585 | Var. 5670 | Var. 5755 | Var. 5840 | Var. 5925 | Var. 6010 |
| | 175 ± 10 | Var. 5501 | Var. 5586 | Var. 5671 | Var. 5756 | Var. 5841 | Var. 5926 | Var. 6011 |
| | 180 ± 10 | Var. 5502 | Var. 5587 | Var. 5672 | Var. 5757 | Var. 5842 | Var. 5927 | Var. 6012 |
| | 190 ± 10 | Var. 5503 | Var. 5588 | Var. 5673 | Var. 5758 | Var. 5843 | Var. 5928 | Var. 6013 |
| | 25 | Var. 5504 | Var. 5589 | Var. 5674 | Var. 5759 | Var. 5844 | Var. 5929 | Var. 6014 |
| | 30 | Var. 5505 | Var. 5590 | Var. 5675 | Var. 5760 | Var. 5845 | Var. 5930 | Var. 6015 |
| | 40 | Var. 5506 | Var. 5591 | Var. 5676 | Var. 5761 | Var. 5846 | Var. 5931 | Var. 6016 |
| | 50 | Var. 5507 | Var. 5592 | Var. 5677 | Var. 5762 | Var. 5847 | Var. 5932 | Var. 6017 |
| | 60 | Var. 5508 | Var. 5593 | Var. 5678 | Var. 5763 | Var. 5848 | Var. 5933 | Var. 6018 |
| | 70 | Var. 5509 | Var. 5594 | Var. 5679 | Var. 5764 | Var. 5849 | Var. 5934 | Var. 6019 |
| | 75 | Var. 5510 | Var. 5595 | Var. 5680 | Var. 5765 | Var. 5850 | Var. 5935 | Var. 6020 |
| | 80 | Var. 5511 | Var. 5596 | Var. 5681 | Var. 5766 | Var. 5851 | Var. 5936 | Var. 6021 |
| | 90 | Var. 5512 | Var. 5597 | Var. 5682 | Var. 5767 | Var. 5852 | Var. 5937 | Var. 6022 |
| | 100 | Var. 5513 | Var. 5598 | Var. 5683 | Var. 5768 | Var. 5853 | Var. 5938 | Var. 6023 |

TABLE 9-continued

Exemplary embodiments for the combination of sugar or sugar alcohol and non-ionic surfactant concentrations useful for the stabilization of furin (e.g., rfurin) compositions.

| | Sugar or Sugar Alcohol (%) | | | | | | |
|---|---|---|---|---|---|---|---|
| | 14% | 15% | 16% | 17% | 18% | 19% | 20% |
| 110 | Var. 5514 | Var. 5599 | Var. 5684 | Var. 5769 | Var. 5854 | Var. 5939 | Var. 6024 |
| 120 | Var. 5515 | Var. 5600 | Var. 5685 | Var. 5770 | Var. 5855 | Var. 5940 | Var. 6025 |
| 125 | Var. 5516 | Var. 5601 | Var. 5686 | Var. 5771 | Var. 5856 | Var. 5941 | Var. 6026 |
| 130 | Var. 5517 | Var. 5602 | Var. 5687 | Var. 5772 | Var. 5857 | Var. 5942 | Var. 6027 |
| 140 | Var. 5518 | Var. 5603 | Var. 5688 | Var. 5773 | Var. 5858 | Var. 5943 | Var. 6028 |
| 150 | Var. 5519 | Var. 5604 | Var. 5689 | Var. 5774 | Var. 5859 | Var. 5944 | Var. 6029 |
| 160 | Var. 5520 | Var. 5605 | Var. 5690 | Var. 5775 | Var. 5860 | Var. 5945 | Var. 6030 |
| 170 | Var. 5521 | Var. 5606 | Var. 5691 | Var. 5776 | Var. 5861 | Var. 5946 | Var. 6031 |
| 175 | Var. 5522 | Var. 5607 | Var. 5692 | Var. 5777 | Var. 5862 | Var. 5947 | Var. 6032 |
| 180 | Var. 5523 | Var. 5608 | Var. 5693 | Var. 5778 | Var. 5863 | Var. 5948 | Var. 6033 |
| 190 | Var. 5524 | Var. 5609 | Var. 5694 | Var. 5779 | Var. 5864 | Var. 5949 | Var. 6034 |
| 200 | Var. 5525 | Var. 5610 | Var. 5695 | Var. 5780 | Var. 5865 | Var. 5950 | Var. 6035 |

Var. = Variation

1. Sugars and Sugar Alcohols

Advantageously, it was found that the addition of sugar and/or sugar alcohol to furin compositions (e.g., rfurin compositions) increases the storage stability of the composition. For example, as shown in FIGS. 17 to 20 and 22 to 25, the inclusion of as little as 2% sugar and/or sugar alcohol can increase the storage stability of a furin composition by at least 20%. And the inclusion of 10% sugar and/or sugar alcohol can increase the storage stability of a furin composition by at least 75%. Accordingly, in one aspect of the present disclosure, a storage stable composition of furin (e.g., rfurin) contains a stabilizing amount of sugar and/or sugar alcohol.

In one embodiment, the storage stable composition of furin (e.g., rfurin) contains monosaccharide sugar. In a particular embodiment, the monosaccharide sugar is selected from the group consisting of a diose sugar, a triose sugar, a tetrose sugar, a pentose sugar, a hexose sugar, a heptose sugar, and an octose sugar. In a particular embodiment, the sugar is a pentose sugar, a hexose sugar, or a combination thereof. In a specific embodiment, the sugar is a hexose sugar.

In another embodiment, the storage stable composition of furin (e.g., rfurin) contains a disaccharide sugar. In a particular embodiment, the disaccharide sugar is selected from disaccharide sugars formed from pentose and/or hexose monosaccharides. In another particular embodiment, the sugar is selected from disaccharide sugars formed from hexose monosaccharides. In one embodiment, the sugar is sucrose, trehalose, or a combination thereof. In one specific embodiment, the sugar is sucrose. In another specific embodiment, the sugar is trehalose. In one embodiment, the sugar is formulated as trehalose dihydrate.

In another embodiment, the storage stable composition of furin (e.g., rfurin) contains a sugar alcohol. In a particular embodiment, the sugar alcohol is selected from glycol, glycerol, erythritol, threitol, ribitol, fucitol, iditol, volmitol, isomalt, maltitol, lactitol, mannitol, sorbitol, inositol, galactitol, dulcitol, xylitol, and arabitol. In another particular embodiment, the sugar alcohol is mannitol.

In yet another embodiment, the stable composition of furin (e.g., rfurin) contains a mixture of sugar and sugar alcohol. In one embodiment, the mixture contains at least two of a monosaccharide, a disaccharide, and a sugar alcohol. In another embodiment, the mixture contains at least two of a pentose sugar, a hexose sugar, a disaccharide formed from pentose and/or hexose monosaccharides, and a sugar alcohol. In another embodiment, the mixture contains at least two of sucrose, trehalose, and mannitol.

In one embodiment, the sugar or sugar alcohol is present at a concentration of from 2% to 20%, 2% to 17.5%, 2% to 15%, 2% to 12.5%, 2% to 10%, 2% to 9%, 2% to 8%, 2% to 7%, 5% to 20%, 5% to 17.5%, 5% to 15%, 5% to 12.5%, 5% to 10%, 7.5% to 20%, 7.5% to 17.5%, 7.5% to 15%, 7.5% to 12.5%, 10% to 20%, 10% to 17.5%, 10% to 15%, 4±2%, 5±2%, 6±2%, 7±2%, 8±2%, 9±2%, 10±2%, 11±2%, 12±2%, 13±2%, 14±2%, 15±2%, 16±2%, 17±2%, 18±2%, 3±1%, 4±1%, 5±1%, 6±1%, 7±1%, 8±1%, 9±1%, 10±1%, 11±1%, 12±1%, 13±1%, 14±1%, 15±1%, 16±1%, 17±1%, 18±1%, 19±1%, 2%, 3%, 4%, 5%, 6%, 7%, 8%, 9%, 10%, 11%, 12%, 13%, 14%, 15%, 16%, 17%, 18%, 19%, or 20%. In one embodiment, the sugar or sugar alcohol is selected from sucrose, trehalose, mannitol, and a combination thereof. In a specific embodiment, the sugar or sugar alcohol is trehalose.

In one embodiment, a stabilized furin (e.g., rfurin) composition comprises from 50 mM to 500 mM of a pharmaceutically acceptable salt, from 0.5 mM to 5 mM calcium; from 2% to 20% sugar or sugar alcohol, from 10 to 200 mM buffering agent, and a pH from 5.5 to 7.5. In one embodiment, the storage stable furin composition further comprises from 10 ppm to 200 ppm non-ionic surfactant. In a specific embodiment, the sugar or sugar alcohol is selected from sucrose, trehalose, mannitol, and a combination thereof. In one embodiment, the pH of the composition is from 5.5 to 7.0. In another embodiment, the pH of the composition is from 5.5 to 6.5. In another embodiment, the pH of the composition is 6.0±0.2. In a specific embodiment, the pH of the composition is 6.0. In a specific embodiment, the composition contains from 8,000 U/mL to 500,000 U/mL rfurin.

In one embodiment, a stabilized furin (e.g., rfurin) composition comprises from 50 to 500 mM of a pharmaceutically acceptable salt, from 0.5 mM to 5 mM calcium; from 2% to 20% sugar or sugar alcohol, from 10 ppm to 100 ppm non-ionic surfactant, from 10 mM to 200 mM buffering agent, and a pH from 5.5 to 7.5. In a specific embodiment, the sugar or sugar alcohol is selected from sucrose, trehalose, mannitol, and a combination thereof. In one embodiment, the pH of the composition is from 5.5 to 7.0. In another embodiment, the pH of the composition is from 5.5 to 6.5. In another embodiment, the pH of the composition is 6.0±0.2. In a specific embodiment, the pH of the composition is 6.0. In a specific embodiment, the composition contains from 8,000 U/mL to 500,000 U/mL rfurin.

In one embodiment, a stabilized furin (e.g., rfurin) composition comprises from 50 to 500 mM of a pharmaceutically acceptable salt, from 0.5 mM to 5 mM calcium; from 2% to 20% trehalose, from 10 ppm to 100 ppm non-ionic surfactant, from 10 mM to 200 mM buffering agent, and a pH from 5.5 to 7.5. In one embodiment, the pH of the composition is from 5.5 to 7.0. In another embodiment, the pH of the composition is from 5.5 to 6.5. In another embodiment, the pH of the composition is 6.0±0.2. In a specific embodiment, the pH of the composition is 6.0. In a specific embodiment, the composition contains from 8,000 U/mL to 500,000 U/mL rfurin.

In one embodiment, a stabilized furin (e.g., rfurin) composition comprises from 50 to 500 mM of a pharmaceutically acceptable salt, from 0.5 mM to 5 mM calcium; a combination of sugar or sugar alcohol and non-ionic surfactant selected from variations 1 to 6035 found in Table 1 to Table 9, from 10 mM to 200 mM buffering agent, and a pH from 5.5 to 7.5. In a specific embodiment, the sugar or sugar alcohol is selected from sucrose, trehalose, mannitol, and a combination thereof. In one embodiment, the pH of the composition is from 5.5 to 7.0. In another embodiment, the pH of the composition is from 5.5 to 6.5. In another embodiment, the pH of the composition is 6.0±0.2. In a specific embodiment, the pH of the composition is 6.0. In a specific embodiment, the composition contains from 8,000 U/mL to 500,000 U/mL rfurin.

In one embodiment, a stabilized furin (e.g., rfurin) composition comprises from 50 to 500 mM of a pharmaceutically acceptable salt, from 0.5 mM to 5 mM calcium; a combination of trehalose and non-ionic surfactant selected from variations 1 to 6035 found in Table 1 to Table 9, from 10 mM to 200 mM buffering agent, and a pH from 5.5 to 7.5. In one embodiment, the pH of the composition is from 5.5 to 7.0. In another embodiment, the pH of the composition is from 5.5 to 6.5. In another embodiment, the pH of the composition is 6.0±0.2. In a specific embodiment, the pH of the composition is 6.0. In a specific embodiment, the composition contains from 8,000 U/mL to 500,000 U/mL rfurin.

In one embodiment, a stabilized furin (e.g., rfurin) composition comprises from 100 to 300 mM of a pharmaceutically acceptable salt, from 0.5 mM to 2 mM calcium; from 2% to 20% sugar or sugar alcohol, from 10 mM to 200 mM buffering agent, and a pH from 5.5 to 7.5. In one embodiment, the storage stable furin composition further comprises from 10 ppm to 200 ppm non-ionic surfactant. In a specific embodiment, the sugar or sugar alcohol is selected from sucrose, trehalose, mannitol, and a combination thereof. In one embodiment, the pH of the composition is from 5.5 to 7.0. In another embodiment, the pH of the composition is from 5.5 to 6.5. In another embodiment, the pH of the composition is 6.0±0.2. In a specific embodiment, the pH of the composition is 6.0. In a specific embodiment, the composition contains from 8,000 U/mL to 500,000 U/mL rfurin.

In one embodiment, a stabilized furin (e.g., rfurin) composition comprises from 100 mM to 300 mM of a pharmaceutically acceptable salt, from 0.5 mM to 2 mM calcium; from 2% to 20% sugar or sugar alcohol, from 10 ppm to 100 ppm non-ionic surfactant, from 10 to 200 mM buffering agent, and a pH from 5.5 to 7.5. In a specific embodiment, the sugar or sugar alcohol is selected from sucrose, trehalose, mannitol, and a combination thereof. In one embodiment, the pH of the composition is from 5.5 to 7.0. In another embodiment, the pH of the composition is from 5.5 to 6.5. In another embodiment, the pH of the composition is 6.0±0.2. In a specific embodiment, the pH of the composition is 6.0. In a specific embodiment, the composition contains from 8,000 U/mL to 500,000 U/mL rfurin.

In one embodiment, a stabilized furin (e.g., rfurin) composition comprises from 100 mM to 300 mM of a pharmaceutically acceptable salt, from 0.5 mM to 2 mM calcium; from 2% to 20% trehalose, from 10 ppm to 100 ppm non-ionic surfactant, from 10 to 200 mM buffering agent, and a pH from 5.5 to 7.5. In one embodiment, the pH of the composition is from 5.5 to 7.0. In another embodiment, the pH of the composition is from 5.5 to 6.5. In another embodiment, the pH of the composition is 6.0±0.2. In a specific embodiment, the pH of the composition is 6.0. In a specific embodiment, the composition contains from 8,000 U/mL to 500,000 U/mL rfurin.

In one embodiment, a stabilized furin (e.g., rfurin) composition comprises from 100 to 300 mM of a pharmaceutically acceptable salt, from 0.5 mM to 2 mM calcium; a combination of sugar or sugar alcohol and non-ionic surfactant selected from variations 1 to 6035 found in Table 1 to Table 9, from 10 mM to 200 mM buffering agent, and a pH from 5.5 to 7.5. In a specific embodiment, the sugar or sugar alcohol is selected from sucrose, trehalose, mannitol, and a combination thereof. In one embodiment, the pH of the composition is from 5.5 to 7.0. In another embodiment, the pH of the composition is from 5.5 to 6.5. In another embodiment, the pH of the composition is 6.0±0.2. In a specific embodiment, the pH of the composition is 6.0. In a specific embodiment, the composition contains from 8,000 U/mL to 500,000 U/mL rfurin.

In one embodiment, a stabilized furin (e.g., rfurin) composition comprises from 100 to 300 mM of a pharmaceutically acceptable salt, from 0.5 mM to 2 mM calcium; a combination of trehalose and non-ionic surfactant selected from variations 1 to 6035 found in Table 1 to Table 9, from 10 mM to 200 mM buffering agent, and a pH from 5.5 to 7.5. In one embodiment, the pH of the composition is from 5.5 to 7.0. In another embodiment, the pH of the composition is from 5.5 to 6.5. In another embodiment, the pH of the composition is 6.0±0.2. In a specific embodiment, the pH of the composition is 6.0. In a specific embodiment, the composition contains from 8,000 U/mL to 500,000 U/mL rfurin.

In one embodiment, a stabilized furin (e.g., rfurin) composition comprises 190±50 mM of a pharmaceutically acceptable salt, from 0.5 mM to 2 mM calcium; 10±5% sugar or sugar alcohol, 90±25 mM buffering agent, and a pH from 5.5 to 7.5. In one embodiment, the storage stable furin composition further comprises from 10 to 200 ppm non-ionic surfactant. In a specific embodiment, the sugar or sugar alcohol is selected from sucrose, trehalose, mannitol, and a combination thereof. In one embodiment, the pH of the composition is from 5.5 to 7.0. In another embodiment, the pH of the composition is from 5.5 to 6.5. In another embodiment, the pH of the composition is 6.0±0.2. In a specific embodiment, the pH of the composition is 6.0. In a specific embodiment, the composition contains from 8,000 U/mL to 500,000 U/mL rfurin. In another specific embodiment, the composition contains 10±2% sugar or sugar alcohol. In another specific embodiment, the composition contains 10±1% sugar or sugar alcohol. In another specific embodiment, the composition contains 10% sugar or sugar alcohol.

In one embodiment, a stabilized furin (e.g., rfurin) composition comprises 190±50 mM of a pharmaceutically acceptable salt, from 0.5 mM to 2 mM calcium; 10±5% sugar or sugar alcohol, from 10 to 100 ppm non-ionic surfactant, 90±25 mM buffering agent, and a pH from 5.5 to 7.5. In a specific embodiment, the sugar or sugar alcohol is selected from sucrose, trehalose, mannitol, and a combination thereof. In one embodiment, the pH of the composition is from 5.5 to 7.0. In another embodiment, the pH of the composition is from 5.5 to 6.5. In another embodiment, the pH of the composition is 6.0±0.2. In a specific embodiment, the pH of the composition is 6.0. In a specific embodiment, the composition contains from 8,000 U/mL to 500,000 U/mL rfurin. In another specific embodiment, the composition contains 10±2% sugar or sugar alcohol. In another specific embodiment, the composition contains 10±1% sugar or sugar alcohol. In another specific embodiment, the composition contains 10% sugar or sugar alcohol.

In one embodiment, a stabilized furin (e.g., rfurin) composition comprises 190±50 mM of a pharmaceutically acceptable salt, from 0.5 mM to 2 mM calcium; 10±5% trehalose, from 10 to 100 ppm non-ionic surfactant, 90±25 mM buffering agent, and a pH from 5.5 to 7.5. In one embodiment, the pH of the composition is from 5.5 to 7.0. In another embodiment, the pH of the composition is from 5.5 to 6.5. In another embodiment, the pH of the composition is 6.0±0.2. In a specific embodiment, the pH of the composition is 6.0. In a specific embodiment, the composition contains from 8,000 U/mL to 500,000 U/mL rfurin. In another specific embodiment, the composition contains 10±2% trehalose. In another specific embodiment, the composition contains 10±1% trehalose. In another specific embodiment, the composition contains 10% trehalose.

In one embodiment, a stabilized furin (e.g., rfurin) composition comprises 190±50 mM of a pharmaceutically acceptable salt, from 0.5 mM to 2 mM calcium; a combination of sugar or sugar alcohol and non-ionic surfactant selected from variations 1 to 6035 found in Table 1 to Table 9, 90±25 mM buffering agent, and a pH from 5.5 to 7.5. In a specific embodiment, the sugar or sugar alcohol is selected from sucrose, trehalose, mannitol, and a combination thereof. In one embodiment, the pH of the composition is from 5.5 to 7.0. In another embodiment, the pH of the composition is from 5.5 to 6.5. In another embodiment, the pH of the composition is 6.0±0.2. In a specific embodiment, the pH of the composition is 6.0. In a specific embodiment, the composition contains from 8,000 U/mL to 500,000 U/mL rfurin.

In one embodiment, a stabilized furin (e.g., rfurin) composition comprises 190±50 mM of a pharmaceutically acceptable salt, from 0.5 mM to 2 mM calcium; a combination of trehalose and non-ionic surfactant selected from variations 1 to 6035 found in Table 1 to Table 9, from 90±25 mM buffering agent, and a pH from 5.5 to 7.5. In one embodiment, the pH of the composition is from 5.5 to 7.0. In another embodiment, the pH of the composition is from 5.5 to 6.5. In another embodiment, the pH of the composition is 6.0±0.2. In a specific embodiment, the pH of the composition is 6.0. In a specific embodiment, the composition contains from 8,000 U/mL to 500,000 U/mL rfurin.

In one embodiment, a stabilized furin (e.g., rfurin) composition comprises 190 mM of a pharmaceutically acceptable salt, 0.9 mM calcium; 10±5% sugar or sugar alcohol, 91 mM buffering agent, and a pH of 6.0±0.2. In one embodiment, the storage stable furin composition further comprises from 10 to 200 ppm non-ionic surfactant. In a specific embodiment, the sugar or sugar alcohol is selected from sucrose, trehalose, mannitol, and a combination thereof. In one embodiment, the pH of the composition is 6.0. In a specific embodiment, the composition contains from 8,000 U/mL to 500,000 U/mL rfurin. In another specific embodiment, the composition contains 10±2% sugar or sugar alcohol. In another specific embodiment, the composition contains 10±1% sugar or sugar alcohol. In another specific embodiment, the composition contains 10% sugar or sugar alcohol.

In one embodiment, a stabilized furin (e.g., rfurin) composition comprises 190 mM of a pharmaceutically acceptable salt, 0.9 mM calcium; 10±5% sugar or sugar alcohol, 75 ppm non-ionic surfactant, 91 mM buffering agent, and a pH from of 6.0±0.2. In a specific embodiment, the sugar or sugar alcohol is selected from sucrose, trehalose, mannitol, and a combination thereof. In one embodiment, the pH of the composition is 6.0. In a specific embodiment, the composition contains from 8,000 U/mL to 500,000 U/mL rfurin. In another specific embodiment, the composition contains 10±2% sugar or sugar alcohol. In another specific embodiment, the composition contains 10±1% sugar or sugar alcohol. In another specific embodiment, the composition contains 10% sugar or sugar alcohol.

In one embodiment, a stabilized furin (e.g., rfurin) composition comprises 190 mM of a pharmaceutically acceptable salt, 0.9 mM calcium; 10±5% trehalose, 75 ppm non-ionic surfactant, 91 mM buffering agent, and a pH of 6.0±0.2. In one embodiment, the pH of the composition is 6.0. In a specific embodiment, the composition contains from 8,000 U/mL to 500,000 U/mL rfurin. In another specific embodiment, the composition contains 10±2% trehalose. In another specific embodiment, the composition contains 10±1% trehalose. In another specific embodiment, the composition contains 10% trehalose.

In one embodiment, a stabilized furin (e.g., rfurin) composition comprises 190 mM of a pharmaceutically acceptable salt, 0.9 mM calcium; a combination of sugar or sugar alcohol and non-ionic surfactant selected from variations 1 to 6035 found in Table 1 to Table 9, 91 mM buffering agent, and a pH of 6.0±0.2. In a specific embodiment, the sugar or sugar alcohol is selected from sucrose, trehalose, mannitol, and a combination thereof. In one embodiment, the pH of the composition is 6.0. In a specific embodiment, the composition contains from 8,000 U/mL to 500,000 U/mL rfurin.

In one embodiment, a stabilized furin (e.g., rfurin) composition comprises 190 mM of a pharmaceutically acceptable salt, 0.9 mM calcium; a combination of trehalose and non-ionic surfactant selected from variations 1 to 6035 found in Table 1 to Table 9, 91 mM buffering agent, and a pH of 6.0±0.2. In one embodiment, the pH of the composition is 6.0. In a specific embodiment, the composition contains from 8,000 U/mL to 500,000 U/mL rfurin.

In some embodiments, stabilizing agents used in the formulations of the present disclosure are selected from a group that includes, without limitation: sucrose, trehalose, mannitol, raffinose, and arginine. These agents are present in the formulations of the present invention in an amount of from 0.1% to 20%. In certain embodiments, the stabilizing agent is present in an amount of from 5% to 15%, or about 10%. In further embodiments, formulations of the present disclosure include stabilizing agents in an amount of from 0.5% to 19%, 1% to 18%, 1.5% to 17%, 2.0% to 16%, 2.5% to 15%, 3.0% to 14%, 3.5% to 13%, 4.0% to 12%, 4.5% to 11%, 5.0% to 10%, 5.5% to 9%, or 6.0% to 8%. Certain formulations include mannitol, sucrose, and/or trehalose in combination with one or more of any other formulation components disclosed herein.

2. Non-Ionic Surfactants

Advantageously, it was found that the addition of sugar non-ionic surfactant to furin compositions (e.g., rfurin compositions) increases the stability of the composition to mechanical stress. For example, as shown in FIGS. 31 to 42, the inclusion of as little as 10 ppm non-ionic surfactant can increase the stability of a furin composition subjected to mechanical stress by at least 25%. And the inclusion of 50 ppm non-ionic surfactant can increase the stability of a furin composition subjected to mechanical stress by at least 40%. Accordingly, in one aspect of the present disclosure, a storage stable composition of furin (e.g., rfurin) contains a stabilizing amount of non-ionic surfactant.

In one embodiment, storage stable compositions of furin (e.g., rfurin) are provided which contain a non-ionic surfactant selected from a non-ionic water soluble monoglyceride, a non-ionic water soluble diglyceride, a non-ionic water soluble triglyceride, a non-ionic water soluble monofatty acid esters of polyethyelene glycol, a non-ionic water soluble difatty acid esters of polyethyelene glycol, a non-ionic water soluble sorbitan fatty acid ester, a non-ionic polyglycolyzed glyceride, a non-ionic water soluble triblock copolymer, and a combination thereof. In one embodiment, the non-ionic surfactant is a non-ionic water soluble sorbitan fatty acid ester. In a specific embodiment, the non-ionic surfactant is polysorbate 80 (polyoxyethylene (20) sorbitan monooleate).

In one embodiment, the non-ionic surfactant is present at a concentration of from 10 to 200 ppm, 10 to 175 ppm, 10 to 150 ppm, 10 to 125 ppm, 10 to 100 ppm, 10 to 90 ppm, 10 to 80 ppm, 10 to 75 ppm, 10 to 70 ppm, 10 to 60 ppm, 10 to 50 ppm, 10 to 25 ppm, 25 to 200 ppm, 25 to 175 ppm, 25 to 150 ppm, 25 to 125 ppm, 25 to 100 ppm, 25 to 90 ppm, 25 to 80 ppm, 25 to 70 ppm, 25 to 60 ppm, 25 to 50 ppm, 50 to 200 ppm, 50 to 175 ppm, 50 to 150 ppm, 50 to 125 ppm, 50 to 90 ppm, 50 to 80 ppm, 75 to 200 ppm, 75 to 175 ppm, 75 to 150 ppm, 100 to 200 ppm, 100 to 175 ppm, 50±25 ppm, 60±25 ppm, 70±25 ppm, 75±25 ppm, 80±25 ppm, 90±25 ppm, 100±25 ppm, 125±25 ppm, 150±25 ppm, 175±25 ppm, 30±10 ppm, 40±10 ppm, 50±10 ppm, 60±10 ppm, 70±10 ppm, 75±10 ppm, 80±10 ppm, 90±10 ppm, 100±10 ppm, 110±10 ppm, 120±10 ppm, 125±10 ppm, 130±10 ppm, 140±10 ppm, 150±10 ppm, 160±10 ppm, 170±10 ppm, 175±10 ppm, 180±10 ppm, 190±10 ppm, 25 ppm, 30 ppm, 40 ppm, 50 ppm, 60 ppm, 70 ppm, 75 ppm, 80 ppm, 90 ppm, 100 ppm, 110 ppm, 120 ppm, 125 ppm, 130 ppm, 140 ppm, 150 ppm, 160 ppm, 170 ppm, 175 ppm, 180 ppm, 190 ppm, or 200 ppm. In one embodiment, the non-ionic surfactant is a non-ionic water soluble sorbitan fatty acid ester. In a specific embodiment, the non-ionic surfactant is polysorbate 80 (polyoxyethylene (20) sorbitan monooleate).

In one embodiment, a stabilized furin (e.g., rfurin) composition comprises from 50 mM to 500 mM of a pharmaceutically acceptable salt, from 0.5 mM to 5 mM calcium; from 10 ppm to 200 ppm non-ionic surfactant, from 10 to 200 mM buffering agent, and a pH from 5.5 to 7.5. In one embodiment, the storage stable furin composition further comprises from 2% to 20% sugar or sugar alcohol. In one specific embodiment, the non-ionic surfactant is a non-ionic water soluble sorbitan fatty acid ester. In a specific embodiment, the non-ionic surfactant is polysorbate 80 (polyoxyethylene (20) sorbitan monooleate). In one embodiment, the pH of the composition is from 5.5 to 7.0. In another embodiment, the pH of the composition is from 5.5 to 6.5. In another embodiment, the pH of the composition is 6.0±0.2. In a specific embodiment, the pH of the composition is 6.0. In a specific embodiment, the composition contains from 8,000 U/mL to 500,000 U/mL rfurin.

In one embodiment, a stabilized furin (e.g., rfurin) composition comprises from 50 to 500 mM of a pharmaceutically acceptable salt, from 0.5 mM to 5 mM calcium; from 2% to 10% sugar or sugar alcohol, from 10 ppm to 200 ppm non-ionic surfactant, from 10 mM to 200 mM buffering agent, and a pH from 5.5 to 7.5. In one specific embodiment, the non-ionic surfactant is a non-ionic water soluble sorbitan fatty acid ester. In a specific embodiment, the non-ionic surfactant is polysorbate 80 (polyoxyethylene (20) sorbitan monooleate). In one embodiment, the pH of the composition is from 5.5 to 7.0. In another embodiment, the pH of the composition is from 5.5 to 6.5. In another embodiment, the pH of the composition is 6.0±0.2. In a specific embodiment, the pH of the composition is 6.0. In a specific embodiment, the composition contains from 8,000 U/mL to 500,000 U/mL rfurin.

In one embodiment, a stabilized furin (e.g., rfurin) composition comprises from 50 to 500 mM of a pharmaceutically acceptable salt, from 0.5 mM to 5 mM calcium; from 2% to 10% sugar or sugar alcohol, from 10 ppm to 200 ppm non-ionic water soluble sorbitan fatty acid ester, from 10 mM to 200 mM buffering agent, and a pH from 5.5 to 7.5. In a specific embodiment, the non-ionic water soluble sorbitan fatty acid ester is polysorbate 80 (polyoxyethylene (20) sorbitan monooleate). In one embodiment, the pH of the composition is from 5.5 to 7.0. In another embodiment, the pH of the composition is from 5.5 to 6.5. In another embodiment, the pH of the composition is 6.0±0.2. In a specific embodiment, the pH of the composition is 6.0. In a specific embodiment, the composition contains from 8,000 U/mL to 500,000 U/mL rfurin.

In one embodiment, a stabilized furin (e.g., rfurin) composition comprises from 50 to 500 mM of a pharmaceutically acceptable salt, from 0.5 mM to 5 mM calcium; a combination of sugar or sugar alcohol and non-ionic surfactant selected from variations 1 to 6035 found in Table 1 to Table 9, from 10 mM to 200 mM buffering agent, and a pH from 5.5 to 7.5. In a specific embodiment, the non-ionic surfactant is a non-ionic water soluble sorbitan fatty acid ester. In another specific embodiment, the sugar or sugar alcohol is selected from sucrose, trehalose, mannitol, and a combination thereof. In yet another specific embodiment, the non-ionic surfactant is a non-ionic water soluble sorbitan fatty acid ester and the sugar or sugar alcohol is selected from sucrose, trehalose, mannitol, and a combination thereof. In one embodiment, the pH of the composition is from 5.5 to 7.0. In another embodiment, the pH of the composition is from 5.5 to 6.5. In another embodiment, the pH of the composition is 6.0±0.2. In a specific embodiment, the pH of the composition is 6.0. In a specific embodiment, the composition contains from 8,000 U/mL to 500,000 U/mL rfurin.

In one embodiment, a stabilized furin (e.g., rfurin) composition comprises from 50 to 500 mM of a pharmaceutically acceptable salt, from 0.5 mM to 5 mM calcium; a combination of sugar or sugar alcohol and a non-ionic water soluble sorbitan fatty acid ester selected from variations 1 to 6035 found in Table 1 to Table 9, from 10 mM to 200 mM buffering agent, and a pH from 5.5 to 7.5. In a specific embodiment, the non-ionic surfactant is polysorbate 80 (polyoxyethylene (20) sorbitan monooleate). In another specific embodiment, the sugar or sugar alcohol is trehalose. In yet another specific embodiment, the non-ionic water soluble sorbitan fatty acid ester is polysorbate 80 (polyoxyethylene (20) sorbitan monooleate) and the sugar or sugar alcohol is trehalose. In one embodiment, the pH of the composition is from 5.5 to 7.0. In another embodiment, the pH of the composition is from 5.5 to 6.5. In another embodiment, the pH of the composition is 6.0±0.2. In a specific embodiment, the pH of the composition is 6.0. In a specific embodiment, the composition contains from 8,000 U/mL to 500,000 U/mL rfurin.

In one embodiment, a stabilized furin (e.g., rfurin) composition comprises from 100 to 300 mM of a pharmaceutically acceptable salt, from 0.5 mM to 2 mM calcium; from 10 ppm to 200 ppm non-ionic surfactant, from 10 mM to 200 mM buffering agent, and a pH from 5.5 to 7.5. In one embodiment, the storage stable furin composition further comprises from 2% to 20% sugar or sugar alcohol. In one embodiment, the non-ionic surfactant is a non-ionic water soluble sorbitan fatty acid ester. In a specific embodiment, the non-ionic surfactant is polysorbate 80 (polyoxyethylene (20) sorbitan monooleate). In one embodiment, the pH of the composition is from 5.5 to 7.0. In another embodiment, the pH of the composition is from 5.5 to 6.5. In another embodiment, the pH of the composition is 6.0±0.2. In a specific embodiment, the pH of the composition is 6.0. In a specific embodiment, the composition contains from 8,000 U/mL to 500,000 U/mL rfurin.

In one embodiment, a stabilized furin (e.g., rfurin) composition comprises from 100 mM to 300 mM of a pharmaceutically acceptable salt, from 0.5 mM to 2 mM calcium; from 2% to 10% sugar or sugar alcohol, from 10 ppm to 200 ppm non-ionic surfactant, from 10 to 200 mM buffering agent, and a pH from 5.5 to 7.5. In one embodiment, the non-ionic surfactant is a non-ionic water soluble sorbitan fatty acid ester. In a specific embodiment, the non-ionic surfactant is polysorbate 80 (polyoxyethylene (20) sorbitan monooleate). In one embodiment, the pH of the composition is from 5.5 to 7.0. In another embodiment, the pH of the composition is from 5.5 to 6.5. In another embodiment, the pH of the composition is 6.0±0.2. In a specific embodiment, the pH of the composition is 6.0. In a specific embodiment, the composition contains from 8,000 U/mL to 500,000 U/mL rfurin.

In one embodiment, a stabilized furin (e.g., rfurin) composition comprises from 100 mM to 300 mM of a pharmaceutically acceptable salt, from 0.5 mM to 2 mM calcium; from 2% to 10% sugar or sugar alcohol, from 10 ppm to 200 ppm non-ionic water soluble sorbitan fatty acid ester, from 10 to 200 mM buffering agent, and a pH from 5.5 to 7.5. In a specific embodiment, the non-ionic water soluble sorbitan fatty acid ester is polysorbate 80 (polyoxyethylene (20) sorbitan monooleate). In one embodiment, the pH of the composition is from 5.5 to 7.0. In another embodiment, the pH of the composition is from 5.5 to 6.5. In another embodiment, the pH of the composition is 6.0±0.2. In a specific embodiment, the pH of the composition is 6.0. In a specific embodiment, the composition contains from 8,000 U/mL to 500,000 U/mL rfurin.

In one embodiment, a stabilized furin (e.g., rfurin) composition comprises from 100 to 300 mM of a pharmaceutically acceptable salt, from 0.5 mM to 2 mM calcium; a combination of sugar or sugar alcohol and non-ionic surfactant selected from variations 1 to 6035 found in Table 1 to Table 9, from 10 mM to 200 mM buffering agent, and a pH from 5.5 to 7.5. In a specific embodiment, the non-ionic surfactant is a non-ionic water soluble sorbitan fatty acid ester. In another specific embodiment, the sugar or sugar alcohol is selected from sucrose, trehalose, mannitol, and a combination thereof. In yet another specific embodiment, the non-ionic surfactant is a non-ionic water soluble sorbitan fatty acid ester and the sugar or sugar alcohol is selected from sucrose, trehalose, mannitol, and a combination thereof. In one embodiment, the pH of the composition is from 5.5 to 7.0. In another embodiment, the pH of the composition is from 5.5 to 6.5. In another embodiment, the pH of the composition is 6.0±0.2. In a specific embodiment, the pH of the composition is 6.0. In a specific embodiment, the composition contains from 8,000 U/mL to 500,000 U/mL rfurin.

In one embodiment, a stabilized furin (e.g., rfurin) composition comprises from 100 to 300 mM of a pharmaceutically acceptable salt, from 0.5 mM to 2 mM calcium; a combination of sugar or sugar alcohol and non-ionic water soluble sorbitan fatty acid ester selected from variations 1 to 6035 found in Table 1 to Table 9, from 10 mM to 200 mM buffering agent, and a pH from 5.5 to 7.5. In a specific embodiment, the non-ionic water soluble sorbitan fatty acid ester is polysorbate 80 (polyoxyethylene (20) sorbitan monooleate). In another specific embodiment, the sugar or sugar alcohol is trehalose. In yet another specific embodiment, the non-ionic water soluble sorbitan fatty acid ester is polysorbate 80 (polyoxyethylene (20) sorbitan monooleate) and the sugar or sugar alcohol is trehalose. In one embodiment, the pH of the composition is from 5.5 to 7.0. In another embodiment, the pH of the composition is from 5.5 to 6.5. In another embodiment, the pH of the composition is 6.0±0.2. In a specific embodiment, the pH of the composition is 6.0. In a specific embodiment, the composition contains from 8,000 U/mL to 500,000 U/mL rfurin.

In one embodiment, a stabilized furin (e.g., rfurin) composition comprises 190±50 mM of a pharmaceutically acceptable salt, from 0.5 mM to 2 mM calcium; 75±25% non-ionic surfactant, 90±25 mM buffering agent, and a pH from 5.5 to 7.5. In one embodiment, the storage stable furin composition further comprises from 2% to 20% sugar or sugar alcohol. In one embodiment, the non-ionic surfactant is a non-ionic water soluble sorbitan fatty acid ester. In a specific embodiment, the non-ionic surfactant is polysorbate 80 (polyoxyethylene (20) sorbitan monooleate). In one embodiment, the pH of the composition is from 5.5 to 7.0. In another embodiment, the pH of the composition is from 5.5 to 6.5. In another embodiment, the pH of the composition is 6.0±0.2. In a specific embodiment, the pH of the composition is 6.0. In a specific embodiment, the composition contains from 8,000 U/mL to 500,000 U/mL rfurin. In one specific embodiment, the composition contains 75±15 ppm non-ionic surfactant. In another specific embodiment, the composition contains 75±5 ppm non-ionic surfactant. In another specific embodiment, the composition contains 75 ppm non-ionic surfactant.

In one embodiment, a stabilized furin (e.g., rfurin) composition comprises 190±50 mM of a pharmaceutically acceptable salt, from 0.5 mM to 2 mM calcium; from 2% to 10% sugar or sugar alcohol, 75±25 ppm non-ionic surfactant, 90±25 mM buffering agent, and a pH from 5.5 to 7.5. In one embodiment, the non-ionic surfactant is a non-ionic water soluble sorbitan fatty acid ester. In a specific embodiment, the non-ionic surfactant is polysorbate 80 (polyoxyethylene (20) sorbitan monooleate). In one embodiment, the pH of the composition is from 5.5 to 7.0. In another embodiment, the pH of the composition is from 5.5 to 6.5. In another embodiment, the pH of the composition is 6.0±0.2. In a specific embodiment, the pH of the composition is 6.0. In a specific embodiment, the composition contains from 8,000 U/mL to 500,000 U/mL rfurin. In one specific embodiment, the composition contains 75±15 ppm non-ionic surfactant. In another specific embodiment, the composition contains 75±5 ppm non-ionic surfactant. In another specific embodiment, the composition contains 75 ppm non-ionic surfactant.

In one embodiment, a stabilized furin (e.g., rfurin) composition comprises 190±50 mM of a pharmaceutically acceptable salt, from 0.5 mM to 2 mM calcium; from 2% to 10% sugar or sugar alcohol, 75±25 ppm non-ionic water soluble sorbitan fatty acid ester, 90±25 mM buffering agent, and a pH from 5.5 to 7.5. In a specific embodiment, the non-ionic water soluble sorbitan fatty acid ester is polysorbate 80 (polyoxyethylene (20) sorbitan monooleate). In another specific embodiment, the sugar or sugar alcohol is trehalose. In yet another specific embodiment, the non-ionic water soluble sorbitan fatty acid ester is polysorbate 80 (polyoxyethylene (20) sorbitan monooleate) and the sugar or sugar alcohol is trehalose. In one embodiment, the pH of the composition is from 5.5 to 7.0. In another embodiment, the pH of the composition is from 5.5 to 6.5. In another embodiment, the pH of the composition is 6.0±0.2. In a specific embodiment, the pH of the composition is 6.0. In a specific embodiment, the composition contains from 8,000 U/mL to 500,000 U/mL rfurin. In one specific embodiment, the composition contains 75±15 ppm non-ionic water soluble sorbitan fatty acid ester. In another specific embodiment, the composition contains 75±5 ppm non-ionic water soluble sorbitan fatty acid ester. In another specific embodiment, the composition contains 75 ppm non-ionic water soluble sorbitan fatty acid ester.

In one embodiment, a stabilized furin (e.g., rfurin) composition comprises 190±50 mM of a pharmaceutically acceptable salt, from 0.5 mM to 2 mM calcium; a combination of sugar or sugar alcohol and non-ionic surfactant selected from variations 1 to 6035 found in Table 1 to Table 9, 90±25 mM buffering agent, and a pH from 5.5 to 7.5. In a specific embodiment, the non-ionic surfactant is a non-ionic water soluble sorbitan fatty acid ester. In another specific embodiment, the sugar or sugar alcohol is selected from sucrose, trehalose, mannitol, and a combination thereof. In yet another specific embodiment, the non-ionic surfactant is a non-ionic water soluble sorbitan fatty acid ester and the sugar or sugar alcohol is selected from sucrose, trehalose, mannitol, and a combination thereof. In one embodiment, the pH of the composition is from 5.5 to 7.0. In another embodiment, the pH of the composition is from 5.5 to 6.5. In another embodiment, the pH of the composition is 6.0±0.2. In a specific embodiment, the pH of the composition is 6.0. In a specific embodiment, the composition contains from 8,000 U/mL to 500,000 U/mL rfurin.

In one embodiment, a stabilized furin (e.g., rfurin) composition comprises 190±50 mM of a pharmaceutically acceptable salt, from 0.5 mM to 2 mM calcium; a combination of sugar or sugar alcohol and non-ionic water soluble sorbitan fatty acid ester selected from variations 1 to 6035 found in Table 1 to Table 9, from 90±25 mM buffering agent, and a pH from 5.5 to 7.5. In a specific embodiment, the non-ionic water soluble sorbitan fatty acid ester is polysorbate 80 (polyoxyethylene (20) sorbitan monooleate). In another specific embodiment, the sugar or sugar alcohol is trehalose. In yet another specific embodiment, the non-ionic water soluble sorbitan fatty acid ester is polysorbate 80 (polyoxyethylene (20) sorbitan monooleate) and the sugar or sugar alcohol is trehalose. In one embodiment, the pH of the composition is from 5.5 to 7.0. In another embodiment, the pH of the composition is from 5.5 to 6.5. In another embodiment, the pH of the composition is 6.0±0.2. In a specific embodiment, the pH of the composition is 6.0. In a specific embodiment, the composition contains from 8,000 U/mL to 500,000 U/mL rfurin.

In one embodiment, a stabilized furin (e.g., rfurin) composition comprises 190 mM of a pharmaceutically acceptable salt, 0.9 mM calcium; 75±25% non-ionic surfactant, 91 mM buffering agent, and a pH of 6.0±0.2. In one embodiment, the storage stable furin composition further comprises from 2% to 10% sugar or sugar alcohol. In one embodiment, the non-ionic surfactant is a non-ionic water soluble sorbitan fatty acid ester. In a specific embodiment, the non-ionic surfactant is polysorbate 80 (polyoxyethylene (20) sorbitan monooleate). In one embodiment, the pH of the composition is 6.0. In a specific embodiment, the composition contains from 8,000 U/mL to 500,000 U/mL rfurin. In one specific embodiment, the composition contains 75±15 ppm non-ionic surfactant. In another specific embodiment, the composition contains 75±5 ppm non-ionic surfactant. In another specific embodiment, the composition contains 75 ppm non-ionic surfactant.

In one embodiment, a stabilized furin (e.g., rfurin) composition comprises 190 mM of a pharmaceutically acceptable salt, 0.9 mM calcium; 10% sugar or sugar alcohol, 75±25 ppm non-ionic surfactant, 91 mM buffering agent, and a pH from of 6.0±0.2. In one embodiment, the non-ionic surfactant is a non-ionic water soluble sorbitan fatty acid ester. In a specific embodiment, the non-ionic surfactant is polysorbate 80 (polyoxyethylene (20) sorbitan monooleate). In one embodiment, the pH of the composition is 6.0. In a specific embodiment, the composition contains from 8,000 U/mL to 500,000 U/mL rfurin. In one specific embodiment, the composition contains 75±15 ppm non-ionic surfactant. In another specific embodiment, the composition contains 75±5 ppm non-ionic surfactant. In another specific embodiment, the composition contains 75 ppm non-ionic surfactant.

In one embodiment, a stabilized furin (e.g., rfurin) composition comprises 190 mM of a pharmaceutically acceptable salt, 0.9 mM calcium; 10% sugar or sugar alcohol, 75±25 ppm non-ionic water soluble sorbitan fatty acid ester, 91 mM buffering agent, and a pH of 6.0±0.2. In one embodiment, the pH of the composition is 6.0. In a specific embodiment, the non-ionic water soluble sorbitan fatty acid ester is polysorbate 80 (polyoxyethylene (20) sorbitan monooleate). In another specific embodiment, the sugar or sugar alcohol is trehalose. In yet another specific embodiment, the non-ionic water soluble sorbitan fatty acid ester is polysorbate 80 (polyoxyethylene (20) sorbitan monooleate) and the sugar or sugar alcohol is trehalose. In a specific embodiment, the composition contains from 8,000 U/mL to 500,000 U/mL rfurin. In one specific embodiment, the composition contains 75±15 ppm non-ionic water soluble sorbitan fatty acid ester. In another specific embodiment, the composition contains 75±5 ppm non-ionic water soluble sorbitan fatty acid ester. In another specific embodiment, the composition contains 75 ppm non-ionic water soluble sorbitan fatty acid ester.

In one embodiment, a stabilized furin (e.g., rfurin) composition comprises 190 mM of a pharmaceutically acceptable salt, 0.9 mM calcium; a combination of sugar or sugar alcohol and non-ionic surfactant selected from variations 1 to 6035 found in Table 1 to Table 9, 91 mM buffering agent, and a pH of 6.0±0.2. In a specific embodiment, the non-ionic surfactant is a non-ionic water soluble sorbitan fatty acid ester. In another specific embodiment, the sugar or sugar alcohol is selected from sucrose, trehalose, mannitol, and a combination thereof. In yet another specific embodiment, the non-ionic surfactant is a non-ionic water soluble sorbitan fatty acid ester and the sugar or sugar alcohol is selected from sucrose, trehalose, mannitol, and a combination thereof. In one embodiment, the pH of the composition is 6.0. In a specific embodiment, the composition contains from 8,000 U/mL to 500,000 U/mL rfurin.

In one embodiment, a stabilized furin (e.g., rfurin) composition comprises 190 mM of a pharmaceutically acceptable salt, 0.9 mM calcium; a combination of sugar or sugar alcohol and non-ionic water soluble sorbitan fatty acid ester selected from variations 1 to 6035 found in Table 1 to Table 9, 91 mM buffering agent, and a pH of 6.0±0.2. In a specific embodiment, the non-ionic water soluble sorbitan fatty acid ester is polysorbate 80 (polyoxyethylene (20) sorbitan monooleate). In another specific embodiment, the sugar or sugar alcohol is trehalose. In yet another specific embodiment, the non-ionic water soluble sorbitan fatty acid ester is polysorbate 80 (polyoxyethylene (20) sorbitan monooleate) and the sugar or sugar alcohol is trehalose. In one embodiment, the pH of the composition is 6M. In a specific embodiment, the composition contains from 8,000 U/mL to 500,000 U/mL rfurin.

The furin (e.g., rfurin) compositions of the present invention also preferably include a surfactant, preferably a non-ionic surfactant, and preferably in an amount from 0.1 ppm to 150 ppm, or from 65 ppm to 80 ppm, or at about 75 ppm. In further embodiments, the furin (e.g., rfurin) compositions include a surfactant in an amount of from 0.5 ppm to 140 ppm, 1.0 ppm to 130 ppm, 10 ppm to 120 ppm, 20 ppm to 110 ppm, 30 ppm to 100 ppm, 40 ppm to 95 ppm, 50 ppm to 90 ppm, 55 ppm to 85 ppm, 60 ppm to 80 ppm, or 70 ppm to 75 ppm. In certain embodiments, the surfactant is chosen from the group consisting of polysorbate 20, polysorbate 40, polysorbate 60, polysorbate 80, pluronic polyols, glycerol, glucamides (such as Mega 8), tritons, and Brij 35 (polyoxyethylene 23 lauryl ether). Several grades of pluronic polyols (sold under the trade name Pluronic, manufactured by the BASF Wyandotte Corporation) are available. These polyols, of diversified molecular weight (from 1,000 to over 16,000) and physico-chemical properties have been used as surfactants. Pluronic F-38, of a molecular weight of 5,000 and Pluronic F-68, molecular weight 9,000, both contain (by weight) 80 percent hydrophilic polyoxyethylene groups and 20 percent hydrophobic polyoxypropylene groups. In one embodiment, the surfactant is polysorbate 80. In a particular embodiment, the polysorbate 80 is vegetable-derived polysorbate 80.

B. Pharmaceutically Acceptable Salts

The stabilized compositions of furin (e.g., rfurin) provided herein generally include a pharmaceutically acceptable salt at a concentration tolerated by the furin polypeptide during storage. In one embodiment, the pharmaceutically acceptable salt is a chloride salt. In a specific embodiment, the pharmaceutically acceptable salt is a monovalent chloride salt. In a more specific embodiment, the pharmaceutically acceptable salt is sodium chloride, potassium chloride, or a combination thereof.

In one embodiment, the concentration of pharmaceutically acceptable salt in a stabilized furin (e.g., rfurin) composition provided herein is from 10 mM to 500 mM. In another embodiment, the concentration of pharmaceutically acceptable salt is from 100 mM to 300 mM. In another embodiment, the concentration of pharmaceutically acceptable salt is from 150 mM to 250 mM. In yet other embodiments, the concentration of pharmaceutically acceptable salt in the stabilized furin (e.g., rfurin) compositions provided herein is selected from variations 6036 to 6180 found in Table 10.

TABLE 10

Exemplary pharmaceutically acceptable salt concentrations useful for the stabilization of furin (e.g., rfurin) compositions.

| | |
|---|---|
| 10 mM to 500 mM | Var. 6036 |
| 100 mM to 300 mM | Var. 6037 |
| 150 mM to 250 mM | Var. 6038 |
| 50 mM to 500 mM | Var. 6039 |
| 50 mM to 450 mM | Var. 6040 |
| 50 mM to 400 mM | Var. 6041 |
| 100 to 400 mM | Var. 6042 |
| 100 mM to 350 mM | Var. 6043 |
| 100 mM to 250 mM | Var. 6044 |
| 100 mM to 200 mM | Var. 6045 |
| 150 mM to 400 mM | Var. 6046 |
| 150 mM to 350 mM | Var. 6047 |
| 150 mM to 300 mM | Var. 6048 |
| 150 mM to 250 mM | Var. 6049 |
| 150 mM to 200 mM | Var. 6050 |
| 175 mM to 225 mM | Var. 6051 |
| 175 mM to 200 mM | Var. 6052 |
| 100 ± 25 mM | Var. 6053 |
| 150 ± 25 mM | Var. 6054 |
| 200 ± 25 mM | Var. 6055 |
| 250 ± 25 mM | Var. 6056 |
| 300 ± 25 mM | Var. 6057 |
| 350 ± 25 mM | Var. 6058 |
| 400 ± 25 mM | Var. 6059 |

TABLE 10-continued

Exemplary pharmaceutically acceptable salt concentrations useful for the stabilization of furin (e.g., rfurin) compositions.

| | |
|---|---|
| 450 ± 25 mM | Var. 6060 |
| 190 ± 150 mM | Var. 6061 |
| 190 ± 125 mM | Var. 6062 |
| 190 ± 100 mM | Var. 6063 |
| 190 ± 90 mM | Var. 6064 |
| 190 ± 80 mM | Var. 6065 |
| 190 ± 70 mM | Var. 6066 |
| 190 ± 60 mM | Var. 6067 |
| 190 ± 50 mM | Var. 6068 |
| 190 ± 40 mM | Var. 6069 |
| 190 ± 30 mM | Var. 6070 |
| 190 ± 25 mM | Var. 6071 |
| 190 ± 20 mM | Var. 6072 |
| 190 ± 15 mM | Var. 6073 |
| 190 ± 10 mM | Var. 6074 |
| 190 ± 5 mM | Var. 6075 |
| 190 ± 2 mM | Var. 6076 |
| 100 ± 5 mM | Var. 6077 |
| 105 ± 5 mM | Var. 6078 |
| 110 ± 5 mM | Var. 6079 |
| 115 ± 5 mM | Var. 6080 |
| 120 ± 5 mM | Var. 6081 |
| 125 ± 5 mM | Var. 6082 |
| 130 ± 5 mM | Var. 6083 |
| 135 ± 5 mM | Var. 6084 |
| 140 ± 5 mM | Var. 6085 |
| 145 ± 5 mM | Var. 6086 |
| 150 ± 5 mM | Var. 6087 |
| 155 ± 5 mM | Var. 6088 |
| 160 ± 5 mM | Var. 6089 |
| 165 ± 5 mM | Var. 6090 |
| 170 ± 5 mM | Var. 6091 |
| 175 ± 5 mM | Var. 6092 |
| 180 ± 5 mM | Var. 6093 |
| 185 ± 5 mM | Var. 6094 |
| 186 ± 5 mM | Var. 6095 |
| 187 ± 5 mM | Var. 6096 |
| 188 ± 5 mM | Var. 6097 |
| 189 ± 5 mM | Var. 6098 |
| 190 ± 5 mM | Var. 6099 |
| 191 ± 5 mM | Var. 6100 |
| 192 ± 5 mM | Var. 6101 |
| 193 ± 5 mM | Var. 6102 |
| 194 ± 5 mM | Var. 6103 |
| 195 ± 5 mM | Var. 6104 |
| 196 ± 5 mM | Var. 6105 |
| 197 ± 5 mM | Var. 6106 |
| 198 ± 5 mM | Var. 6107 |
| 199 ± 5 mM | Var. 6108 |
| 200 ± 5 mM | Var. 6109 |
| 205 ± 5 mM | Var. 6110 |
| 210 ± 5 mM | Var. 6111 |
| 215 ± 5 mM | Var. 6112 |
| 220 ± 5 mM | Var. 6113 |
| 225 ± 5 mM | Var. 6114 |
| 230 ± 5 mM | Var. 6115 |
| 235 ± 5 mM | Var. 6116 |
| 240 ± 5 mM | Var. 6117 |
| 245 ± 5 mM | Var. 6118 |
| 250 ± 5 mM | Var. 6119 |
| 255 ± 5 mM | Var. 6120 |
| 260 ± 5 mM | Var. 6121 |
| 265 ± 5 mM | Var. 6122 |
| 270 ± 5 mM | Var. 6123 |
| 275 ± 5 mM | Var. 6124 |
| 280 ± 5 mM | Var. 6125 |
| 285 ± 5 mM | Var. 6126 |
| 290 ± 5 mM | Var. 6127 |
| 295 ± 5 mM | Var. 6128 |
| 300 ± 5 mM | Var. 6129 |
| 175 mM | Var. 6130 |
| 176 mM | Var. 6131 |
| 177 mM | Var. 6132 |
| 178 mM | Var. 6133 |
| 179 mM | Var. 6134 |
| 180 mM | Var. 6135 |
| 181 mM | Var. 6136 |

TABLE 10-continued

Exemplary pharmaceutically acceptable salt concentrations useful for the stabilization of furin (e.g., rfurin) compositions.

| | |
|---|---|
| 182 mM | Var. 6137 |
| 183 mM | Var. 6138 |
| 184 mM | Var. 6139 |
| 185 mM | Var. 6140 |
| 186 mM | Var. 6141 |
| 187 mM | Var. 6142 |
| 188 mM | Var. 6143 |
| 189 mM | Var. 6144 |
| 190 mM | Var. 6145 |
| 191 mM | Var. 6146 |
| 192 mM | Var. 6147 |
| 193 mM | Var. 6148 |
| 194 mM | Var. 6149 |
| 195 mM | Var. 6150 |
| 196 mM | Var. 6151 |
| 197 mM | Var. 6152 |
| 198 mM | Var. 6153 |
| 199 mM | Var. 6154 |
| 200 mM | Var. 6155 |
| 201 mM | Var. 6156 |
| 202 mM | Var. 6157 |
| 203 mM | Var. 6158 |
| 204 mM | Var. 6159 |
| 205 mM | Var. 6160 |
| 206 mM | Var. 6161 |
| 207 mM | Var. 6162 |
| 208 mM | Var. 6163 |
| 209 mM | Var. 6164 |
| 210 mM | Var. 6165 |
| 211 mM | Var. 6166 |
| 212 mM | Var. 6167 |
| 213 mM | Var. 6168 |
| 214 mM | Var. 6169 |
| 215 mM | Var. 6170 |
| 216 mM | Var. 6171 |
| 217 mM | Var. 6172 |
| 218 mM | Var. 6173 |
| 219 mM | Var. 6174 |
| 220 mM | Var. 6175 |
| 221 mM | Var. 6176 |
| 222 mM | Var. 6177 |
| 223 mM | Var. 6178 |
| 224 mM | Var. 6179 |
| 225 mM | Var. 6180 |

Var. = Variation

In one embodiment, a stabilized furin (e.g., rfurin) composition comprises a pharmaceutically acceptable salt at a concentration selected from variations 6036 to 6180 found in Table 10, from 0.5 mM to 5 mM calcium, from 10 ppm to 200 ppm non-ionic surfactant, from 10 to 200 mM buffering agent, and a pH from 5.5 to 7.5. In one embodiment, the storage stable furin composition further comprises from 2% to 20% sugar or sugar alcohol. In one embodiment, the non-ionic surfactant is a non-ionic water soluble sorbitan fatty acid ester. In a specific embodiment, the non-ionic surfactant is polysorbate 80 (polyoxyethylene (20) sorbitan monooleate). In one embodiment, the pharmaceutically acceptable salt is sodium chloride, potassium chloride, or a combination thereof. In a specific embodiment, pharmaceutically acceptable salt is sodium chloride. In another specific embodiment, pharmaceutically acceptable salt is potassium chloride. In one embodiment, the pH of the composition is from 5.5 to 7.0. In another embodiment, the pH of the composition is from 5.5 to 6.5. In another embodiment, the pH of the composition is 6.0±0.2. In a specific embodiment, the pH of the composition is 6.0. In a specific embodiment, the composition contains from 8,000 U/mL to 500,000 U/mL rfurin.

In one embodiment, a stabilized furin (e.g., rfurin) composition comprises a pharmaceutically acceptable salt at a concentration selected from variations 6036 to 6180 found in Table 10, from 0.5 mM to 5 mM calcium, from 2% to 20% sugar or sugar alcohol, from 10 to 200 mM buffering agent, and a pH from 5.5 to 7.5. In one embodiment, the storage stable furin composition further comprises from 10 ppm to 200 ppm non-ionic surfactant. In one embodiment, the sugar or sugar alcohol is selected from sucrose, trehalose, mannitol, and a combination thereof. In a specific embodiment, the sugar or sugar alcohol is trehalose. In one embodiment, the pharmaceutically acceptable salt is sodium chloride, potassium chloride, or a combination thereof. In a specific embodiment, pharmaceutically acceptable salt is sodium chloride. In another specific embodiment, pharmaceutically acceptable salt is potassium chloride. In one embodiment, the pH of the composition is from 5.5 to 7.0. In another embodiment, the pH of the composition is from 5.5 to 6.5. In another embodiment, the pH of the composition is 6.0±0.2. In a specific embodiment, the pH of the composition is 6.0. In a specific embodiment, the composition contains from 8,000 U/mL to 500,000 U/mL rfurin.

In one embodiment, a stabilized furin (e.g., rfurin) composition comprises a pharmaceutically acceptable salt at a concentration selected from variations 6036 to 6180 found in Table 10, from 0.5 mM to 5 mM calcium, from 2% to 20% sugar or sugar alcohol, from 10 ppm to 200 ppm non-ionic surfactant, from 10 to 200 mM buffering agent, and a pH from 5.5 to 7.5. In one embodiment, the non-ionic surfactant is a non-ionic water soluble sorbitan fatty acid ester. In a specific embodiment, the non-ionic surfactant is polysorbate 80 (polyoxyethylene (20) sorbitan monooleate). In one embodiment, the sugar or sugar alcohol is selected from sucrose, trehalose, mannitol, and a combination thereof. In a specific embodiment, the sugar or sugar alcohol is trehalose. In a specific embodiment, the non-ionic surfactant is polysorbate 80 (polyoxyethylene (20) sorbitan monooleate) and the sugar or sugar alcohol is trehalose. In one embodiment, the pharmaceutically acceptable salt is sodium chloride, potassium chloride, or a combination thereof. In a specific embodiment, pharmaceutically acceptable salt is sodium chloride. In another specific embodiment, pharmaceutically acceptable salt is potassium chloride. In one embodiment, the pH of the composition is from 5.5 to 7.0. In another embodiment, the pH of the composition is from 5.5 to 6.5. In another embodiment, the pH of the composition is 6.0±0.2. In a specific embodiment, the pH of the composition is 6.0. In a specific embodiment, the composition contains from 8,000 U/mL to 500,000 U/mL rfurin.

In one embodiment, a stabilized furin (e.g., rfurin) composition comprises a pharmaceutically acceptable salt at a concentration selected from variations 6036 to 6180 found in Table 10, from 0.5 mM to 5 mM calcium, from 2% to 10% sugar or sugar alcohol, from 10 ppm to 100 ppm non-ionic surfactant, from 10 to 200 mM buffering agent, and a pH from 5.5 to 7.5. In one embodiment, the non-ionic surfactant is a non-ionic water soluble sorbitan fatty acid ester. In a specific embodiment, the non-ionic surfactant is polysorbate 80 (polyoxyethylene (20) sorbitan monooleate). In one embodiment, the sugar or sugar alcohol is selected from sucrose, trehalose, mannitol, and a combination thereof. In a specific embodiment, the sugar or sugar alcohol is trehalose. In a specific embodiment, the non-ionic surfactant is polysorbate 80 (polyoxyethylene (20) sorbitan monooleate) and the sugar or sugar alcohol is trehalose. In one embodiment, the pharmaceutically acceptable salt is sodium chloride, potassium chloride, or a combination thereof. In a specific embodiment, pharmaceutically acceptable salt is sodium chloride. In another specific embodiment, pharmaceutically acceptable salt is potassium chloride. In one embodiment, the pH of the composition is from 5.5 to 7.0. In another embodiment, the pH of the composition is from 5.5 to 6.5. In another embodiment, the pH of the composition is 6.0±0.2. In a specific embodiment, the pH of the composition is 6.0. In a specific embodiment, the composition contains from 8,000 U/mL to 500,000 U/mL rfurin.

In one embodiment, a stabilized furin (e.g., rfurin) composition comprises a pharmaceutically acceptable salt at a concentration selected from variations 6036 to 6180 found in Table 10, from 0.5 mM to 2 mM calcium, 10±5% sugar or sugar alcohol, 75±25 ppm non-ionic surfactant, from 10 to 200 mM buffering agent, and a pH from 5.5 to 7.5. In one embodiment, the non-ionic surfactant is a non-ionic water soluble sorbitan fatty acid ester. In a specific embodiment, the non-ionic surfactant is polysorbate 80 (polyoxyethylene (20) sorbitan monooleate). In one embodiment, the sugar or sugar alcohol is selected from sucrose, trehalose, mannitol, and a combination thereof. In a specific embodiment, the sugar or sugar alcohol is trehalose. In a specific embodiment, the non-ionic surfactant is polysorbate 80 (polyoxyethylene (20) sorbitan monooleate) and the sugar or sugar alcohol is trehalose. In one embodiment, the pharmaceutically acceptable salt is sodium chloride, potassium chloride, or a combination thereof. In a specific embodiment, pharmaceutically acceptable salt is sodium chloride. In another specific embodiment, pharmaceutically acceptable salt is potassium chloride. In one embodiment, the concentration of the buffering agent is 90±25 mM. In one embodiment, the pH of the composition is from 5.5 to 7.0. In another embodiment, the pH of the composition is from 5.5 to 6.5. In another embodiment, the pH of the composition is 6.0±0.2. In a specific embodiment, the pH of the composition is 6.0. In a specific embodiment, the composition contains from 8,000 U/mL to 500,000 U/mL rfurin.

In one embodiment, a stabilized furin (e.g., rfurin) composition comprises a pharmaceutically acceptable salt at a concentration selected from variations 6036 to 6180 found in Table 10, from 0.9 mM calcium, 10% sugar or sugar alcohol, 75 ppm non-ionic surfactant, from 91 mM buffering agent, and a pH of 6.0±0.2. In one embodiment, the non-ionic surfactant is a non-ionic water soluble sorbitan fatty acid ester. In a specific embodiment, the non-ionic surfactant is polysorbate 80 (polyoxyethylene (20) sorbitan monooleate). In one embodiment, the sugar or sugar alcohol is selected from sucrose, trehalose, mannitol, and a combination thereof. In a specific embodiment, the sugar or sugar alcohol is trehalose. In a specific embodiment, the non-ionic surfactant is polysorbate 80 (polyoxyethylene (20) sorbitan monooleate) and the sugar or sugar alcohol is trehalose. In one embodiment, the pharmaceutically acceptable salt is sodium chloride, potassium chloride, or a combination thereof. In a specific embodiment, pharmaceutically acceptable salt is sodium chloride. In another specific embodiment, pharmaceutically acceptable salt is potassium chloride. In a specific embodiment, the pH of the composition is 6.0. In a specific embodiment, the composition contains from 8,000 U/mL to 500,000 U/mL rfurin.

In some embodiments, monovalent chloride salts, such as sodium chloride and potassium chloride, are used in formulations of the present disclosure. Although the formulation component comprising monovalent chloride salts is described primarily in terms of sodium chloride, it will be appreciated that any monovalent chloride salt, including potassium chloride, may be used in accordance with the descriptions herein for sodium chloride. In certain embodiments, sodium chloride is included in the present formulations at an amount of from 50 to 500 mM. In other embodiments, sodium chloride is included in the formulations at an amount of from 100 to 300 mM, from 150 to 250 mM, or at about 190 mM. In further embodiments, sodium chloride is included in the present formulations in an amount of from 100 to 300 mM, 110 to 280 mM, 120 to 260 mM, 130 to 240 mM, 140 to 220 mM, 150 to 200 mM, or 160 to 180 mM. In a specific embodiment, the formulation includes 190 mM sodium chloride in combination with one or more of any other formulation components disclosed herein.

C. Buffering Agents

Figure 11:
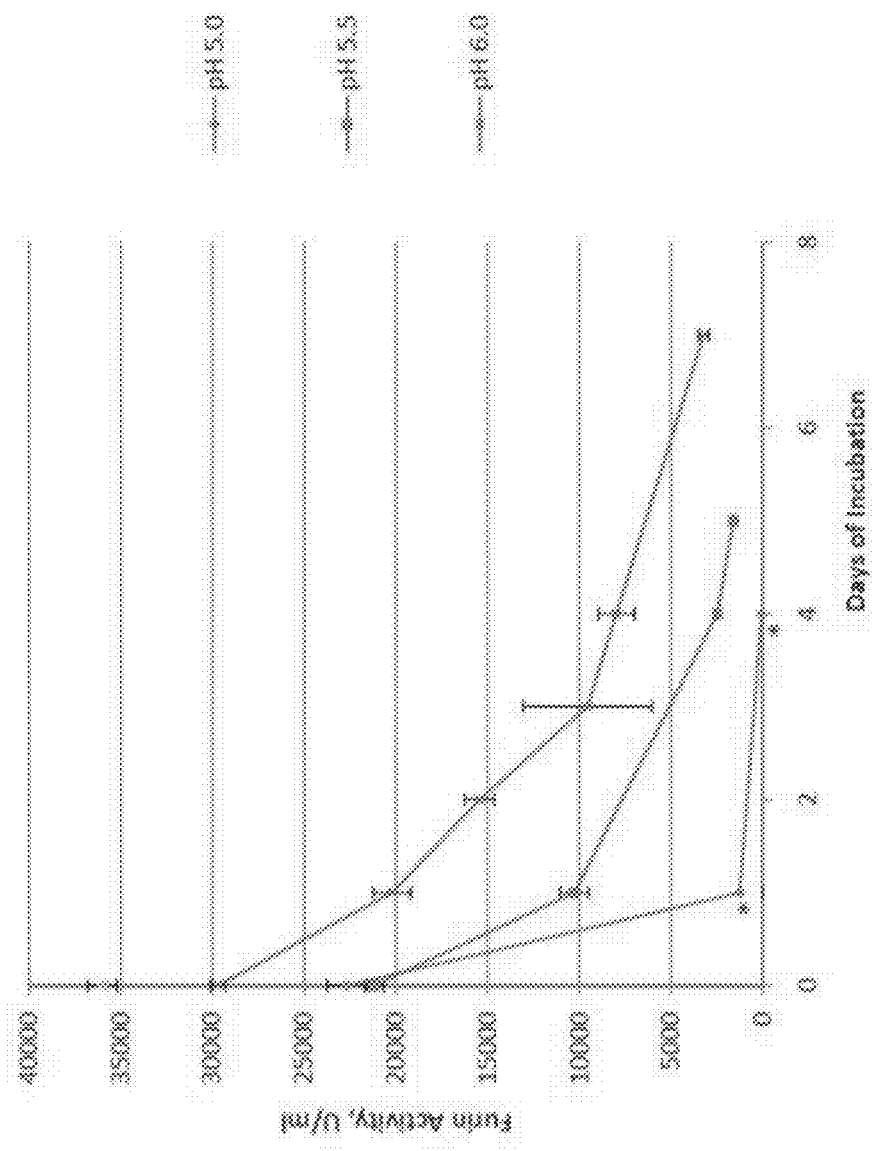
Figure 12:
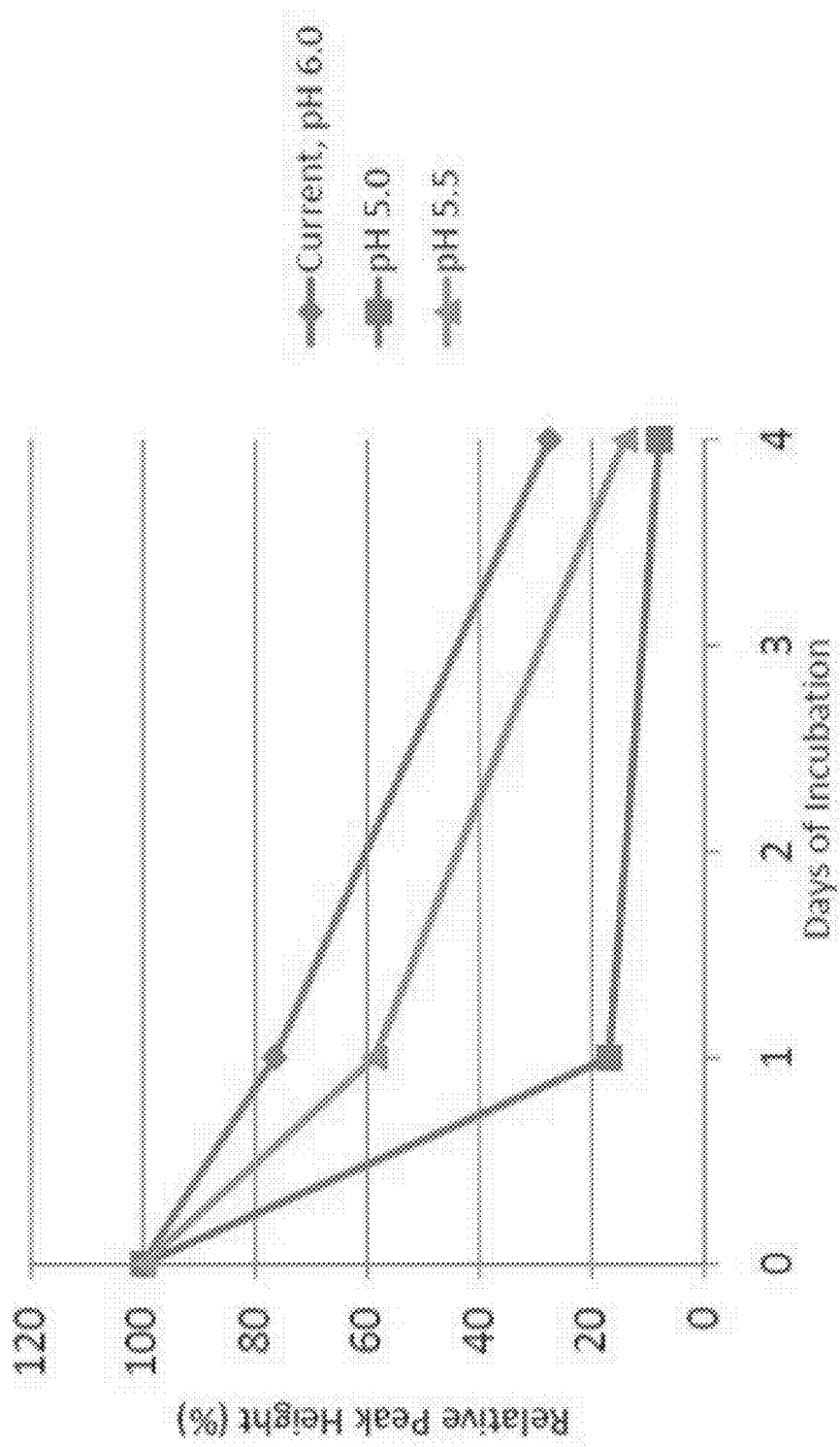
Figure 17:
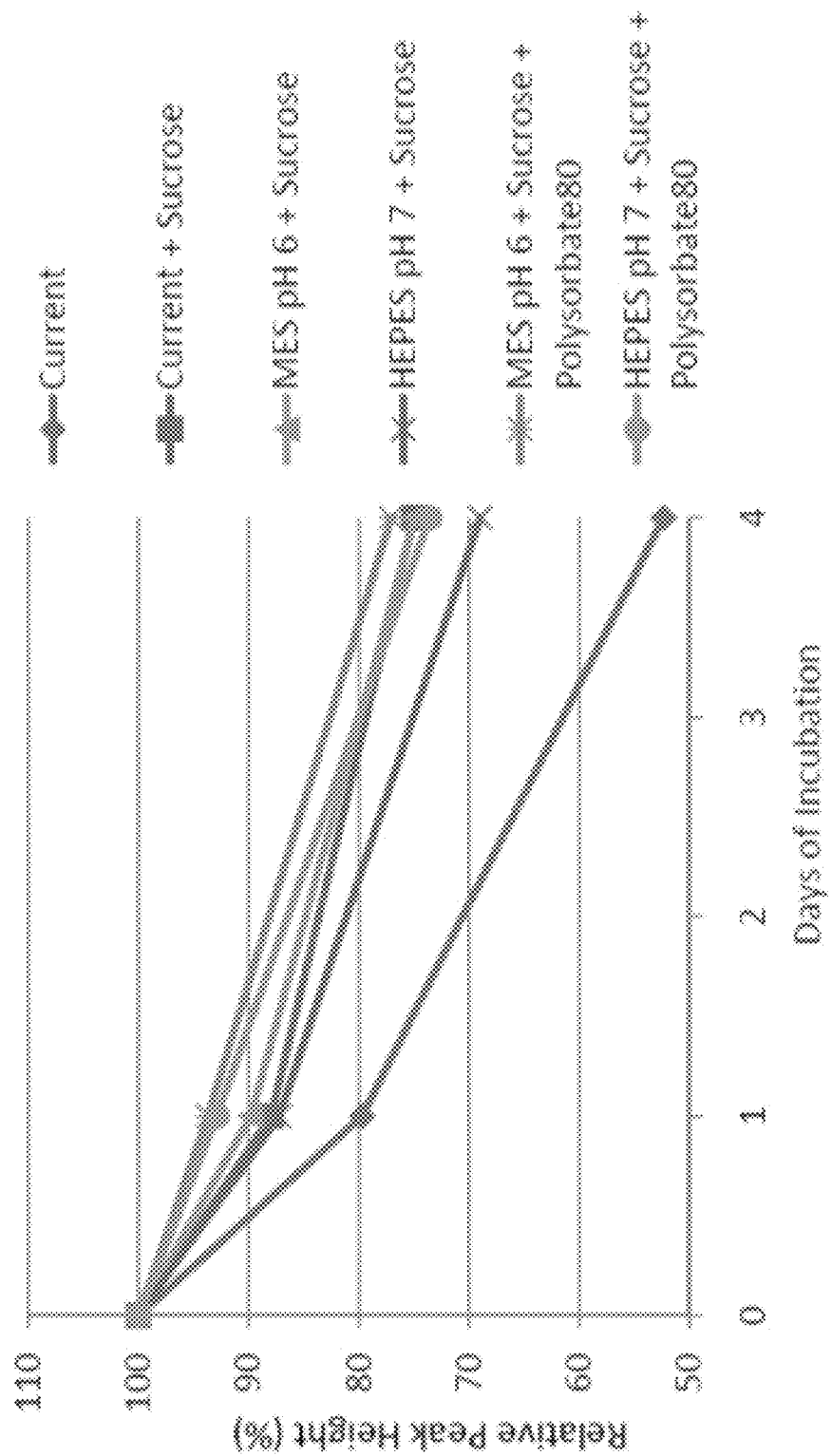

Advantageously, it was found that furin (e.g., rfurin) compositions are stabilized at pH 6.0 to 7.0. For example, it is shown in FIGS. 11 and 12 that furin compositions formulated at pH 5.5 are stabilized as compared to furin compositions formulated at pH 5.0. Also shown is that furin compositions formulated at pH 6.0 are further stabilized as compared to compositions formulated at pH 5.5. Furthermore, as shown in FIG. 17, furin (e.g., rfurin) compositions formulated at pH 7.0 have similar stability to compositions formulated at pH 6.0.

Accordingly, in certain embodiments, the stabilized furin (e.g., rfurin) compositions provided herein are formulated at a pH from 5.5 to 7.5. In a specific embodiment, a stabilized furin (e.g., rfurin) composition is formulated at a pH from 6.0 to 7.0. In another specific embodiment, a stabilized furin composition is formulated at pH 6.0±0.2. In a more specific embodiment, a stabilized furin composition is formulated at pH 6.0. In yet other embodiments, a stabilized furin composition is formulated at pH selected from variations 6181 to 6403 found in Table 11.

TABLE 11

Exemplary pH ranges useful for the stabilization of furin (e.g., rfurin) compositions.

| | |
|---|---|
| 5.5-8.0 | Var. 6181 |
| 5.5-7.9 | Var. 6182 |
| 5.5-7.8 | Var. 6183 |
| 5.5-7.6 | Var. 6184 |
| 5.5-7.5 | Var. 6185 |
| 5.5-7.4 | Var. 6186 |
| 5.5-7.3 | Var. 6187 |
| 5.5-7.2 | Var. 6188 |
| 5.5-7.1 | Var. 6189 |
| 5.5-7.0 | Var. 6190 |
| 5.5-6.9 | Var. 6191 |
| 5.5-6.8 | Var. 6192 |
| 5.5-6.7 | Var. 6193 |
| 5.5-6.6 | Var. 6194 |
| 5.5-6.5 | Var. 6195 |
| 5.5-6.4 | Var. 6196 |
| 5.5-6.3 | Var. 6197 |
| 5.5-6.2 | Var. 6198 |
| 5.5-6.1 | Var. 6199 |
| 5.5-6.0 | Var. 6200 |
| 5.6-8.0 | Var. 6201 |
| 5.6-7.9 | Var. 6202 |
| 5.6-7.8 | Var. 6203 |
| 5.6-7.6 | Var. 6204 |
| 5.6-7.5 | Var. 6205 |
| 5.6-7.4 | Var. 6206 |
| 5.6-7.3 | Var. 6207 |
| 5.6-7.2 | Var. 6208 |
| 5.6-7.1 | Var. 6209 |
| 5.6-7.0 | Var. 6210 |
| 5.6-6.9 | Var. 6211 |
| 5.6-6.8 | Var. 6212 |
| 5.6-6.7 | Var. 6213 |
| 5.6-6.6 | Var. 6214 |
| 5.6-6.5 | Var. 6215 |
| 5.6-6.4 | Var. 6216 |
| 5.6-6.3 | Var. 6217 |
| 5.6-6.2 | Var. 6218 |
| 5.6-6.1 | Var. 6219 |

TABLE 11-continued

| Exemplary pH ranges useful for the stabilization of furin (e.g., rfurin) compositions. | |
|---|---|
| 5.6-6.0 | Var. 6220 |
| 5.7-8.0 | Var. 6221 |
| 5.7-7.9 | Var. 6222 |
| 5.7-7.8 | Var. 6223 |
| 5.7-7.6 | Var. 6224 |
| 5.7-7.5 | Var. 6225 |
| 5.7-7.4 | Var. 6226 |
| 5.7-7.3 | Var. 6227 |
| 5.7-7.2 | Var. 6228 |
| 5.7-7.1 | Var. 6229 |
| 5.7-7.0 | Var. 6230 |
| 5.7-6.9 | Var. 6231 |
| 5.7-6.8 | Var. 6232 |
| 5.7-6.7 | Var. 6233 |
| 5.7-6.6 | Var. 6234 |
| 5.7-6.5 | Var. 6235 |
| 5.7-6.4 | Var. 6236 |
| 5.7-6.3 | Var. 6237 |
| 5.7-6.2 | Var. 6238 |
| 5.7-6.1 | Var. 6239 |
| 5.7-6.0 | Var. 6240 |
| 5.8-8.0 | Var. 6241 |
| 5.8-7.9 | Var. 6242 |
| 5.8-7.8 | Var. 6243 |
| 5.8-7.6 | Var. 6244 |
| 5.8-7.5 | Var. 6245 |
| 5.8-7.4 | Var. 6246 |
| 5.8-7.3 | Var. 6247 |
| 5.8-7.2 | Var. 6248 |
| 5.8-7.1 | Var. 6249 |
| 5.8-7.0 | Var. 6250 |
| 5.8-6.9 | Var. 6251 |
| 5.8-6.8 | Var. 6252 |
| 5.8-6.7 | Var. 6253 |
| 5.8-6.6 | Var. 6254 |
| 5.8-6.5 | Var. 6255 |
| 5.8-6.4 | Var. 6256 |
| 5.8-6.3 | Var. 6257 |
| 5.8-6.2 | Var. 6258 |
| 5.8-6.1 | Var. 6259 |
| 5.8-6.0 | Var. 6260 |
| 5.9-8.0 | Var. 6261 |
| 5.9-7.9 | Var. 6262 |
| 5.9-7.8 | Var. 6263 |
| 5.9-7.6 | Var. 6264 |
| 5.9-7.5 | Var. 6265 |
| 5.9-7.4 | Var. 6266 |
| 5.9-7.3 | Var. 6267 |
| 5.9-7.2 | Var. 6268 |
| 5.9-7.1 | Var. 6269 |
| 5.9-7.0 | Var. 6270 |
| 5.9-6.9 | Var. 6271 |
| 5.9-6.8 | Var. 6272 |
| 5.9-6.7 | Var. 6273 |
| 5.9-6.6 | Var. 6274 |
| 5.9-6.5 | Var. 6275 |
| 5.9-6.4 | Var. 6276 |
| 5.9-6.3 | Var. 6277 |
| 5.9-6.2 | Var. 6278 |
| 5.9-6.1 | Var. 6279 |
| 5.9-6.0 | Var. 6280 |
| 6.0-8.0 | Var. 6281 |
| 6.0-7.9 | Var. 6282 |
| 6.0-7.8 | Var. 6283 |
| 6.0-7.6 | Var. 6284 |
| 6.0-7.5 | Var. 6285 |
| 6.0-7.4 | Var. 6286 |
| 6.0-7.3 | Var. 6287 |
| 6.0-7.2 | Var. 6288 |
| 6.0-7.1 | Var. 6289 |
| 6.0-7.0 | Var. 6290 |
| 6.0-6.9 | Var. 6291 |
| 6.0-6.8 | Var. 6292 |
| 6.0-6.7 | Var. 6293 |
| 6.0-6.6 | Var. 6294 |
| 6.0-6.5 | Var. 6295 |
| 6.0-6.4 | Var. 6296 |

TABLE 11-continued

| Exemplary pH ranges useful for the stabilization of furin (e.g., rfurin) compositions. | |
|---|---|
| 6.0-6.3 | Var. 6297 |
| 6.0-6.2 | Var. 6298 |
| 6.0-6.1 | Var. 6299 |
| 5.7 ± 0.2 | Var. 6300 |
| 5.8 ± 0.2 | Var. 6301 |
| 5.9 ± 0.2 | Var. 6302 |
| 6.0 ± 0.2 | Var. 6303 |
| 6.1 ± 0.2 | Var. 6304 |
| 6.2 ± 0.2 | Var. 6305 |
| 6.3 ± 0.2 | Var. 6306 |
| 6.4 ± 0.2 | Var. 6307 |
| 6.5 ± 0.2 | Var. 6308 |
| 6.6 ± 0.2 | Var. 6309 |
| 6.7 ± 0.2 | Var. 6310 |
| 6.8 ± 0.2 | Var. 6311 |
| 6.9 ± 0.2 | Var. 6312 |
| 7.0 ± 0.2 | Var. 6313 |
| 7.1 ± 0.2 | Var. 6314 |
| 7.2 ± 0.2 | Var. 6315 |
| 7.3 ± 0.2 | Var. 6316 |
| 7.4 ± 0.2 | Var. 6317 |
| 7.5 ± 0.2 | Var. 6318 |
| 7.6 ± 0.2 | Var. 6319 |
| 7.7 ± 0.2 | Var. 6320 |
| 7.8 ± 0.2 | Var. 6321 |
| 5.6 ± 0.1 | Var. 6322 |
| 5.7 ± 0.1 | Var. 6323 |
| 5.8 ± 0.1 | Var. 6324 |
| 5.9 ± 0.1 | Var. 6325 |
| 6.0 ± 0.1 | Var. 6326 |
| 6.1 ± 0.1 | Var. 6327 |
| 6.2 ± 0.1 | Var. 6328 |
| 6.3 ± 0.1 | Var. 6329 |
| 6.4 ± 0.1 | Var. 6330 |
| 6.5 ± 0.1 | Var. 6331 |
| 6.6 ± 0.1 | Var. 6332 |
| 6.7 ± 0.1 | Var. 6333 |
| 6.8 ± 0.1 | Var. 6334 |
| 6.9 ± 0.1 | Var. 6335 |
| 7.0 ± 0.1 | Var. 6336 |
| 7.1 ± 0.1 | Var. 6337 |
| 7.2 ± 0.1 | Var. 6338 |
| 7.3 ± 0.1 | Var. 6339 |
| 7.4 ± 0.1 | Var. 6340 |
| 7.5 ± 0.1 | Var. 6341 |
| 7.6 ± 0.1 | Var. 6342 |
| 7.7 ± 0.1 | Var. 6343 |
| 7.8 ± 0.1 | Var. 6344 |
| 5.5 | Var. 6345 |
| 5.6 | Var. 6346 |
| 5.7 | Var. 6347 |
| 5.8 | Var. 6348 |
| 5.9 | Var. 6349 |
| 6 | Var. 6350 |
| 6.1 | Var. 6351 |
| 6.2 | Var. 6352 |
| 6.3 | Var. 6353 |
| 6.4 | Var. 6354 |
| 6.5 | Var. 6355 |
| 6.6 | Var. 6356 |
| 6.7 | Var. 6357 |
| 6.8 | Var. 6358 |
| 6.9 | Var. 6359 |
| 7 | Var. 6360 |
| 7.1 | Var. 6361 |
| 7.2 | Var. 6362 |
| 7.3 | Var. 6363 |
| 7.4 | Var. 6364 |
| 7.5 | Var. 6365 |
| 7.6 | Var. 6366 |
| 7.7 | Var. 6367 |
| 7.8 | Var. 6368 |
| 7.9 | Var. 6369 |
| 8 | Var. 6370 |
| 6.0 ± 0.3 | Var. 6371 |
| 6.0 ± 0.4 | Var. 6372 |
| 6.0 ± 0.5 | Var. 6373 |

TABLE 11-continued

Exemplary pH ranges useful for the stabilization of furin (e.g., rfurin) compositions.

| | |
|---|---|
| 6.1 ± 0.3 | Var. 6374 |
| 6.1 ± 0.4 | Var. 6375 |
| 6.1 ± 0.5 | Var. 6376 |
| 6.2 ± 0.3 | Var. 6377 |
| 6.2 ± 0.4 | Var. 6378 |
| 6.2 ± 0.5 | Var. 6379 |
| 6.3 ± 0.3 | Var. 6380 |
| 6.3 ± 0.4 | Var. 6381 |
| 6.3 ± 0.5 | Var. 6382 |
| 6.4 ± 0.3 | Var. 6383 |
| 6.4 ± 0.4 | Var. 6384 |
| 6.4 ± 0.5 | Var. 6385 |
| 6.5 ± 0.3 | Var. 6386 |
| 6.5 ± 0.4 | Var. 6387 |
| 6.5 ± 0.5 | Var. 6388 |
| 6.6 ± 0.3 | Var. 6389 |
| 6.6 ± 0.4 | Var. 6390 |
| 6.6 ± 0.5 | Var. 6391 |
| 6.7 ± 0.3 | Var. 6392 |
| 6.7 ± 0.4 | Var. 6393 |
| 6.7 ± 0.5 | Var. 6394 |
| 6.8 ± 0.3 | Var. 6395 |
| 6.8 ± 0.4 | Var. 6396 |
| 6.8 ± 0.5 | Var. 6397 |
| 6.9 ± 0.3 | Var. 6398 |
| 6.9 ± 0.4 | Var. 6399 |
| 6.9 ± 0.5 | Var. 6400 |
| 7.0 ± 0.3 | Var. 6401 |
| 7.0 ± 0.4 | Var. 6402 |
| 7.0 ± 0.5 | Var. 6403 |

Var. = Variation

In one embodiment, a stabilized furin (e.g., rfurin) composition comprises from 50 to 500 mM of a pharmaceutically acceptable salt, from 0.5 mM to 5 mM calcium, from 10 ppm to 200 ppm non-ionic surfactant, from 10 to 200 mM buffering agent, and a pH selected from variations 6181 to 6403 found in Table 11. In one embodiment, the storage stable furin composition further comprises from 2% to 20% sugar or sugar alcohol. In one embodiment, the non-ionic surfactant is a non-ionic water soluble sorbitan fatty acid ester. In a specific embodiment, the non-ionic surfactant is polysorbate 80 (polyoxyethylene (20) sorbitan monooleate). In a specific embodiment, the composition contains from 8,000 U/mL to 500,000 U/mL rfurin.

In one embodiment, a stabilized furin (e.g., rfurin) composition comprises from 50 to 500 mM of a pharmaceutically acceptable salt, from 0.5 mM to 5 mM calcium, from 2% to 20% sugar or sugar alcohol, from 10 to 200 mM buffering agent, and a pH selected from variations 6181 to 6403 found in Table 11. In one embodiment, the storage stable furin composition further comprises from 10 ppm to 200 ppm non-ionic surfactant. In one embodiment, the sugar or sugar alcohol is selected from sucrose, trehalose, mannitol, and a combination thereof. In a specific embodiment, the sugar or sugar alcohol is trehalose. In a specific embodiment, the composition contains from 8,000 U/mL to 500,000 U/mL rfurin.

In one embodiment, a stabilized furin (e.g., rfurin) composition comprises from 50 to 500 mM of a pharmaceutically acceptable salt, from 0.5 mM to 5 mM calcium, from 2% to 20% sugar or sugar alcohol, from 10 ppm to 200 ppm non-ionic surfactant, from 10 to 200 mM buffering agent, and a pH selected from variations 6181 to 6403 found in Table 11. In one embodiment, the non-ionic surfactant is a non-ionic water soluble sorbitan fatty acid ester. In a specific embodiment, the non-ionic surfactant is polysorbate 80 (polyoxyethylene (20) sorbitan monooleate). In one embodiment, the sugar or sugar alcohol is selected from sucrose, trehalose, mannitol, and a combination thereof. In a specific embodiment, the sugar or sugar alcohol is trehalose. In a specific embodiment, the non-ionic surfactant is polysorbate 80 (polyoxyethylene (20) sorbitan monooleate) and the sugar or sugar alcohol is trehalose. In a specific embodiment, the composition contains from 8,000 U/mL to 500,000 U/mL rfurin.

In one embodiment, a stabilized furin (e.g., rfurin) composition comprises from 50 to 500 mM of a pharmaceutically acceptable salt, from 0.5 mM to 5 mM calcium, from 2% to 10% sugar or sugar alcohol, from 10 ppm to 100 ppm non-ionic surfactant, from 10 to 200 mM buffering agent, and a pH selected from variations 6181 to 6403 found in Table 11. In one embodiment, the non-ionic surfactant is a non-ionic water soluble sorbitan fatty acid ester. In a specific embodiment, the non-ionic surfactant is polysorbate 80 (polyoxyethylene (20) sorbitan monooleate). In one embodiment, the sugar or sugar alcohol is selected from sucrose, trehalose, mannitol, and a combination thereof. In a specific embodiment, the sugar or sugar alcohol is trehalose. In a specific embodiment, the non-ionic surfactant is polysorbate 80 (polyoxyethylene (20) sorbitan monooleate) and the sugar or sugar alcohol is trehalose. In a specific embodiment, the composition contains from 8,000 U/mL to 500,000 U/mL rfurin.

In one embodiment, a stabilized furin (e.g., rfurin) composition comprises from 50 to 300 mM of a pharmaceutically acceptable salt, from 0.5 mM to 2 mM calcium, from 2% to 10% sugar or sugar alcohol, from 10 ppm to 100 ppm non-ionic surfactant, from 10 to 200 mM buffering agent, and a pH selected from variations 6181 to 6403 found in Table 11. In one embodiment, the non-ionic surfactant is a non-ionic water soluble sorbitan fatty acid ester. In a specific embodiment, the non-ionic surfactant is polysorbate 80 (polyoxyethylene (20) sorbitan monooleate). In one embodiment, the sugar or sugar alcohol is selected from sucrose, trehalose, mannitol, and a combination thereof. In a specific embodiment, the sugar or sugar alcohol is trehalose. In a specific embodiment, the non-ionic surfactant is polysorbate 80 (polyoxyethylene (20) sorbitan monooleate) and the sugar or sugar alcohol is trehalose. In a specific embodiment, the composition contains from 8,000 U/mL to 500,000 U/mL rfurin.

In one embodiment, a stabilized furin (e.g., rfurin) composition comprises from 50 to 300 mM of a pharmaceutically acceptable salt, from 0.5 mM to 2 mM calcium, 10±5% sugar or sugar alcohol, 75±25 ppm non-ionic surfactant, from 10 to 200 mM buffering agent, and a pH selected from variations 6181 to 6403 found in Table 11. In one embodiment, the non-ionic surfactant is a non-ionic water soluble sorbitan fatty acid ester. In a specific embodiment, the non-ionic surfactant is polysorbate 80 (polyoxyethylene (20) sorbitan monooleate). In one embodiment, the sugar or sugar alcohol is selected from sucrose, trehalose, mannitol, and a combination thereof. In a specific embodiment, the sugar or sugar alcohol is trehalose. In a specific embodiment, the non-ionic surfactant is polysorbate 80 (polyoxyethylene (20) sorbitan monooleate) and the sugar or sugar alcohol is trehalose. In a specific embodiment, the composition contains from 8,000 U/mL to 500,000 U/mL rfurin.

In one embodiment, a stabilized furin (e.g., rfurin) composition comprises 190±50 mM of a pharmaceutically acceptable salt, from 0.5 mM to 2 mM calcium, 10±5% sugar or sugar alcohol, 75±25 ppm non-ionic surfactant, from 90±25 mM buffering agent, and a pH selected from variations 6181 to 6403 found in Table 11. In one embodiment, the non-ionic surfactant is a non-ionic water soluble sorbitan fatty acid ester. In a specific embodiment, the non-ionic surfactant is polysorbate 80 (polyoxyethylene (20) sorbitan monooleate). In one embodiment, the sugar or sugar alcohol is selected from sucrose, trehalose, mannitol, and a combination thereof. In a specific embodiment, the sugar or sugar alcohol is trehalose. In a specific embodiment, the non-ionic surfactant is polysorbate 80 (polyoxyethylene (20) sorbitan monooleate) and the sugar or sugar alcohol is trehalose. In a specific embodiment, the composition contains from 8,000 U/mL to 500,000 U/mL rfurin.

In one embodiment, a stabilized furin (e.g., rfurin) composition comprises 191 mM of a pharmaceutically acceptable salt, 0.9 mM calcium, 10% sugar or sugar alcohol, 75 ppm non-ionic surfactant, 91 mM buffering agent, and a pH selected from variations 6181 to 6403 found in Table 11. In one embodiment, the non-ionic surfactant is a non-ionic water soluble sorbitan fatty acid ester. In a specific embodiment, the non-ionic surfactant is polysorbate 80 (polyoxyethylene (20) sorbitan monooleate). In one embodiment, the sugar or sugar alcohol is selected from sucrose, trehalose, mannitol, and a combination thereof. In a specific embodiment, the sugar or sugar alcohol is trehalose. In a specific embodiment, the non-ionic surfactant is polysorbate 80 (polyoxyethylene (20) sorbitan monooleate) and the sugar or sugar alcohol is trehalose. In a specific embodiment, the composition contains from 8,000 U/mL to 500,000 U/mL rfurin.

In one embodiment, the stabilized furin (e.g., rfurin) compositions provided herein are formulated at an appropriate pH using one or more buffering agents. In one embodiment, the one or more buffering agent is selected from histidine, imidazole, phosphate, citrate, Tris, acetate (e.g., acetic acid), BIS-Tris Propane, PIPES, MOPS, HEPES, MES, ACES, and a combination thereof. In a particular embodiment, the buffering agent is acetate, HEPES, or a combination thereof. In a specific embodiment, the buffering agent is a combination of acetate and HEPES.

Buffering agent is present in the stabilized furin (e.g., rfurin) compositions at a concentration suitable to maintain the pH of the composition during storage over a period of time (e.g., weeks, months, or years). In one embodiment, the concentration of buffering agent in the formulation is from 10 mM to 300 mM. In another embodiment, the concentration of buffering agent in the formulation is between 10 mM to 200 mM. In a specific embodiment, the concentration of buffering agent in the formulation is 90±25 mM. In yet other embodiments, the concentration of buffering agent in the composition is selected from variations 6404 to 6469 found in Table 12.

TABLE 12

Exemplary buffering agent concentrations (mM) useful for the stabilization of furin (e.g., rfurin) compositions.

| | |
|---|---|
| 10-300 | Var. 6404 |
| 10-275 | Var. 6405 |
| 10-250 | Var. 6406 |
| 10-225 | Var. 6407 |
| 10-200 | Var. 6408 |
| 10-175 | Var. 6409 |
| 10-150 | Var. 6410 |
| 10-125 | Var. 6411 |
| 10-100 | Var. 6412 |
| 25-300 | Var. 6413 |
| 25-275 | Var. 6414 |
| 25-250 | Var. 6415 |
| 25-225 | Var. 6416 |

TABLE 12-continued

Exemplary buffering agent concentrations (mM) useful for the stabilization of furin (e.g., rfurin) compositions.

| | |
|---|---|
| 25-200 | Var. 6417 |
| 25-175 | Var. 6418 |
| 25-150 | Var. 6419 |
| 25-125 | Var. 6420 |
| 25-100 | Var. 6421 |
| 50-300 | Var. 6422 |
| 50-275 | Var. 6423 |
| 50-250 | Var. 6424 |
| 50-225 | Var. 6425 |
| 50-200 | Var. 6426 |
| 50-175 | Var. 6427 |
| 50-150 | Var. 6428 |
| 50-125 | Var. 6429 |
| 50-100 | Var. 6430 |
| 75-300 | Var. 6431 |
| 75-275 | Var. 6432 |
| 75-250 | Var. 6433 |
| 75-225 | Var. 6434 |
| 75-200 | Var. 6435 |
| 75-175 | Var. 6436 |
| 75-150 | Var. 6437 |
| 75-125 | Var. 6438 |
| 75-100 | Var. 6439 |
| 90 ± 75 | Var. 6440 |
| 90 ± 50 | Var. 6441 |
| 90 ± 25 | Var. 6442 |
| 90 ± 10 | Var. 6443 |
| 90 ± 5 | Var. 6444 |
| 90 ± 2 | Var. 6445 |
| 91 ± 10 | Var. 6446 |
| 91 ± 5 | Var. 6447 |
| 91 ± 2 | Var. 6448 |
| 80 | Var. 6449 |
| 81 | Var. 6450 |
| 82 | Var. 6451 |
| 83 | Var. 6452 |
| 84 | Var. 6453 |
| 85 | Var. 6454 |
| 86 | Var. 6455 |
| 87 | Var. 6456 |
| 88 | Var. 6457 |
| 89 | Var. 6458 |
| 90 | Var. 6459 |
| 91 | Var. 6460 |
| 92 | Var. 6461 |
| 93 | Var. 6462 |
| 94 | Var. 6463 |
| 95 | Var. 6464 |
| 96 | Var. 6465 |
| 97 | Var. 6466 |
| 98 | Var. 6467 |
| 99 | Var. 6468 |
| 100 | Var. 6469 |

Var. = Variation

In one embodiment, a stabilized furin (e.g., rfurin) composition comprises from 50 to 500 mM of a pharmaceutically acceptable salt, from 0.5 mM to 5 mM calcium, from 10 ppm to 200 ppm non-ionic surfactant, buffering agent at a concentration selected from variations 6404 to 6469 found in Table 12, and a pH from 5.5 to 7.5. In one embodiment, the storage stable furin composition further comprises from 2% to 20% sugar or sugar alcohol. In one embodiment, the non-ionic surfactant is a non-ionic water soluble sorbitan fatty acid ester. In a specific embodiment, the non-ionic surfactant is polysorbate 80 (polyoxyethylene (20) sorbitan monooleate). In one embodiment, the buffering agent is acetate, HEPES, or a combination thereof. In a specific embodiment, the buffering agent is a combination of acetate and HEPES. In one embodiment, the pH of the composition is from 5.5 to 7.0. In another embodiment, the pH of the composition is from 5.5 to 6.5. In another embodiment, the pH of the composition is 6.0±0.2. In a specific embodiment, the pH of the composition is 6.0. In a specific embodiment, the composition contains from 8,000 U/mL to 500,000 U/mL rfurin.

In one embodiment, a stabilized furin (e.g., rfurin) composition comprises from 50 to 500 mM of a pharmaceutically acceptable salt, from 0.5 mM to 5 mM calcium, from 2% to 20% sugar or sugar alcohol, buffering agent at a concentration selected from variations 6404 to 6469 found in Table 12, and a pH from 5.5 to 7.5. In one embodiment, the storage stable furin composition further comprises from 10 ppm to 200 ppm non-ionic surfactant. In one embodiment, the sugar or sugar alcohol is selected from sucrose, trehalose, mannitol, and a combination thereof. In a specific embodiment, the sugar or sugar alcohol is trehalose. In one embodiment, the buffering agent is acetate, HEPES, or a combination thereof. In a specific embodiment, the buffering agent is a combination of acetate and HEPES. In one embodiment, the pH of the composition is from 5.5 to 7.0. In another embodiment, the pH of the composition is from 5.5 to 6.5. In another embodiment, the pH of the composition is 6.0±0.2. In a specific embodiment, the pH of the composition is 6.0. In a specific embodiment, the composition contains from 8,000 U/mL to 500,000 U/mL rfurin.

In one embodiment, a stabilized furin (e.g., rfurin) composition comprises from 50 to 500 mM of a pharmaceutically acceptable salt, from 0.5 mM to 5 mM calcium, from 2% to 20% sugar or sugar alcohol, from 10 ppm to 200 ppm non-ionic surfactant, buffering agent at a concentration selected from variations 6404 to 6469 found in Table 12, and a pH from 5.5 to 7.5. In one embodiment, the non-ionic surfactant is a non-ionic water soluble sorbitan fatty acid ester. In a specific embodiment, the non-ionic surfactant is polysorbate 80 (polyoxyethylene (20) sorbitan monooleate). In one embodiment, the sugar or sugar alcohol is selected from sucrose, trehalose, mannitol, and a combination thereof. In a specific embodiment, the sugar or sugar alcohol is trehalose. In a specific embodiment, the non-ionic surfactant is polysorbate 80 (polyoxyethylene (20) sorbitan monooleate) and the sugar or sugar alcohol is trehalose. In one embodiment, the buffering agent is acetate, HEPES, or a combination thereof. In a specific embodiment, the buffering agent is a combination of acetate and HEPES. In one embodiment, the pH of the composition is from 5.5 to 7.0. In another embodiment, the pH of the composition is from 5.5 to 6.5. In another embodiment, the pH of the composition is 6.0±0.2. In a specific embodiment, the pH of the composition is 6.0. In a specific embodiment, the composition contains from 8,000 U/mL to 500,000 U/mL rfurin.

In one embodiment, a stabilized furin (e.g., rfurin) composition comprises from 50 to 500 mM of a pharmaceutically acceptable salt, from 0.5 mM to 5 mM calcium, from 2% to 10% sugar or sugar alcohol, from 10 ppm to 100 ppm non-ionic surfactant, buffering agent at a concentration selected from variations 6404 to 6469 found in Table 12, and a pH from 5.5 to 7.5. In one embodiment, the non-ionic surfactant is a non-ionic water soluble sorbitan fatty acid ester. In a specific embodiment, the non-ionic surfactant is polysorbate 80 (polyoxyethylene (20) sorbitan monooleate). In one embodiment, the sugar or sugar alcohol is selected from sucrose, trehalose, mannitol, and a combination thereof. In a specific embodiment, the sugar or sugar alcohol is trehalose. In a specific embodiment, the non-ionic surfactant is polysorbate 80 (polyoxyethylene (20) sorbitan monooleate) and the sugar or sugar alcohol is trehalose. In one embodiment, the buffering agent is acetate, HEPES, or a combination thereof. In a specific embodiment, the buffering agent is a combination of acetate and HEPES. In one embodiment, the pH of the composition is from 5.5 to 7.0. In another embodiment, the pH of the composition is from 5.5 to 6.5. In another embodiment, the pH of the composition is 6.0±0.2. In a specific embodiment, the pH of the composition is 6.0. In a specific embodiment, the composition contains from 8,000 U/mL to 500,000 U/mL rfurin.

In one embodiment, a stabilized furin (e.g., rfurin) composition comprises from 50 to 300 mM of a pharmaceutically acceptable salt, from 0.5 mM to 2 mM calcium, from 2% to 10% sugar or sugar alcohol, from 10 ppm to 100 ppm non-ionic surfactant, buffering agent at a concentration selected from variations 6404 to 6469 found in Table 12, and a pH from 5.5 to 7.5. In one embodiment, the non-ionic surfactant is a non-ionic water soluble sorbitan fatty acid ester. In a specific embodiment, the non-ionic surfactant is polysorbate 80 (polyoxyethylene (20) sorbitan monooleate). In one embodiment, the sugar or sugar alcohol is selected from sucrose, trehalose, mannitol, and a combination thereof. In a specific embodiment, the sugar or sugar alcohol is trehalose. In a specific embodiment, the non-ionic surfactant is polysorbate 80 (polyoxyethylene (20) sorbitan monooleate) and the sugar or sugar alcohol is trehalose. In one embodiment, the buffering agent is acetate, HEPES, or a combination thereof. In a specific embodiment, the buffering agent is a combination of acetate and HEPES. In one embodiment, the pH of the composition is from 5.5 to 7.0. In another embodiment, the pH of the composition is from 5.5 to 6.5. In another embodiment, the pH of the composition is 6.0±0.2. In a specific embodiment, the pH of the composition is 6.0. In a specific embodiment, the composition contains from 8,000 U/mL to 500,000 U/mL rfurin.

In one embodiment, a stabilized furin (e.g., rfurin) composition comprises from 50 to 300 mM of a pharmaceutically acceptable salt, from 0.5 mM to 2 mM calcium, 10±5% sugar or sugar alcohol, 75±25 ppm non-ionic surfactant, buffering agent at a concentration selected from variations 6404 to 6469 found in Table 12, and a pH from 5.5 to 7.5. In one embodiment, the non-ionic surfactant is a non-ionic water soluble sorbitan fatty acid ester. In a specific embodiment, the non-ionic surfactant is polysorbate 80 (polyoxyethylene (20) sorbitan monooleate). In one embodiment, the sugar or sugar alcohol is selected from sucrose, trehalose, mannitol, and a combination thereof. In a specific embodiment, the sugar or sugar alcohol is trehalose. In a specific embodiment, the non-ionic surfactant is polysorbate 80 (polyoxyethylene (20) sorbitan monooleate) and the sugar or sugar alcohol is trehalose. In one embodiment, the buffering agent is acetate, HEPES, or a combination thereof. In a specific embodiment, the buffering agent is a combination of acetate and HEPES. In one embodiment, the pH of the composition is from 5.5 to 7.0. In another embodiment, the pH of the composition is from 5.5 to 6.5. In another embodiment, the pH of the composition is 6.0±0.2. In a specific embodiment, the pH of the composition is 6.0. In a specific embodiment, the composition contains from 8,000 U/mL to 500,000 U/mL rfurin.

In one embodiment, a stabilized furin (e.g., rfurin) composition comprises 190±50 mM of a pharmaceutically acceptable salt, from 0.5 mM to 2 mM calcium, 10±5% sugar or sugar alcohol, 75±25 ppm non-ionic surfactant, buffering agent at a concentration selected from variations 6404 to 6469 found in Table 12, and a pH from 5.5 to 7.5. In one embodiment, the non-ionic surfactant is a non-ionic water soluble sorbitan fatty acid ester. In a specific embodiment, the non-ionic surfactant is polysorbate 80 (polyoxyethylene (20) sorbitan monooleate). In one embodiment, the sugar or sugar alcohol is selected from sucrose, trehalose, mannitol, and a combination thereof. In a specific embodiment, the sugar or sugar alcohol is trehalose. In a specific embodiment, the non-ionic surfactant is polysorbate 80 (polyoxyethylene (20) sorbitan monooleate) and the sugar or sugar alcohol is trehalose. In one embodiment, the buffering agent is acetate, HEPES, or a combination thereof. In a specific embodiment, the buffering agent is a combination of acetate and HEPES. In one embodiment, the pH of the composition is from 5.5 to 7.0. In another embodiment, the pH of the composition is from 5.5 to 6.5. In another embodiment, the pH of the composition is 6.0±0.2. In a specific embodiment, the pH of the composition is 6.0. In a specific embodiment, the composition contains from 8,000 U/mL to 500,000 U/mL rfurin.

In one embodiment, a stabilized furin (e.g., rfurin) composition comprises 191 mM of a pharmaceutically acceptable salt, 0.9 mM calcium, 10% sugar or sugar alcohol, 75 ppm non-ionic surfactant, buffering agent at a concentration selected from variations 6404 to 6469 found in Table 12, and a pH from 5.5 to 7.5. In one embodiment, the non-ionic surfactant is a non-ionic water soluble sorbitan fatty acid ester. In a specific embodiment, the non-ionic surfactant is polysorbate 80 (polyoxyethylene (20) sorbitan monooleate). In one embodiment, the sugar or sugar alcohol is selected from sucrose, trehalose, mannitol, and a combination thereof. In a specific embodiment, the sugar or sugar alcohol is trehalose. In a specific embodiment, the non-ionic surfactant is polysorbate 80 (polyoxyethylene (20) sorbitan monooleate) and the sugar or sugar alcohol is trehalose. In one embodiment, the buffering agent is acetate, HEPES, or a combination thereof. In a specific embodiment, the buffering agent is a combination of acetate and HEPES. In one embodiment, the pH of the composition is from 5.5 to 7.0. In another embodiment, the pH of the composition is from 5.5 to 6.5. In another embodiment, the pH of the composition is 6.0±0.2. In a specific embodiment, the pH of the composition is 6.0. In a specific embodiment, the composition contains from 8,000 U/mL to 500,000 U/mL rfurin.

Buffers may also be present in formulations of the invention in combination with one or more of any other formulation components described herein. As shown in the Examples, the highly stabilized formulations of the present invention show increased stability at pH 6.0. In certain embodiments, the pH of the highly stabilized formulations should preferably be maintained in the range of from 6.0 to 8.0, or at a pH of about 6.0. The buffering agent can be any physiologically acceptable chemical entity or combination of chemical entities which have the capacity to act as buffers, including, without limitation: histidine, imidazole, phosphate, citrate, Tris, Acetate, BIS-Tris Propane, PIPES, MOPS, HEPES, MES, and ACES. The full chemical designations of many of these buffering agents are listed in Table 1 below. In certain embodiments, if calcium is present in the formulation at a concentration above about 5 mM, phosphate is not used as a buffering agent. In some embodiments, the buffering agent is included in a concentration of from 10 mM to 200 mM, or 10 to 100 mM, or 30-60 mM, or about 46 mM. In further embodiments, an individual buffering agent is included in a concentration of from 15 to 95 mM, 20 to 90 mM, 25 to 85 mM, 30 to 80 mM, 35 to 75 mM, 40 to 70 mM, 45 to 65 mM, or 50 to 60 mM. In certain embodiments, the formulation contains two buffering agents.

TABLE 13

Exemplary Buffering Agents

| Tris | tris-(hydroxymethyl)-aminomethane |
| BIS-Tris Propane | 1,3-bis-[tris-(hydroxy-methyl)methylamino]-propane |
| PIPES | piperazine-N,N'-bis-(2-ethanesulfonic acid) |

TABLE 13-continued

Exemplary Buffering Agents

| MOPS | 3-{N-morpholino) propanesulfonic acid |
| HEPES | N-2-hydroxyethyl-piperazine-N'-2-ethanesulfonic acid |
| MES | 2-(N-morpholino) ethanesulfonic acid |
| ACES | N-2-acetamido-2-aminoethanesulfonic acid |

In certain aspects the present formulations include a carboxylic acid in combination with one or more of the formulation components described herein. In further aspects, the carboxylic acid is preferably acetic acid (e.g., acetate). In certain embodiments, the formulation includes from 20 mM to 100 mM acetic acid, or from 30 mM to 50 mM, or about 45 mM acetic acid or any other carboxylic acid. In further embodiments, the formulation includes from 25 mM to 90 mM, 30 mM to 80 mM, 35 mM to 70 mM, 40 mM to 60 mM, or 45 mM to 50 mM acetic acid or any other carboxylic acid.

D. Additional Formulation Components

The highly stabilized formulations of the present disclosure include furin, e.g., rfurin, and one or more of stabilizing agents, buffering agents, sodium chloride, salts, and other excipients. Such components are described in further detail below. As will be appreciated, any of the formulation components described herein can be used singly or in any combination.

The highly stabilized Furin formulations of the present disclosure show increased stability toward shear (agitation), lyophilization, and freeze/thaw stress as well as resistance to product loss or denaturation at container surfaces as compared to control or starting formulations.

Furin is included in formulations of the present disclosure in concentrations from 5,000 to 500,000 U/mL. In certain embodiments, Furin is included in concentrations from 5,500 to 55,000, from 6,000 to 50,000, from 6,500 to 45,000, from 7,000 to 40,000, from 7,500 to 35,000, from 8,000 to 30,000, from 8,500 to 25,000, from 9,000 to 20,000, from 9,500 to 15,000, and about 10,000 U/mL. In yet other embodiments, furin is included in the formulations of the present disclosure at a concentration selected from variations 6470 to 6533 found in Table 14, reported in thousands of Units of furin activity per mL. In specific embodiments, the furin contained in the highly stabilized formulations of the present disclosure is rfurin.

TABLE 14

Exemplary furin (e.g., rfurin) concentrations (expressed in thousands of Units furin activity per mL) used in the stabilized compositions provided herein.

| 1-1,000 | Var. 6470 |
| 1-900 | Var. 6471 |
| 1-800 | Var. 6472 |
| 1-700 | Var. 6473 |
| 1-600 | Var. 6474 |
| 1-500 | Var. 6475 |
| 1-450 | Var. 6476 |
| 1-400 | Var. 6477 |
| 1-350 | Var. 6478 |
| 1-300 | Var. 6479 |
| 1-250 | Var. 6480 |
| 1-200 | Var. 6481 |
| 1-150 | Var. 6482 |
| 1-100 | Var. 6483 |
| 1-52 | Var. 6484 |
| 1-50 | Var. 6485 |
| 5-1,000 | Var. 6486 |
| 5-900 | Var. 6487 |
| 5-800 | Var. 6488 |
| 5-700 | Var. 6489 |
| 5-600 | Var. 6490 |
| 5-500 | Var. 6491 |

TABLE 14-continued

Exemplary furin (e.g., rfurin) concentrations (expressed in thousands of Units furin activity per mL) used in the stabilized compositions provided herein.

| Range | Variation |
|---|---|
| 5-450 | Var. 6492 |
| 5-400 | Var. 6493 |
| 5-350 | Var. 6494 |
| 5-300 | Var. 6495 |
| 5-250 | Var. 6496 |
| 5-200 | Var. 6497 |
| 5-150 | Var. 6498 |
| 5-100 | Var. 6499 |
| 5-52 | Var. 6500 |
| 5-50 | Var. 6501 |
| 8-1,000 | Var. 6502 |
| 8-900 | Var. 6503 |
| 8-800 | Var. 6504 |
| 8-700 | Var. 6505 |
| 8-600 | Var. 6506 |
| 8-500 | Var. 6507 |
| 8-450 | Var. 6508 |
| 8-400 | Var. 6509 |
| 8-350 | Var. 6510 |
| 8-300 | Var. 6511 |
| 8-250 | Var. 6512 |
| 8-200 | Var. 6513 |
| 8-150 | Var. 6514 |
| 8-100 | Var. 6515 |
| 8-52 | Var. 6516 |
| 8-50 | Var. 6517 |
| 10-1,000 | Var. 6518 |
| 10-900 | Var. 6519 |
| 10-800 | Var. 6520 |
| 10-700 | Var. 6521 |
| 10-600 | Var. 6522 |
| 10-500 | Var. 6523 |
| 10-450 | Var. 6524 |
| 10-400 | Var. 6525 |
| 10-350 | Var. 6526 |
| 10-300 | Var. 6527 |
| 10-250 | Var. 6528 |
| 10-200 | Var. 6529 |
| 10-150 | Var. 6530 |
| 10-100 | Var. 6531 |
| 10-52 | Var. 6532 |
| 10-50 | Var. 6533 |

Var. = Variation

In another embodiment, the furin (e.g., rfurin) concentration of a stabilized composition provided herein can be expressed as the mass of furin present in the composition. In one embodiment, furin (e.g., rfurin) is present in a stabilized composition as described herein at a concentration from 100 ng/mL to 100 mg/mL. In another embodiment, furin (e.g., rfurin) is present in a stabilized composition as described herein at a concentration from 1 µg/mL to 10 mg/mL. In another embodiment, furin (e.g., rfurin) is present in a stabilized composition as described herein at a concentration from 1 µg/mL to 1 mg/mL. In yet other embodiments, furin (e.g., rfurin) is present in a stabilized composition as described herein at a concentration selected from variations 6534 to 6638 found in Table 15. In specific embodiments, the furin contained in the highly stabilized formulations of the present disclosure is rfurin.

TABLE 15

Exemplary furin (e.g., rfurin) concentrations used in the stabilized compositions provided herein.

| Range | Variation |
|---|---|
| 100 ng/mL to 100 mg/mL | Var. 6534 |
| 100 ng/mL to 50 mg/mL | Var. 6535 |
| 100 ng/mL to 25 mg/mL | Var. 6536 |
| 100 ng/mL to 10 mg/mL | Var. 6537 |
| 100 ng/mL to 5 mg/mL | Var. 6538 |
| 100 ng/mL to 1 mg/mL | Var. 6539 |
| 100 ng/mL to 500 µg/mL | Var. 6540 |
| 100 ng/mL to 250 µg/mL | Var. 6541 |
| 100 ng/mL to 100 µg/mL | Var. 6542 |
| 100 ng/mL to 50 µg/mL | Var. 6543 |
| 100 ng/mL to 25 µg/mL | Var. 6544 |
| 100 ng/mL to 10 µg/mL | Var. 6545 |
| 100 ng/mL to 5 µg/mL | Var. 6546 |
| 100 ng/mL to 1 µg/mL | Var. 6547 |
| 1 µg/mL to 100 mg/mL | Var. 6548 |
| 1 µg/mL to 50 mg/mL | Var. 6549 |
| 1 µg/mL to 25 mg/mL | Var. 6550 |
| 1 µg/mL to 10 mg/mL | Var. 6551 |
| 1 µg/mL to 5 mg/mL | Var. 6552 |
| 1 µg/mL to 1 mg/mL | Var. 6553 |
| 1 µg/mL to 500 µg/mL | Var. 6554 |
| 1 µg/mL to 250 µg/mL | Var. 6555 |
| 1 µg/mL to 100 µg/mL | Var. 6556 |
| 1 µg/mL to 50 µg/mL | Var. 6557 |
| 1 µg/mL to 25 µg/mL | Var. 6558 |
| 1 µg/mL to 10 µg/mL | Var. 6559 |
| 1 µg/mL to 5 µg/mL | Var. 6560 |
| 5 µg/mL to 100 mg/mL | Var. 6561 |
| 5 µg/mL to 50 mg/mL | Var. 6562 |
| 5 µg/mL to 25 mg/mL | Var. 6563 |
| 5 µg/mL to 10 mg/mL | Var. 6564 |
| 5 µg/mL to 5 mg/mL | Var. 6565 |
| 5 µg/mL to 1 mg/mL | Var. 6566 |
| 5 µg/mL to 500 µg/mL | Var. 6567 |
| 5 µg/mL to 250 µg/mL | Var. 6568 |
| 5 µg/mL to 100 µg/mL | Var. 6569 |
| 5 µg/mL to 50 µg/mL | Var. 6570 |
| 5 µg/mL to 25 µg/mL | Var. 6571 |
| 5 µg/mL to 10 µg/mL | Var. 6572 |
| 10 µg/mL to 100 mg/mL | Var. 6573 |
| 10 µg/mL to 50 mg/mL | Var. 6574 |
| 10 µg/mL to 25 mg/mL | Var. 6575 |
| 10 µg/mL to 10 mg/mL | Var. 6576 |
| 10 µg/mL to 5 mg/mL | Var. 6577 |
| 10 µg/mL to 1 mg/mL | Var. 6578 |
| 10 µg/mL to 500 µg/mL | Var. 6579 |
| 10 µg/mL to 250 µg/mL | Var. 6580 |
| 10 µg/mL to 100 µg/mL | Var. 6581 |
| 10 µg/mL to 50 µg/mL | Var. 6582 |
| 10 µg/mL to 25 µg/mL | Var. 6583 |
| 25 µg/mL to 100 mg/mL | Var. 6584 |
| 25 µg/mL to 50 mg/mL | Var. 6585 |
| 25 µg/mL to 25 mg/mL | Var. 6586 |
| 25 µg/mL to 10 mg/mL | Var. 6587 |
| 25 µg/mL to 5 mg/mL | Var. 6588 |
| 25 µg/mL to 1 mg/mL | Var. 6589 |
| 25 µg/mL to 500 µg/mL | Var. 6590 |
| 25 µg/mL to 250 µg/mL | Var. 6591 |
| 25 µg/mL to 100 µg/mL | Var. 6592 |
| 25 µg/mL to 50 µg/mL | Var. 6593 |
| 50 µg/mL to 100 mg/mL | Var. 6594 |
| 50 µg/mL to 50 mg/mL | Var. 6595 |
| 50 µg/mL to 25 mg/mL | Var. 6596 |
| 50 µg/mL to 10 mg/mL | Var. 6597 |
| 50 µg/mL to 5 mg/mL | Var. 6598 |
| 50 µg/mL to 1 mg/mL | Var. 6599 |
| 50 µg/mL to 500 µg/mL | Var. 6600 |
| 50 µg/mL to 250 µg/mL | Var. 6601 |
| 50 µg/mL to 100 µg/mL | Var. 6602 |
| 100 µg/mL to 100 mg/mL | Var. 6603 |
| 100 µg/mL to 50 mg/mL | Var. 6604 |
| 100 µg/mL to 25 mg/mL | Var. 6605 |
| 100 µg/mL to 10 mg/mL | Var. 6606 |
| 100 µg/mL to 5 mg/mL | Var. 6607 |
| 100 µg/mL to 1 mg/mL | Var. 6608 |
| 100 µg/mL to 500 µg/mL | Var. 6609 |
| 100 µg/mL to 250 µg/mL | Var. 6610 |
| 250 µg/mL to 100 mg/mL | Var. 6611 |
| 250 µg/mL to 50 mg/mL | Var. 6612 |
| 250 µg/mL to 25 mg/mL | Var. 6613 |
| 250 µg/mL to 10 mg/mL | Var. 6614 |

TABLE 15-continued

Exemplary furin (e.g., rfurin) concentrations used in the stabilized compositions provided herein.

| | |
|---|---|
| 250 µg/mL to 5 mg/mL | Var. 6615 |
| 250 µg/mL to 1 mg/mL | Var. 6616 |
| 250 µg/mL to 500 µg/mL | Var. 6617 |
| 500 µg/mL to 100 mg/mL | Var. 6618 |
| 500 µg/mL to 50 mg/mL | Var. 6619 |
| 500 µg/mL to 25 mg/mL | Var. 6620 |
| 500 µg/mL to 10 mg/mL | Var. 6621 |
| 500 µg/mL to 5 mg/mL | Var. 6622 |
| 500 µg/mL to 1 mg/mL | Var. 6623 |
| 1 mg/mL to 100 mg/mL | Var. 6624 |
| 1 mg/mL to 50 mg/mL | Var. 6625 |
| 1 mg/mL to 25 mg/mL | Var. 6626 |
| 1 mg/mL to 10 mg/mL | Var. 6627 |
| 1 mg/mL to 5 mg/mL | Var. 6628 |
| 5 mg/mL to 100 mg/mL | Var. 6629 |
| 5 mg/mL to 50 mg/mL | Var. 6630 |
| 5 mg/mL to 25 mg/mL | Var. 6631 |
| 5 mg/mL to 10 mg/mL | Var. 6632 |
| 10 mg/mL to 100 mg/mL | Var. 6633 |
| 10 mg/mL to 50 mg/mL | Var. 6634 |
| 10 mg/mL to 25 mg/mL | Var. 6635 |
| 25 mg/mL to 100 mg/mL | Var. 6636 |
| 25 mg/mL to 50 mg/mL | Var. 6637 |
| 50 mg/mL to 100 mg/mL | Var. 6638 |

Var. = Variation

In some aspects of the present disclosure, furin (e.g., rfurin) formulations include calcium or another divalent metal cations. In further aspects, the divalent cation is present as a salt, preferably a chloride salt. In certain embodiments, from 0.1 mM to 10 mM of a divalent cation salt can be used, or from 0.5 mM to 2 mM, or about 0.92 mM. In still further embodiments, from 0.5 mM to 9 mM, from 1 mM to 8 mM, from 1.5 mM to 7 mM, from 2 mM to 6 mM, from 2.5 mM to 5 mM, or from 3 mM to 4.5 mM divalent cation salt is used in formulations of the invention. When calcium salt is used, it is preferably calcium chloride, but can also be other calcium salts such as calcium gluconate, calcium glubionate, or calcium gluceptate. Divalent cations, including calcium, can be included in combination with one or more other formulation components disclosed herein. Non-limiting examples of divalent metal cations useful in the formulations provided herein include calcium, barium, manganese, magnesium, cobalt, copper, nickel, and zinc.

In some embodiments, the furin (e.g., rfurin) formulations include an antioxidant. The addition of antioxidants to aqueous and lyophilized formulations has been found to improve the stability of these formulations, and thus extend their shelf lives. The antioxidants used must be compatible for use with a pharmaceutical preparation, and in addition are preferably water soluble. When adding antioxidants to a formulation, it is preferable to add such antioxidants as late in the process prior to lyophilization as possible, in order to avoid spontaneous oxidation of the antioxidant. Table 2 below lists suitable antioxidants, which are available commercially through companies such as Calbiochem and Sigma.

TABLE 16

Exemplary Antioxidants

N-Acetyl-L-Cysteine/Homocysteine
Glutathione
6-hydroxy-2,5,7,8-tetramethylchroman-2-carboxylic acid (Trolox)
Lipoic acid
Methionine
Sodium Thiosulfate
Platinum TABLE 16-continued Exemplary Antioxidants Glycme-glycine-histidme (tripeptide)
Butylatedhydroxytoluene (BHT)

Concentrations in the range of about 0.05 mg/ml to more than 1.0 mg/ml of antioxidants can be used, and it is believed that higher concentrations would also be useful (up to the point of any toxic effects or adverse manufacturing effects, such as a depression of the glass transition temperature of the lyophilized product). Accordingly, in one embodiment, the furin (e.g., rfurin) composition comprises from 0.05 mg/mL to 1.0 mg/mL antioxidant. In other embodiments, the furin (e.g., rfurin) composition comprises from 0.05 to 0.5 mg/mL, 0.1 mg/mL to 0.9 mg/mL, 0.1 mg/mL to 0.8 mg/mL, 0.1 mg/mL to 0.7 mg/mL, 0.1 mg/mL to 0.6 mg/mL, 0.1 mg/mL to 0.5 mg/mL, 0.1 mg/mL to 0.4 mg/mL, 0.1 mg/mL to 0.3 mg/mL, 0.1 mg/mL to 0.2 mg/mL, 0.2 mg/mL to 0.9 mg/mL, 0.2 mg/mL to 0.8 mg/mL, 0.2 mg/mL to 0.7 mg/mL, 0.2 mg/mL to 0.6 mg/mL, 0.2 mg/mL to 0.5 mg/mL, 0.2 mg/mL to 0.4 mg/mL, 0.2 mg/mL to 0.3 mg/mL, 0.3 mg/mL to 0.7 mg/mL, 0.4 mg/mL to 0.6 mg/mL antioxidant.

E. Formulation Development

In certain aspects of the present disclosure, highly stabilized formulations of furin (e.g., rfurin) are prepared by providing a starting (control) furin formulation and adding components to achieve a desired level of component concentrations. For example, the addition of one part 750 ppm non-ionic surfactant to 9 parts furin composition lacking non-ionic surfactant to provide a final formulation comprising 75 ppm non-ionic surfactant. This process is also called "spiking in" to a starting formulation.

In certain embodiments, to produce the highly stabilized furin (e.g., rfurin) formulations of the present disclosure, furin is contained in a starting formulation and a buffer composition is spiked into the starting formulation. In other embodiments, the highly stabilized furin (e.g., rfurin) formulation is formed using dialysis according to methods known in the art. In some embodiments, the methods of formulation involve spiking a concentrated buffer composition into a starting formulation of furin. In one embodiment, polysorbate 80 is added to the starting formulation prior to the addition of other components, particularly prior to the addition of trehalose, in order to protect Furin against agitation during mixing.

In an exemplary embodiment, furin (e.g., rfurin) bulk drug substance (BDS) is contained in a starting formulation of 10 mM sodium acetate, 230 mM sodium chloride, 1 mM calcium chloride, pH 6.0. In one embodiment, the following components are spiked into the starting formulation: 1% polysorbate 80, 500 mM HEPES, 400 mM acetic acid, 1 mM $CaCl_2$, pH 6.0 and trehalose dihydrate powder to attain the following composition: 46 mM HEPES, 45 mM acetic acid, 190 mM NaCl, 0.92 mM CaCl2, 75 ppm polysorbate 80, 10% w/w trehalose dihydrate, pH 6.0. The increase in acetic acid and the addition of HEPES results in greater stability of the pH. Although at pH 6.0 both acetic acid and HEPES are outside of their highest buffering capacity, the high concentration of these chemicals greatly increases the buffering capacity of the highly stabilized formulation. In certain embodiments, the polysorbate 80 is added to the starting formulation prior to the other components to protect furin from aggregation and adsorption to container surfaces during mixing when the other reagents are added. In certain embodiments, the furin in the starting formulation is mixed with polysorbate 80 and/or any other components except for trehalose. Trehalose and any remaining components are added after polysorbate 80 is added to protect furin from aggregation and adsorption during mixing.

In certain embodiments, the stabilized formulation is combined with a diluent so that the formulation can be used in methods such as an rVWF maturation process. In further embodiments, a stabilized diluent is prepared by spiking a starting diluent (50 mM HEPES, 150 mM NaCl, 1 mM CaCl$_2$, pH 7.0) with polysorbate 80 to 75 ppm. The combination of the highly stabilized furin (e.g., rfurin) formulation of the present disclosure with this stabilized diluent increases furin recovery in the rVWF maturation step by three to four times compared to the use of the starting furin and diluent formulations.

In certain embodiments, the highly stabilized furin formulations of the present disclosure are lyophilized. During lyophilization, the formulation is converted from being in an aqueous phase to being in an amorphous solid phase, which is thought to protect the protein from chemical and/or conformational instability. In further embodiments, the lyophilized preparation not only contains an amorphous phase, but also includes a component which crystallizes during lyophilization.

One or more components of highly stabilized formulations may in some embodiments be dispersed in the amorphous phase of the lyophilized cake. In addition, the apparent glass transition temperature (Tg') of the amorphous phase is preferably relatively high during freeze-drying, and the glass transition temperature (Tg) of the solid is likewise preferably high during storage.

IV. Methods for Diluting Aqueous Compositions of Recombinant Furin

In one aspect, the present disclosure provides methods for diluting aqueous compositions of furin (e.g., rfurin). The following embodiments are based in part on the discovery that inclusion of a non-ionic surfactant in a buffer used to dilute furin (e.g., rfurin) results in the recovery of 3-4 times more furin activity as compared to dilution with a buffer lacking the non-ionic surfactant.

In one embodiment, the method includes adding a dilution buffer containing non-ionic surfactant to a furin (e.g., rfurin) composition, to form a diluted furin (e.g., rfurin) composition. In some embodiments, the dilution buffer is added at a ratio of from 1:1 (dilution buffer:furin composition) to 1,000:1 (dilution buffer:furin composition). In another embodiment, the dilution buffer is added at a ratio of from 1:1 (dilution buffer:furin composition) to 500:1 (dilution buffer:furin composition). In another embodiment, the dilution buffer is added at a ratio of from 1:1 (dilution buffer:furin composition) to 250:1 (dilution buffer:furin composition). In another embodiment, the dilution buffer is added at a ratio of from 1:1 (dilution buffer:furin composition) to 200:1 (dilution buffer:furin composition). In another embodiment, the dilution buffer is added at a ratio of from 1:1 (dilution buffer:furin composition) to 100:1 (dilution buffer:furin composition). In another embodiment, the dilution buffer is added at a ratio of from 1:1 (dilution buffer:furin composition) to 50:1 (dilution buffer:furin composition).

In one embodiment, the method comprises a first step of adding a non-ionic surfactant to a furin (e.g., rfurin) composition and a second step of adding a dilution buffer to the furin (e.g., rfurin) composition containing the non-ionic surfactant, to form a diluted furin composition. In one embodiment, the surfactant will be added to the furin composition at a final concentration of X-fold a desired concentration in the diluted furin composition, where X is the dilution factor. For example, if a final concentration of 10 ppm non-ionic surfactant is desired in a furin composition to be diluted 100-fold, the non-ionic surfactant is added to the starting furin composition at a final concentration of 1,000 ppm (10 ppm×100-fold dilution), and the composition is subsequently diluted by adding 99 parts dilution buffer per 1 part starting solution (accounting for volume added during addition of the non-ionic surfactant).

In certain embodiments, the furin (e.g., rfurin) composition is diluted from 1-fold to 1,000-fold, from 1-fold to 500-fold, from 1-fold to 250-fold, from 1-fold to 200-fold, from 1-fold to 100-fold, from 1-fold to 50-fold, from 1-fold to 10-fold, from 10-fold to 1,000-fold, from 10-fold to 500-fold, from 10-fold to 250-fold, from 10-fold to 200-fold, from 10-fold to 100-fold, from 10-fold to 50-fold, from 50-fold to 1,000-fold, from 50-fold to 500-fold, from 50-fold to 250-fold, from 50-fold to 200-fold, from 50-fold to 100-fold, from 100-fold to 1,000-fold, from 100-fold to 500-fold, from 100-fold to 250-fold, from 100-fold to 200-fold, from 200-fold to 1,000-fold, from 200-fold to 500-fold, or from 200-fold to 250-fold.

A. Furin Dilution Buffer

In one embodiment, the furin dilution buffer will include a pharmaceutically acceptable salt, non-ionic surfactant, and a buffering agent. In one embodiment, the dilution buffer further includes calcium. In another embodiment, the dilution buffer further includes a sugar and/or sugar alcohol.

In one embodiment, pharmaceutically acceptable salt is present in the dilution buffer at a concentration of from 10 mM to 500 mM. In another embodiment, the concentration of pharmaceutically acceptable salt is from 100 mM to 300 mM. In another embodiment, the concentration of pharmaceutically acceptable salt is from 150 mM to 250 mM. In yet other embodiments, the concentration of pharmaceutically acceptable salt in the furin dilution buffer is selected from variations 6036 to 6180 found in Table 10. In one embodiment, the pharmaceutically acceptable salt is sodium chloride, potassium chloride, or a combination thereof. In a specific embodiment, pharmaceutically acceptable salt is sodium chloride. In another specific embodiment, pharmaceutically acceptable salt is potassium chloride.

In one embodiment, the dilution buffer has a pH of from 5.5 to 7.5. In one embodiment, the pH of the dilution buffer is from 5.5 to 7.0. In another embodiment, the pH of the dilution buffer is from 5.5 to 6.5. In another embodiment, the pH of the dilution buffer is 6.0±0.2. In a specific embodiment, the pH of the dilution buffer is 6.0. In other embodiments, the dilution buffer has a pH selected from variations 6181 to 6403 found in Table 11.

In one embodiment, buffering agent is present in the dilution buffer at a concentration of from 10 mM to 300 mM. In another embodiment, the concentration of buffering agent in the dilution buffer is between 10 mM to 200 mM. In other embodiments, the concentration of buffering agent in the dilution buffer is selected from variations 6404 to 6469 found in Table 12. In one embodiment, the buffering agent is acetate, HEPES, or a combination thereof. In a specific embodiment, the buffering agent is a combination of acetate and HEPES.

In some embodiments, the furin dilution buffer includes calcium or another divalent metal cation. In one embodiment, the divalent cation is added as a salt, preferably a chloride salt. In certain embodiments, the concentration of divalent cation (e.g., calcium) in the dilution buffer is from 0.1 mM to 10 mM, from 0.5 mM to 2 mM, or about 0.92 mM. In still further embodiments, from 0.5 mM to 9 mM, from 1 mM to 8 mM, from 1.5 mM to 7 mM, from 2 mM to 6 mM, from 2.5 mM to 5 mM, or from 3 mM to 4.5 mM divalent cation is used in the dilution buffer. When calcium salt is used, it is preferably calcium chloride, but can also be other calcium salts such as calcium gluconate, calcium glubionate, or calcium gluceptate. Divalent cations, including calcium, can be included in combination with one or more other formulation components disclosed herein. Non-limiting examples of divalent metal cations useful in the dilution buffers provided herein include calcium, barium, manganese, magnesium, cobalt, copper, nickel, and zinc.

In some embodiments, the furin dilution buffer includes a sugar and/or sugar alcohol. In one embodiment, the dilution buffer contains a monosaccharide sugar. In a particular embodiment, the monosaccharide sugar is selected from the group consisting of a diose sugar, a triose sugar, a tetrose sugar, a pentose sugar, a hexose sugar, a heptose sugar, and an octose sugar. In a particular embodiment, the sugar is a pentose sugar, a hexose sugar, or a combination thereof. In a specific embodiment, the sugar is a hexose sugar.

In another embodiment, the dilution buffer contains a disaccharide sugar. In a particular embodiment, the disaccharide sugar is selected from disaccharide sugars formed from pentose and/or hexose monosaccharides. In another particular embodiment, the sugar is selected from disaccharide sugars formed from hexose monosaccharides. In one embodiment, the sugar is sucrose, trehalose, or a combination thereof. In one specific embodiment, the sugar is sucrose. In another specific embodiment, the sugar is trehalose. In one embodiment, the sugar is formulated as trehalose dihydrate.

In another embodiment, the dilution buffer contains a sugar alcohol. In a particular embodiment, the sugar alcohol is selected from glycol, glycerol, erythritol, threitol, ribitol, fucitol, iditol, volmitol, isomalt, maltitol, lactitol, mannitol, sorbitol, inositol, galactitol, dulcitol, xylitol, and arabitol. In another particular embodiment, the sugar alcohol is mannitol.

In yet another embodiment, the dilution buffer contains a mixture of sugar and sugar alcohol. In one embodiment, the mixture contains at least two of a monosaccharide, a disaccharide, and a sugar alcohol. In another embodiment, the mixture contains at least two of a pentose sugar, a hexose sugar, a disaccharide formed from pentose and/or hexose monosaccharides, and a sugar alcohol. In another embodiment, the mixture contains at least two of sucrose, trehalose, and mannitol.

In one embodiment, the sugar or sugar alcohol is present in the dilution buffer at a concentration of from 2% to 20%, 2% to 17.5%, 2% to 15%, 2% to 12.5%, 2% to 10%, 2% to 9%, 2% to 8%, 2% to 7%, 5% to 20%, 5% to 17.5%, 5% to 15%, 5% to 12.5%, 5% to 10%, 7.5% to 20%, 7.5% to 17.5%, 7.5% to 15%, 7.5% to 12.5%, 10% to 20%, 10% to 17.5%, 10% to 15%, 4±2%, 5±2%, 6±2%, 7±2%, 8±2%, 9±2%, 10±2%, 11±2%, 12±2%, 13±2%, 14±2%, 15±2%, 16±2%, 17±2%, 18±2%, 3±1%, 4±1%, 5±1%, 6±1%, 7±1%, 8±1%, 9±1%, 10±1%, 11±1%, 12±1%, 13±1%, 14±1%, 15±1%, 16±1%, 17±1%, 18±1%, 19±1%, 2%, 3%, 4%, 5%, 6%, 7%, 8%, 9%, 10%, 11%, 12%, 13%, 14%, 15%, 16%, 17%, 18%, 19%, or 20%. In one embodiment, the sugar or sugar alcohol is selected from sucrose, trehalose, mannitol, and a combination thereof. In a specific embodiment, the sugar or sugar alcohol is trehalose.

In one embodiment, storage stable compositions of furin (e.g., rfurin) are provided which contain a non-ionic surfactant selected from a non-ionic water soluble monoglyceride, a non-ionic water soluble diglyceride, a non-ionic water soluble triglyceride, a non-ionic water soluble monofatty acid esters of polyethyelene glycol, a non-ionic water soluble difatty acid esters of polyethyelene glycol, a non-ionic water soluble sorbitan fatty acid ester, a non-ionic polyglycolyzed glyceride, a non-ionic water soluble triblock copolymer, and a combination thereof. In one embodiment, the non-ionic surfactant is a non-ionic water soluble sorbitan fatty acid ester. In a specific embodiment, the non-ionic surfactant is polysorbate 80 (polyoxyethylene (20) sorbitan monooleate).

1. Non-Ionic Surfactants

In one embodiment, the furin dilution buffer, or non-ionic surfactant solution added prior to dilution, contains a non-ionic surfactant selected from a non-ionic water soluble monoglyceride, a non-ionic water soluble diglyceride, a non-ionic water soluble triglyceride, a non-ionic water soluble monofatty acid esters of polyethyelene glycol, a non-ionic water soluble difatty acid esters of polyethyelene glycol, a non-ionic water soluble sorbitan fatty acid ester, a non-ionic polyglycolyzed glyceride, a non-ionic water soluble triblock copolymer, and a combination thereof. In one embodiment, the non-ionic surfactant is a non-ionic water soluble sorbitan fatty acid ester. In a specific embodiment, the non-ionic surfactant is polysorbate 80 (polyoxyethylene (20) sorbitan monooleate).

In one embodiment, the non-ionic surfactant is present in the dilution buffer at a concentration of from 10 to 200 ppm, 10 to 175 ppm, 10 to 150 ppm, 10 to 125 ppm, 10 to 100 ppm, 10 to 90 ppm, 10 to 80 ppm, 10 to 75 ppm, 10 to 70 ppm, 10 to 60 ppm, 10 to 50 ppm, 10 to 25 ppm, 25 to 200 ppm, 25 to 175 ppm, 25 to 150 ppm, 25 to 125 ppm, 25 to 100 ppm, 25 to 90 ppm, 25 to 80 ppm, 25 to 70 ppm, 25 to 60 ppm, 25 to 50 ppm, 50 to 200 ppm, 50 to 175 ppm, 50 to 150 ppm, 50 to 125 ppm, 50 to 90 ppm, 50 to 80 ppm, 75 to 200 ppm, 75 to 175 ppm, 75 to 150 ppm, 100 to 200 ppm, 100 to 175 ppm, 50±25 ppm, 60±25 ppm, 70±25 ppm, 75±25 ppm, 80±25 ppm, 90±25 ppm, 100±25 ppm, 125±25 ppm, 150±25 ppm, 175±25 ppm, 30±10 ppm, 40±10 ppm, 50±10 ppm, 60±10 ppm, 70±10 ppm, 75±10 ppm, 80±10 ppm, 90±10 ppm, 100±10 ppm, 110±10 ppm, 120±10 ppm, 125±10 ppm, 130±10 ppm, 140±10 ppm, 150±10 ppm, 160±10 ppm, 170±10 ppm, 175±10 ppm, 180±10 ppm, 190±10 ppm, 25 ppm, 30 ppm, 40 ppm, 50 ppm, 60 ppm, 70 ppm, 75 ppm, 80 ppm, 90 ppm, 100 ppm, 110 ppm, 120 ppm, 125 ppm, 130 ppm, 140 ppm, 150 ppm, 160 ppm, 170 ppm, 175 ppm, 180 ppm, 190 ppm, or 200 ppm. In one embodiment, the non-ionic surfactant is a non-ionic water soluble sorbitan fatty acid ester. In a specific embodiment, the non-ionic surfactant is polysorbate 80 (polyoxyethylene (20) sorbitan monooleate).

In one embodiment, the target concentration of non-ionic surfactant after dilution is from 10 to 200 ppm, 10 to 175 ppm, 10 to 150 ppm, 10 to 125 ppm, 10 to 100 ppm, 10 to 90 ppm, 10 to 80 ppm, 10 to 75 ppm, 10 to 70 ppm, 10 to 60 ppm, 10 to 50 ppm, 10 to 25 ppm, 25 to 200 ppm, 25 to 175 ppm, 25 to 150 ppm, 25 to 125 ppm, 25 to 100 ppm, 25 to 90 ppm, 25 to 80 ppm, 25 to 70 ppm, 25 to 60 ppm, 25 to 50 ppm, 50 to 200 ppm, 50 to 175 ppm, 50 to 150 ppm, 50 to 125 ppm, 50 to 90 ppm, 50 to 80 ppm, 75 to 200 ppm, 75 to 175 ppm, 75 to 150 ppm, 100 to 200 ppm, 100 to 175 ppm, 50±25 ppm, 60±25 ppm, 70±25 ppm, 75±25 ppm, 80±25 ppm, 90±25 ppm, 100±25 ppm, 125±25 ppm, 150±25 ppm, 175±25 ppm, 30±10 ppm, 40±10 ppm, 50±10 ppm, 60±10 ppm, 70±10 ppm, 75±10 ppm, 80±10 ppm, 90±10 ppm, 100±10 ppm, 110±10 ppm, 120±10 ppm, 125±10 ppm, 130±10 ppm, 140±10 ppm, 150±10 ppm, 160±10 ppm, 170±10 ppm, 175±10 ppm, 180±10 ppm, 190±10 ppm, 25 ppm, 30 ppm, 40 ppm, 50 ppm, 60 ppm, 70 ppm, 75 ppm, 80 ppm, 90 ppm, 100 ppm, 110 ppm, 120 ppm, 125 ppm, 130 ppm, 140 ppm, 150 ppm, 160 ppm, 170 ppm, 175 ppm, 180 ppm, 190 ppm, or 200 ppm. In one embodiment, the non-ionic surfactant is a non-ionic water soluble sorbitan fatty acid ester. In a specific embodiment, the non-ionic surfactant is polysorbate 80 (polyoxyethylene (20) sorbitan monooleate).

In one embodiment, the inclusion of a non-ionic surfactant in a furin dilution buffer, or addition prior to dilution, increases the furin activity recovered in a diluted furin composition by at least 10%, as compared to the activity recovered in a furin composition diluted without use of the non-ionic surfactant, or with the use of the non-ionic surfactant at a lower concentration. In other embodiments, the furin activity recovered after dilution using a non-ionic surfactant is at least 15%, 20%, 25%, 30%, 35%, 40%, 45%, 50%, 55%, 60%, 65%, 70%, 75%, 80%, 85%, 90%, 95%, 100%, 125%, 150%, 175%, 2-fold, 3-fold, 4-fold, 5-fold, or more greater than the furin activity recovered after dilution without the non-ionic surfactant, or using a lower concentration of the non-ionic surfactant.

V. Stability Assays

As discussed herein, the highly stabilized furin (e.g., rfurin) formulations of the present disclosure show improved stability as compared to control formulations. In one embodiment, improved stability includes retention of a higher percentage of activity than control formulations in various stability assays. Such assays can be used to determine if a formulation is a highly stabilized formulation. In some embodiments, the highly stabilized formulation has at least 5%, 10%, 20%, 30%, 40%, 50%, 55%, 60%, 65%, 70%, 75%, 80%, 85%, 90%, 95%, 96%, 97%, 98%, 99% or greater activity than a control formulation when assessed by any of the stability assays discussed herein or known in the art.

In further aspects, furin (e.g., rfurin) formulations are tested under stressor conditions, such as storage at high temperature, agitation, freeze/thaw cycles, or some combination thereof. After such stressors, the formulations are assayed using any of the methods described herein or known in the art to determine the stability under these conditions.

In one aspect, furin activity assays are used to assess the stability of a formulation. In some embodiments, a furin activity assays involve a measurement of substrate cleavage. In one embodiment, the substrate is Boc-Arg-Val-Arg-Arg-AMC (SEQ ID NO:1; AMC=7-amino-4-methoxy coumarin), which is cleaved by furin, liberating 7-amino-4-methoxy coumarin. The assay is performed, for example, on an ELISA plate. The furin activity in a sample is determined from a standard curve created, for example, from a quality control (QC) furin standard. The activity values are generally calculated as mean values from two dilutions, each in duplicate.

In another aspect, size exclusion chromatography (SEC) is used to evaluate the stability of a furin (e.g., rfurin) formulation. In such assays, stability is indicated by the height of the peak corresponding to monomeric furin. A reduction in monomer peak height means the product is being lost (unstable) and the generation of higher molecular weight peaks indicates that aggregation is occurring and lower molecular weight peaks means the product is degrading. In an exemplary embodiment, after 4 days at 37° C., the relative peak height of a control furin formulation was 58.5%, but in a highly stabilized formulation, the relative peak height was 74.8% (FIG. 48). Thus, the highly stabilized formulation maintained the stability of furin in the composition and retained a larger percentage of the peak height as compared to that seen prior to storage at four days at a higher (37° C.) temperature.

In another aspect, qualitative assays such as Western Blot analyses, are used to evaluate the stability of a Furin formulation. For example, FIG. 26 shows that after 5 days at 35° C., a greater percent of the signal is present as the intact furin molecule rather than the degraded species in the stabilized formulation (lane 11), as compared to a non-stabilized formulation (lane 5).

In still another aspect, qualitative assays such as UV spectra are used to evaluate stability. Such assays are particularly useful when the stressor used is agitation. The UV spectra can indicate the presence of aggregate—the presence of an aggregate is an indication of instability. For example, FIG. 36 shows a major displacement of the spectra upward (indicating aggregation) when the control formulation is agitated. FIGS. 41 and 42 show the protective power of a highly stabilized formulation in that, with agitation, the spectra of the agitated sample is not displaced upward, but overlays the non-agitated sample, which indicates that aggregation was not formed when the formulation was placed under stress through agitation.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press), Stryer, L. (1995) Biochemistry (4th Ed.) Freeman, Highly stabilized York, Gait, "Oligonucleotide Synthesis: A Practical Approach" 1984, IRL Press, London, Nelson and Cox (2000), Lehninger, Principles of Biochemistry 3rd Ed., W. H. Freeman Pub., Highly stabilized York, N.Y. and Berg et al. (2002) Biochemistry, 5th Ed., W. H. Freeman Pub., Highly stabilized York, N.Y., all of which are herein incorporated in their entirety by reference for all purposes.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

Although the present invention is described primarily with reference to specific embodiments, it is also envisioned that other embodiments will become apparent to those skilled in the art upon reading the present disclosure, and it is intended that such embodiments be contained within the present inventive methods.

EXAMPLES

Example 1

Storage Stability of Aqueous Rfurin Formulations

The stability of a control furin formulation was tested at three different temperatures: room temperature (e.g., 25° C.), 37° C., and 45° C. These studies at elevated temperatures were used to study accelerated stability, which is comparable to long term studies of stability at lower temperatures. The samples were tested at time zero, then after 1, 2, 3, 4, and 7 days of incubation. Analyses included the furin activity assay, SEC, and western blotting.

Briefly, several 5 mL polypropylene vials were filled with 3 mL of rfurin and incubated at three different temperatures: ambient (room), 37° C. and 45° C. One vial from each incubation condition was taken out at time zero, then after 1, 2, 3, 4, and 7 days. 200 μL aliquots were made into 0.65 mL polypropylene vials and frozen at −80° C. awaiting analyses.

The stability of several furin formulations was determined under these conditions. Specifics of the various formulations are given in Table 17.

Figure 1:
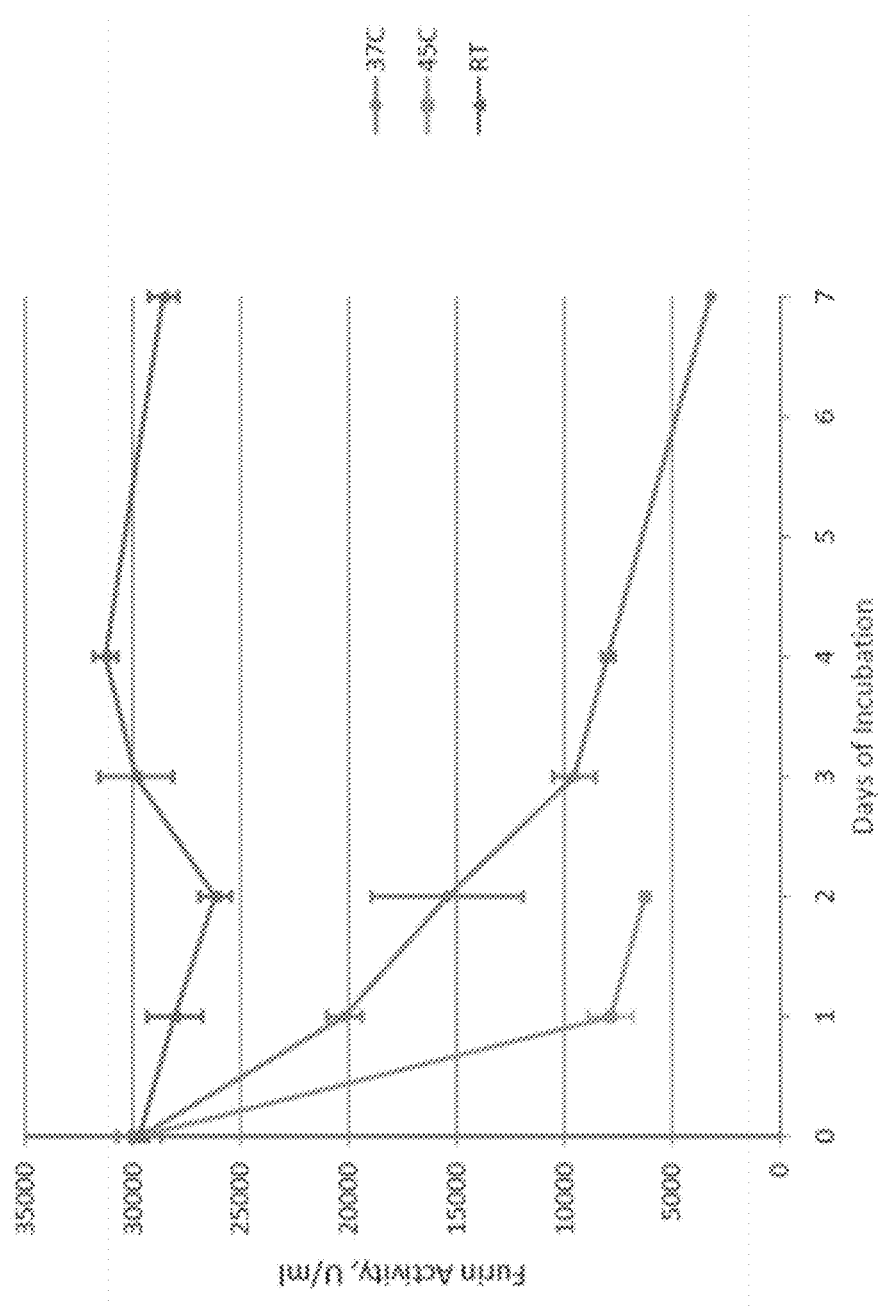
Figure 2:
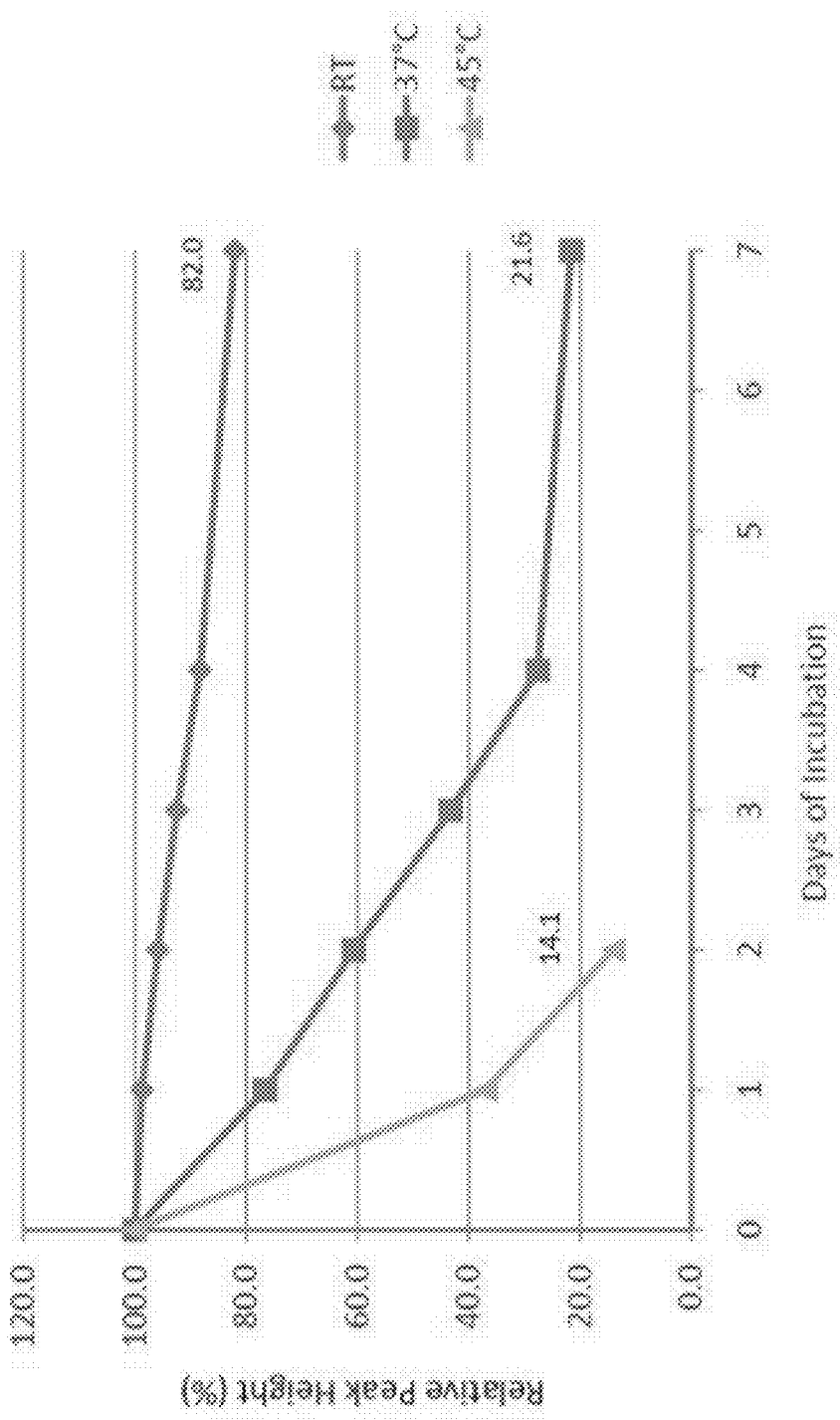
Figure 3:
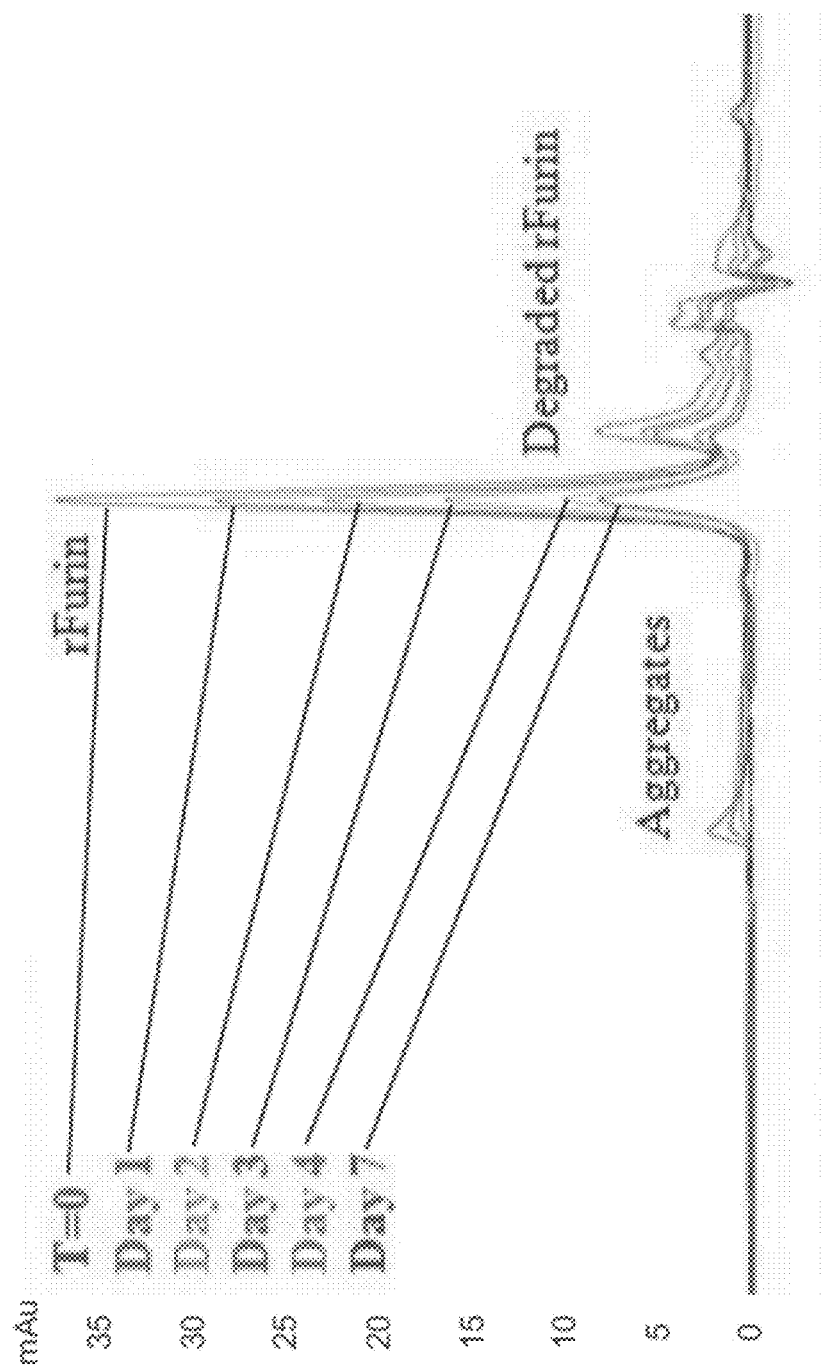
Figure 4:
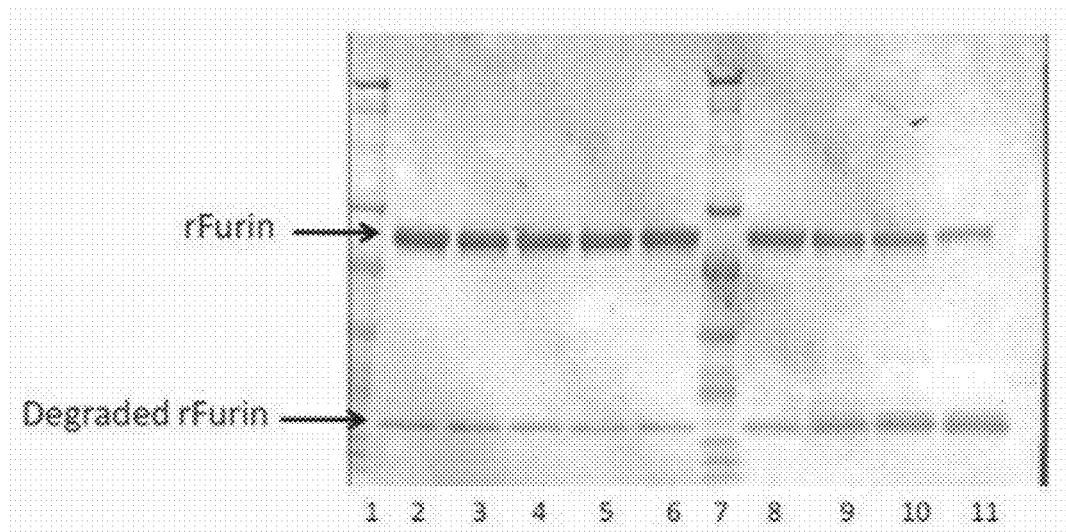
Figure 5:
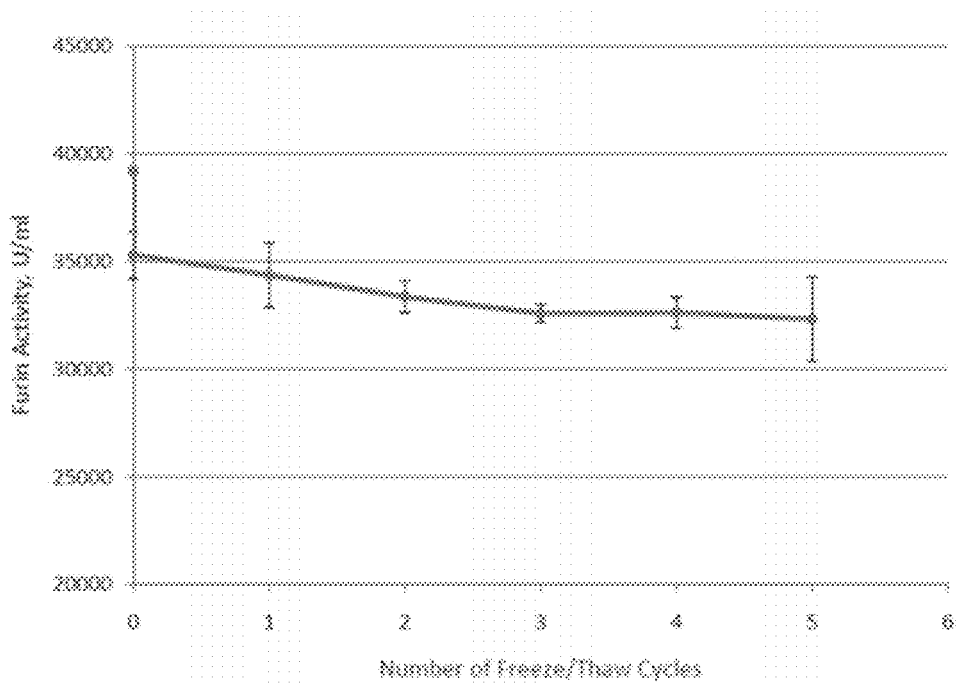

TABLE 17

Furin formulations tested for stability during storage at elevated temperatures.

| | |
|---|---|
| Control Formulation | 10 mM Acetate<br>230 mM sodium chloride<br>1 mM calcium chloride<br>pH 6.0 |
| Test Formulation #1 | 46 mM HEPES<br>45 mM Acetate<br>190 mM sodium chloride<br>0.92 mM calcium chloride<br>75 ppm polysorbate 80<br>10% (w/w) trehalose dehydrate<br>pH 6.0 |
| Test Formulation #2 | 46 mM HEPES<br>45 mM Acetate<br>190 mM sodium chloride<br>0.92 mM calcium chloride<br>10% (w/w) trehalose dehydrate<br>pH 6.0 |
| Test Formulation #3 | 46 mM HEPES<br>45 mM Acetate<br>190 mM sodium chloride<br>0.92 mM calcium chloride<br>10 ppm polysorbate 80<br>10% (w/w) trehalose dehydrate<br>pH 6.0 |
| Test Formulation #4 | 46 mM HEPES<br>45 mM Acetate<br>190 mM sodium chloride<br>0.92 mM calcium chloride<br>25 ppm polysorbate 80<br>10% (w/w) trehalose dehydrate<br>pH 6.0 |
| Test Formulation #5 | 46 mM HEPES<br>45 mM Acetate<br>190 mM sodium chloride<br>0.92 mM calcium chloride<br>50 ppm polysorbate 80<br>10% (w/w) trehalose dehydrate<br>pH 6.0 |
| Test Formulation #6 | 46 mM HEPES<br>45 mM Acetate<br>190 mM sodium chloride<br>0.92 mM calcium chloride<br>100 ppm polysorbate 80<br>10% (w/w) trehalose dehydrate<br>pH 6.0 |

One method of assessing stability is through a furin activity assay. In this assay, the activity of furin is determined from the rate of a substrate cleavage. The substrate, Boc-Arg-Val-Arg-Arg-AMC (SEQ ID NO:1; AMC=7-amino-4-methoxy coumarin), is cleaved by furin and a fluorescent AMC is liberated. The assay is performed, for example, on an ELISA plate. The furin activity in a sample is determined from a standard curve created, for example, from a quality control rfurin standard. The activity values were calculated as mean values from two dilutions, each in duplicate.

rFurin stability at 37° C. in the highly stabilized formulation. The purpose of this experiment was to test rfurin stability in a stabilized formulation containing 75 ppm polysorbate 80. There was a small change in the composition of this sample because trehalose dihydrate ($C_{12}H_{22}O_{11}*2H_2O$, FW 378.33) was used, rather than, nonhydrated trehalose ($C_{12}H_{22}O_{11}$, FW 342.30). Use of the trehalose dihydrate created a slightly more dilute sample. Agitation studies suggested that the polysorbate 80 concentration should be kept between 50 ppm and 100 ppm to provide the best protection against rfurin denaturation induced by agitation. In this study, a rfurin sample in test formulation #1 was spiked with polysorbate 80 to 75 ppm and incubated at 37° C. for four days. An rfurin sample formulated with the control formulation served as a control.

Analyses by the Furin activity assay (FIG. 1) show loss of activity in the samples in the control formulation that were incubated at 37° C. and 45° C. Since the 45° C. sample was highly degraded and aggregated after just two days, the sample was not tested after that time. For the samples incubated at room temperature, the data was inconclusive as a result of the amount of variability in the assay, but the data suggested that the rfurin activity was relatively stable, with the activity after 7 days roughly equivalent to T=0.

In contrast to the data in the control formulation, analyses by the furin activity assay (FIG. 46) show that rfurin in test formulation #1 retained more of its activity than in the control formulation. After four days of incubation at 37° C., rfurin retained 76.7% of its original activity, while the control formulation preserved only 55.5% of its original activity (FIG. 47).

Size exclusion chromatograph (SEC) was also used to assess the stability of various furin formulations. For SEC methods, the following equipment and materials were used:

Agilent HPLC 1100 Series equipped with a temperature controlled autosampler and a Photo-Diode Array detector Autosampler 100 μL polypropylene vials Size Exclusion Chromatography column from TOSOH Bioscience, TSKgel G3000SW×1, 7.8 mm ID×30 cm, 5 μm In addition, following conditions were used for the SEC method:

Mobile Phase: 50 mM MOPS, 200 mM sodium sulfate, 0.02% sodium azide, pH 7.0

Flow Rate: 0.5 mL/min

Run Time: 30 min

Sample Volume: 100 μL

Autosampler Temperature: 4° C.

Column Temperature: Ambient

Single wavelength absorption at 280 nm (Reference off) was used to create chromatographs. After manual integration, the height of the main peak at 19 min, corresponding to the rfurin content of the formulation, was used to evaluate stability. The reason for using the peak height instead of the peak area was that the chromatographic peaks were often not baseline separated, which could lead to large errors. Only one injection of each sample was conducted. Repeated analyses of the rfurin control formulation showed less than 2% variation in the peak height (data not shown).

The SEC results correlated with the furin activity assay results reported above. Analyses by SEC (FIG. 2) show that the height of the rfurin monomer peak (retention time 19 min) of the control formulation decreased with the time of incubation for all temperatures. The rate of the rfurin monomer peak decrease was relatively low in the samples incubated at room temperature, as 82% of the peak height remained after seven days of incubation. However, at 37° C., the height of the rfurin monomer peak dropped to 21.6%, of the original height, after seven days of incubation. At 45° C., after two days of incubation, the main peak decreased to 14.1%. Consistent with the loss of rfurin monomer content, other chromatographic peaks began to appear over time (FIG. 3), corresponding to aggregates (eluting at earlier time points) and degradation products (eluting at later time points). These additional peaks indicate both degradation and aggregation of rfurin in the control formulation. Increased degradation at 37° C. compared to room temperature storage was also confirmed by Western Blotting (FIG. 4). rFurin degradation may be caused by proteases that were co-purified with rfurin, or by the autocatalytic activity of rfurin itself.

In contrast, SEC analysis confirmed the increased stability of test formulation #1 (FIG. 48), containing trehalose, as compared to the control formulation, which does not contain a sugar or sugar alcohol. FIG. 48 shows that test formulation #1 maintained 74.8% of rfurin monomer peak height of the starting solution after incubation at 37° C. for 4 days, as compared to the control formulation, which maintained only 58.5% of rfurin monomer peak height of the starting solution during the same incubation.

Example 2

Storage Stability of Aqueous Rfurin Formulations Upon Freeze/Thaw

Figure 6:
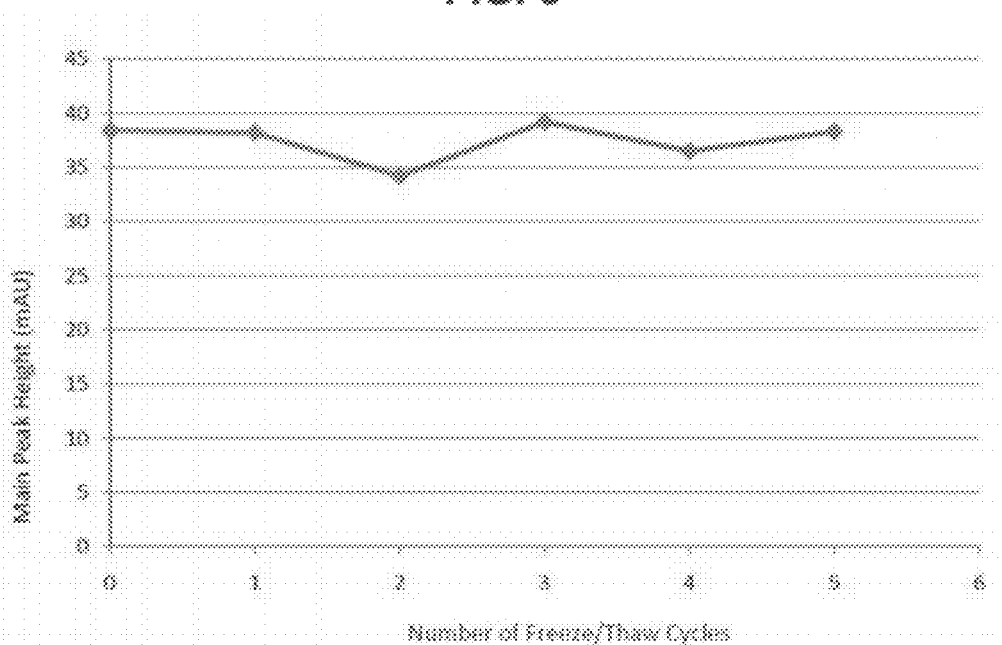

The stability of the control formulation and test formulations #2-6 were tested by a freeze/thaw study. Five freeze/thaw cycles were completed and samples were analyzed by the furin activity assay and SEC. Investigating the impact of freeze/thaw is important because rfurin samples in this study and rfurin BDS are stored frozen. Freeze/thaw experiments using the control formulation (n=4) demonstrate a minor loss of furin activity (approximately 7%) after a total of five freeze/thaw cycles. While there appears to be a downward trend, this may be due to true loss of protein or a reflection of assay variability. Regardless, this data supports the ability to freeze and thaw the rFurin, not only once, but multiple times, with little to no loss of activity. Likewise, SEC analysis of the oligomeric state of furin in the control formulation showed no loss in monomeric content over the course of the freeze/thaw experiment (FIG. 6).

Since rFurin is generally stored frozen, the impact of a thawing method was evaluated. Analyses by the activity assay (Figure) demonstrate no significant difference between the two thawing methods: thawing at 4° C. overnight, or at room temperature for 2 hours.

Taken together, these data suggest that rfurin in the control formulation is relatively stable for short periods at room temperature. Furthermore, loss of activity upon storage at elevated temperatures correlates to both rfurin degradation and aggregation. In addition, rfurin in the control formulation retained its activity well even after five freeze/thaw cycles.

Freeze/Thaw Study of rFurin in a highly stabilized Formulation. The freeze/thaw study was carried out using the same set of samples as the previous Freeze/thaw study; the stability of rfurin in test formulations #2 (0 ppm polysorbate 80), #3 (10 ppm polysorbate 80), #4 (25 ppm polysorbate 80), #5 (50 ppm polysorbate 80), and #6 (100 ppm polysorbate 80) was evaluated. Furin in the control formulation served as a control. Consistent with the prior analysis of the control formulation, analysis of furin activity (FIG. 43) demonstrated no significant loss of activity after five freeze/thaw cycles in any of the tested formulations. Analyses of the rfurin monomer content by SEC (FIGS. 44 and 45) demonstrated only a small trend of sample deterioration after freeze/thaw. Even after five freeze/thaw cycles, all samples retained more than 95% of their original activity.

Example 3

Storage Stability of Aqueous Rfurin Formulations Upon Mechanical Stress

Without being limited by theory, one potential mechanism of the agitation effect on rfurin samples is that it induces denaturation of rfurin, exposing hydrophobic surfaces. The hydrophobic surfaces are attracted to other hydrophobic surfaces, such as other denatured rFurin proteins which induces aggregation, or causing adsorption to hydrophobic surfaces on sample tubes and materials.

The agitation study was not designed to mimic the true process of rfurin use, but to overstress the sample. To be considered stabilized, a formulation of rfurin performs at least as well as the control formulation, and a highly stabilized formulation performs better than the control formulation.

Figure 7:
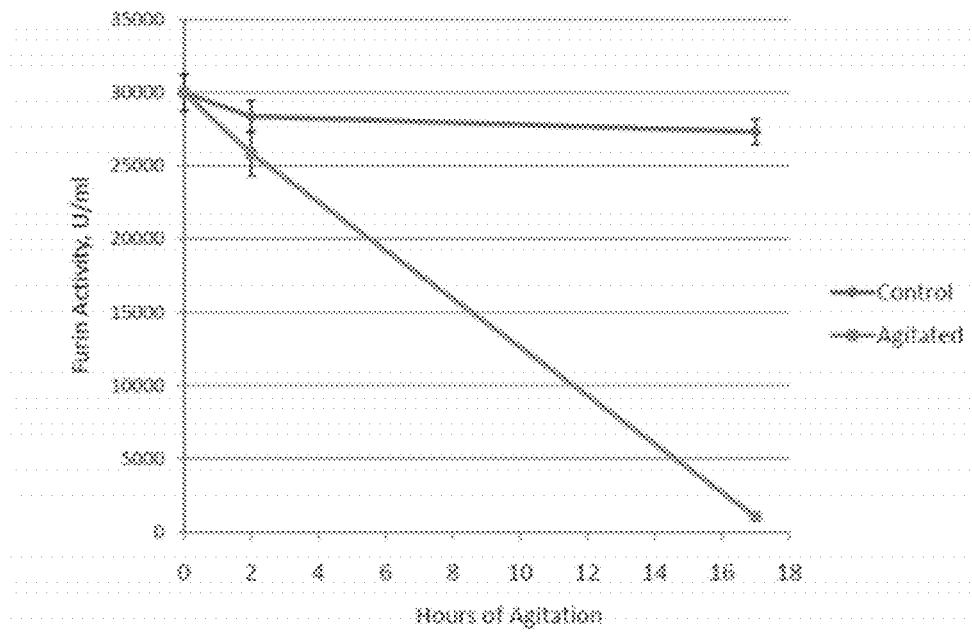
Figure 8:
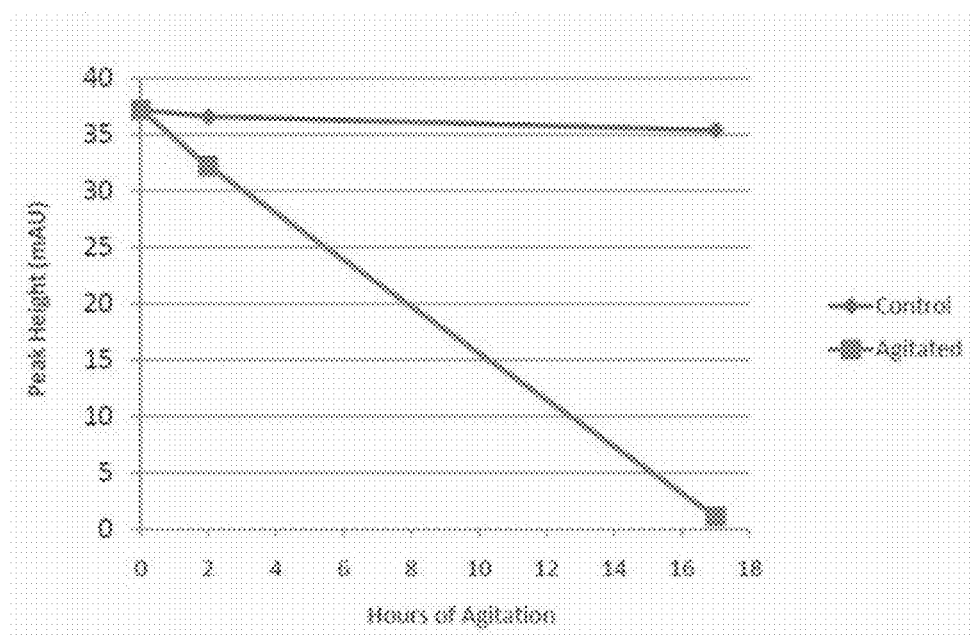
Figure 9:
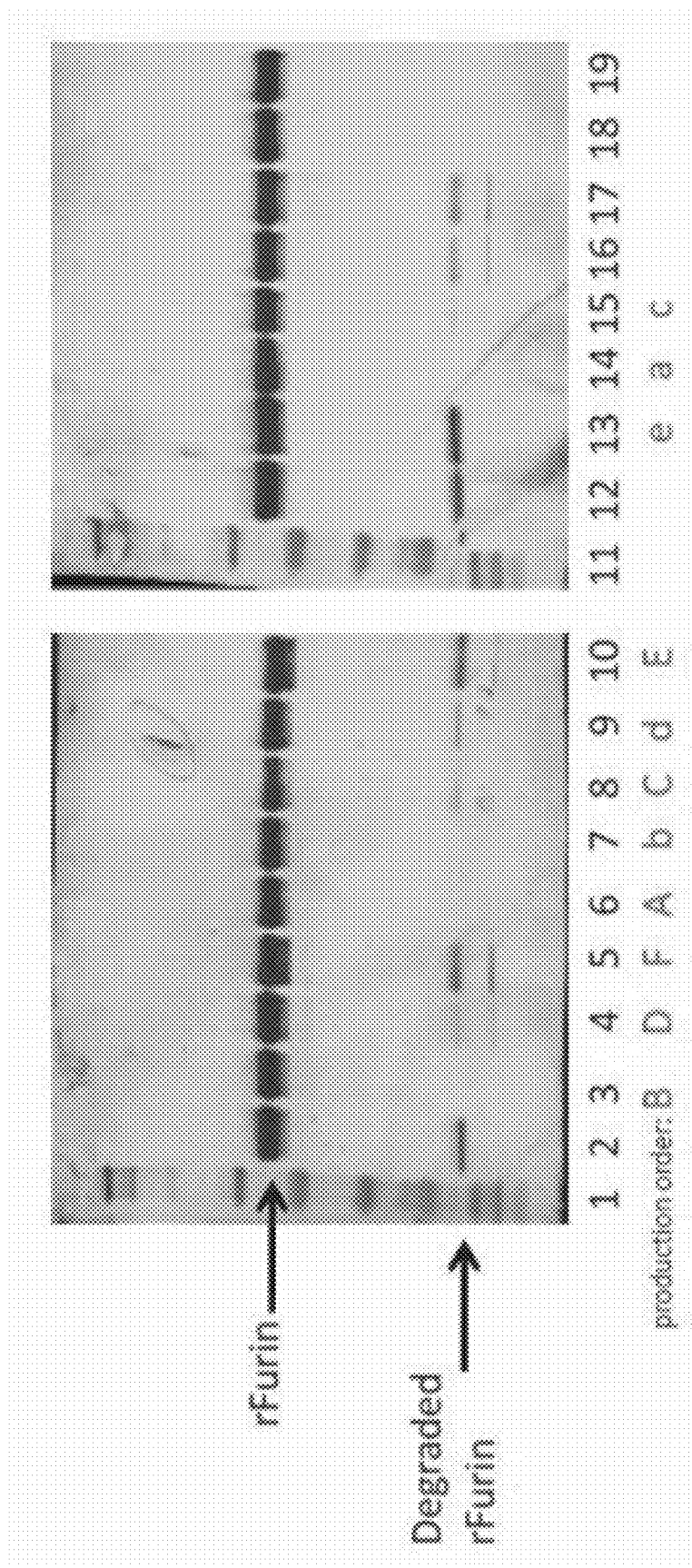
Figure 10:
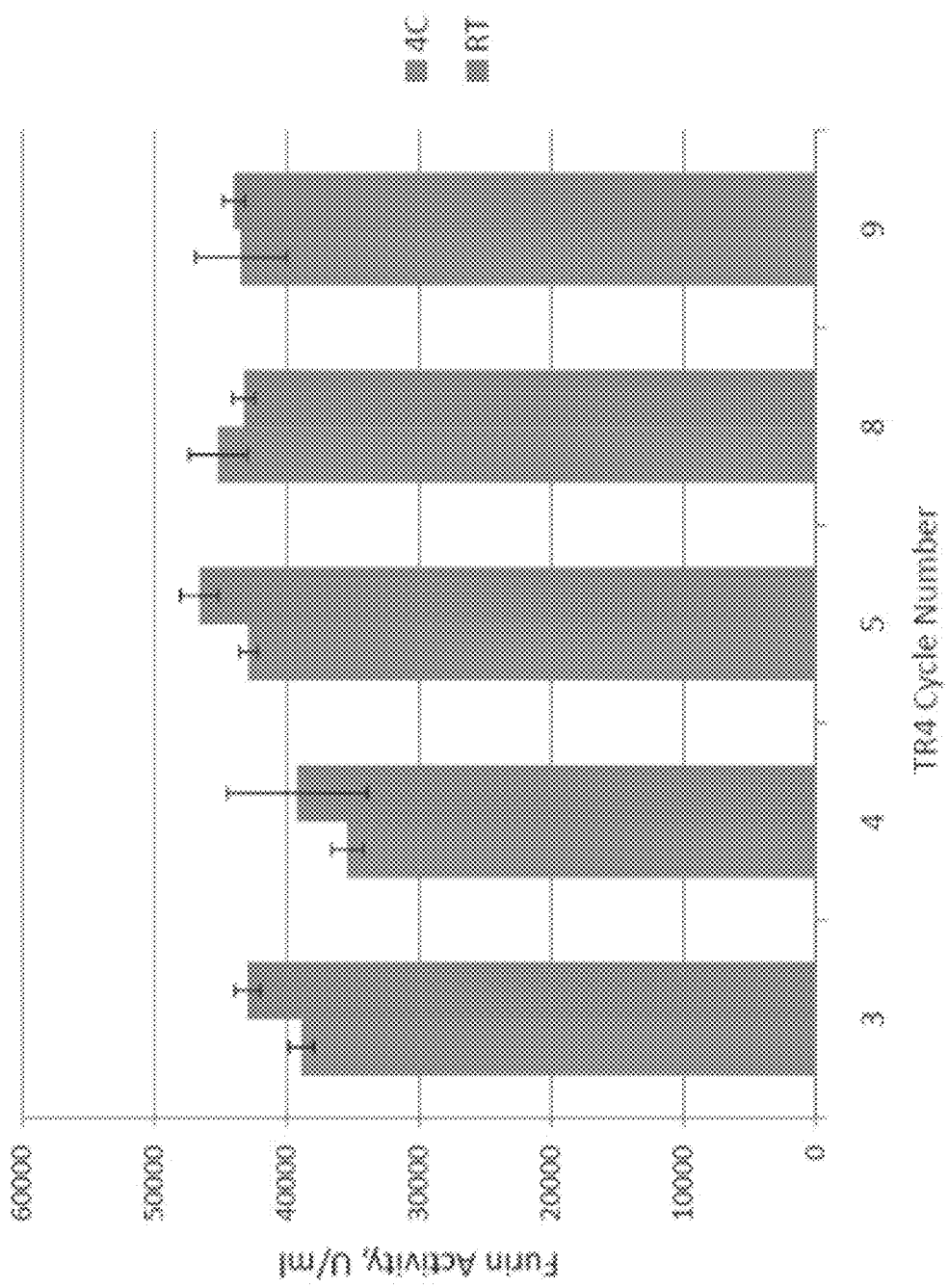

The agitation study was carried out by shaking a rfurin sample in a bottle containing Teflon balls. Samples were taken after 2 and 17 hours of agitation and analyzed by furin activity assay and SEC. As shown in the results for both the furin activity assay and SEC analysis (FIGS. 7 and 8, respectively), rfurin in the control formulation is fairly resistant to agitation for a limited period of time. After two hours of vigorous agitation, such as might occur during a diafiltration step, more than 85% of rfurin was still active in the control formulation. However, after 17 hours of agitation, as might occur during shipping of a sample, less than 10% of the rfurin content remained active.

The effect was then tested on furin test formulations #2 to 6, which were created by spiking nine parts of a rFurin sample with one part of 500 mM HEPES, 400 mM acetic acid, 1 mM CaCl2, pH 6 plus 10% w/w trehalose plus varied amounts of polysorbate 80.

This agitation study was carried out by shaking the test rfurin formulations and control formulation containing bottles with Teflon balls for three hours. Test formulations containing the following levels of polysorbate 80 were evaluated: none, 10 ppm, 25 ppm, 50 ppm, or 100 ppm. As shown in FIG. 31, polysorbate 80 in the test formulations provided significant protection to rfurin during agitation. After three hours of agitation, the activity of rFurin in the samples containing polysorbate 80 ranged from 31,499±1,218 U/mL to 36,787±847 U/mL, while the sample in the formulations without polysorbate 80 had 17,835±1,706 U/mL of Furin activity. The sample in the control formulation (10 mM sodium acetate, 230 mM sodium chloride, 1 mM calcium chloride, pH 6.0) had an activity of 24,368±1,135 U/mL.

Analyses by SEC confirmed the beneficial effect of polysorbate 80 in this study (FIG. 32). After three hours of agitation, the peak heights of rfurin in the samples containing polysorbate 80 ranged from 37.5 mAU to 35.9 mAU, while the height of the rFurin peak in the formulation without polysorbate 80 was 22.1 mAU. The height of the rFurin peak in the control formulation was 29.9 mAU. The effect of polysorbate 80 is also shown in FIGS. 33 and 34. The small trend suggests that the addition of 10 ppm and 25 ppm polysorbate 80, while still beneficial, is not as effective as use of 50 ppm or 100 ppm polysorbate 80. The SEC profile for the agitated sample in the control formulation (FIG. 35) does not show any additional peaks compared to the non-agitated sample. This would suggest that surface adsorption was the main reason for the activity loss. However, the UV absorption spectra (FIG. 36), show that the agitated sample has a slanted and elevated profile, which is a sign of light scattering and obscuration caused by the presence of aggregates. Light obscuration is generally caused by vary large aggregates that are more opaque than smaller molecules, which cause an elevation of the UV spectra. This phenomenon cannot be distinguished from absorption by a spectrophotometer because its detector measures the amount of light that passes through a sample. Since less light gets to the detector, it is reported as absorption; hence the absorption profile is elevated.

Light can also be scattered by aggregates, which would also decrease the amount of light getting into a detector. The shorter the wave length, the more light is scattered (the amount of scattered light is inversely proportional to the fourth power on the wavelength). This means that the shorter the wavelength the less light gets to a detector; hence the absorption profile is slanted. It is likely that the aggregates were present in this sample, but the SEC analysis was unable to detect them. These kinds of problems with SEC analyses are not uncommon as protein aggregates are often too large to pass through the column, or are absorbed by the column matrix. The UV absorption spectrum of the rfurin sample in the formulation without polysorbate 80 (FIG. 37) shows a similar elevated profile. Again, no aggregates were detected in the SEC analysis of this sample (FIG. 38). The samples formulated with polysorbate 80 show less aggregation than those without polysorbate 80 when analyzed by the UV absorption spectra (FIGS. 39 to 42). Although a UV spectrum cannot quantify the amount of aggregates, again, a small trend can be observed hinting that the samples with polysorbate 80 at 50 ppm and 100 ppm were better in protecting rFurin from aggregation than 10 ppm or 25 ppm. The data suggest that polysorbate 80 included in the formulation at a level of 75 ppm would be effective, as this concentration is in the middle of a wide plateau (50-10 ppm) and would represent a robust condition.

The UV spectrophotometry analysis was conducted using the following equipment and materials:
Agilent 8453 Spectrophotometer
Quartz cuvette 1 cm light pathway The spectrophotometry analysis was conducted by first placing 0.5 mL of an appropriate formulation in a cuvette and measured as a blank. Then, 0.5 mL of a rfurin sample was placed in a cuvette, and the scan was taken from 240 nm to 400 nm.

Example 4

Impact of pH, Sucrose and Polysorbate 80 on rFurin Stability rFurin samples were spiked with various buffers in order to adjust the pH to 5.0, 5.5, 6.0, 7.0 and 8.0. In addition, sucrose and/or polysorbate 80 were added to the samples at pH 6.0, 7.0 and 8.0. The samples were incubated at 37° C. and tested by the furin activity assay and SEC.

Figure 13:
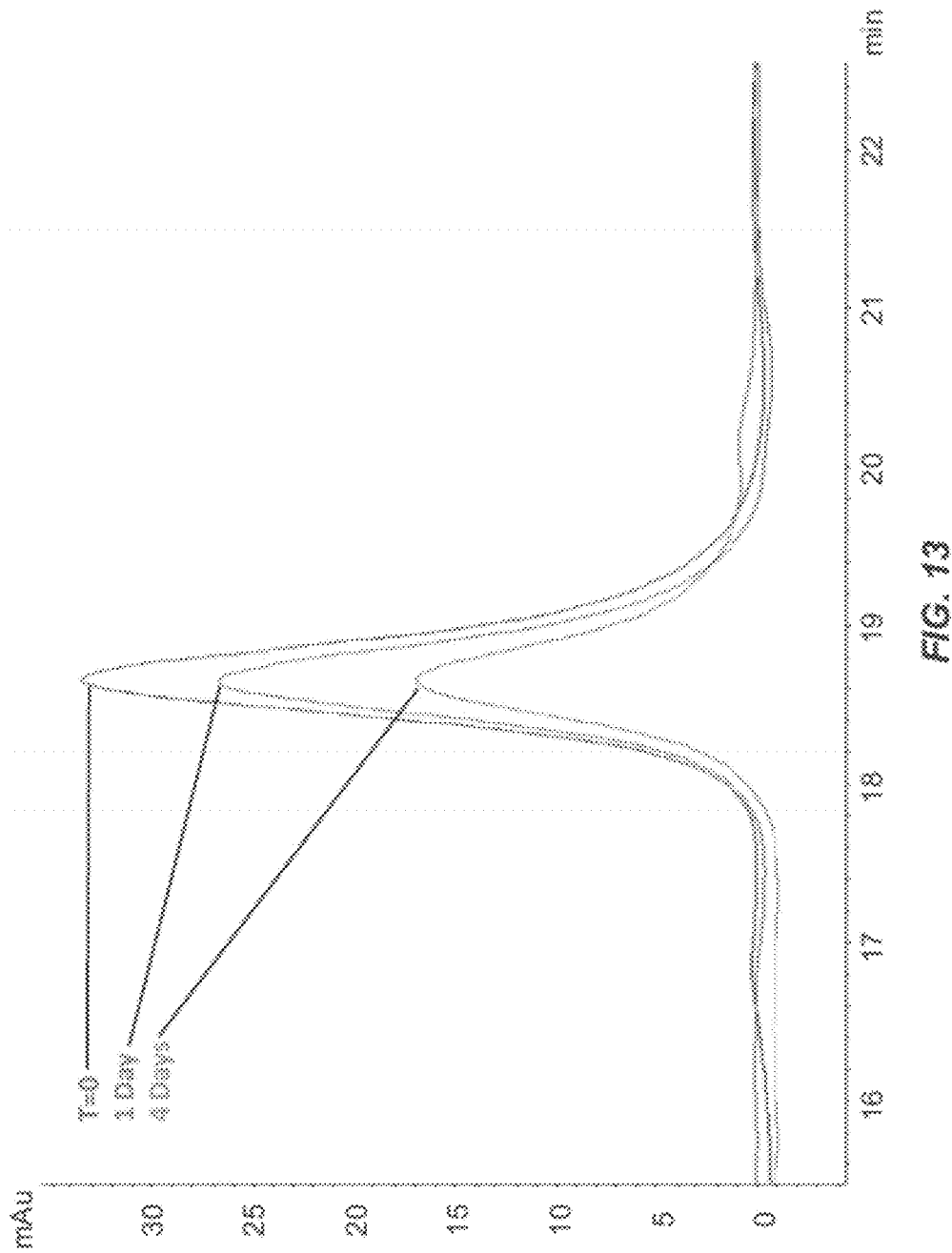
Figure 14:
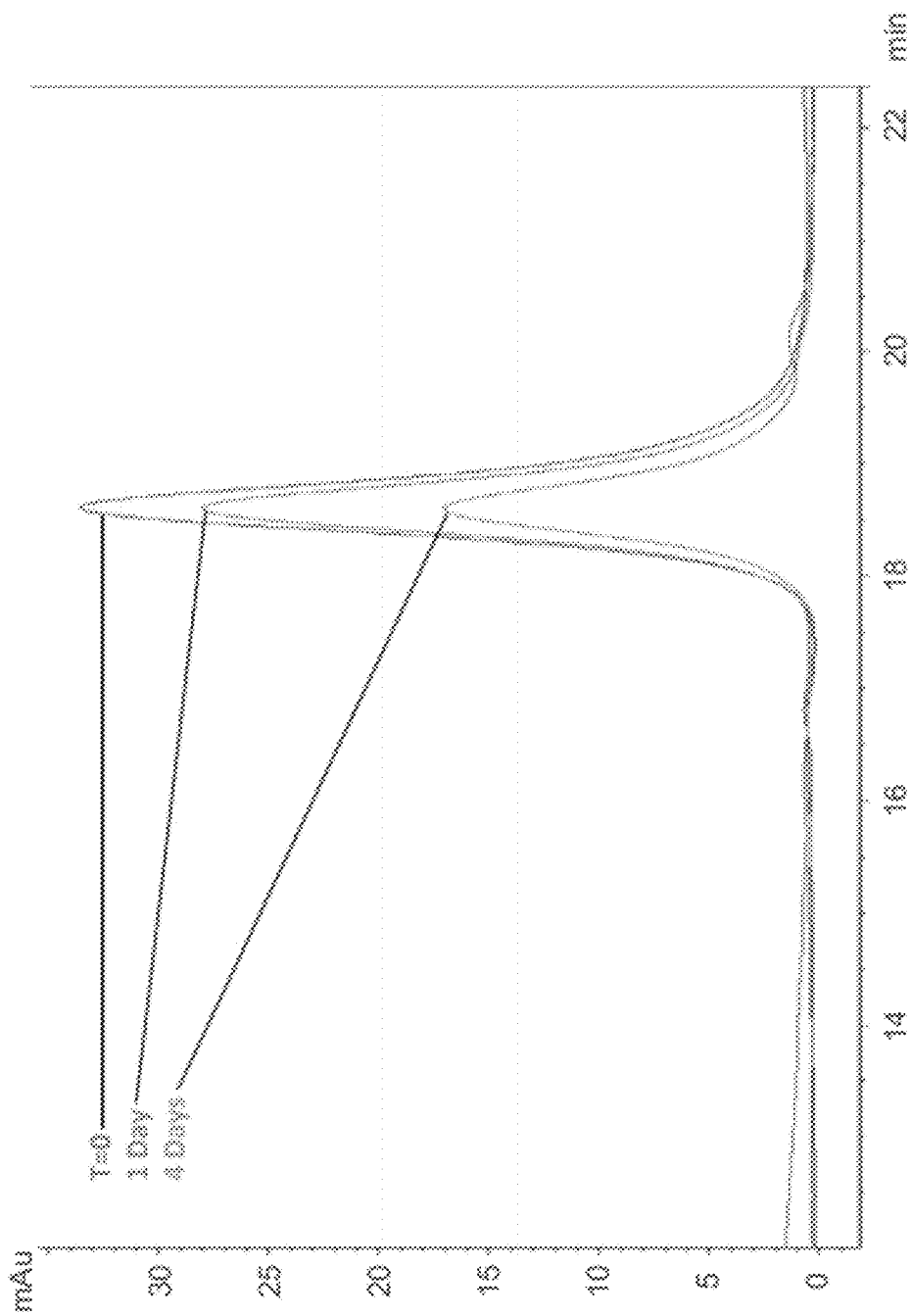
Figure 15:
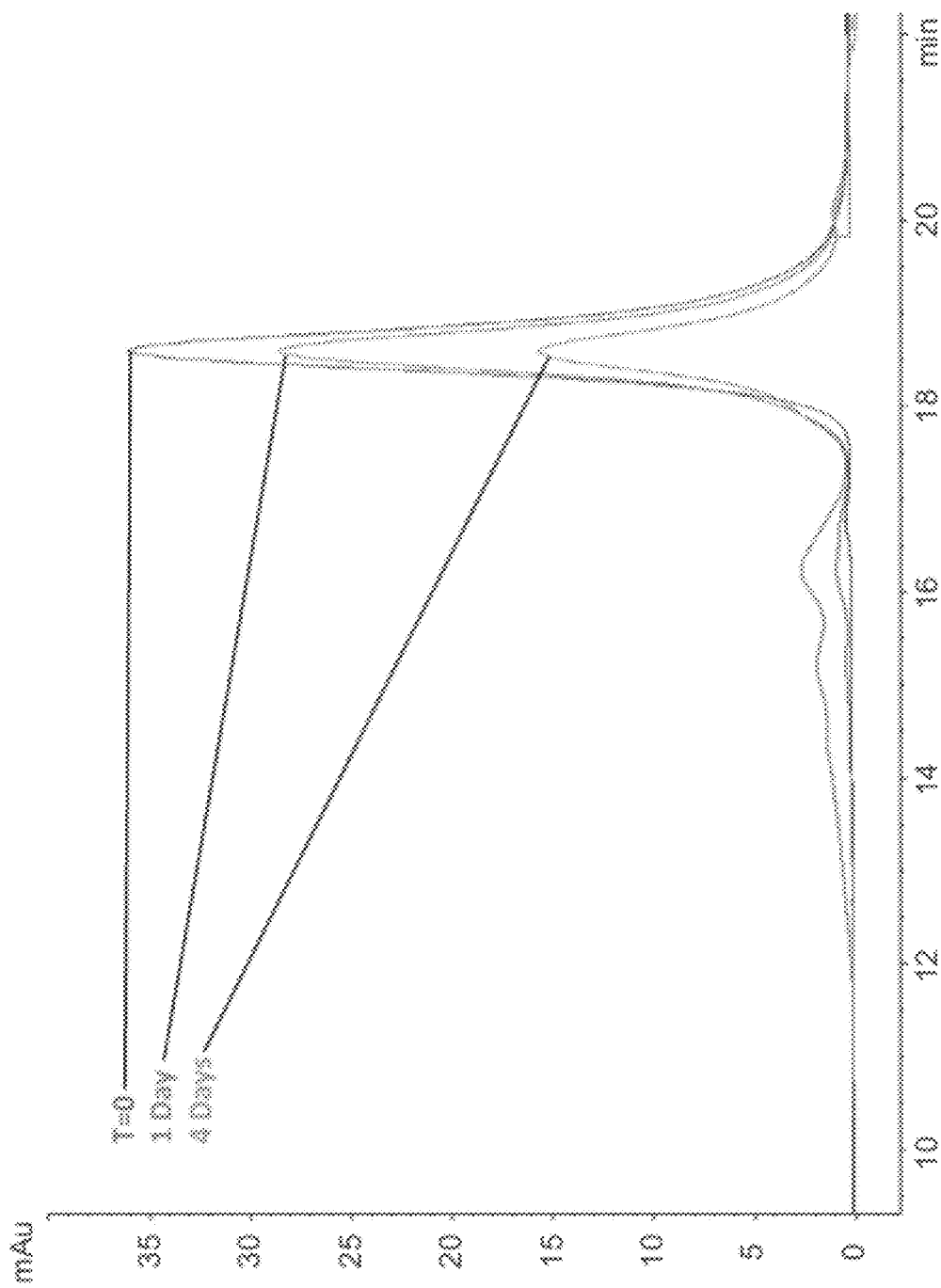
Figure 16:
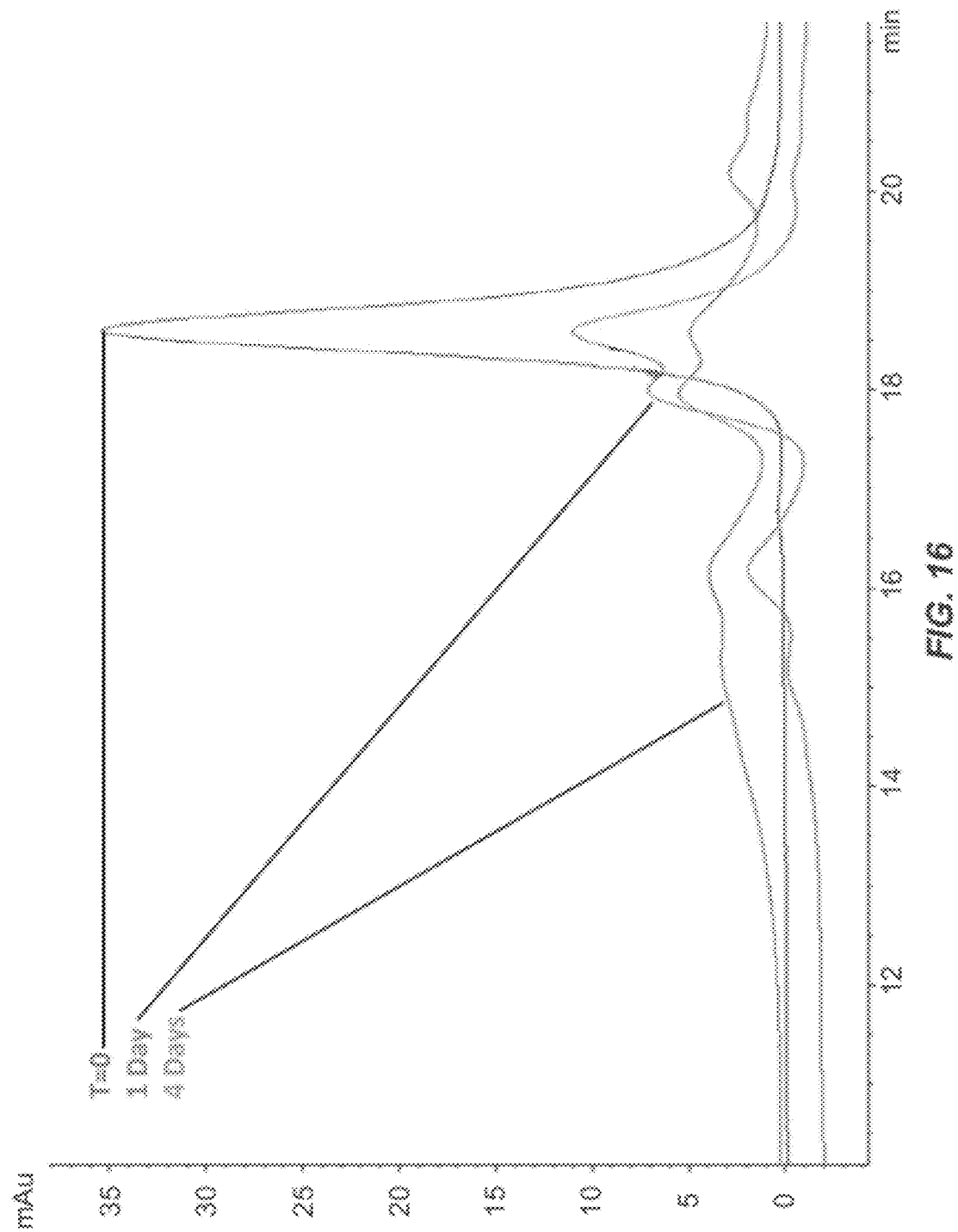
Figure 18:
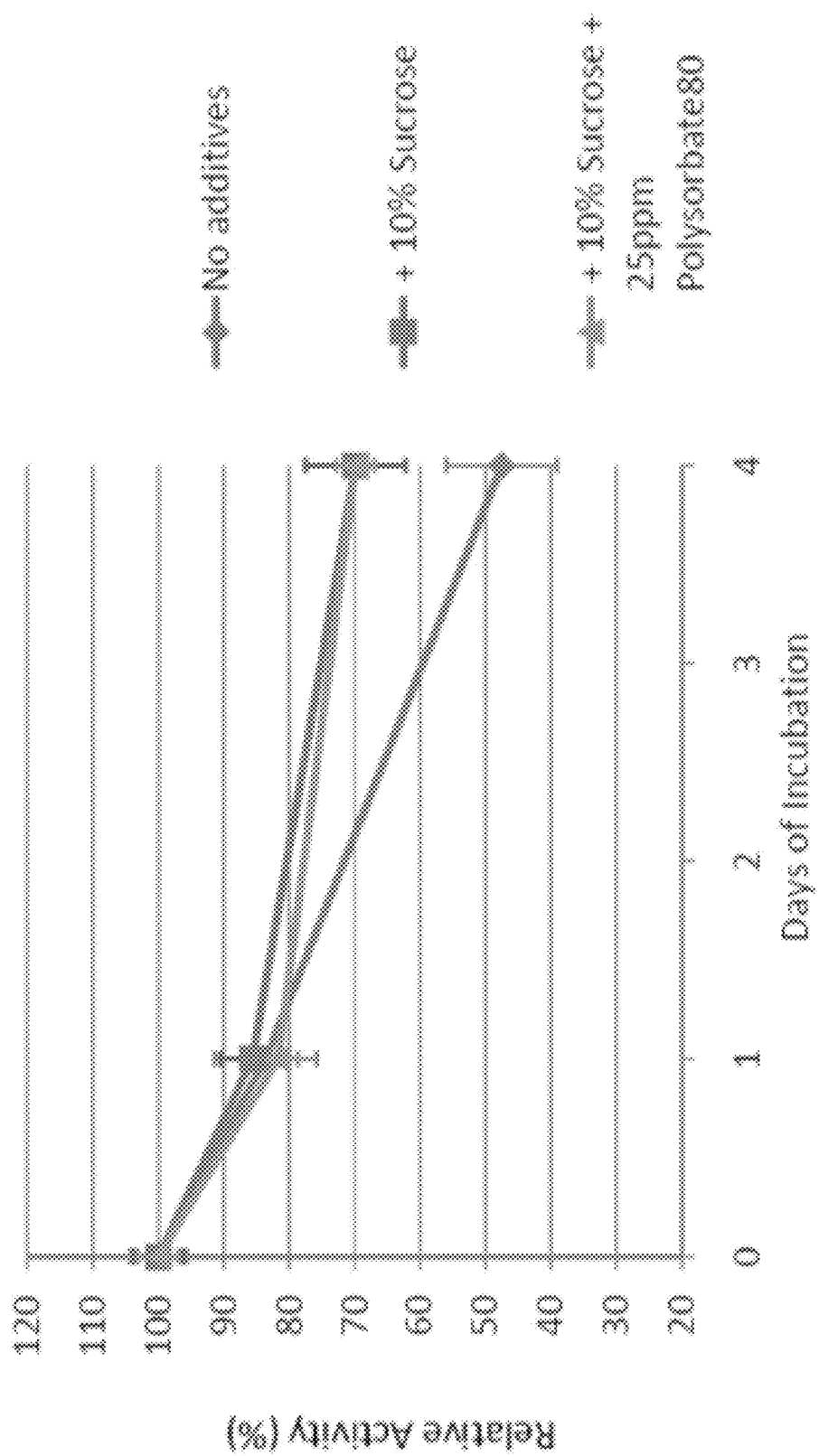

Both the furin activity assay (FIG. 11) and SEC (FIG. 12) showed that at 37° C. the rfurin was more stable at pH 6.0 than at pH 5.0 or 5.5. The samples at pH 6.0, in both the control formulation (FIG. 13) and in MES (FIG. 14), were more stable than those formulated in pH 7.0 or 8.0 (FIGS. 15 and 16) when analyzed by SEC. The addition of sucrose to the samples in pH 6.0 and 7.0 had a beneficial effect on rfurin stability. The SEC analyses (FIG. 17) showed that after four days of incubation at 37° C., the peak heights of the samples containing sucrose were on average at 75% of T=0, as compared to 52% without the sucrose. Analyses by the furin activity assay confirmed the results of the SEC experiments (FIGS. 18 and 19). The addition of sucrose improved rfurin stability in both the control formulation and in MES pH 6.0 (FIGS. 18 and 19), with similar stability seen using either buffer (FIG. 20). The effects of polysorbate 80 on rfurin stability in a sucrose-containing formulation at 37° C. were minimal, if any, as shown in FIGS. 17, 18, and 19.

These data suggest that at 37° C. rfurin is most stable in the pH 6.0 formulations compared to pH 5.0, 5.5, 7.0 and 8.0. The data further show that sucrose had a beneficial effect on rfurin stability at 37° C. In addition, no significant difference was seen in rfurin stability between the control buffer (acetate) or MES at pH 6.0 in the presence of 10% sucrose. Finally, there was no significant effect of polysorbate 80 on rfurin stability in a sucrose formulation at 37° C.

Example 5

Comparison of Furin Formulation Stability in Sucrose and Mannitol

As seen in Example 4, the addition of sucrose slowed down rfurin degradation and/or activity loss at 37° C. While sucrose is not used in downstream applications such as the rVWF process, other sugars and/or sugar alcohols are, such as mannitol. The addition of mannitol to the rfurin formulation, rather than sucrose, would therefore not introduce a new raw material to the vWF process. This study was conducted to determine whether the addition of mannitol would have a beneficial effect on rfurin stability. The test formulation also possessed an improved buffering capacity by addition of HEPES and acetic acid to final concentrations of 50 mM each at pH 6.0. A stabilized formulation was created by spiking a rfurin sample with 10% of 500 mM HEPES, 400 mM acetic acid, 1 mM $CaCl_2$, pH 6, and then, adding either sucrose, mannitol, and/or polysorbate 80. Analyses by both the furin activity assay (FIG. 21) and SEC (FIG. 22) showed that after four days of incubation at 37° C., mannitol and sucrose had similar stabilizing effects on rfurin formulations. Again, the effect of polysorbate 80 on these formulations was not significant. Although the activity data (FIG. 21) show that the sample containing mannitol and polysorbate 80 after 4 days of incubation at 37° C. was better than other samples, not only does this sample not follow the overall pattern, but also the SEC analyses (Figure) did not confirm it. It is likely that this result was an outlier.

Example 6

Comparison of Furin Formulation Stability in Sucrose and Trehalose

Various publications have shown that mannitol accelerates the denaturation of proteins during freezing, which raised some concerns about its inclusion in the rfurin formulation buffer. No such problems have been reported with trehalose, another sugar already part of the rVWF production process. This study was conducted to determine whether addition of trehalose would have a beneficial effect on rfurin stability. In addition, various concentrations of polysorbate 80 were evaluated. Analyses using the furin activity assay (FIGS. 23 and 24) showed that after 5 days of incubation at 37° C., the sample containing 10% sucrose retained 66.2%±2.9% of its original activity while the sample containing 10% trehalose retained 60.1%±4%. The difference between these samples is not significant. Both samples were significantly better in preserving rfurin activity than the control formulation, which retained only 37.5%±4.2% of its original activity.

Analyses by SEC (FIG. 25) confirmed the activity analyses. The rfurin peak for the sample in 10% sucrose retained 78.3% of its height compared to 75.1% for the sample in 10% trehalose and 44.2% for the control formulation. Also, analyses by western blotting (FIG. 26) showed the least degradation in the samples containing 10% sucrose or 10% trehalose. Note that the samples are presented as pairs, with day 0 followed by day 5 for each of the formulations.

Both the furin activity assay (FIG. 27) and SEC (FIG. 28) analyses show that 10% trehalose was better than 5% or 2% in preserving rfurin activity at 37° C. These findings were also confirmed by western blotting (FIG. 26). The impact of polysorbate 80 on rfurin stability at 37° C. was minimal according to the analyses by the furin activity assay and SEC (FIGS. 29 and 30, respectively).

SEC and furin activity assays were conducted as described above. Western blotting was performed using the following equipment and materials:

- Goat anti-Furin (peptide) primary antibody (Cat#SC-12484) from Santa Cruz Biotechnology, Inc.
- Rabbit anti-goat IgG-HRP conjugate secondary antibody (Cat#A5420) from Sigma
- Pierce Metal Enhanced Substrate Kit containing DAB/Metal Concentrate 10×,
- Pierce (Cat#1856090) and Stable Peroxidase Buffer, Pierce (Cat#185591)
- 4-20% Tris-Glycine gel (Cat#EC6025BOX) from Invitrogen
- NuPAGE® Sample Reducing Agent (0.5M DTT, 10×, Cat#NP0004) from Invitrogen
- Non-Reducing Sample Buffer (4×, Cat#84788) from Thermo
- PBS (Cat#P4417) from Sigma
- Tween 20 (Cat#9480) from EMD Chemicals
- BSA (Cat#A7906) from Sigma
- Gel transfer device (iBLOT Cat#IB401001) from Invitrogen
- PVDF (Immobilon-P, Cat#IPVH07850) transfer membrane from Millipore A polyclonal antibody was used in this study instead of a monoclonal to increase detection of rFurin degradation products. 5 μl of a sample was combined with 1 μl of 10×DTT, and 4 μl of 4× non-reducing dye. The sample was heated at 70° C. to 75° C. for 10 minutes. 10 μl of the sample was loaded to 4-20% SDS-PAGE gel, and run at 150 V for 60 to 70 minutes. The protein gel was transferred to PVDF membrane using the iBLOT at 20 V for 6 minutes. The PVDF membrane was then blocked with PBS buffer containing 0.1% TWEEN 20 and 3% BSA for 1 hour. The membrane was incubated for one hour in the primary antibody diluted 125 fold with the same buffer. The membrane was washed with PBST buffer for five minutes, three times each. The membrane was incubated for one hour in the secondary antibody diluted 10,000 fold with the same buffer as the primary antibody. The incubation time was 1 hour. The blot was washed using PBST buffer for five minutes, three times each. The blot was developed in 10 mL of premixed chromagenic substrate (1 ml concentrate plus 9 ml of Stable Peroxidase Buffer) followed by the wash with water for 10 minutes.

Example 7

Effects of Stabilizing Agents Upon Dilution of Furin Compositions

The rFurin dilution study was carried out to compare a starting formulation and its diluent to a stabilized formulation and a stabilized diluent. The study mimicked the dilution method that used in the rVWF maturation process. Briefly, rfurin BDS was passed through a filter followed by the addition of a 200-fold volume of the diluent. The main difference between the test dilution method and the starting dilution method is that in the test (highly stabilized) method, 75 ppm polysorbate 80 is present in both the rfurin BDS and the diluent, while in the starting method, there is no polysorbate 80 in either the rfurin BDS or the diluent.

Two dilution experiments were carried out, and both have shown that the combination of the stabilized formulation with its stabilized diluent was superior to the starting furin and diluent formulations. In the first experiment, the test method using the stabilized formulations recovered 83% to 87% of the expected rfurin activity, while the control methods recovered only 21% to 22% (Table 18). In this experiment, the rfurin sample was passed through a filter and followed by a 200-fold volume of a diluent. The filtrate was collected to a bag and then transferred to a graduated cylinder.

TABLE 18

Experimental results of rfurin dilution experiments performed with and without non-ionic surfactant.

| Sample | | Activity (IU) | St. Dev. | Dilution Factor | Expected Activity (IU) | Recovery (% Activity) |
|---|---|---|---|---|---|---|
| Starting Material | | 25,953 | 1,118 | 1 | N/A | N/A |
| Control Formulation | From a Bag | 27.264 | 2.815 | 200 | 129.8 | 21.0 |
| After Filtration | From a Cylinder | 28.3 | 1.56 | 200 | 129.8 | 21.8 |
| New Formulation | From a Bag | 108.137 | 6.611 | 200 | 129.8 | 83.3 |
| After Filtration | From a Cylinder | 113.4 | 5.21 | 200 | 129.8 | 87.4 |

In the second experiment, the test method recovered 80% of the expected rfurin activity, while the control method recovered only 27% (Table 19). In this experiment, the rfurin sample was passed through a filter and followed by a 200-fold volume of a diluent. The filtrate was collected to a cylinder. The combination of the stabilized rfurin formulation and the stabilized diluent increased rfurin recovery three to four times compared to the control method. The improved recovery is, without being limited by theory, linked to the presence of polysorbate 80.

TABLE 19

Experimental results of rfurin dilution experiments performed with and without non-ionic surfactant.

| Sample | Activity (IU) | St. Dev. | Dilution Factor | Expected Activity (IU) | Recovery (% Activity) |
|---|---|---|---|---|---|
| Starting Material | 32,379 | 1,654 | N/A | N/A | N/A |
| Control Formulation After Filtration | 44.267 | 1.607 | 200 | 161.9 | 27.3 |
| New Formulation After Filtration | 129.646 | 11.514 | 200 | 161.9 | 80.1 |

Example 8

Characteristics of Stabilized Formulation Stock Buffer

The stock buffer for the stabilized rfurin formulation (500 mM HEPES, 400 mM acetic acid, 1 mM $CaCl_2$, pH 6.0) can be made consistently (Table 20). The RSD's for pH and conductivity were <0.3%. The pH was slightly and indirectly correlated with temperature, dropping 0.014 units per degree Celsius, while conductivity was directly correlated with temperature, raising 0.40 mS/cm per degree C. (FIG. 49). The average temperature of the samples when the pH and conductivity were measured was 27.6° C. In manufacturing, the samples are read at 25±0.5° C. Based on the linear regressions in FIG. 48, the expected pH and conductivity at 25° C. were calculated. The relative standard deviation from Table 20 was applied to this value to determine the expected range (±3 sd). pH at 25° C. is expected to be 6.04 (±0.01). Conductivity at 25° C. is expected to be 19.9±0.2 mS/cm. These expected ranges are based on three lots made under limited circumstances. The specification ranges for the buffer need not be set this strictly. The pH specification will be the same as the final BDS pH specification, 5.90-6.10. The conductivity range will be similar to that used for the previous BDS buffer, e.g., with a range of ±20%, for a specification of 15.9-23.9 mS/cm. The requirements of the rVWF process are generally not of concern in setting the buffer specifications because the rfurin will be diluted 200-fold in the rVWF process. Experimental data in Table 21 and Table 22 correspond to the graphs presented in FIG. 49.

TABLE 20

Characteristics of stabilized formulation stock buffer.

| Reagent | Buffer 1 | Buffer 2 | Buffer 3 | mean | sd | rsd, % | mean + 3 sd | mean − 3 sd |
|---|---|---|---|---|---|---|---|---|
| Water, L | 0.85 | 0.85 | 0.85 | | | | | |
| HEPES, g | 119.15 | 119.15 | 119.15 | | | | | |
| CaCl2, g | 0.111 | 0.111 | 0.111 | | | | | |
| Acetic acid, mL | 23 | 23 | 23 | | | | | |
| 10M NaOH, mL | 39.4 | 39.4 | 39.4 | | | | | |
| pH | 6.011 | 6.003 | 6.005 | 6.006 | 0.004 | 0.07 | 6.019 | 5.994 |
| Cond., mS/cm | 21.23 | 21.15 | 21.11 | 21.16 | 0.06 | 0.29 | 21.35 | 20.98 |
| Temp., C. | 27.5 | 27.6 | 27.6 | 27.6 | 0.06 | 0.21 | 27.7 | 27.4 |

TABLE 21

Dependence of stock buffer conductivity on temperature.

| Temp, C. | Cond, mS/cm |
|---|---|
| 18 | 17.23 |
| 18.4 | 17.42 |
| 18.7 | 17.53 |

TABLE 21-continued

Dependence of stock buffer conductivity on temperature.

| Temp, C. | Cond, mS/cm |
|---|---|
| 19 | 17.63 |
| 19.3 | 17.75 |
| 19.6 | 17.86 |
| 19.7 | 17.91 |
| 20 | 18.03 |
| 20.2 | 17.72 |
| 20.5 | 17.83 |
| 21.6 | 17.86 |
| 24.4 | 19.81 |
| 27.6 | 21.1 |

TABLE 22

Dependence of stock buffer pH on temperature.

| Temp, C. | pH |
|---|---|
| 18 | 6.135 |
| 19.3 | 6.103 |
| 21.6 | 6.088 |
| 27.6 | 6.005 |

REFERENCES

All references cited herein are hereby incorporated by reference herein in their entirety and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments described herein are offered by way of example only, and the application is to be limited only by the terms of the appended claims, along with the full scope of equivalents to which the claims are entitled.

What is claimed:

1. A stabilized aqueous composition of recombinant furin (rfurin), the composition comprising:
   (a) from 8,000 U/mL to 500,000 U/mL rfurin;
   (b) from 190±10 mM of a pharmaceutically acceptable salt;
   (c) from 0.5 mM to 2mM calcium;
   (d) from 2% to 20% sugar or sugar alcohol;
   (e) from 10 to 200 ppm non-ionic surfactant;
   (f) from 10 to 200 mM buffering agent; and
   (g) a pH from 5.5 to 7.5.

2. The composition of claim 1, wherein the pharmaceutically acceptable salt is sodium chloride.

3. The composition of claim 1, comprising 0.9±0.2 mM calcium.

4. The composition of claim 1, comprising 10±2% sugar or sugar alcohol.

5. The composition of claim 1, wherein the sugar or sugar alcohol is selected from the group consisting of sucrose, trehalose, mannitol, and a combination thereof.

6. The composition of claim 1, comprising from 50 ppm to 100 ppm non-ionic surfactant.

7. The composition of claim 1, wherein the non-ionic surfactant is polysorbate-80.

8. The composition of claim 1, comprising 90±10 mM buffering agent.

9. The composition of claim 1, wherein the buffering agent comprises acetate and HEPES.

10. The composition of claim 9, comprising 45±5 mM acetate and 45±5 mM HEPES.

11. The composition of claim 1, having a pH of 6.0±0.2.

12. A stabilized aqueous composition of recombinant furin (rfurin), the composition comprising:
   (a) from 8,000 U/mL to 500,000 U/mL rfurin;
   (b) 190 mM sodium chloride;
   (c) 0.92 mM calcium;
   (d) 10% trehalose;
   (e) 75 ppm polysorbate 80;
   (f) 45 mM acetic acid;
   (g) 46 mM HEPES; and
   (g) a pH from 5.5 to 7.5.

13. The composition of claim 12, having a pH of 6.0±0.2.

14. The composition of claim 1, comprising 0.9±0.2 mM calcium.

15. The composition of claim 1, comprising 10±2% sugar or sugar alcohol.

16. The composition of claim 3, comprising 10±2% sugar or sugar alcohol.

17. The composition of claim 1, comprising from 50 ppm to 100 ppm non-ionic surfactant.

18. The composition of claim 3, comprising from 50 ppm to 100 ppm non-ionic surfactant.

19. The composition of claim 4, comprising from 50 ppm to 100 ppm non-ionic surfactant.

20. The composition of claim 1, comprising 90±10 mM buffering agent.

21. The composition of claim 3, comprising 90±10 mM buffering agent.

22. The composition of claim 4, comprising 90±10 mM buffering agent.

23. The composition of claim 6, comprising 90±10 mM buffering agent.

24. The composition of claim 1, having a pH of 6.0±0.2.

25. The composition of claim 3, having a pH of 6.0±0.2.

26. The composition of claim 4, having a pH of 6.0±0.2.

27. The composition of claim 6, having a pH of 6.0±0.2.

28. The composition of claim 8, having a pH of 6.0±0.2.

* * * * *

SEQUENCE LISTING

```
<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: furin cleavage substrate
<220> FEATURE:
<221> NAME/KEY: MOD_RES
<222> LOCATION: (1)..(1)
<223> OTHER INFORMATION: Modified at the N-terminus by a tert-
      butoxycarbonyl group
<220> FEATURE:
<221> NAME/KEY: MOD_RES
<222> LOCATION: (4)..(4)
<223> OTHER INFORMATION: Modified at the C-terminus by 7-amino-4-methoxy
      coumarin

<400> SEQUENCE: 1

Arg Val Arg Arg
1
```